United States Patent
Dilger et al.

(10) Patent No.: US 10,273,236 B2
(45) Date of Patent: Apr. 30, 2019

(54) MACROCYCLIC FACTOR XIA INHIBITORS BEARING HETEROCYCLIC GROUPS

(71) Applicant: Bristol-Myers Squibb Company, Princeton, NJ (US)

(72) Inventors: Andrew K. Dilger, Ewing, NJ (US); James R. Corte, Yardley, PA (US); Indawati De Lucca, Pennington, NJ (US); Tianan Fang, Newtown, PA (US); Wu Yang, Princeton Junction, NJ (US); Yufeng Wang, Belle Mead, NJ (US); Kumar Balashanmuga Pabbisetty, Piscataway, NJ (US); William R. Ewing, Yardley, PA (US); Yeheng Zhu, Stockton, NJ (US); Ruth R. Wexler, Belle Mead, NJ (US); Donald J. P. Pinto, Churchville, PA (US); Michael J. Orwat, New Hope, PA (US); Leon M. Smith, II, Somerset, NJ (US)

(73) Assignee: Bristol-Myers Squibb, Princeton, NJ (US)

( * ) Notice: Subject to any disclaimer, the term of this patent is extended or adjusted under 35 U.S.C. 154(b) by 0 days.

(21) Appl. No.: 15/946,837

(22) Filed: Apr. 6, 2018

(65) Prior Publication Data
US 2018/0222907 A1    Aug. 9, 2018

Related U.S. Application Data

(63) Continuation of application No. 15/680,729, filed on Aug. 18, 2017, now abandoned, which is a continuation of application No. 15/115,319, filed as application No. PCT/US2015/013647 on Jan. 30, 2015, now abandoned.

(60) Provisional application No. 61/933,948, filed on Jan. 31, 2014.

(51) Int. Cl.
*C07D 471/18* (2006.01)
*C07D 487/08* (2006.01)

(52) U.S. Cl.
CPC ......... *C07D 471/18* (2013.01); *C07D 487/08* (2013.01)

(58) Field of Classification Search
CPC ............................. C07D 471/18; C07D 487/08
See application file for complete search history.

(56) References Cited

U.S. PATENT DOCUMENTS

| 5,624,936 A | 4/1997 | deSolms |
| 5,869,682 A | 2/1999 | deSolms |
| 6,951,840 B2 | 10/2005 | Belvo et al. |
| 7,544,699 B2 | 6/2009 | Mjalli et al. |
| 8,940,720 B2 | 1/2015 | Corte et al. |
| 9,453,018 B2 | 9/2016 | Dilger et al. |

FOREIGN PATENT DOCUMENTS

| DE | 40 34 829 A1 | 5/1992 |
| EP | 0 525 420 B1 | 5/1999 |
| EP | 1 016 663 A1 | 7/2000 |
| EP | 1 125 925 A1 | 8/2001 |
| FR | 1525186 | 5/1968 |
| FR | 7155 M | 2/1970 |
| GB | 2497806 A | 6/2013 |
| JP | 2015-120685 A | 7/2015 |
| KR | 2015-0136294 A | 12/2015 |
| WO | WO 93/20099 A2 | 10/1993 |
| WO | WO 96/34010 A2 | 10/1996 |
| WO | WO 97/36891 A1 | 10/1997 |
| WO | WO 99/15530 A1 | 4/1999 |
| WO | WO 99/47545 A2 | 9/1999 |
| WO | WO 99/61444 A2 | 12/1999 |
| WO | WO 00/18733 A1 | 4/2000 |

(Continued)

OTHER PUBLICATIONS

U.S. Appl. No. 15/115,314, filed Jul. 29, 2016, Corte, James R.
U.S. Appl. No. 15/115,319, filed Jul. 29, 2016, Dilger, Andrew K.
U.S. Appl. No. 15/115,327, filed Jul. 29, 2016, Corte, James R.
Approaches of Classic Medicinal Chemistry, Optimizing Drug Binding Affinity: (Semi) Empirical Studies, http://www.chem.uzh.ch/zerbe/MedChem/MedChem4_MedChem.pdf (Mar. 18, 2012).

(Continued)

*Primary Examiner* — Bruck Kifle
(74) *Attorney, Agent, or Firm* — Mintz Levin Cohn Ferris Glovsky and Popeo, P.C.

(57) ABSTRACT

The present invention provides compounds of Formula (Ia):

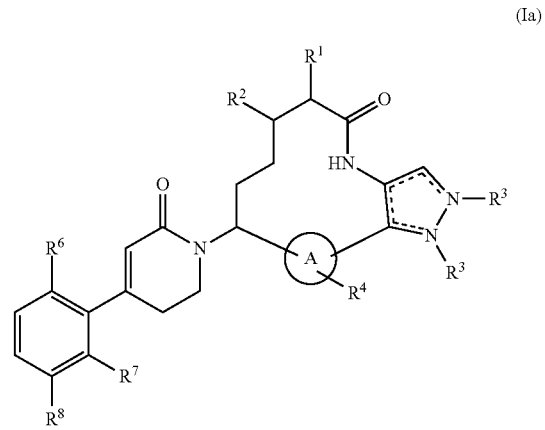

(Ia)

or stereoisomers, tautomers, or pharmaceutically acceptable salts thereof, wherein all the variables are as defined herein. These compounds are selective factor XIa inhibitors or dual inhibitors of FXIa and plasma kallikrein. This invention also relates to pharmaceutical compositions comprising these compounds and methods of treating thromboembolic and/or inflammatory disorders using the same.

11 Claims, No Drawings

(56) References Cited

FOREIGN PATENT DOCUMENTS

| WO | WO 00/40571 A1 | 7/2000 |
|---|---|---|
| WO | WO 00/61608 A2 | 10/2000 |
| WO | WO 01/85695 A1 | 11/2001 |
| WO | WO 02/18369 A2 | 3/2002 |
| WO | WO 03/011222 A2 | 2/2003 |
| WO | WO 03/041641 A2 | 5/2003 |
| WO | WO 03/106438 A1 | 12/2003 |
| WO | WO 2004/080971 A1 | 9/2004 |
| WO | WO 2004/094372 A2 | 11/2004 |
| WO | WO 2005/014533 A2 | 2/2005 |
| WO | WO 2005/099709 A2 | 10/2005 |
| WO | WO 2005/123050 A2 | 12/2005 |
| WO | WO 2005/123680 A1 | 12/2005 |
| WO | WO 2006/017295 A2 | 2/2006 |
| WO | WO 2006/076575 A2 | 7/2006 |
| WO | WO 2006/089005 A2 | 8/2006 |
| WO | WO 2007/047608 A2 | 4/2007 |
| WO | WO 2007/054453 A2 | 5/2007 |
| WO | WO 2007/070816 A2 | 6/2007 |
| WO | WO 2007/070818 A1 | 6/2007 |
| WO | WO 2007/070826 A1 | 6/2007 |
| WO | WO 2007/076431 A1 | 7/2007 |
| WO | WO 2008/076805 A2 | 6/2008 |
| WO | WO 2008/079836 A2 | 7/2008 |
| WO | WO 2008/157162 A1 | 12/2008 |
| WO | WO 2009/114677 A1 | 9/2009 |
| WO | WO 2010/151317 A1 | 12/2010 |
| WO | WO 2011/002520 A2 | 1/2011 |
| WO | WO 2011/017296 A1 | 2/2011 |
| WO | WO 2011/100401 A1 | 8/2011 |
| WO | WO 2011/100402 A1 | 8/2011 |
| WO | WO 2013/009527 A2 | 1/2013 |
| WO | WO 2013/022814 A1 | 2/2013 |
| WO | WO 2013/022818 A1 | 2/2013 |
| WO | WO 2013/055984 A1 | 4/2013 |
| WO | WO 2013/056034 A1 | 4/2013 |
| WO | WO 2013/056060 A1 | 4/2013 |
| WO | WO 2013/093484 A1 | 6/2013 |
| WO | WO 2013/111107 A1 | 8/2013 |
| WO | WO 2013/111108 A1 | 8/2013 |
| WO | WO 2013/118805 A1 | 8/2013 |
| WO | WO 2013/167669 A1 | 11/2013 |
| WO | WO 2013/174937 A1 | 11/2013 |
| WO | WO 2014/014050 A1 | 1/2014 |
| WO | WO 2014/022766 A1 | 2/2014 |
| WO | WO 2014/022767 A1 | 2/2014 |
| WO | WO 2014/059202 A1 | 4/2014 |
| WO | WO 2014/059203 A1 | 4/2014 |
| WO | WO 2014/059214 A1 | 4/2014 |
| WO | WO 2014/108679 A1 | 7/2014 |
| WO | WO 2014/108685 A1 | 7/2014 |
| WO | WO 2014/120346 A1 | 8/2014 |
| WO | WO 2014/154794 A1 | 10/2014 |
| WO | WO 2014/160668 A1 | 10/2014 |
| WO | WO 2015/011087 A1 | 1/2015 |
| WO | WO 2015/044163 A1 | 4/2015 |
| WO | WO 2015/044165 A1 | 4/2015 |
| WO | WO 2015/044167 A1 | 4/2015 |
| WO | WO 2015/044169 A1 | 4/2015 |
| WO | WO 2015/044170 A1 | 4/2015 |
| WO | WO 2015/044172 A1 | 4/2015 |
| WO | WO 2015/044173 A1 | 4/2015 |
| WO | WO 2015/044174 A1 | 4/2015 |
| WO | WO 2015/047973 A1 | 4/2015 |
| WO | WO 2015/054087 A1 | 4/2015 |
| WO | WO 2015/107724 A1 | 7/2015 |
| WO | WO 2015/116882 A1 | 8/2015 |
| WO | WO 2015/116885 A1 | 8/2015 |
| WO | WO 2015/116886 A1 | 8/2015 |
| WO | WO 2015/120062 A2 | 8/2015 |
| WO | WO 2015/120777 A1 | 8/2015 |
| WO | WO 2015/123090 A1 | 8/2015 |
| WO | WO 2015/123091 A1 | 8/2015 |
| WO | WO 2015/123093 A1 | 8/2015 |
| WO | WO 2015/134998 A1 | 9/2015 |
| WO | WO 2015/160634 A1 | 10/2015 |
| WO | WO 2015/160636 A1 | 10/2015 |
| WO | WO 2015/183709 A1 | 12/2015 |
| WO | WO 2016/046157 A1 | 3/2016 |
| WO | WO 2016/053455 A1 | 4/2016 |
| WO | WO 2016/093285 A1 | 6/2016 |
| WO | WO 2016/205482 A1 | 12/2016 |

OTHER PUBLICATIONS

Boger, D.L. et al., "Thermal Atropisomerism of Aglucovancomycin Derivatives: Preparation of $(M,M,M)$- and $(P,M,M)$-Aglucovancomycins", J. Am. Chem. Soc., vol. 120, No. 35, pp. 8920-8926 (1998).

Caballero, J. et al., "Quantitative Structure-Activity Relationship Modeling of Growth Hormone Secretagogues Agonist Activity of Some Tetrahydroisoquinoline 1-Carboxamides", Chem. Biol. Drug. Des., vol. 69, pp. 48-55 (2007).

Chan, J.C.Y. et al., "The Characterization of Mice with a Targeted Combined Deficiency of Protein C and Factor XI", American Journal of Pathology, vol. 158, No. 2, pp. 469-479 (2001).

Chen, X. et al., Chapter 32: "The use of bioisosteric groups in lead optimization", Annual Reports in Medicinal Chemistry, vol. 38, pp. 333-346, Elsevier Inc., publ. (2003).

Cho, J.E. et al., "Characterization of Binding Mode for Human Coagulation Factor XI (FXI) Inhibitors", Bull. Korean Chem. Soc., vol. 34, No. 4, pp. 1212-1220 (2013).

Crosby, J.R. et al., "Antithrombotic Effect of Antisense Factor XI Oligonucleotide Treatment in Primates", Arterioscler. Thromb. Vasc. Biol., vol. 33, pp. 1670-1678 (2013), and vol. 33, pp. e127 and e130 (errata) (2013).

Evans, D.A. et al., "Total Syntheses of Vancomycin and Eremomycin Aglycons", Angew. Chem. Int. Ed., vol. 37, No. 19, pp. 2700-2704 (1998).

Gailani, D., "Gene Targeting in Hemostasis, Factor XI", Frontiers in Bioscience, vol. 6, pp. 201-207 (2001).

Gailani, D. et al., "A murine model of factor XI deficiency", Blood Coagulation and Fibrinolysis, vol. 8, pp. 134-144 (1997).

Gruber, A. et al., "Factor XI-dependence of surface- and tissue factor-initiated thrombus propagation in primates", Blood, vol. 102, No. 3, pp. 953-955 (2003).

Hoffman, M., "A cell-based model of coagulation and the role of factor VIIa", Blood Reviews, vol. 17, pp. S1-S5 (2003).

Jiang, G. et al., "Highly Efficient Oxidation of Amines to Imines by Singlet Oxygen and Its Application in Ugi-Type Reactions", Organic Letters, vol. 11, No. 20, pp. 4568-4571 (2009).

Li, J.J. et al., "Tetrahydroisoquinoline 1-carboxamides as growth hormone secretagogues", Bioorganic & Medicinal Chemistry Letters, vol. 15, pp. 1799-1802 (2005).

Matafonov, A. et al., "Evidence for factor IX-independent roles for factor XIa in blood coagulation", Journal of Thrombosis and Haemostasis, vol. 11, pp. 2118-2127 (2013).

MayoClinic.com, "Pulmonary Embolism: Prevention", http://www.mayoclinic.com/health/pulmonary-embolism/DS00429/DSECTION=prevention, accessed May 20, 2013.

Meijers, J.C.M. et al., "High Levels of Coagulation Factor XI as a Risk Factor for Venous Thrombosis", The New England Journal of Medicine, vol. 342, pp. 696-701 (2000).

Meng, D. et al., "Development of a novel tricyclic class of potent and selective FIXa inhibitors", Bioorganic & Medicinal Chemistry Letters (2015), doi: http://dx.doi.org/10.1016/j.bmcl.2015.07.078.

Minnema, M.C. et al., "Activation of Clotting Factors XI and IX in Patients with Acute Myocardial Infarction", Arterioscler. Thromb. Vasc. Biol., vol. 20, pp. 2489-2493 (2000).

Murakami, T. et al., "Evaluation of Factor XIa-$\alpha_1$-Antitrypsin in Plasma, a Contact Phase-Activated Coagulation Factor-Inhibitor Complex, in Patients with Coronary Artery Disease", Arteriosclerosis, Thrombosis, and Vascular Biology, vol. 15, No. 8, pp. 1107-1113 (1995).

(56) References Cited

OTHER PUBLICATIONS

Ngouansavanh, T. et al., "IBX-Mediated Oxidative Ugi-Type Multicomponent Reactions: Application to the N and C1 Functionalization of Tetrahydroisoquinoline", Angew. Chem. Int. Ed., vol. 46, pp. 5775-5778 (2007).

Rosen, E.D. et al., "FXI is Essential for Thrombus Formation Following $FeCl_3$-Induced Injury of the Carotid Artery in the Mouse", Thromb. Haemost., vol. 87, pp. 774-776 (2002).

Schumacher, W.A. et al., "Inhibition of Factor XIa as a New Approach to Anticoagulation", Arterioscler. Thromb. Vasc. Biol., vol. 30, pp. 388-392 (2010).

Schuster, I. et al., "Convenient Synthesis of 1,2,3,4-Tetrahydroisoquinoline-1-Carboxylic Acid Derivatives via Isocyanide-Based Three-Component Reactions", Synthetic Communications, vol. 40, pp. 2488-2498 (2010).

Schuster, I. et al., "Synthesis of 1,2,3,4-Tetrahydroisoquinoline-1-Carboxylic Acid Derivatives Via Ugi Reactions", Letters in Organic Chemistry, vol. 4, No. 2, pp. 102-108 (2007).

Schuster, I. et al., "Synthesis of 1,2,3,4-Tetrahydroisoquinoline-1-carboxylic Acid Derivatives via Ugi Reactions", Magyar Kémiai Folyóirat (Hungarian Journal of Chemistry), vol. 116, No. 3, pp. 126-130 (2010).

Walsh, P.N., "Platelets and Factor XI Bypass the Contact System of Blood Coagulation", Thrombosis and Haemostasis, vol. 82, No. 2, pp. 234-242 (1999).

Wang, X. et al., "Effects of factor IX or factor XI deficiency on ferric chloride-induced carotid artery occlusion in mice", Journal of Thrombosis and Haemostasis, vol. 3, pp. 695-702 (2005).

Wu, Y.-J. et al., "Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain", Bioorganic & Medicinal Chemistry Letters, vol. 23, pp. 6188-6191 (2013).

Chinese Office Action dated Jan. 17, 2018, Application No. 2015800177593.

MACROCYCLIC FACTOR XIA INHIBITORS BEARING HETEROCYCLIC GROUPS

CROSS REFERENCE TO RELATED APPLICATIONS

This application is a continuation of U.S. application Ser. No. 15/680,729, filed Aug. 18, 2017 which is a continuation of U.S. application Ser. No. 15/115,319, filed Jul. 29, 2016, which is the 371 National Stage of International Application No. PCT/US2015/013647, filed Jan. 30, 2015, which claims the priority benefit of U.S. provisional patent application No. 61/933,948, filed on Jan. 31, 2014, the contents of which are incorporated herein in their entirety.

FIELD OF THE INVENTION

The present invention relates generally to novel macrocyclic compounds, and their analogues thereof, which are factor XIa inhibitors or dual inhibitors of factor XIa and plasma kallikrein, compositions containing them, and methods of using them, for example, for the treatment or prophylaxis of thromboembolic disorders, or for the treatment of retinal vascular permeability associated with diabetic retinopathy and diabetic macular edema.

BACKGROUND OF THE INVENTION

Thromboembolic diseases remain the leading cause of death in developed countries despite the availability of anticoagulants such as warfarin (COUMADIN®), heparin, low molecular weight heparins (LMWH), and synthetic pentasaccharides and antiplatelet agents such as aspirin and clopidogrel (PLAVIX®). The oral anticoagulant warfarin, inhibits the post-translational maturation of coagulation factors VII, IX, X and prothrombin, and has proven effective in both venous and arterial thrombosis. However, its usage is limited due to its narrow therapeutic index, slow onset of therapeutic effect, numerous dietary and drug interactions, and a need for monitoring and dose adjustment. Thus discovering and developing safe and efficacious oral anticoagulants for the prevention and treatment of a wide range of thromboembolic disorders has become increasingly important.

One approach is to inhibit thrombin generation by targeting the inhibition of coagulation factor XIa (FXIa). Factor XIa is a plasma serine protease involved in the regulation of blood coagulation, which is initiated in vivo by the binding of tissue factor (TF) to factor VII (FVII) to generate factor VIIa (FVIIa). The resulting TF:FVIIa complex activates factor IX (FIX) and factor X (FX) that leads to the production of factor Xa (FXa). The generated FXa catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Gailani, D. et al., *Arterioscler. Thromb. Vasc. Biol.*, 27:2507-2513 (2007).) The resulting burst of thrombin converts fibrinogen to fibrin that polymerizes to form the structural framework of a blood clot, and activates platelets, which are a key cellular component of coagulation (Hoffman, M., *Blood Reviews*, 17:S1-S5 (2003)). Therefore, factor XIa plays a key role in propagating this amplification loop and is thus an attractive target for anti-thrombotic therapy.

An alternative way of initiation of coagulation is operative when blood is exposed to artificial surfaces. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI.

Plasma prekallikrein is a zymogen of a trypsin-like serine protease and is present in plasma at 35 to 50 μg/mL. The gene structure is similar to that of factor XI. Overall, the amino acid sequence of plasma kallikrein has 58% homology to factor XI. Plasma kallikrein is thought to play a role in a number of inflammatory disorders. The major inhibitor of plasma kallikrein is the serpin C1 esterase inhibitor. Patients who present with a genetic deficiency in C1 esterase inhibitor suffer from hereditary angioedema (HAE) which results in intermittent swelling of face, hands, throat, gastrointestinal tract and genitals. Blisters formed during acute episodes contain high levels of plasma kallikrein which cleaves high molecular weight kininogen liberating bradykinin leading to increased vascular permeability. Treatment with a large protein plasma kallikrein inhibitor has been shown to effectively treat HAE by preventing the release of bradykinin which causes increased vascular permeability (Lehmann, "Ecallantide (DX-88), a plasma kallikrein inhibitor for the treatment of hereditary angioedema and the prevention of blood loss in on-pump cardiothoracic surgery", *Expert Opin. Biol. Ther.*, 8:1187-1199 (2008)).

The plasma kallikrein-kinin system is abnormally abundant in patients with advanced diabetic macular edema. It has been recently published that plasma kallikrein contributes to retinal vascular dysfunctions in diabetic rats (Clermont, A. et al., "Plasma kallikrein mediates retinal vascular dysfunction and induces retinal thickening in diabetic rats", *Diabetes*, 60:1590-1598 (2011)). Furthermore, administration of the plasma kallikrein inhibitor ASP-440 ameliorated both retinal vascular permeability and retinal blood flow abnormalities in diabetic rats. Therefore, a plasma kallikrein inhibitor should have utility as a treatment to reduce retinal vascular permeability associated with diabetic retinopathy and diabetic macular edema. Other complications of diabetes such as cerebral hemorrhage, nephropathy, cardiomyopathy and neuropathy, all of which have associations with plasma kallikrein may also be considered as targets for a plasma kallikrein inhibitor.

To date, no small molecule synthetic plasma kallikrein inhibitor has been approved for medical use. The large protein plasma kallikrein inhibitors present risks of anaphylactic reactions, as has been reported for Ecallantide. Thus there remains a need for compounds that inhibit plasma kallikrein, that do not induce anaphylaxis and that are orally available. Furthermore, the molecules in the known art feature a highly polar and ionizable guanidine or amidine functionality. It is well known that such functionalities may be limiting to gut permeability and therefore to oral availability.

SUMMARY OF THE INVENTION

The present invention provides novel macrocyclic compounds, their analogues, including stereoisomers, tautomers, pharmaceutically acceptable salts, or solvates thereof, which are useful as selective factor XIa inhibitors or dual inhibitors of factor XIa and plasma kallikrein.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used in the treatment and/or prophylaxis of thromboembolic disorders.

The compounds of the invention may be used in the treatment of retinal vascular permeability associated with diabetic retinopathy and diabetic macular edema.

The compounds of the present invention may be used in therapy.

The compounds of the present invention may be used for the manufacture of a medicament for the treatment and/or prophylaxis of a thromboembolic disorder.

The compounds of the invention can be used alone, in combination with other compounds of the present invention, or in combination with one or more, preferably one to two other agent(s).

These and other features of the invention will be set forth in expanded form as the disclosure continues.

DETAILED DESCRIPTION OF THE INVENTION

I. Compounds of the Invention

In one aspect, the present invention provides, inter alia, compounds of Formula (I):

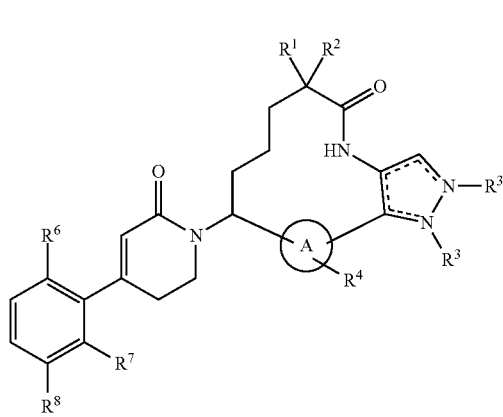

(I)

or stereoisomers, tautomers, pharmaceutically acceptable salts, solvates, or prodrugs thereof, wherein:
--- is an optional bond;
ring A is independently selected from

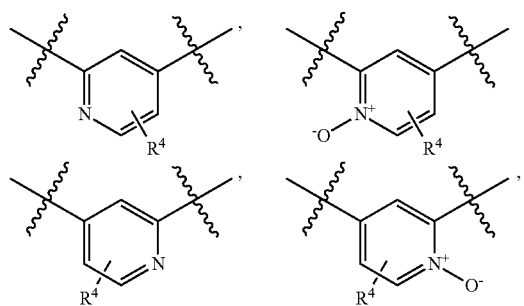

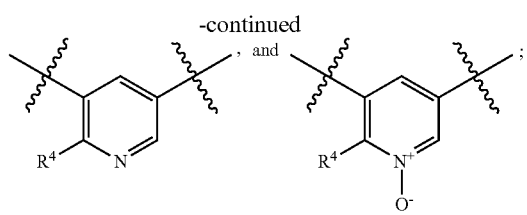

, and $R^1$ and $R^2$ are independently selected from H, F, $C_{1-4}$ alkyl, alkoxy, and hydroxyl;
$R^3$, at each occurrence, is absent or independently selected from H, $C_{1-4}$alkyl, $C_{1-4}$haloalkyl, —$(CH_2)_n$—$OR^5$, —$(CH_2)_n$—$C(O)OR^5$, and $C_{3-6}$ cycloalkyl;
$R^4$ is independently selected from H, OH, F, $OC_{1-4}$ alkyl, $C_{1-4}$ alkyl, and CN;
$R^5$ is independently selected from H and $C_{1-4}$ alkyl;
$R^6$ is independently selected from H, F, Cl, Br, CN, $OCH_3$, $CH_3$, $C(O)CH_3$, $CF_3$, $OCHF_2$, $NHC(O)C_{1-4}$ alkyl, aryl, $C_{3-6}$ cycloalkyl, and 4-6 membered heterocycle substituted with $R^9$;
$R^7$ is independently selected from H and F;
$R^8$ is independently selected from H, F, Cl, and $OCH_3$;
$R^9$ is independently selected from H, $C_{1-4}$ alkyl and halogen; and
n, at each occurrence, is an integer independently selected from 0, 1, and 2.

In another aspect, the present invention provides compounds of Formula (II):

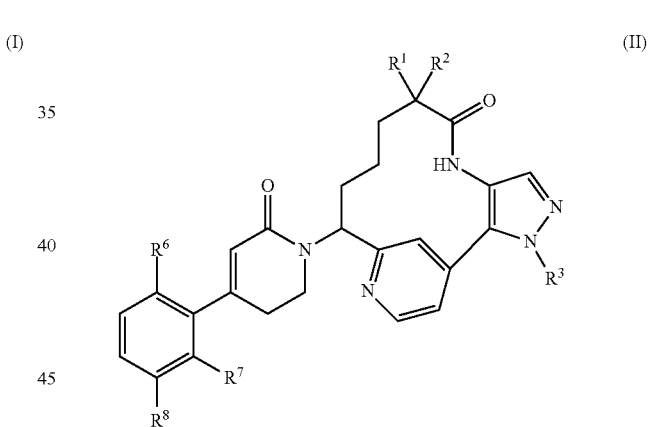

(II)

or stereoisomers, tautomers, pharmaceutically acceptable salts, solvates, or prodrugs thereof, wherein:
$R^1$ and $R^2$ are independently selected from H and $C_{1-4}$ alkyl;
$R^3$ is independently selected from H, $C_{1-4}$alkyl, $C_{1-4}$haloalkyl, —$(CH_2)_n$—$OR^5$, —$(CH_2)_n$—$C(O)OR^5$, and $C_{3-6}$ cycloalkyl;
$R^5$ is independently selected from H and $C_{1-4}$ alkyl;
$R^6$ is independently selected from H, F, $CF_3$, and triazole substituted with $R^9$;
$R^7$ is independently selected from H and F;
$R^8$ is independently selected from H, F, and Cl;
$R^9$ is independently selected from H and halogen; and
n, at each occurrence, is an integer independently selected from 0, 1, and 2.

In another aspect, the present invention provides compounds of Formula (II), or stereoisomers, tautomers, pharmaceutically acceptable salts, solvates, or prodrugs thereof, wherein:

$R^1$ and $R^2$ are independently selected from H and $CH_3$;
$R^3$ is independently selected from H, $CH_3$, $CH_2CH_3$, $-CH_2CHF_2$, $-CH_2CF_3$, $-(CH_2)_n-OH$, $-(CH_2)_n-C(O)OH$, and cyclopropyl;
$R^6$ is independently selected from F, $CF_3$, and

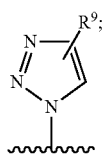

$R^7$ is independently selected from H and F;
$R^8$ is independently selected from H, F, and Cl;
$R^9$ is independently selected from H and Cl; and
n, at each occurrence, is an integer independently selected from 0, 1, and 2.

In another aspect, the present invention provides compounds of Formula (III):

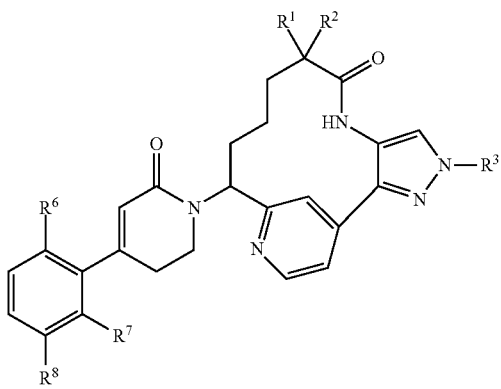

(III)

or stereoisomers, tautomers, pharmaceutically acceptable salts, solvates, or prodrugs thereof, wherein:
$R^1$ and $R^2$ are independently selected from H and $C_{1-4}$ alkyl;
$R^3$ is independently selected from H, $-(CH_2)_n-C(O)OH$;
$R^6$ is independently selected from H, F, $CF_3$, and triazole substituted with $R^9$;
$R^7$ is independently selected from H and F;
$R^8$ is independently selected from H, F, and Cl;
$R^9$ is independently selected from H and halogen; and
n, at each occurrence, is an integer independently selected from 0, 1, and 2.

In another aspect, the present invention provides compounds of Formula (II), or stereoisomers, tautomers, pharmaceutically acceptable salts, solvates, or prodrugs thereof, wherein:
$R^6$ is independently selected from F, $CF_3$ and

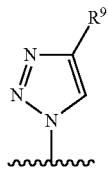

$R^7$ is independently selected from H and F;
$R^8$ is Cl;
$R^9$ is independently selected from H and Cl; and
other variables are as defined in Formula (II).

In another aspect, the present invention provides compounds of Formula (II), or stereoisomers, tautomers, pharmaceutically acceptable salts, solvates, or prodrugs thereof, wherein:
$R^6$ is independently selected from F, $CF_3$ and

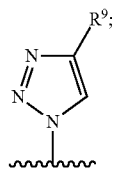

$R^7$ is independently selected from H and F;
$R^8$ is Cl;
$R^9$ is independently selected from H and Cl; and
other variables are as defined in Formula (III).

In another aspect, the present invention provides compounds of Formula (Ia):

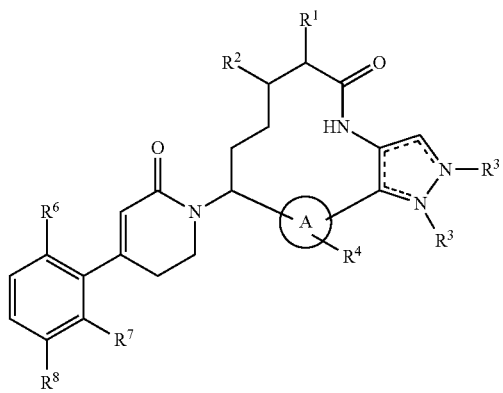

(Ia)

or stereoisomers, tautomers, pharmaceutically acceptable salts, solvates, or prodrugs thereof, wherein:
--- is an optional bond;
ring A is independently selected from

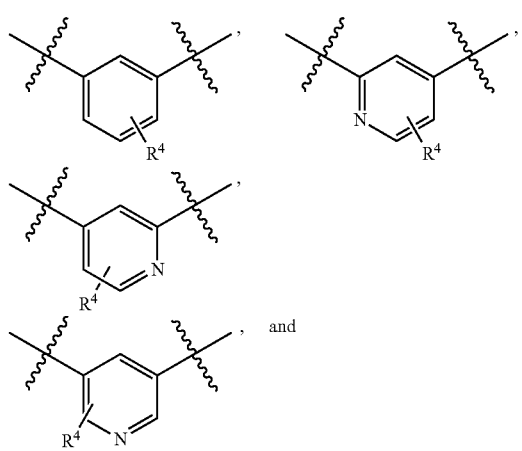

-continued

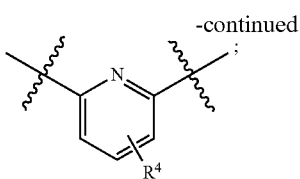

R¹ is independently selected from H, F, OH, and C$_{1-4}$ alkyl;
R² is independently selected from H, F, and OH;
R³ is absent or independently selected from H, C$_{1-4}$alkyl, C$_{1-4}$haloalkyl, —(CH$_2$)$_n$—OR⁵, —(CH$_2$)$_n$—C(O)OR⁵, C$_{3-6}$ cycloalkyl optionally substituted with halogen, and 5- to 6-membered heteroaryl comprising carbon atoms and 1-2 nitrogen atoms and optionally substituted with R¹; provided only one R³ group is present on the ring;
R⁴ is independently selected from H, OH, F, OC$_{1-4}$ alkyl, C$_{1-4}$ alkyl, and CN;
R⁵ is independently selected from H and C$_{1-4}$ alkyl;
R⁶ is independently selected from H, F, Cl, Br, CN, OCH$_3$, CH$_3$, C(O)CH$_3$, CHF$_2$, CCH$_3$F$_2$, CF$_3$, OCHF$_2$, NHC(O)C$_{1-4}$ alkyl, C$_{3-6}$ cycloalkyl, and 5-membered heterocycle substituted with R⁹;
R⁷ is independently selected from H and F;
R⁸ is independently selected from H, F, Cl, and OCH$_3$;
R⁹ is independently selected from H, cyano, C$_{1-4}$ alkyl, haloalkyl, and halogen; and
n, at each occurrence, is an integer selected from 1 and 2.

In another aspect, the present invention provides compounds of Formula (IIa):

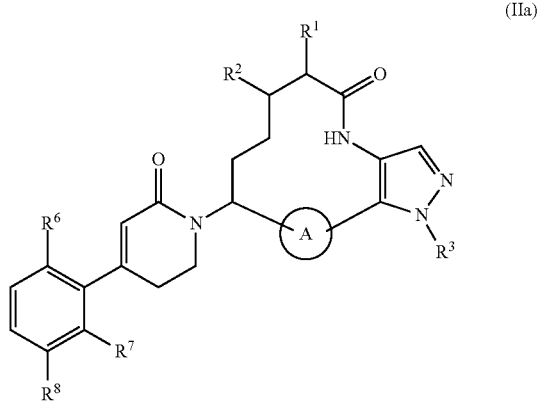

or stereoisomers, tautomers, pharmaceutically acceptable salts, solvates, or prodrugs thereof, wherein:
ring A is independently selected from

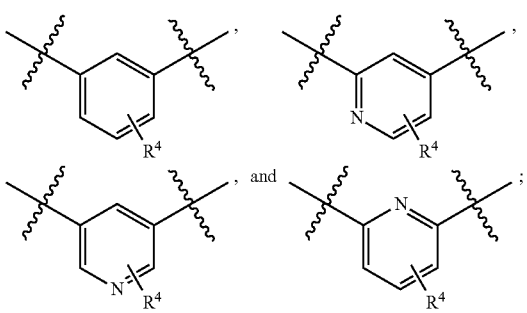

R¹ is independently selected from H and C$_{1-3}$alkyl;
R² is independently selected from H and F;
R³ is independently selected from H, C$_{1-3}$alkyl, C$_{1-3}$haloalkyl, —(CH$_2$)$_n$—OR⁵, —(CH$_2$)$_n$—C(O)OR⁵, and C$_{3-4}$ cycloalkyl optionally substituted with halogen;
R⁴ is independently selected from H and F;
R⁵ is independently selected from H and C$_{1-4}$ alkyl;
R⁶ is independently selected from H, F, Cl, Br, CN, CF$_3$, C(O)CH$_3$, CHF$_2$, CCH$_3$F$_2$, CF$_3$, OCHF$_2$,

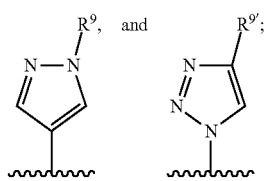

R⁷ is independently selected from H and F;
R⁸ is independently selected from H, F, Cl, and OCH$_3$;
R⁹ is independently selected from H, CHF$_2$, and CF$_3$;
R⁹' is independently selected from H, F, Cl, CN, CHF$_2$, and CF$_3$; and
n, at each occurrence, is an integer selected from 1 and 2.

In another aspect, the present invention provides compounds of Formula (IIa) or stereoisomers, tautomers, pharmaceutically acceptable salts, solvates, or prodrugs thereof, wherein:
R¹ is independently selected from H, CH$_3$, and CH(CH$_3$)$_2$;
R² is independently selected from H and F;
R³ is independently selected from H, CH$_3$, CD$_3$, CH$_2$CH$_3$, —CHF$_2$, —CH$_2$CHF$_2$, —CH$_2$CF$_3$, —CH$_2$CH$_2$OH, CH$_2$CH$_2$OC(CH$_3$)$_3$, —CH$_2$C(O)OH, cyclopropyl optionally substituted with F, and cyclobutyl;
R⁶ is independently selected from H, F, Cl, Br, CN, CF$_3$, C(O)CH$_3$, CHF$_2$, CCH$_3$F$_2$, CF$_3$, OCHF$_2$,

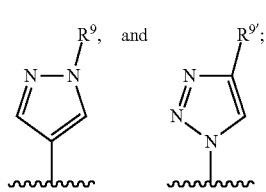

R⁷ is independently selected from H and F;
R⁸ is independently selected from H, F, Cl, and OCH$_3$;
R⁹ is independently selected from H, CHF$_2$, and CF$_3$; and
R⁹' is independently selected from H, F, Cl, CN, CHF$_2$, and CF$_3$.

In another aspect, the present invention provides compounds of Formula (IIIa):

(IIIa)

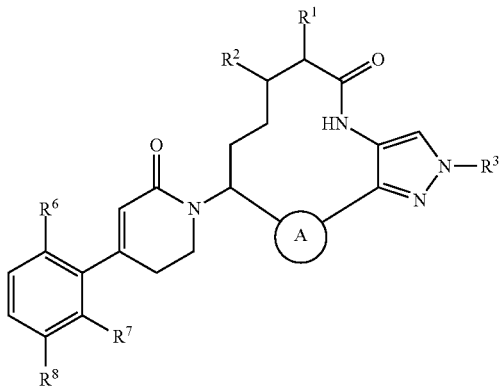

or stereoisomers, tautomers, pharmaceutically acceptable salts, solvates, or prodrugs thereof, wherein:
ring A is independently selected from

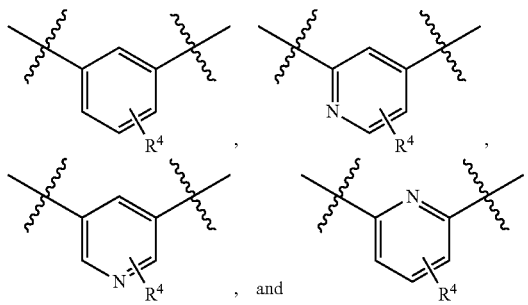

$R^1$ is independently selected from H, $CH_3$, and $CH(CH_3)_2$;
$R^2$ is independently selected from H and F;
$R^3$ is independently selected from H, $CH_2C(=O)OH$, $CH_2C(=O)OCH_2CH_3$,

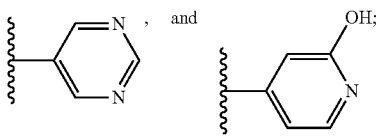 [SMILES: *c1cncnc1 ; *c1ccnc(O)c1]

$R^4$ is independently selected from H and F;
$R^6$ is independently selected from H, F, Cl, Br, CN, $CF_3$, $C(O)CH_3$, $CHF_2$, $CCH_3F_2$, $CF_3$, $OCHF_2$,

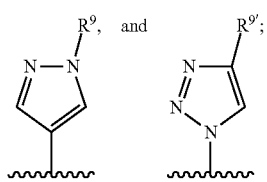

$R^7$ is independently selected from H and F;
$R^8$ is independently selected from H, F, Cl, and $OCH_3$;
$R^9$ is independently selected from H, $CHF_2$, and $CF_3$; and
$R^{9'}$ is independently selected from H, F, Cl, CN, $CHF_2$, and $CF_3$.

In another aspect, the present invention provides compounds of Formula (Ia), or stereoisomers, tautomers, pharmaceutically acceptable salts, solvates, or prodrugs thereof, wherein:
$R^3$ is independently selected from H, $CH_3$, $CD_3$, $CH_2CH_3$, $CHF_2$, $CH_2CHF_2$, $CH_2CF_3$, $CH_2CH_2OH$, $CH_2CH_2OC(CH_3)_3$, $CH_2C(O)OH$, $CH_2C(=O)OH$, $CH_2C(=O)OCH_2CH_3$, cyclopropyl optionally substituted with F, and cyclobutyl,

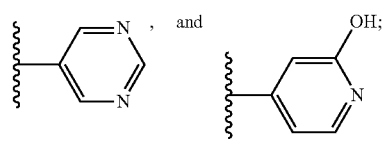

$R^6$ is independently selected from H, F, Cl, Br, CN, $CF_3$, $C(O)CH_3$, $CHF_2$, $CCH_3F_2$, $CF_3$, $OCHF_2$,

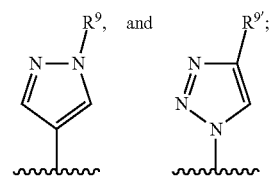

$R^7$ is independently selected from H and F;
$R^8$ is Cl;
$R^9$ is independently selected from H, $CHF_2$, and $CF_3$; and
$R^{9'}$ is independently selected from H, F, Cl, CN, $CHF_2$, and $CF_3$; and
other variables are as defined in Formula (Ia).

In another aspect, the present invention provides compounds of Formula (IV):

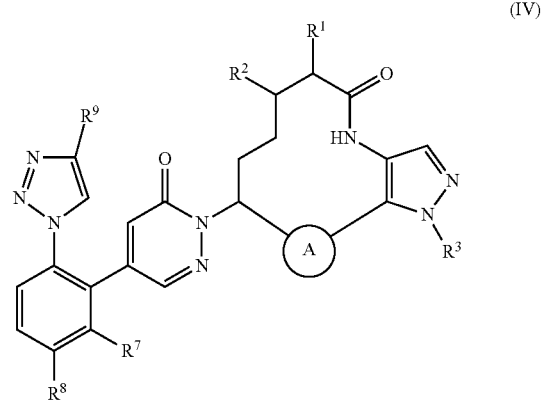

(IV)

or stereoisomers, tautomers, pharmaceutically acceptable salts, solvates, or prodrugs thereof, wherein:
ring A is independently selected from

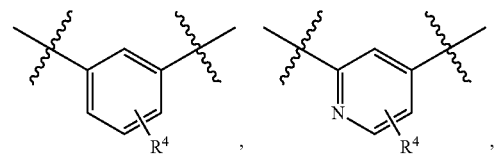

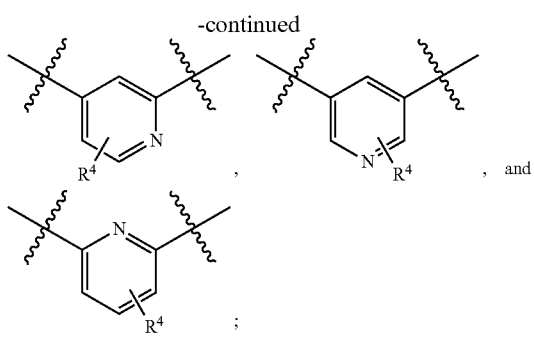

$R^1$ is independently selected from H and $C_{1-3}$alkyl;
$R^2$ is independently selected from H and F;
$R^3$ is independently selected from H, $CD_3$, $CHF_2$, and $CH_3$;
$R^4$ is independently selected from H and halogen;
$R^7$ is independently selected from H and F;
$R^8$ is independently selected from H, F, Cl, and $OCH_3$; and
$R^9$ is independently selected from H, F, Cl, CN, and $CF_3$.

In another aspect, the present invention provides compounds of Formula (V):

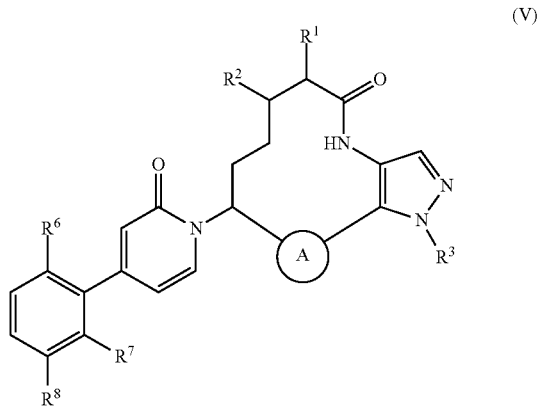

or stereoisomers, tautomers, pharmaceutically acceptable salts, solvates, or prodrugs thereof, wherein:
ring A is independently selected from

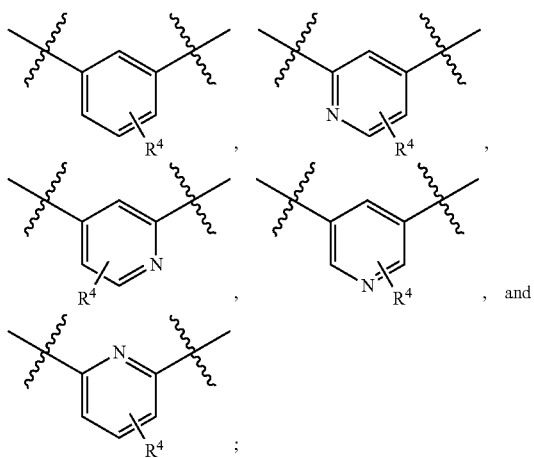

$R^1$ is independently selected from H and $C_{1-3}$alkyl;
$R^2$ is independently selected from H and F;
$R^3$ is independently selected from H, $CD_3$, $CHF_2$, and $CH_3$;
$R^4$ is independently selected from H and halogen;
$R^6$ is independently selected from H, F, Cl, Br, CN, $CF_3$, $C(O)CH_3$, $CHF_2$, $CCH_3F_2$, $CF_3$, $OCHF_2$,

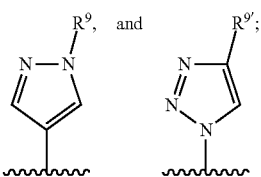

$R^7$ is independently selected from H and F;
$R^8$ is independently selected from H, F, Cl, and $OCH_3$;
$R^9$ is independently selected from H, $CHF_2$, and $CF_3$; and
$R^{9'}$ is independently selected from H, F, Cl, CN, $CHF_2$, and $CF_3$.

In another embodiment, $R^1$ is independently selected from the group consisting of H, OH, and $C_{1-4}$ alkyl; $R^2$ is, independently at each occurrence, selected from the group consisting of H and F.

In another embodiment, $R^1$ is independently selected from the group consisting of H and methyl, ethyl, and isopropyl; $R^2$ is H or F.

In another aspect, the present invention provides a compound selected from any subset list of compounds exemplified in the present application.

In another embodiment, the present invention provides a compound selected from

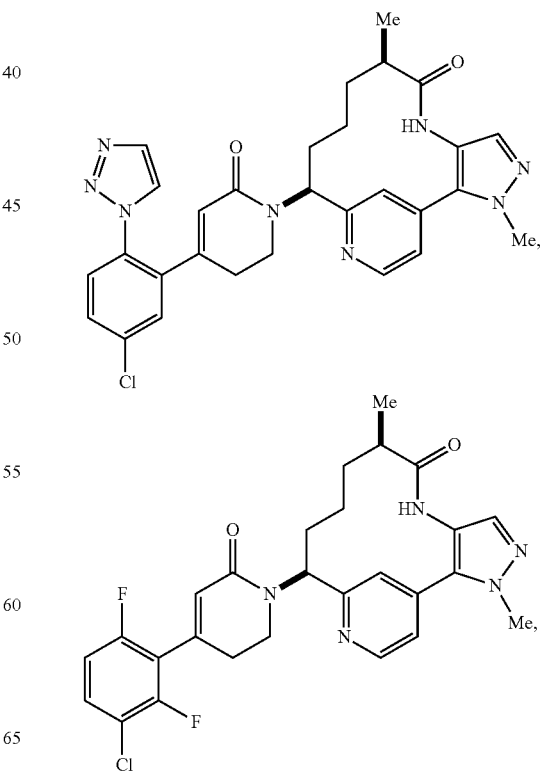

13
-continued
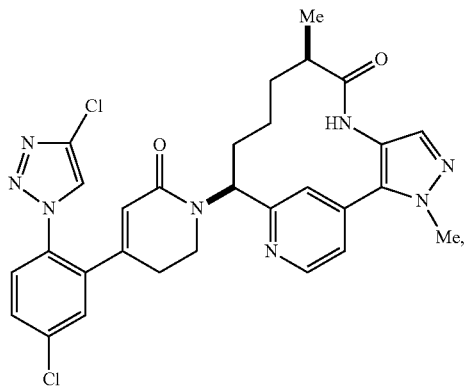
14
-continued
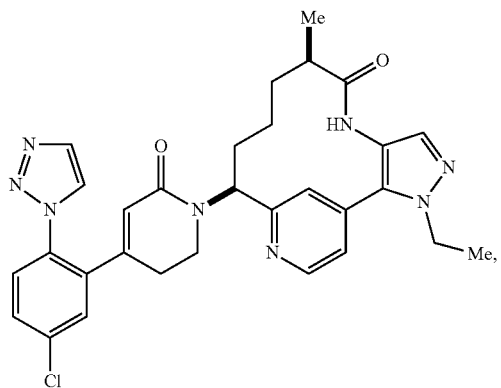
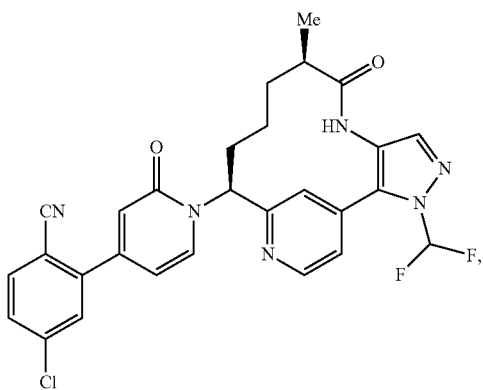
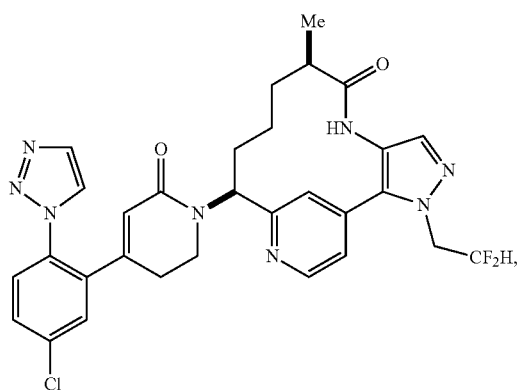
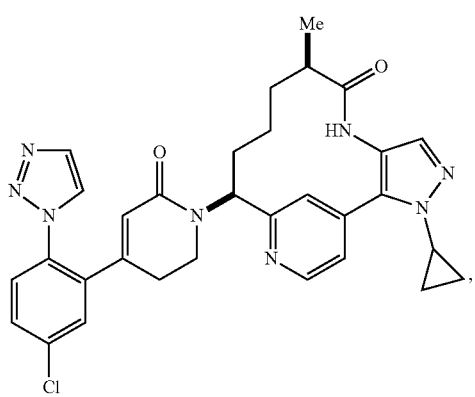
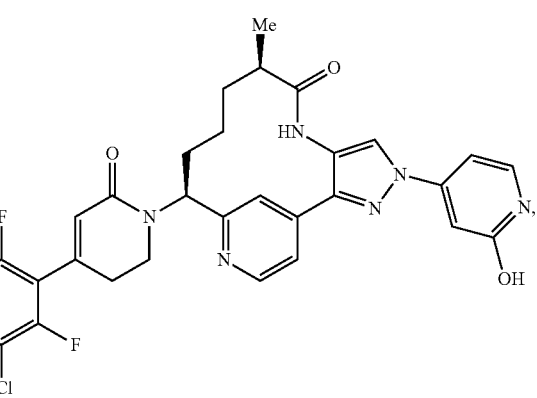
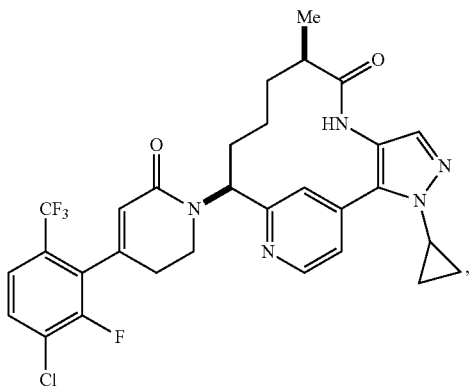
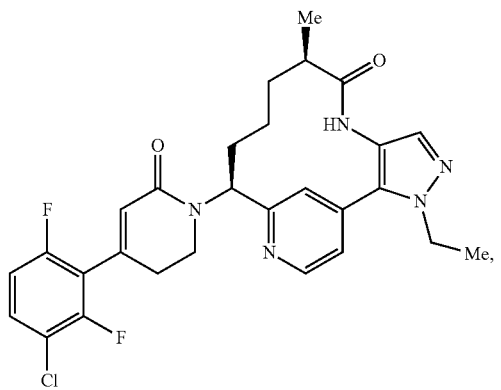

15
-continued
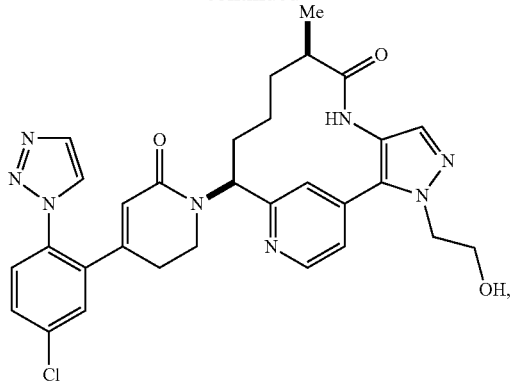
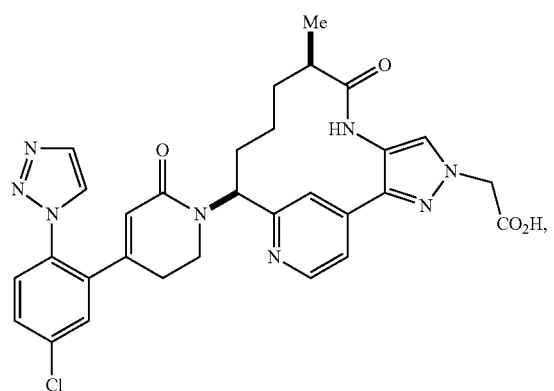
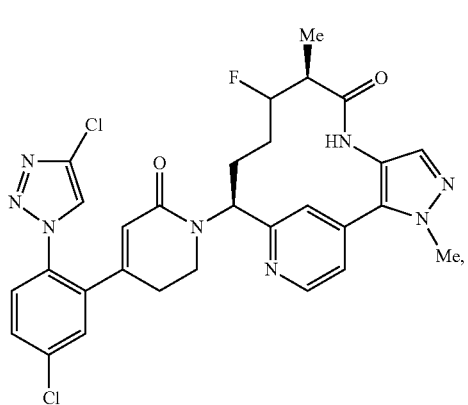
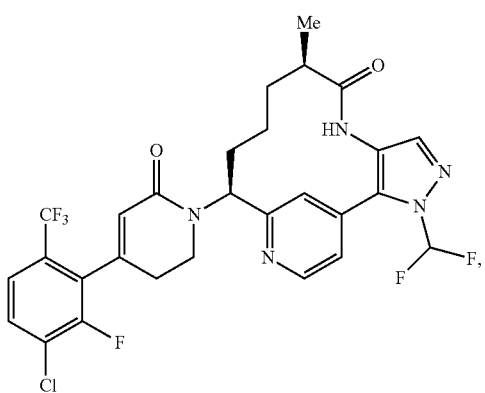
16
-continued
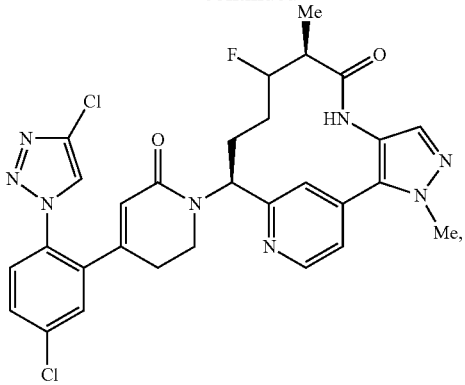
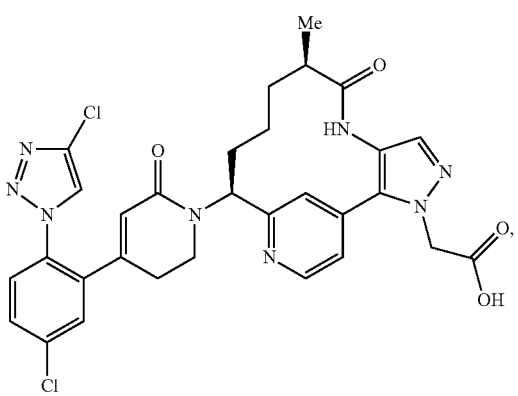
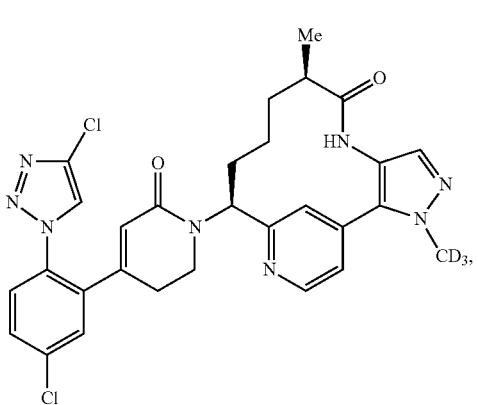

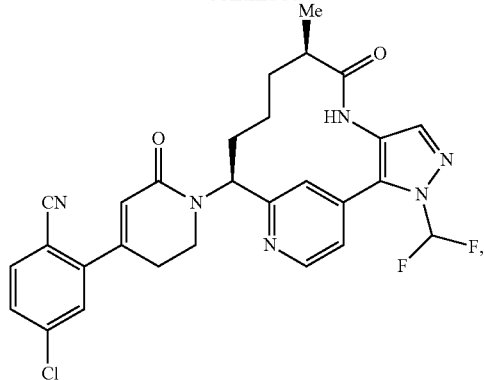
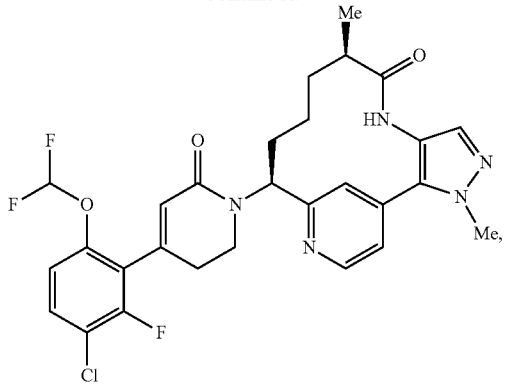

-continued
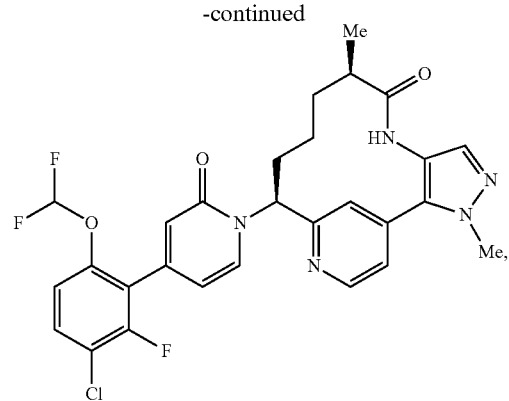
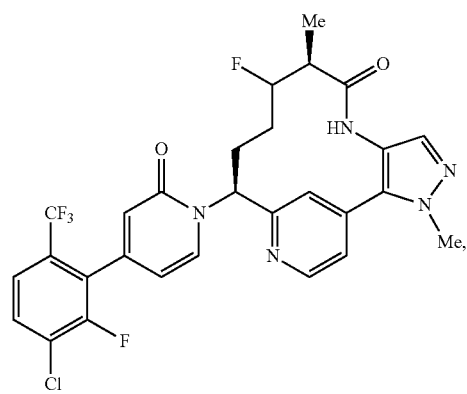
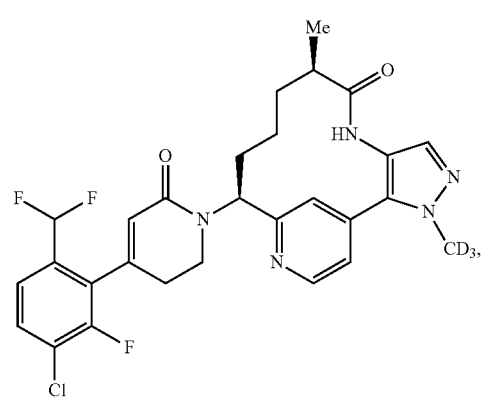
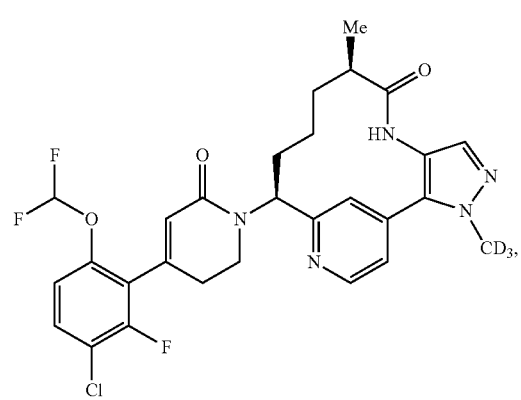
-continued
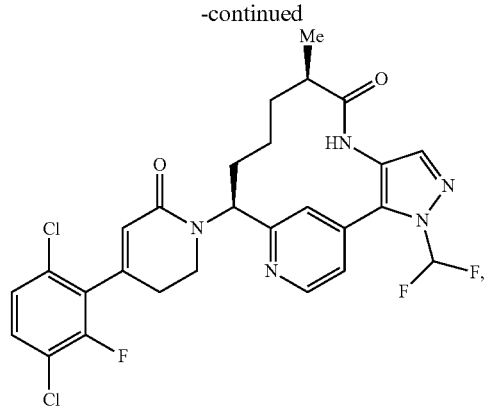
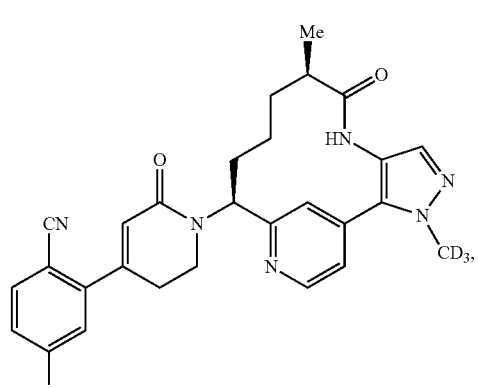
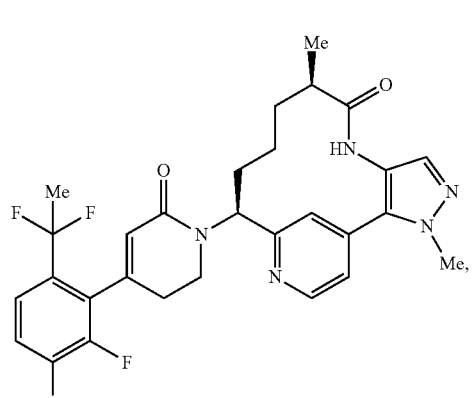
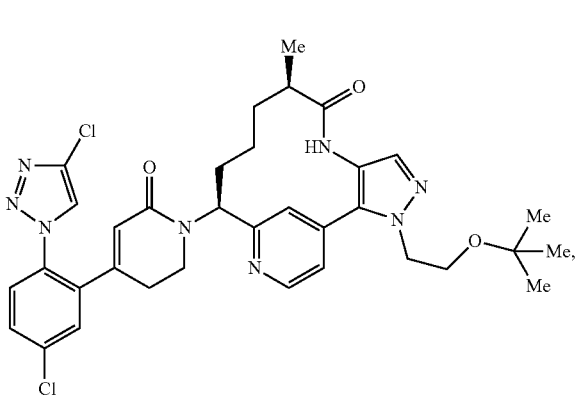

21
-continued
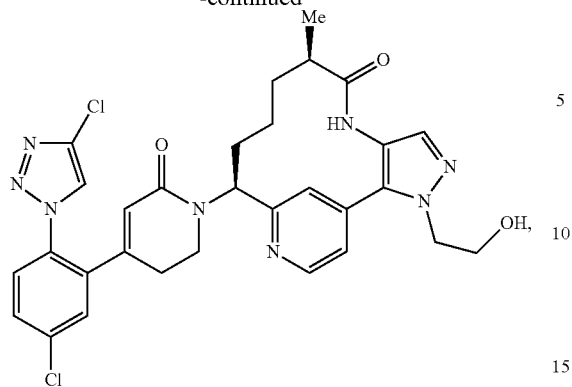
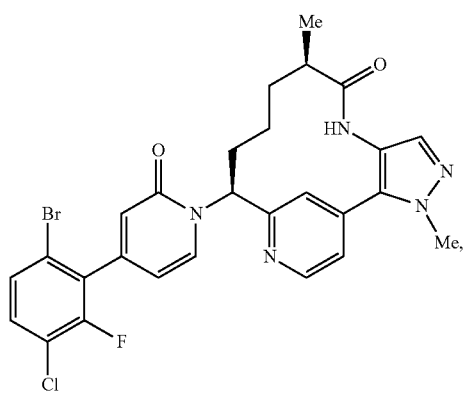
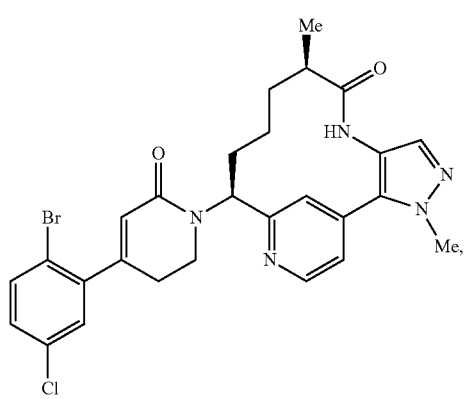
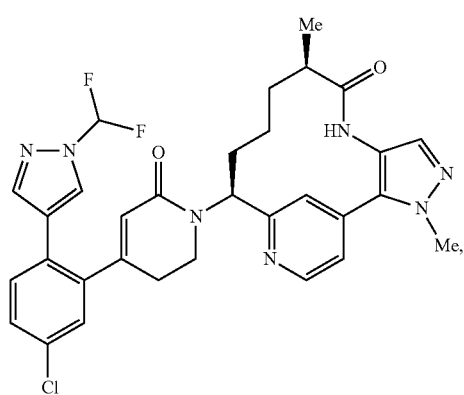
22
-continued
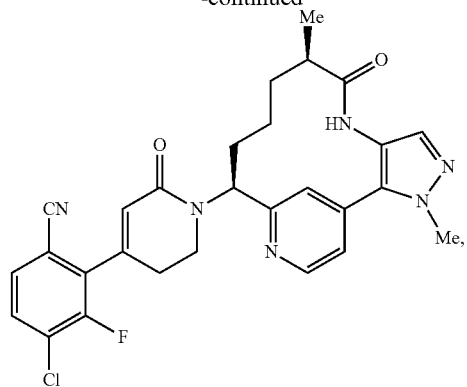
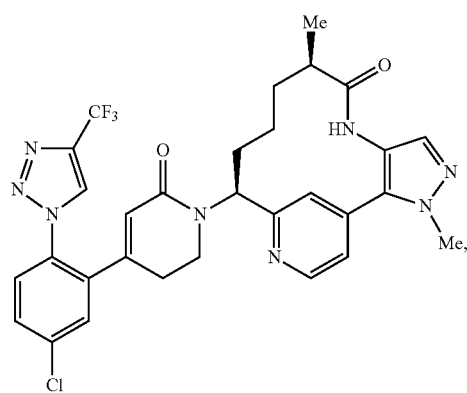
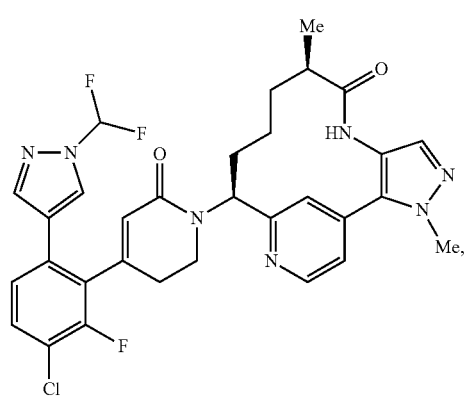
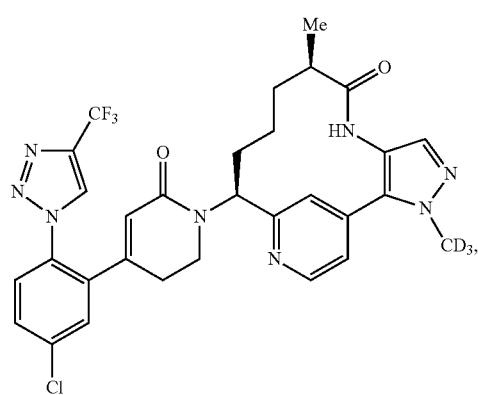

23
-continued
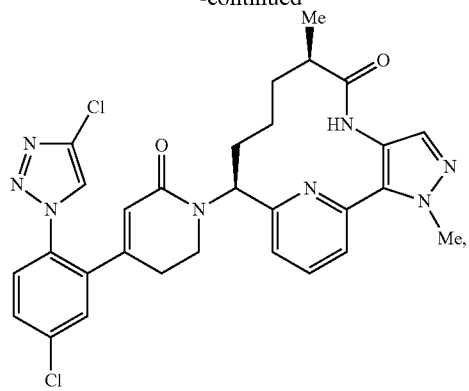
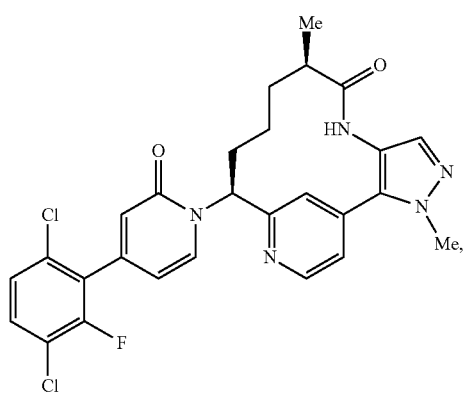
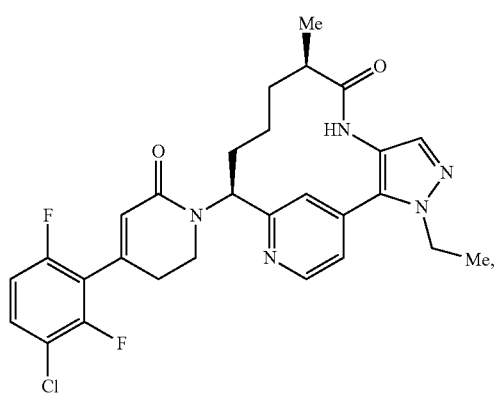
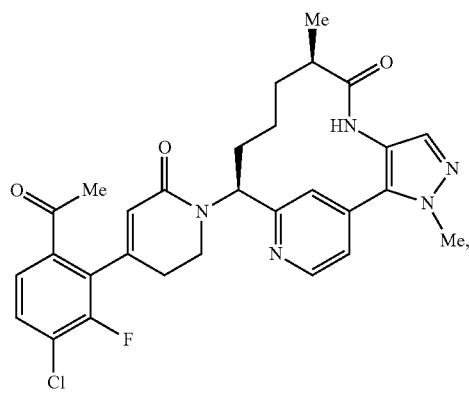
24
-continued
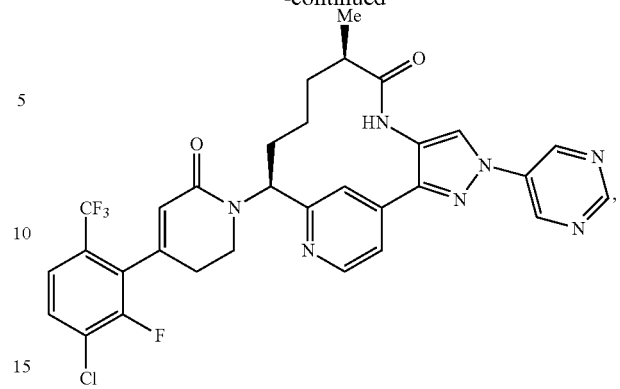
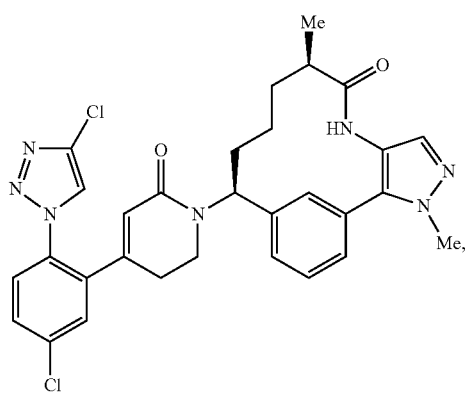
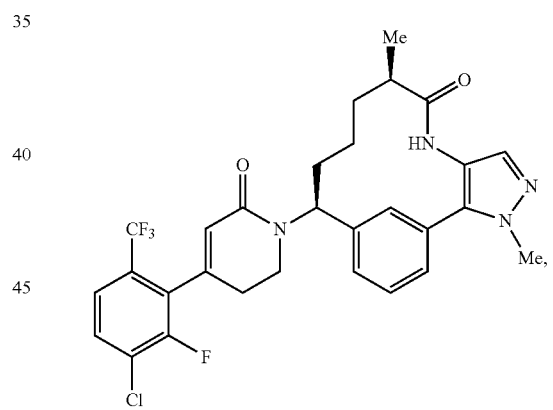
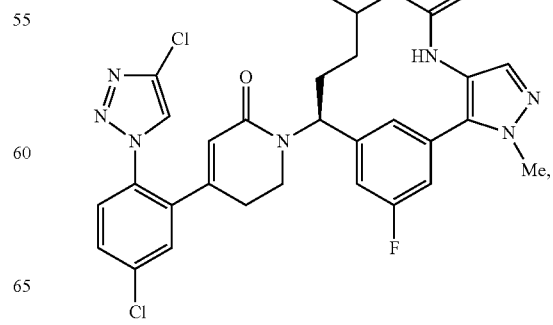

-continued
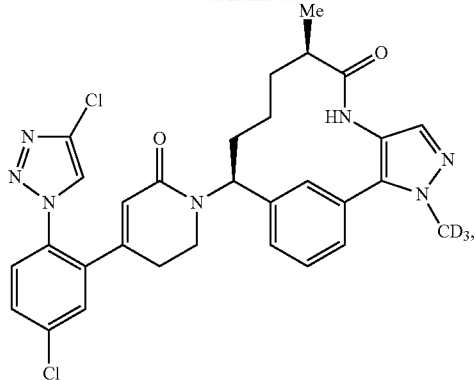
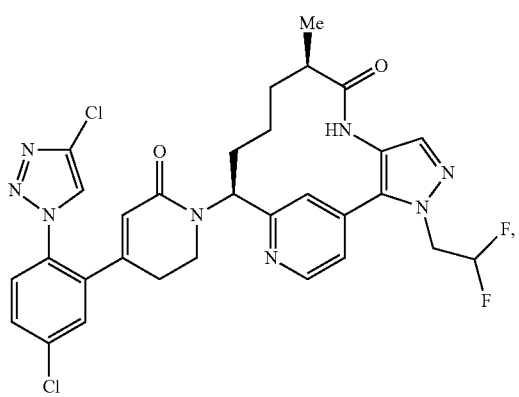
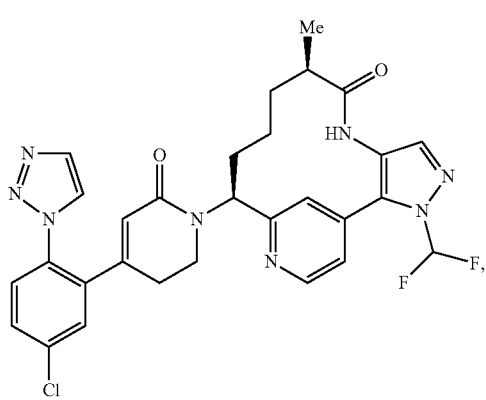
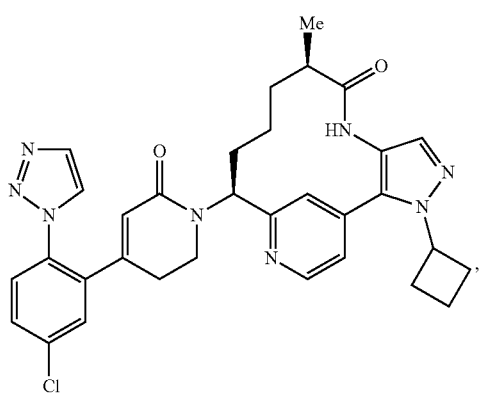
-continued
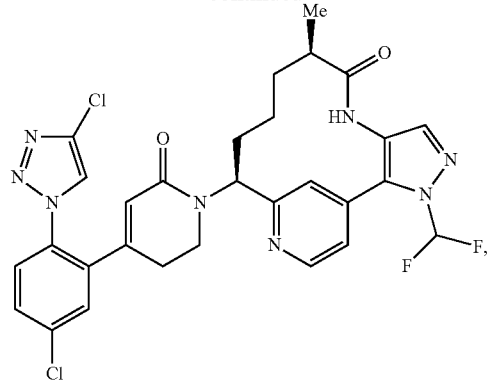
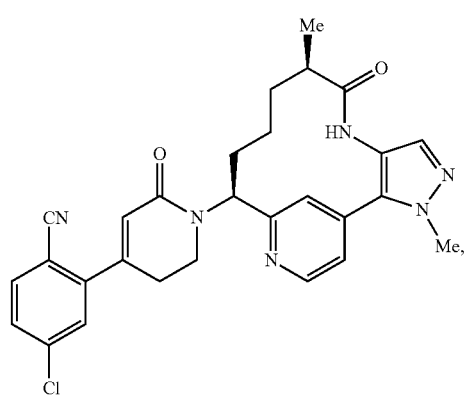
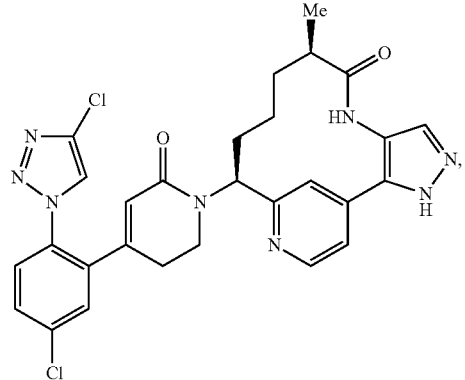

-continued

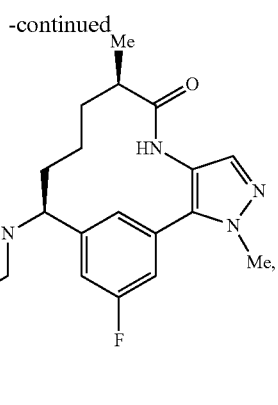

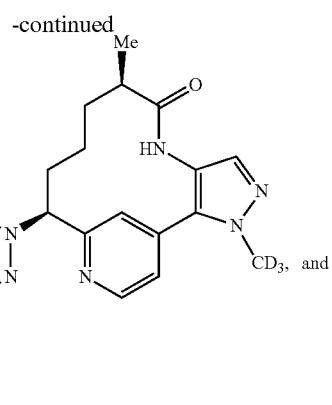

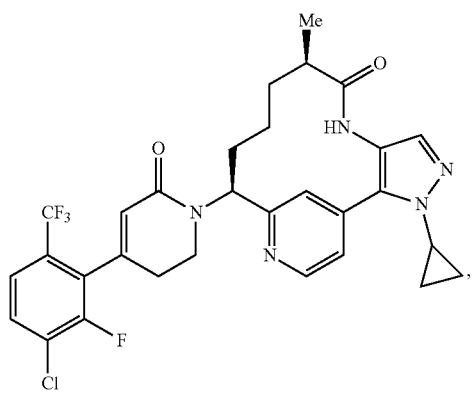

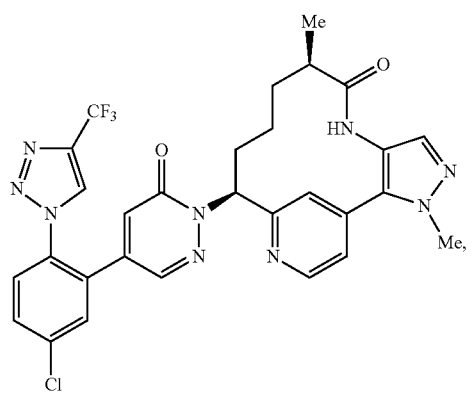

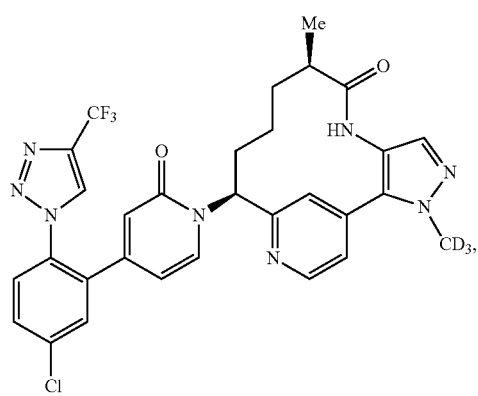

or stereoisomers, tautomers, pharmaceutically acceptable salts, solvates, or prodrugs thereof.

II. Other Embodiments of the Invention

In another embodiment, the present invention provides a composition comprising at least one of the compounds of the present invention or a stereoisomer, a tautomer, a pharmaceutically acceptable salt, or a solvate thereof.

In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate, thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition further comprising additional therapeutic agent(s). In a preferred embodiment, the present invention provides pharmaceutical composition, wherein the additional therapeutic agent(s) are an anti-platelet agent or a combination thereof. Preferably, the anti-platelet agent(s) are clopidogrel and/or aspirin, or a combination thereof.

In another embodiment, the present invention provides a method for the treatment and/or prophylaxis of a thromboembolic disorder comprising administering to a patient in need of such treatment and/or prophylaxis a therapeutically effective amount of at least one of the compounds of the present invention or a stereoisomer, a tautomer, a pharmaceutically acceptable salt, or a solvate thereof.

In another embodiment, the present invention provides a compound of the present invention or a stereoisomer, a tautomer, a pharmaceutically acceptable salt, or a solvate thereof, for use in therapy.

In another embodiment, the present invention provides a compound of the present invention or a stereoisomer, a tautomer, a pharmaceutically acceptable salt, or a solvate thereof, for use in therapy for the treatment and/or prophylaxis of a thromboembolic disorder.

In another embodiment, the present invention also provides the use of a compound of the present invention or a stereoisomer, a tautomer, a pharmaceutically acceptable salt, or a solvate thereof, for the manufacture of a medicament for the treatment and/or prophylaxis of a thromboembolic disorder.

In another embodiment, the present invention provides a method for treatment and/or prophylaxis of a thromboembolic disorder, comprising: administering to a patient in need thereof a therapeutically effective amount of a first and second therapeutic agent, wherein the first therapeutic agent is a compound of the present invention or a stereoisomer, a tautomer, a pharmaceutically acceptable salt, or a solvate thereof, and the second therapeutic agent is at least one agent selected from a factor Xa inhibitor such as apixaban, rivaroxaban, betrixaban, edoxaban, an anticoagulant agent, an anti-platelet agent, a thrombin inhibiting agent such as dabigatran, a thrombolytic agent, and a fibrinolytic agent. Preferably, the second therapeutic agent is at least one agent selected from warfarin, unfractionated heparin, low molecular weight heparin, synthetic pentasaccharide, hirudin, argatroban, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, desulfatohirudin, tissue plasminogen activator, modified tissue plasminogen activator, anistreplase, urokinase, and streptokinase. Preferably, the second therapeutic agent is at least one anti-platelet agent. Preferably, the anti-platelet agent(s) are clopidogrel and/or aspirin, or a combination thereof.

The thromboembolic disorder includes arterial cardiovascular thromboembolic disorders, venous cardiovascular thromboembolic disorders, arterial cerebrovascular thromboembolic disorders, and venous cerebrovascular thromboembolic disorders. Examples of the thromboembolic disorder include, but are not limited to, unstable angina, an acute coronary syndrome, atrial fibrillation, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

In another embodiment, the present invention provides a method for the treatment and/or prophylaxis of an inflammatory disorder comprising: administering to a patient in need of such treatment and/or prophylaxis a therapeutically effective amount of at least one of the compounds of the present invention or a stereoisomer, a tautomer, a pharmaceutically acceptable salt, or a solvate thereof. Examples of the inflammatory disorder include, but are not limited to, sepsis, acute respiratory distress syndrome, and systemic inflammatory response syndrome.

In another embodiment, the present invention provides a method for the prophylaxis of a disease or condition in which plasma kallikrein activity is implicated comprising administering to a patient in need of such treatment and/or prophylaxis a therapeutically effective amount of at least one of the compounds of the present invention or a stereoisomer, a tautomer, a pharmaceutically acceptable salt, or a solvate thereof.

The disease or condition in which plasma kallikrein activity is implicated includes, but not limited to, impaired visual acuity, diabetic retinopathy, diabetic macular edema, hereditary angioedema, diabetes, pancreatitis, nephropathy, cardio myopathy, neuropathy, inflammatory bowel disease, arthritis, inflammation, septic shock, hypotension, cancer, adult respiratory distress syndrome, disseminated intravascular coagulation, and cardiopulmonary bypass surgery.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in treatment and/or prophylaxis of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also to be understood that each individual element of the embodiments is its own independent embodiment. Furthermore, any element of an embodiment is meant to be combined with any and all other elements from any embodiment to describe an additional embodiment.

III. Chemistry

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The term "stereoisomer" refers to isomers of identical constitution that differ in the arrangement of their atoms in space. Enantiomers and diastereomers are examples of stereoisomers. The term "enantiomer" refers to one of a pair of molecular species that are mirror images of each other and are not superimposable. The term "diastereomer" refers to stereoisomers that are not mirror images. The term "racemate" or "racemic mixture" refers to a composition composed of equimolar quantities of two enantiomeric species, wherein the composition is devoid of optical activity.

The symbols "R" and "S" represent the configuration of substituents around a chiral carbon atom(s). The isomeric descriptors "R" and "S" are used as described herein for indicating atom configuration(s) relative to a core molecule and are intended to be used as defined in the literature (IUPAC Recommendations 1996, *Pure and Applied Chemistry*, 68:2193-2222 (1996)).

The term "chiral" refers to the structural characteristic of a molecule that makes it impossible to superimpose it on its mirror image. The term "homochiral" refers to a state of enantiomeric purity. The term "optical activity" refers to the degree to which a homochiral molecule or nonracemic mixture of chiral molecules rotates a plane of polarized light.

As used herein, the term "alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

The term "alkoxy" or "alkyloxy" refers to an —O-alkyl group. "$C_1$ to $C_6$ alkoxy" or "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Alkoxy also includes deuteroalkyoxy such as $OCD_3$. Similarly, "alkylthio" or "thioalkoxy" represents an alkyl group as defined above with the indicated number of carbon atoms attached through a sulphur bridge; for example methyl-S— and ethyl-S—.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens.

Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

The term "carbonyl", as used herein, refers to —C(O)—.
The term "cyano", as used herein, refers to —CN.
The term "cycloalkylamino", as used herein, refers to —NHR wherein R is a cycloalkyl group.
The term "haloalkyl", as used herein, refers to an alkyl group substituted by one, two, three, or four halogen atoms.
The term "carbonyl" refers to C(=O).
The term "carboxy" refers to C(=O)OH.
The term "haloalkylcarbonyl", as used herein, refers to a haloalkyl group attached to the parent molecular moiety through a carbonyl group.
The term "hydroxy" or "hydroxyl" refers to OH.

The term "cycloalkyl" refers to cyclized alkyl groups, including mono-, bi- or poly-cyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl".

As used herein, "carbocycle" or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl". A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

As used herein, the term "bicyclic carbocycle" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary*, 13th Edition, John Wiley & Sons, Inc., New York (1997). "$C_6$ or $C_{10}$ aryl" or "$C_{6-10}$ aryl" refers to phenyl and naphthyl. Unless otherwise specified, "aryl", "$C_6$ or $C_{10}$ aryl" or "$C_{6-10}$ aryl" or "aromatic residue" may be unsubstituted or substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

The term "benzyl", as used herein, refers to a methyl group on which one of the hydrogen atoms is replaced by a phenyl group, wherein said phenyl group may optionally be substituted with 1 to 5 groups, preferably 1 to 3 groups, OH, $OCH_3$, Cl, F, Br, I, CN, $NO_2$, $NH_2$, $N(CH_3)H$, $N(CH_3)_2$, $CF_3$, $OCF_3$, $C(=O)CH_3$, $SCH_3$, $S(=O)CH_3$, $S(=O)_2CH_3$, $CH_3$, $CH_2CH_3$, $CO_2H$, and $CO_2CH_3$.

As used herein, the term "heterocycle" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Examples of 5- to 10-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Examples of 5- to 6-membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxadiazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "bicyclic heterocycle" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocycle, a 6-membered heterocycle or a carbocycle (provided the first ring is not benzo when the second ring is a carbocycle).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocycle exceeds 1, then these heteroatoms are not adjacent to one another. It is preferred that the total number of S and O atoms in the heterocycle is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydro-quinolinyl, 2,3-dihydrobenzofuranyl, chromanyl, 1,2,3,4-tetrahydro-quinoxalinyl, and 1,2,3,4-tetrahydro-quinazolinyl.

As used herein, the term "aromatic heterocyclic group" or "heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

Bridged rings are also included in the definition of heterocycle. A bridged ring occurs when one or more atoms (i.e., C, O, N, or S) link two non-adjacent carbon or nitrogen atoms. Examples of bridged rings include, but are not limited to, one carbon atom, two carbon atoms, one nitrogen atom, two nitrogen atoms, and a carbon-nitrogen group. It is noted that a bridge always converts a monocyclic ring into a tricyclic ring.

When a ring is bridged, the substituents recited for the ring may also be present on the bridge.

The term "counterion" is used to represent a negatively charged species such as chloride, bromide, hydroxide, acetate, and sulfate.

When a dotted ring is used within a ring structure, this indicates that the ring structure may be saturated, partially saturated or unsaturated.

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrug derivatives, see:

a) Bundgaard, H., ed., *Design of Prodrugs*, Elsevier (1985), and Widder, K. et al., eds., *Methods in Enzymology,* 112:309-396, Academic Press (1985);

b) Bundgaard, H., Chapter 5: "Design and Application of Prodrugs", *A Textbook of Drug Design and Development*, pp. 113-191, Krosgaard-Larsen, P. et al., eds., Harwood Academic Publishers (1991);

c) Bundgaard, H., *Adv. Drug Deliv. Rev.,* 8:1-38 (1992);

d) Bundgaard, H. et al., *J. Pharm. Sci.,* 77:285 (1988); and
e) Kakeya, N. et al., *Chem. Pharm. Bull.,* 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes.

Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Deuterium has one proton and one neutron in its nucleus and that has twice the mass of ordinary hydrogen. Deuterium can be represented by symbols such as "$^2$H" or "D". The term "deuterated" herein, by itself or used to modify a compound or group, refers to replacement of one or more hydrogen atom(s), which is attached to carbon(s), with a deuterium atom. Isotopes of carbon include $^{13}$C and $^{14}$C.

Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, S(O)$_2$H, or S(O)H group.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "RBF" for round bottom flask, "atm" for atmosphere, "psi" for pounds per square inch, "conc." for concentrate, "RCM" for ring-closing metathesis, "sat" or "sat'd" for saturated, "SFC" for supercritical fluid chromatography "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Me methyl
Et ethyl
Pr propyl
i-Pr isopropyl
Bu butyl
i-Bu isobutyl
t-Bu tert-butyl
Ph phenyl
Bn benzyl
Boc or BOC tert-butyloxycarbonyl
Boc$_2$O di-tert-butyl dicarbonate
AcOH or HOAc acetic acid
AlCl$_3$ aluminum chloride
AIBN azobisisobutyronitrile
BBr$_3$ boron tribromide
aqueous aq
BCl$_3$ boron trichloride
BEMP 2-tert-butylimino-2-diethylamino-1,3-dimethylperhydro-1,3,2-diazaphosphorine
BOP reagent benzotriazol-1-yloxytris(dimethylamino)phosphonium hexafluorophosphate
Burgess reagent 1-methoxy-N-triethylammoniosulfonylmethanimidate
Cbz carbobenzyloxy
DCM or CH$_2$Cl$_2$ dichloromethane
CH$_3$CN or ACN acetonitrile
CDCl$_3$ deutero-chloroform
CHCl$_3$ chloroform
mCPBA or m-CPBA meta-chloroperbenzoic acid
Cs$_2$CO$_3$ cesium carbonate
Cu(OAc)$_2$ copper (II) acetate
Cy$_2$NMe N-cyclohexyl-N-methylcyclohexanamine
CuI copper(I) iodide CuSO₄ copper(II) sulfate
DBU 1,8-diazabicyclo[5.4.0]undec-7-ene
DCE 1,2 dichloroethane
DEA diethylamine
Dess-Martin 1,1,1-tris(acetyloxy)-1,1-dihydro-1,2-beniziodoxol-3-(1H)-one
DIC or DIPCDI diisopropylcarbodiimide
DIEA, DIPEA or diisopropylethylamine Hunig's base
DMAP 4-dimethylaminopyridine
DME 1,2-dimethoxyethane
DMF dimethyl formamide
DMSO dimethyl sulfoxide
cDNA complimentary DNA
Dppp (R)-(+)-1,2-bis(diphenylphosphino)propane
DuPhos (+)-1,2-bis((2S,5S)-2,5-diethylpholano)benzene
EDC N-(3-dimethylaminopropyl)-N'-ethylcarbodiimide
EDCI N-(3-dimethylaminopropyl)-N'-ethylcarbodiimide hydrochloride
EDTA ethylenediaminetetraacetic acid
(S,S)-EtDuPhosRh(I) (+)-1,2-bis((2S,5S)-2,5-diethylphospholano)benzene(1,5-cyclooctadiene)rhodium(I) trifluoromethanesulfonate
Et₃N or TEA triethylamine
EtOAc ethyl acetate
Et₂O diethyl ether
EtOH ethanol
GMF glass microfiber filter
Grubbs II (1,3-bis(2,4,6-trimethylphenyl)-2-imidazolidinylidene)dichloro(phenylmethylene)(triycyclohexylphosphine)ruthenium
HCl hydrochloric acid
HATU O-(7-azabenzotriazol-1-yl)-N,N,N',N'-tetramethyluronium hexafluorophosphate
HEPES 4-(2-hydroxyethyl)piperazine-1-ethanesulfonic acid
Hex hexane
HOBt or HOBT 1-hydroxybenzotriazole
H₂O₂ hydrogen peroxide
H₂SO₄ sulfuric acid
IBX 2-iodoxybenzoic acid
InCl₃ Indium(III) chloride
Jones reagent CrO₃ in aqueous H₂SO₄, 2 M
K₂CO₃ potassium carbonate
K₂HPO₄ potassium phosphate dibasic
K₃PO₄ potassium phosphate tribasic
KOAc potassium acetate
K₃PO₄ potassium phosphate
LAH lithium aluminum hydride
LG leaving group
LiOH lithium hydroxide
MeOH methanol
MgSO₄ magnesium sulfate
MsOH or MSA methylsulfonic acid
NaCl sodium chloride
NaH sodium hydride
NaHCO₃ sodium bicarbonate
Na₂CO₃ sodium carbonate
NaOH sodium hydroxide
Na₂SO₃ sodium sulfite
Na₂SO₄ sodium sulfate
NBS N-bromosuccinimide
NCS N-chlorosuccinimide
NH₃ ammonia
NH₄Cl ammonium chloride
NH₄OH ammonium hydroxide
NH₄COOH ammonium formate
NMM N-methylmorpholine
OTf triflate or trifluoromethanesulfonate
Pd₂(dba)₃ tris(dibenzylideneacetone)dipalladium(0)
Pd(OAc)₂ palladium(II) acetate
Pd/C palladium on carbon
Pd(dppf)Cl₂ [1,1'-bis(diphenylphosphino)-ferrocene]dichloropalladium(II)
Ph₃PCl₂ triphenylphosphine dichloride
PG protecting group
POCl₃ phosphorus oxychloride
i-PrOH or IPA isopropanol
PS Polystyrene
rt room temperature
SEM-Cl 2-(trimethysilyl)ethoxymethyl chloride
SiO₂ silica oxide
SnCl₂ tin(II) chloride
TBAI tetra-n-butylammonium iodide
TBN t-butyl nitrite
TFA trifluoroacetic acid
THF tetrahydrofuran
TMSCHN₂ trimethylsilyldiazomethane
T3P® propane phosphonic acid anhydride
TRIS tris (hydroxymethyl) aminomethane
pTsOH p-toluenesulfonic acid The compounds of the present invention can be prepared in a number of ways known to one skilled in the art of organic synthesis, which are described in more detail in Section VI.

IV. Biology

While blood coagulation is essential to the regulation of an organism's hemostasis, it is also involved in many pathological conditions. In thrombosis, a blood clot, or thrombus, may form and obstruct circulation locally, causing ischemia and organ damage. Alternatively, in a process known as embolism, the clot may dislodge and subsequently become trapped in a distal vessel, where it again causes ischemia and organ damage. Diseases arising from pathological thrombus formation are collectively referred to as thromboembolic disorders and include acute coronary syndrome, unstable angina, myocardial infarction, atrial fibrillation, thrombosis in the cavity of the heart, ischemic stroke, deep vein thrombosis, peripheral occlusive arterial disease, transient ischemic attack, and pulmonary embolism. In addition, thrombosis occurs on artificial surfaces in contact with blood, including catheters, stents, artificial heart valves, and hemodialysis membranes.

Some conditions contribute to the risk of developing thrombosis. For example, alterations of the vessel wall, changes in the flow of blood, and alterations in the composition of the vascular compartment. These risk factors are collectively known as Virchow's triad. (Colman, R. W. et al., eds., *Hemostasis and Thrombosis, Basic Principles and Clinical Practice*, Fifth Edition, p. 853, Lippincott Williams & Wilkins (2006)).

Antithrombotic agents are frequently given to patients at risk of developing thromboembolic disease because of the presence of one or more predisposing risk factors from Virchow's triad to prevent formation of an occlusive thrombus (primary prevention). For example, in an orthopedic surgery setting (e.g., hip and knee replacement), an antithrombotic agent is frequently administered prior to a surgical procedure. The antithrombotic agent counterbalances the prothrombotic stimulus exerted by vascular flow alterations (stasis), potential surgical vessel wall injury, as well as changes in the composition of the blood due to the acute phase response related to surgery. Another example of the use of an antithrombotic agent for primary prevention is dosing with aspirin, a platelet activation inhibitor, in patients at risk for developing thrombotic cardiovascular disease. Well recognized risk factors in this setting include age, male gender, hypertension, diabetes mellitus, lipid alterations, and obesity.

Antithrombotic agents are also indicated for secondary prevention, following an initial thrombotic episode. For example, patients with mutations in factor V (also known as factor V Leiden) and additional risk factors (e.g., pregnancy), are dosed with anticoagulants to prevent the reoccurrence of venous thrombosis. Another example entails secondary prevention of cardiovascular events in patients with a history of acute myocardial infarction or acute coronary syndrome. In a clinical setting, a combination of aspirin and clopidogrel (or other thienopyridines) may be used to prevent a second thrombotic event.

Antithrombotic agents are also given to treat the disease state (i.e., by arresting its development) after it has already started. For example, patients presenting with deep vein thrombosis are treated with anticoagulants (i.e., heparin, warfarin, or LMWH) to prevent further growth of the venous occlusion. Over time, these agents also cause a regression of the disease state because the balance between prothrombotic factors and anticoagulant/profibrinolytic pathways is changed in favor of the latter. Examples on the arterial vascular bed include the treatment of patients with acute myocardial infarction or acute coronary syndrome with aspirin and clopidogrel to prevent further growth of vascular occlusions and eventually leading to a regression of thrombotic occlusions.

Thus, antithrombotic agents are used widely for primary and secondary prevention (i.e., prophylaxis or risk reduction) of thromboembolic disorders, as well as treatment of an already existing thrombotic process. Drugs that inhibit blood coagulation, or anticoagulants, are "pivotal agents for prevention and treatment of thromboembolic disorders" (Hirsh, J. et al., *Blood*, 105:453-463 (2005)).

An alternative way of initiation of coagulation is operative when blood is exposed to artificial surfaces (e.g., during hemodialysis, "on-pump" cardiovascular surgery, vessel grafts, bacterial sepsis), on cell surfaces, cellular receptors, cell debris, DNA, RNA, and extracellular matrices. This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Alternatively, the serine protease prolylcarboxylpeptidase can activate plasma kallikrein complexed with high molecular weight kininogen in a multiprotein complex formed on the surface of cells and matrices (Shariat-Madar et al., *Blood*, 108:192-199 (2006)). Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R., "Contact Activation Pathway", *Hemostasis and Thrombosis*, pp. 103-122, Lippincott Williams & Wilkins (2001); Schmaier, A. H., "Contact Activation", *Thrombosis and Hemorrhage*, pp. 105-128 (1998)). The biological relevance of the contact activation system for thromboembolic diseases is supported by the phenotype of factor XII deficient mice. More specifically, factor XII deficient mice were protected from thrombotic vascular occlusion in several thrombosis models as well as stroke models and the phenotype of the XII deficient mice was identical to XI deficient mice (Renne et al., *J. Exp. Med.*, 202:271-281 (2005); Kleinschmitz et al., *J. Exp. Med.*, 203:513-518 (2006)). The fact that factor XI is down-stream from factor XIIa, combined with the identical phenotype of the XII and XI deficient mice suggest that the contact activation system could play a major role in factor XI activation in vivo.

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D., *Trends Cardiovasc. Med.*, 10:198-204 (2000)).

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al., *Thromb. Res.*, 101:329-354 (2001).) Thus, inhibitors of factor XIa are expected to be anticoagulant and profibrinolytic.

Further evidence for the anti-thromboembolic effects of targeting factor XI is derived from mice deficient in factor XI. It has been demonstrated that complete fXI deficiency protected mice from ferric chloride ($FeCl_3$)-induced carotid artery thrombosis (Rosen et al., *Thromb. Haemost.*, 87:774-777 (2002); Wang et al., *J. Thromb. Haemost.*, 3:695-702 (2005)). Also, factor XI deficiency rescues the perinatal lethal phenotype of complete protein C deficiency (Chan et al., *Amer. J. Pathology*, 158:469-479 (2001)). Furthermore, baboon cross-reactive, function blocking antibodies to human factor XI protect against baboon arterialvenous shunt thrombosis (Gruber et al., *Blood*, 102:953-955 (2003)). Evidence for an antithrombotic effect of small molecule inhibitors of factor XIa is also disclosed in published U.S. Patent Publication No. 2004/0180855 A1. Taken together, these studies suggest that targeting factor XI will reduce the propensity for thrombotic and thromboembolic diseases.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of aPTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The aPTT (intrinsic system) is prolonged in a gene dose-dependent fashion. Interestingly, even after severe stimulation of the coagulation system (tail transection), the bleeding time is not significantly prolonged compared to wild-type and heterozygous litter mates. (Gailani, D., *Frontiers in Bioscience*, 6:201-207 (2001); Gailani, D. et al., *Blood Coagulation and Fibrinolysis*, 8:134-144 (1997).) Taken together, these observations suggest that high levels of inhibition of factor XIa should be well tolerated. This is in contrast to gene targeting experiments with other coagulation factors, excluding factor XII.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al., *Arterioscler. Thromb. Vasc. Biol.*, 20:2489-2493 (2000)). A second study establishes a positive correlation between the extent of coronary arteriosclerosis and factor XIa in complex with alpha 1 antitrypsin (Murakami, T. et al., *Arterioscler. Thromb. Vasc. Biol.*, 15:1107-1113 (1995)). In another study, Factor XI levels above the 90th percentile in patients were associated with a 2.2-fold increased risk for venous thrombosis (Meijers, J. C. M. et al., *N. Engl. J Med.*, 342:696-701 (2000)).

Also, it is preferred to find new compounds with improved activity in in vitro clotting assays, compared with known serine protease inhibitors, such as the activated partial thromboplastin time (aPTT) or prothrombin time (PT) assay. (for a description of the aPTT and PT assays see, Goodnight, S. H. et al., "Screening Tests of Hemostasis", *Disorders of Thrombosis and Hemostasis: A Clinical Guide*, Second Edition, pp. 41-51, McGraw-Hill, New York (2001)).

It is also desirable and preferable to find compounds with advantageous and improved characteristics compared with known serine protease inhibitors, in one or more of the following categories that are given as examples, and are not intended to be limiting: (a) pharmacokinetic properties, including oral bioavailability, half life, and clearance; (b) pharmaceutical properties; (c) dosage requirements; (d) factors that decrease blood concentration peak-to-trough characteristics; (e) factors that increase the concentration of active drug at the receptor; (f) factors that decrease the liability for clinical drug-drug interactions; (g) factors that decrease the potential for adverse side-effects, including selectivity versus other biological targets; and (h) factors that improve manufacturing costs or feasibility.

Pre-clinical studies demonstrated significant antithrombotic effects of small molecule factor XIa inhibitors in rabbit and rat model of arterial and venous thrombosis, at doses that preserved hemostasis. Wong P. C. et al., *Journal of Thrombosis and Thrombolysis*, 32(2):129-137 (August 2011); Schumacher, W. A. et al., *Eur. J. Pharmacol.*, 167-174 (2007)). Furthermore, it was observed that in vitro prolongation of the aPTT by specific XIa inhibitors is a good predictor of efficacy in our thrombosis models. Thus, the in vitro aPTT test can be used as a surrogate for efficacy in vivo. Pre-clinical and clinical studies using FXI antisense (ASO) has been shown to be effective in various venous and arterial thrombosis models, comparable to warfarin or enoxaparin without increased bleeding (Bueller et al., DOI: 10.1056/NEJMoa1405760 (2014)).

As used herein, the term "patient" encompasses all mammalian species.

As used herein, "treating" or "treatment" cover the treatment of a disease-state in a mammal, particularly in a human, and include: (a) inhibiting the disease-state, i.e., arresting it development; and/or (b) relieving the disease-state, i.e., causing regression of the disease state.

As used herein, "prophylaxis" or "prevention" covers the preventive treatment of a subclinical disease-state in a mammal, particularly in a human, aimed at reducing the probability of the occurrence of a clinical disease-state. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state.

As used herein, "risk reduction" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination to inhibit factor XIa and/or plasma kallikrein and/or to prevent or treat the disorders listed herein. When applied to a combination, the term refers to combined amounts of the active ingredients that result in the preventive or therapeutic effect, whether administered in combination, serially, or simultaneously.

The term "thrombosis", as used herein, refers to formation or presence of a thrombus (pl. thrombi); clotting within a blood vessel that may cause ischemia or infarction of tissues supplied by the vessel. The term "embolism", as used herein, refers to sudden blocking of an artery by a clot or foreign material that has been brought to its site of lodgment by the blood current. The term "thromboembolism", as used herein, refers to obstruction of a blood vessel with thrombotic material carried by the blood stream from the site of origin to plug another vessel. The term "thromboembolic disorders" entails both "thrombotic" and "embolic" disorders (defined above).

The term "thromboembolic disorders" as used herein includes arterial cardiovascular thromboembolic disorders, venous cardiovascular or cerebrovascular thromboembolic disorders, and thromboembolic disorders in the chambers of the heart or in the peripheral circulation. The term "thromboembolic disorders" as used herein also includes specific disorders selected from, but not limited to, unstable angina or other acute coronary syndromes, atrial fibrillation, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. The medical implants or devices include, but are not limited to: prosthetic valves, artificial valves, indwelling catheters, stents, blood oxygenators, shunts, vascular access ports, ventricular assist devices and artificial hearts or heart chambers, and vessel grafts. The procedures include, but are not limited to: cardiopulmonary bypass, percutaneous coronary intervention, and hemodialysis. In another embodiment, the term "thromboembolic disorders" includes acute coronary syndrome, stroke, deep vein thrombosis, and pulmonary embolism.

In another embodiment, the present invention provides a method for the treatment of a thromboembolic disorder, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the treatment of a thromboembolic disorder, wherein the thromboembolic disorder is selected from acute coronary syndrome, stroke, venous thrombosis, atrial fibrillation, and thrombosis resulting from medical implants and devices.

In another embodiment, the present invention provides a method for the primary prophylaxis of a thromboembolic disorder, wherein the thromboembolic disorder is selected from unstable angina, an acute coronary syndrome, atrial fibrillation, myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the primary prophylaxis of a thromboembolic disorder, wherein the thromboembolic disorder is selected from acute coronary syndrome, stroke, venous thrombosis, and thrombosis resulting from medical implants and devices.

In another embodiment, the present invention provides a method for the secondary prophylaxis of a thromboembolic disorder, wherein the thromboembolic disorder is selected from unstable angina, an acute coronary syndrome, atrial fibrillation, recurrent myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis. In another embodiment, the present invention provides a method for the secondary prophylaxis of a thromboembolic disorder, wherein the thromboembolic disorder is selected from acute coronary syndrome, stroke, atrial fibrillation and venous thrombosis.

The term "stroke", as used herein, refers to embolic stroke or atherothrombotic stroke arising from occlusive thrombosis in the carotid communis, carotid interna, or intracerebral arteries.

It is noted that thrombosis includes vessel occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy.

Thromboembolic disorders are frequently associated with patients with atherosclerosis. Risk factors for atherosclerosis include but are not limited to male gender, age, hypertension, lipid disorders, and diabetes mellitus. Risk factors for atherosclerosis are at the same time risk factors for complications of atherosclerosis, i.e., thromboembolic disorders.

Similarly, arterial fibrillation is frequently associated with thromboembolic disorders. Risk factors for arterial fibrillation and subsequent thromboembolic disorders include cardiovascular disease, rheumatic heart disease, nonrheumatic mitral valve disease, hypertensive cardiovascular disease, chronic lung disease, and a variety of miscellaneous cardiac abnormalities as well as thyrotoxicosis.

Diabetes mellitus is frequently associated with atherosclerosis and thromboembolic disorders. Risk factors for the more common type 2 include but are not limited to are family history, obesity, physical inactivity, race/ethnicity, previously impaired fasting glucose or glucose tolerance test, history of gestational diabetes mellitus or delivery of a "big baby", hypertension, low HDL cholesterol, and polycystic ovary syndrome.

Risk factors for congenital thrombophilia include gain of function mutations in coagulation factors or loss of function mutations in the anticoagulant- or fibrinolytic pathways.

Thrombosis has been associated with a variety of tumor types, e.g., pancreatic cancer, breast cancer, brain tumors, lung cancer, ovarian cancer, prostate cancer, gastrointestinal malignancies, and Hodgkins or non-Hodgkins lymphoma. Recent studies suggest that the frequency of cancer in patients with thrombosis reflects the frequency of a particular cancer type in the general population (Levitan, N. et al., *Medicine* (Baltimore), 78(5):285-291 (1999); Levine M. et al., *N. Engl. J. Med.*, 334(11):677-681 (1996); Blom, J. W. et al., *JAMA*, 293(6):715-722 (2005)). Hence, the most common cancers associated with thrombosis in men are prostate, colorectal, brain, and lung cancer, and in women are breast, ovary, and lung cancer. The observed rate of venous thromboembolism (VTE) in cancer patients is significant. The varying rates of VTE between different tumor types are most likely related to the selection of the patient population. Cancer patients at risk for thrombosis may possess any or all of the following risk factors: (i) the stage of the cancer (i.e., presence of metastases), (ii) the presence of central vein catheters, (iii) surgery and anticancer therapies including chemotherapy, and (iv) hormones and anti-angiogenic drugs. Thus, it is common clinical practice to dose patients having advanced tumors with heparin or low molecular heparin to prevent thromboembolic disorders. A number of low molecular heparin preparations have been approved by the FDA for these indications.

There are three main clinical situations when considering the prevention of VTE in a medical cancer patient: (i) the patient is bedridden for prolonged periods of time; (ii) the ambulatory patient is receiving chemotherapy or radiation; and (iii) the patient is with indwelling central vein catheters. Unfractionated heparin (UFH) and low molecular weight heparin (LMWH) are effective antithrombotic agents in cancer patients undergoing surgery. (Mismetti, P. et al., *British Journal of Surgery*, 88:913-930 (2001).)

A. In Vitro Assays

The effectiveness of compounds of the present invention as inhibitors of the coagulation Factors XIa, VIIa, IXa, Xa, XIIa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin), which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 25-200 pM (Haematologic Technologies) and the synthetic substrate S-2366 (pyroGlu-Pro-Arg-pNA; Chromogenix or AnaSpec) at a concentration of 0.0002-0.001 M.

Factor VIIa determinations were made in 0.005 M calcium chloride, 0.15 M sodium chloride, 0.05 M HEPES buffer containing 0.1% PEG 8000 at a pH of 7.5. Determinations were made using purified human Factor VIIa (Haematologic Technologies) or recombinant human Factor VIIa (Novo Nordisk) at a final assay concentration of 0.5-10 nM, recombinant soluble tissue factor at a concentration of 10-40 nM and the synthetic substrate H-D-Ile-Pro-Arg-pNA (S-2288; Chromogenix or BMPM-2; AnaSpec) at a concentration of 0.001-0.0075 M.

Factor IXa determinations were made in 0.005 M calcium chloride, 0.1 M sodium chloride, 0.0000001 M Refludan (Berlex), 0.05 M TRIS base and 0.5% PEG 8000 at a pH of 7.4. Refludan was added to inhibit small amounts of thrombin in the commercial preparations of human Factor IXa. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M.

Factor Xa determinations were made in 0.1 M sodium phosphate buffer at a pH of 7.5 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.00035 M.

Factor XIIa determinations were made in 0.05 M HEPES buffer at pH 7.4 containing 0.145 M NaCl, 0.05 M KCl, and 0.1% PEG 8000. Determinations were made using purified human Factor XIIa at a final concentration of 4 nM (American Diagnostica) and the synthetic substrate SPECTROZYME® #312 (H-D-CHT-Gly-L-Arg-pNA.2AcOH; American Diagnostica) at a concentration of 0.00015 M.

Plasma kallikrein determinations were made in 0.1 M sodium phosphate buffer at a pH of 7.5 containing 0.1-0.2 M sodium chloride and 0.5% PEG 8000. Determinations were made using purified human plasma kallikrein (Enzyme Research Laboratories) at a final concentration of 200 pM and the synthetic substrate S-2302 (H-(D)-Pro-Phe-Arg-pNA; Chromogenix) at a concentration of 0.00008-0.0004 M.

Thrombin determinations were made in 0.1 M sodium phosphate buffer at a pH of 7.5 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix or AnaSpec) at a concentration of 0.0002-0.0004 M.

The Michaelis constant, $K_m$, for substrate hydrolysis by each protease, was determined at 25° C. or 37° C. in the absence of inhibitor. Values of $K_i$ were determined by allowing the protease to react with the substrate in the presence of the inhibitor.

Reactions were allowed to go for periods of 20-180 minutes (depending on the protease) and the velocities (rate of absorbance or fluorescence change versus time) were measured.

The following relationships were used to calculate $K_i$ values:

$$(V_{max}*S)/(K_m+S)$$

$$(v_o-v_s)/v_s = I/(K_i(1+S/K_m)) \text{ for a competitive inhibitor with one binding site; or}$$

$$v_s/v_o = A+((B-A)/1+((IC_{50}/(I)^n))); \text{ and}$$

$$K_i = IC_{50}/(1+S/K_m) \text{ for a competitive inhibitor}$$

where:
$v_o$ is the velocity of the control in the absence of inhibitor;
$v_s$ is the velocity in the presence of inhibitor;
$V_{max}$ is the maximum reaction velocity;
I is the concentration of inhibitor;
A is the minimum activity remaining (usually locked at zero);
B is the maximum activity remaining (usually locked at 1.0);
n is the Hill coefficient, a measure of the number and cooperativity of potential inhibitor binding sites;
$IC_{50}$ is the concentration of inhibitor that produces 50% inhibition under the assay conditions;
$K_i$ is the dissociation constant of the enzyme: inhibitor complex;
S is the concentration of substrate; and
$K_m$ is the Michaelis constant for the substrate.

The selectivity of a compound may be evaluated by taking the ratio of the $K_i$ value for a given protease with the $K_i$ value for the protease of interest (i.e., selectivity for FXIa versus protease P=$K_i$ for protease P/$K_i$ for FXIa). Compounds with selectivity ratios >20 are considered selective.

The effectiveness of compounds of the present invention as inhibitors of coagulation can be determined using a standard or modified clotting assay. An increase in the plasma clotting time in the presence of inhibitor is indicative of anticoagulation. Relative clotting time is the clotting time in the presence of an inhibitor divided by the clotting time in the absence of an inhibitor. The results of this assay may be expressed as IC1.5× or IC2×, the inhibitor concentration required to increase the clotting time by 1.5-times or 2-times, respectively, relative to the clotting time in the absence of the inhibitor.

The IC1.5× or IC2× is found by linear interpolation from relative clotting time versus inhibitor concentration plots using inhibitor concentration that spans the IC1.5× or IC2×.

Clotting times are determined using citrated normal human plasma as well as plasma obtained from a number of laboratory animal species (e.g., rat or rabbit). A compound is diluted into plasma beginning with a 10 mM DMSO stock solution. The final concentration of DMSO is less than 2%. Plasma clotting assays are performed in an automated coagulation analyzer (Sysmex, Dade-Behring, Ill.). Similarly, clotting times can be determined from laboratory animal species or humans dosed with compounds of the invention.

Activated Partial Thromboplastin Time (aPTT) is determined using ACTIN® (Dade-Behring, Ill.) following the directions in the package insert. Plasma (0.05 mL) is warmed to 37° C. for 1 minute. ACTIN® (0.05 mL) is added to the plasma and incubated for an additional 2 to 5 minutes. Calcium chloride (25 mM, 0.05 mL) is added to the reaction to initiate coagulation. The clotting time is the time in seconds from the moment calcium chloride is added until a clot is detected.

Prothrombin Time (PT) is determined using thromboplastin (Thromboplastin C Plus or Innovin, Dade-Behring, Ill.) following the directions in the package insert. Plasma (0.05 mL) is warmed to 37° C. for 1 minute. Thromboplastin (0.1 mL) is added to the plasma to initiate coagulation. The clotting time is the time in seconds from the moment thromboplastin is added until a clot is detected.

Chymotrypsin determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human chymotrypsin at a final concentration of 0.2-2 nM (Calbiochem) and the synthetic substrate S-2586 (Methoxy-Succinyl-Arg-Pro-Tyr-pNA; Chromogenix) at a concentration of 0.0005-0.005 M.

Trypsin determinations were made in 0.1 M sodium phosphate buffer at a pH of 7.5 containing 0.2 M sodium chloride and 0.5% PEG 8000. Determinations were made using purified human trypsin (Sigma) at a final assay concentration of 0.1-1 nM and the synthetic substrate S-2222 (Bz-Ile-Glu (gamma-OMe, 50%)-Gly-Arg-pNA; Chromogenix) at a concentration of 0.0005-0.005 M.

The exemplified Examples disclosed below were tested in the Factor XIa assay described above and found having Factor XIa inhibitory activity. A range of Factor XIa inhibitory activity (Ki values) of ≤10 μM (10000 nM) was observed.

The exemplified Examples disclosed below were tested in the Plasma Kallikrein assay described above, with some Examples having both Factor XIa and Plasma Kallikrein inhibitory activity. For those Examples where the Plasma Kallikrein inhibitory activity was observed as a (Ki values) of ≤10 μM (10000 nM), the inhibitory activity is reported.

The exemplified Examples disclosed below were tested in the Plasma Kallikrein assay described above, with some Examples having both Factor XIa and Plasma Kallikrein inhibitory activity. For those Examples where the Plasma Kallikrein inhibitory activity was observed as Ki values of ≤10 μM (10000 nM), the inhibitory activity is reported.

The compounds of the present invention exhibit unexpected FXIa inhibitory activity compared to the compounds of Formula (X) in WO 2014/022767 A1 wherein ring B is a pyrazole connected through its carbon atoms to the macrocycle. For example, WO 2014/022767 discloses Example 221 at page 319 with the following chemical structure

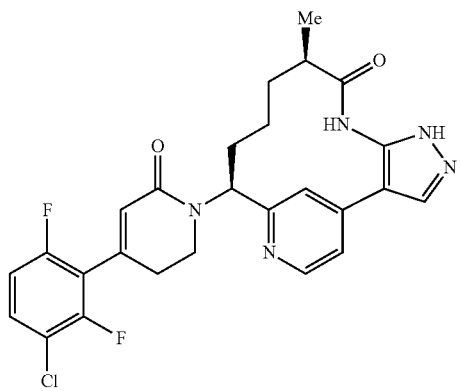 [SMILES: C[C@@H]1CCC[C@H](N2CCC(c3c(F)ccc(Cl)c3F)=CC2=O)c2cc(ccn2)-c2cn[nH]c2NC1=O]

and with a factor XIa Ki value of 1317 nM (Table 1, page 89). In contrast, the factor XIa Ki values of the compounds of the present invention as shown at the end of each example are less than 20 nM. These data illustrate that the compounds of the invention herein, e.g., compounds of Formulae (I), (II), (III), (Ia), (IIa), (IIIa), (IV), and (V) are surprisingly advantageous in inhibiting factor XIa.

B. In Vivo Assays

The effectiveness of compounds of the present invention as antithrombotic agents can be determined using relevant in vivo thrombosis models, including In Vivo Electrically-induced Carotid Artery Thrombosis Models and In Vivo Rabbit Arteriovenous Shunt Thrombosis Models.

a. In Vivo Electrically-Induced Carotid Artery Thrombosis (ECAT) Model

The rabbit ECAT model, described by Wong et al. (*J. Pharmacol. Exp. Ther.*, 295:212-218 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. An electromagnetic flow probe is placed on a segment of an isolated carotid artery to monitor blood flow. Test agents or vehicle will be given (i.v., i.p., s.c., or orally) prior to or after the initiation of thrombosis. Drug treatment prior to initiation of thrombosis is used to model the ability of test agents to prevent and reduce the risk of thrombus formation, whereas dosing after initiation is used to model the ability to treat existing thrombotic disease. Thrombus formation is induced by electrical stimulation of the carotid artery for 3 min at 4 mA using an external stainless-steel bipolar electrode. Carotid blood flow is measured continuously over a 90-min period to monitor thrombus-induced occlusion. Total carotid blood flow over 90 min is calculated by the trapezoidal rule. Average carotid flow over 90 min is then determined by converting total carotid blood flow over 90 min to percent of total control carotid blood flow, which would result if control blood flow had been maintained continuously for 90 min. The $ED_{50}$ (dose that increased average carotid blood flow over 90 min to 50% of the control) of compounds are estimated by a nonlinear least square regression program using the Hill sigmoid $E_{max}$ equation (DeltaGraph; SPSS Inc., Chicago, Ill.).

b. In Vivo Rabbit Arteriovenous (AV) Shunt Thrombosis Model

The rabbit AV shunt model, described by Wong et al. (Wong, P. C. et al., *J Pharmacol. Exp. Ther.* 292:351-357 (2000)), can be used in this study. Male New Zealand White rabbits are anesthetized with ketamine (50 mg/kg+50 mg/kg/h IM) and xylazine (10 mg/kg+10 mg/kg/h IM). These anesthetics are supplemented as needed. The femoral artery, jugular vein and femoral vein are isolated and catheterized. A saline-filled AV shunt device is connected between the femoral arterial and the femoral venous cannulae. The AV shunt device consists of an outer piece of tygon tubing (length=8 cm; internal diameter=7.9 mm) and an inner piece of tubing (length=2.5 cm; internal diameter=4.8 mm). The AV shunt also contains an 8-cm-long 2-0 silk thread (Ethicon, Somerville, N.J.). Blood flows from the femoral artery via the AV-shunt into the femoral vein. The exposure of flowing blood to a silk thread induces the formation of a significant thrombus. Forty minutes later, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose that produces 50% inhibition of thrombus formation) are estimated by a nonlinear least square regression program using the Hill sigmoid $E_{max}$ equation (DeltaGraph; SPSS Inc., Chicago, Ill.).

The anti-inflammatory effect of these compounds can be demonstrated in an Evans Blue dye extravasation assay using C1-esterase inhibitor deficient mice. In this model, mice are dosed with a compound of the present invention, Evans Blue dye is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors).

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

V. Pharmaceutical Compositions, Formulations and Combinations

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to about 1000 mg/kg of body weight, preferably between about 0.01 to about 100 mg/kg of body weight per day, and most preferably between about 0.1 to about 20 mg/kg/day. Intravenously, the most preferred doses will range from about 0.001 to about 10 mg/kg/minute during a constant rate infusion. Compounds of this invention may be administered in a single daily dose, or the total daily dosage may be administered in divided doses of two, three, or four times daily.

Compounds of this invention can also be administered by parenteral administration (e.g., intra-venous, intra-arterial, intramuscularly, or subcutaneously. When administered intra-venous or intra-arterial, the dose can be given continuously or intermittent. Furthermore, formulation can be developed for intramuscularly and subcutaneous delivery that ensure a gradual release of the active pharmaceutical ingredient. In one embodiment, the pharmaceutical composition is a solid formulation, e.g., a spray-dried composition, which may be used as is, or whereto the physician or the patient adds solvents, and/or diluents prior to use.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels. Solid dispersions are also called solid-state dispersions. In some embodiments, any compound described herein is formulated as a spray dried dispersion (SDD). An SDD is a single phase amorphous molecular dispersion of a drug in a polymer matrix. It is a solid solution prepared by dissolving the drug and a polymer in a solvent (e.g., acetone, methanol or the like) and spray drying the solution. The solvent rapidly evaporates from droplets which rapidly solidifies the polymer and drug mixture trapping the drug in amorphous form as an amorphous molecular dispersion.

Dosage forms (pharmaceutical compositions) suitable for administration may contain from about 1 milligram to about 1000 milligrams of active ingredient per dosage unit. In these pharmaceutical compositions the active ingredient will ordinarily be present in an amount of about 0.1-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to about 100 milligrams of the compound of the present invention and about 0.1 to about 100 milligrams per kilogram of patient body weight. For a tablet dosage form, the compounds of this invention generally may be present in an amount of about 5 to about 300 milligrams per dosage unit, and the second anticoagulant in an amount of about 1 to about 500 milligrams per dosage unit.

Where the compounds of the present invention are administered in combination with an anti-platelet agent, by way of general guidance, typically a daily dosage may be about 0.01 to about 300 milligrams of the compound of the present invention and about 50 to about 150 milligrams of the anti-platelet agent, preferably about 0.1 to about 4 milligrams of the compound of the present invention and about 1 to about 3 milligrams of antiplatelet agents, per kilogram of patient body weight.

Where the compounds of the present invention are administered in combination with thrombolytic agent, typically a daily dosage may be about 0.1 to about 100 milligrams of the compound of the present invention, per kilogram of patient body weight and, in the case of the thrombolytic agents, the usual dosage of the thrombolytic agent when administered alone may be reduced by about 50-80% when administered with a compound of the present invention.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

In another embodiment, the present invention provides a pharmaceutical composition further comprising additional therapeutic agent(s) selected from potassium channel openers, potassium channel blockers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anticoagulant agent, an anti-platelet agent, a thrombin inhibiting agent, a thrombolytic agent, a fibrinolytic agent, a calcium channel blocker, a potassium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In another embodiment, the present invention provides a pharmaceutical composition wherein the additional therapeutic agent is an antihypertensive agent selected from ACE inhibitors, AT-1 receptor antagonists, beta-adrenergic receptor antagonists, ETA receptor antagonists, dual ETA/AT-1 receptor antagonists, renin inhibitors (aliskerin) and vasopepsidase inhibitors, an antiarrythmic agent selected from $I_{Kur}$ inhibitors, an anticoagulant selected from thrombin inhibitors, antithrombin-III activators, heparin co-factor II activators, other factor XIa inhibitors, other kallikrein inhibitors, plasminogen activator inhibitor (PAI-1) antagonists, thrombin activatable fibrinolysis inhibitor (TAFI) inhibitors, factor VIIa inhibitors, factor IXa inhibitors, and factor Xa inhibitors, or an antiplatelet agent selected from GPIIb/IIIa blockers, GP Ib/IX blockers, protease activated receptor 1 (PAR-1) antagonists, protease activated receptor4 (PAR-4) antagonists, prostaglandin E2 receptor EP3 antagonists, collagen receptor antagonists, phosphodiesterase-III inhibitors, $P2Y_1$ receptor antagonists, $P2Y_{12}$ antagonists, thromboxane receptor antagonists, cyclooxygense-1 inhibitors, and aspirin, or a combination thereof.

In another embodiment, the present invention provides pharmaceutical composition, wherein the additional therapeutic agent(s) are an anti-platelet agent or a combination thereof.

In another embodiment, the present invention provides a pharmaceutical composition, wherein the additional therapeutic agent is the anti-platelet agent clopidogrel.

The compounds of the present invention can be administered alone or in combination with one or more additional therapeutic agents. By "administered in combination" or "combination therapy" it is meant that the compound of the present invention and one or more additional therapeutic agents are administered concurrently to the mammal being treated. When administered in combination, each component may be administered at the same time or sequentially in any order at different points in time.

Thus, each component may be administered separately but sufficiently closely in time so as to provide the desired therapeutic effect.

Compounds that can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVENOX®), synthetic pentasaccharide, direct acting thrombin inhibitors including hirudin and argatroban, as well as other factor VIIa inhibitors, factor IXa inhibitors, factor Xa inhibitors (e.g., ARIXTRA®, apixaban, rivaroxaban, LY-517717, DU-176b, DX-9065a, and those disclosed in WO 98/57951, WO 03/026652, WO 01/047919, and WO 00/076970), factor XIa inhibitors, and inhibitors of activated TAFI and PAI-1 known in the art.

The term anti-platelet agents (or platelet inhibitory agents), as used herein, denotes agents that inhibit platelet function, for example, by inhibiting the aggregation, adhesion or granule-content secretion of platelets. Such agents include, but are not limited to, the various known non-steroidal anti-inflammatory drugs (NSAIDs) such as acetaminophen, aspirin, codeine, diclofenac, droxicam, fentaynl, ibuprofen, indomethacin, ketorolac, mefenamate, morphine, naproxen, phenacetin, piroxicam, sufentanyl, sulfinpyrazone, sulindac, and pharmaceutically acceptable salts or prodrugs thereof. Of the NSAIDs, aspirin (acetylsalicylic acid or ASA) and piroxicam are preferred. Other suitable platelet inhibitory agents include glycoprotein IIb/IIIa antagonists (e.g., tirofiban, eptifibatide, abciximab, and integrelin), thromboxane-A2-receptor antagonists (e.g., ifetroban), thromboxane-A-synthetase inhibitors, phosphodiesterase-III (PDE-III) inhibitors (e.g., dipyridamole, cilostazol), and PDE-V inhibitors (such as sildenafil), protease-activated receptor 1 (PAR-1) antagonists (e.g., E-5555, SCH-530348, SCH-203099, SCH-529153 and SCH-205831), and pharmaceutically acceptable salts or prodrugs thereof.

Other examples of suitable anti-platelet agents for use in combination with the compounds of the present invention, with or without aspirin, are ADP (adenosine diphosphate) receptor antagonists, preferably antagonists of the purinergic receptors $P2Y_1$ and $P2Y_{12}$, with $P2Y_{12}$ being even more preferred. Preferred $P2Y_{12}$ receptor antagonists include clopidogrel, ticlopidine, prasugrel, ticagrelor, and cangrelor, and pharmaceutically acceptable salts or prodrugs thereof. Ticlopidine and clopidogrel are also preferred compounds since they are known to be more gentle than aspirin on the gastrointestinal tract in use. Clopidogrel is an even more preferred agent.

A preferred example is a triple combination of a compound of the present invention, aspirin, and another anti-platelet agent. Preferably, the anti-platelet agent is clopidogrel or prasugrel, more preferably clopidogrel.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the secretion of platelet granule contents including serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, dabigatran, AZD-0837, and those disclosed in WO 98/37075 and WO 02/044145, and pharmaceutically acceptable salts and prodrugs thereof. Boroarginine derivatives and boropeptides include N-acetyl and peptide derivatives of boronic acid, such as C-terminal a-aminoboronic acid derivatives of lysine, omithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, thrombin inhibitors, inhibitors of factors IXa, Xa, and XIa, PAI-I inhibitors (i.e., inactivators of tissue plasminogen activator inhibitors), inhibitors of activated TAFI, alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable cholesterol/lipid lowering agents and lipid profile therapies for use in combination with the compounds of the present invention include HMG-CoA reductase inhibitors (e.g., pravastatin, lovastatin, simvastatin, fluvastatin, atorvastatin, rosuvastatin, and other statins), low-density lipoprotein (LDL) receptor activity modulators (e.g., HOE-402, PCSK9 inhibitors), bile acid sequestrants (e.g., cholestyramine and colestipol), nicotinic acid or derivatives thereof (e.g., NIASPAN®), GPR109B (nicotinic acid receptor) modulators, fenofibric acid derivatives (e.g., gemfibrozil, clofibrate, fenofibrate and benzafibrate) and other peroxisome proliferator-activated receptors (PPAR) alpha modulators, PPARdelta modulators (e.g., GW-501516), PPARgamma modulators (e.g., rosiglitazone), compounds that have multiple functionality for modulating the activities of various combinations of PPARalpha, PPAR-gamma and PPARdelta, probucol or derivatives thereof (e.g., AGI-1067), cholesterol absorption inhibitors and/or Niemann-Pick C1-like transporter inhibitors (e.g., ezetimibe), cholesterol ester transfer protein inhibitors (e.g., CP-529414), squalene synthase inhibitors and/or squalene epoxidase inhibitors or mixtures thereof, acyl coenzyme A: cholesteryl acyltransferase (ACAT) 1 inhibitors, ACAT2 inhibitors, dual ACAT1/2 inhibitors, ileal bile acid transport inhibitors (or apical sodium co-dependent bile acid transport inhibitors), microsomal triglyceride transfer protein inhibitors, liver-X-receptor (LXR) alpha modulators, LXRbeta modulators, LXR dual alpha/beta modulators, FXR modulators, omega 3 fatty acids (e.g., 3-PUFA), plant stanols and/or fatty acid esters of plant stanols (e.g., sitostanol ester used in BENECOL® margarine), endothelial lipase inhibitors, and HDL functional mimetics which activate reverse cholesterol transport (e.g., apoAI derivatives or apoAI peptide mimetics).

The compounds of the present invention can also be combined with soluble guanylate cyclase inhibitors, Chymase inhibitors, ROMK inhibitors, ACE inhibitors, ATII inhibitors, ATR inhibitors, NEP inhibitors and other compounds to treat heart failure.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 µM against the target protease and greater than or equal to 0.1 µM against the other proteases, may also be used in diagnostic assays involving the quantitation of thrombin, Factor VIIa, IXa, Xa, XIa, and/or plasma kallikrein in serum samples. For example, the amount of Factor XIa in serum samples could be determined by careful titration of protease activity in the presence of the relevant chromogenic substrate, S2366, with a potent Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Other features of the invention will become apparent in the course of the following descriptions of exemplary embodiments that are given for illustration of the invention and are not intended to be limiting thereof. The following Examples have been prepared, isolated and characterized using the methods disclosed herein.

VI. General Synthesis Including Schemes

The compounds of the present invention may be synthesized by many methods available to those skilled in the art of organic chemistry (Maffrand, J. P. et al., *Heterocycles*, 16(1):35-37 (1981)). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Additionally, the various steps in the synthesis may be performed in an alternate sequence in order to give the desired compound or compounds.

Examples of compounds of the present invention prepared by methods described in the general schemes are given in the intermediates and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products. These include, but are not limited to, the incorporation of chiral auxiliary functionalities into racemic intermediates which serve to control the diastereoselectivity of transformations, providing enantio-enriched products upon cleavage of the chiral auxiliary.

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Fourth Edition, Wiley-Interscience (2006)).

Representative compounds of this invention where ring A is a 6-membered heterocycle (example—pyridine) can be derived from intermediates 1h, the synthesis of which is described in Scheme 1. Condensation of aldehyde 1a prepared according to a modified procedure described by Negi (*Synthesis*, 991 (1996)), with (S)-2-methylpropane-2-sulfinamide in the presence of anhydrous copper sulfate or cesium carbonate in a solvent such as DCM gives the sulfinimine 1b (Ellman, J., *J. Org. Chem.*, 64:1278 (1999)). Using a modified procedure described by Kuduk (*Tetrahedron Letters*, 45:6641 (2004)), suitably substituted Grignard reagents, for example allylmagnesium bromide, can be added to sulfinimine 1b to give a sulfinamide 1c, as a mixture of diastereomers which can be separated at various stages of the sequence. The diastereoselectivity for the addition of allylmagnesium bromide to sulfinimine 1b can be improved by employing indium(III) chloride according to a modified procedure of Xu (Xu, M.-H., *Organic Letters*, 10(6): 1259 (2008)). Protecting group interconversion can be accomplished in two steps to give 1d. This chloropyridine can be coupled to 4-nitropyrazoles upon heating with a Pd II salt such as Pd(OAc)$_2$ in the presence of a phosphine ligand and a base such as potassium carbonate in a solvent such as DMF or DMA in a microwave reactor, as described by Sames (Goikhman, R. et al., *J. Am. Chem. Soc.*, 131:3042 (2009)). Zinc/HOAc reduction of the nitropyrazole followed by amidation with an appropriately substituted carboxylic acid provides 1f. Macrocyclization is then accomplished via ring-closing metathesis using the Grubb's second generation ruthenium catalyst to yield 1g. Hydrogenation of the resulting olefin and protecting group cleavage yields amine 1h. Compounds of the formulae 1h can be converted to compounds in this invention according to Schemes 2 and 3.

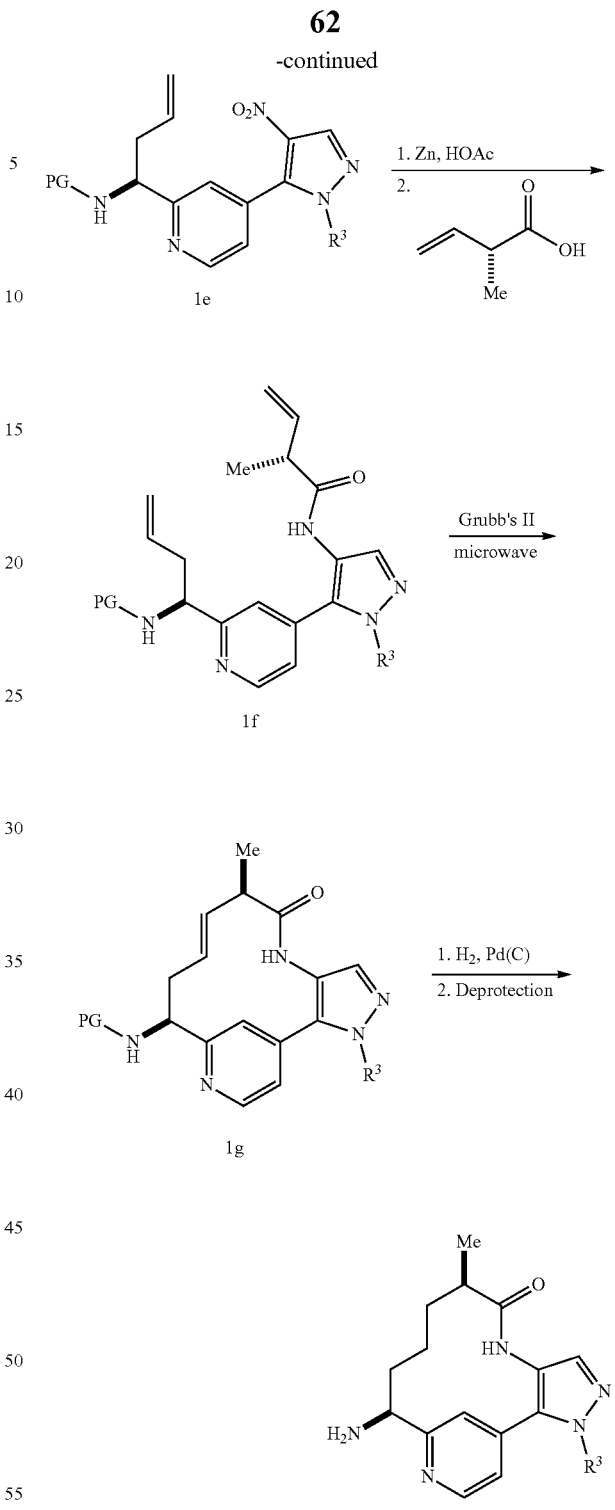

Representative compounds of this invention can be prepared as shown in Scheme 2. Starting from aldehyde 2a, vinyl Grignard addition (yielding allylic alcohol 2b) followed by oxidation gives vinyl ketones 2c. Michael addition of the amines from Scheme 1 followed by acylation with 2d affords compounds 2e, which upon cyclization with base provides the dihydropyridone 2f.

Scheme 2

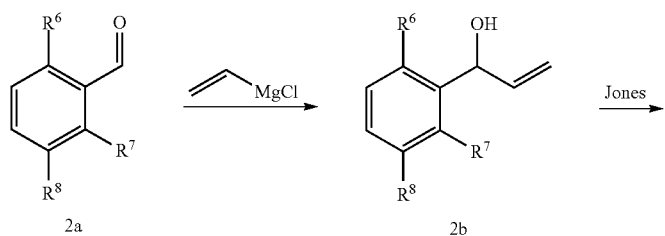

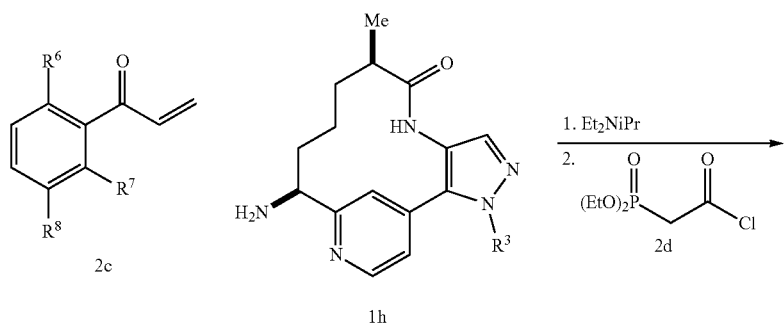

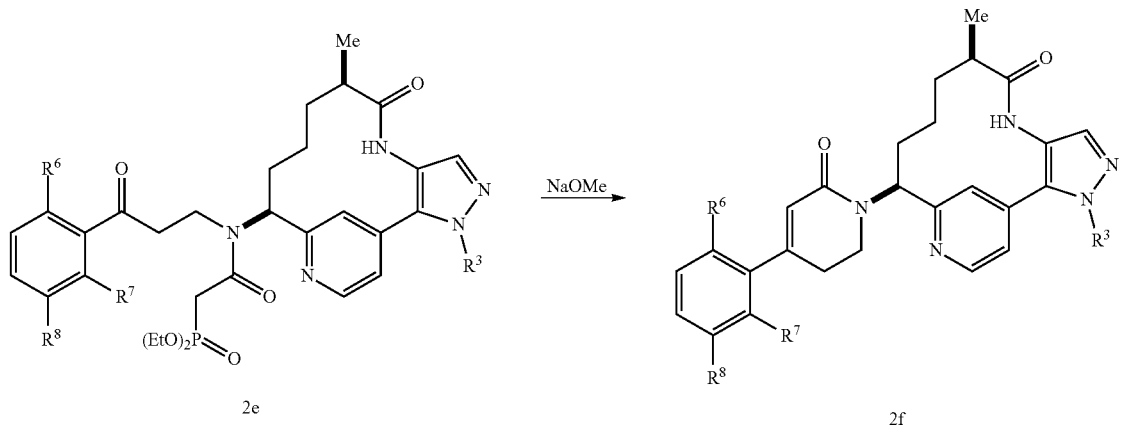

Compounds in this invention bearing alternate regiochemical pyrazole substitution can be synthesized as shown in Scheme 3. When R is an appropriate protective group (example—trimethylsilylethoxymethyl), deprotection of 3a to 3b can be followed by alkylation with an alkyl halide under basic conditions or upon reaction with a boronic acid in the presence of Cu(II) salts such as Cu(OAc)$_2$. In most cases, the alkylation proceeds to give solely the product shown in 3c. In select cases, products of the type shown in Scheme 2 are formed as a minor component.

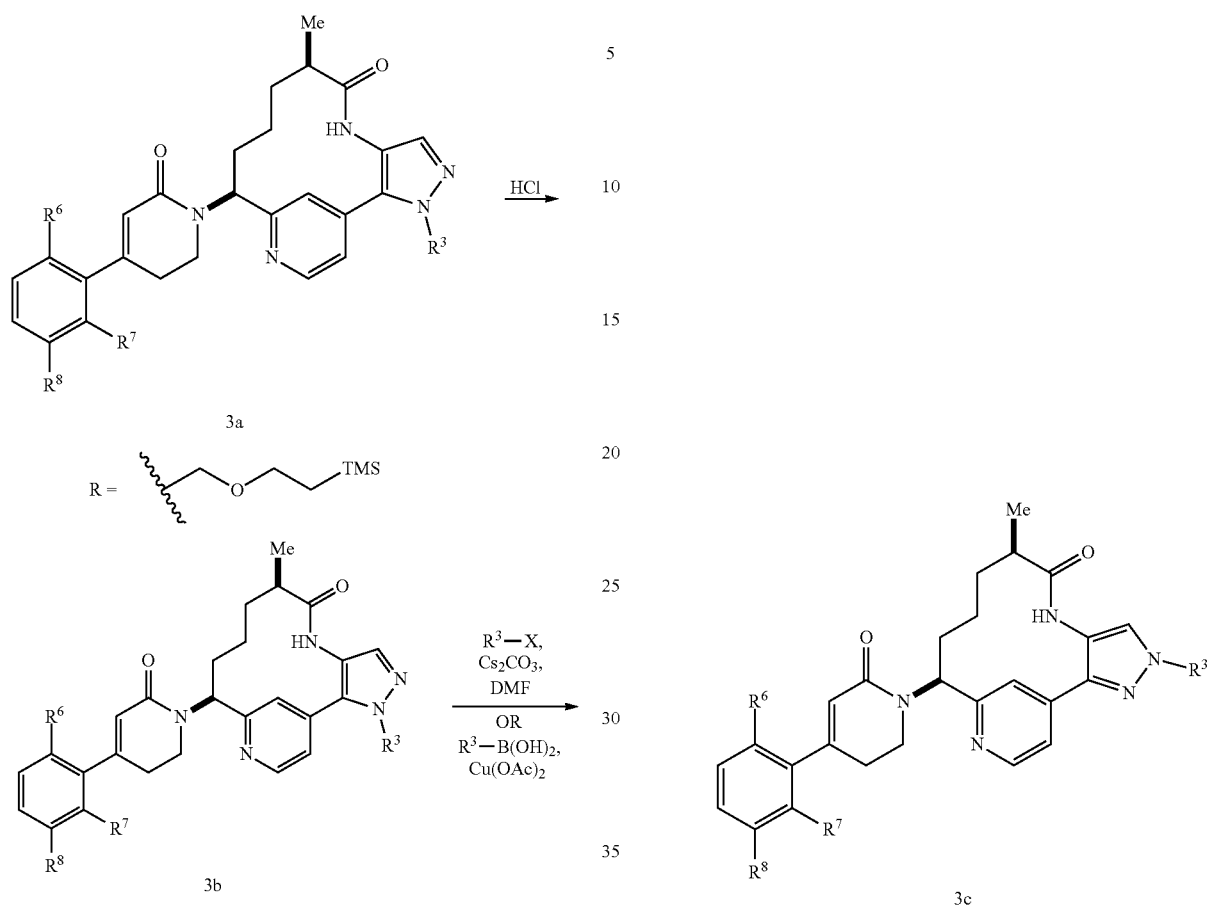
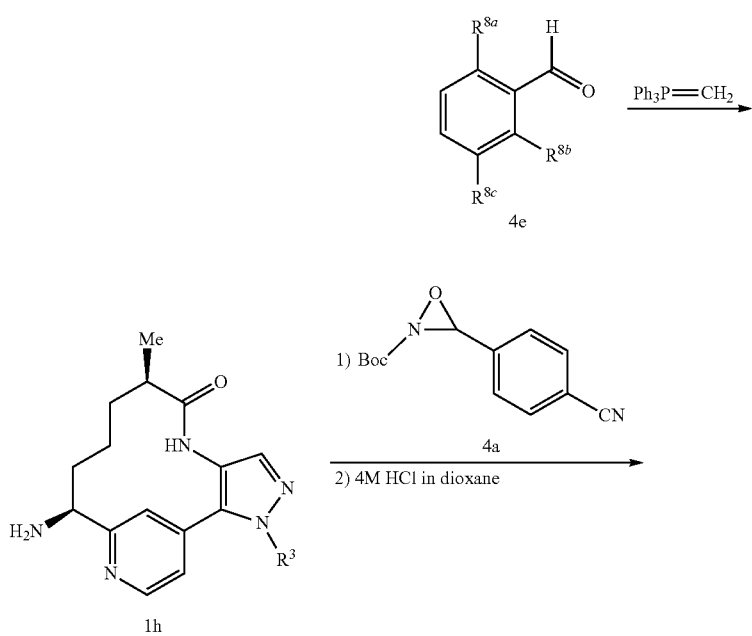

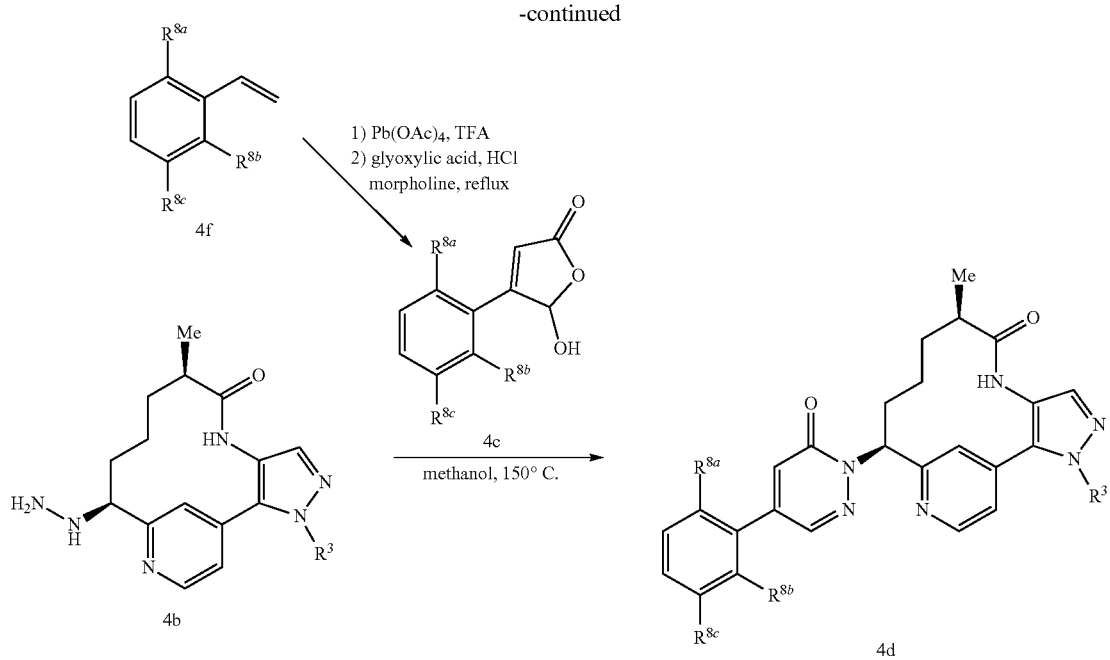

Representative pyridazinone compounds of this invention can be prepared as shown in Scheme 4. Using a modified procedure described by Vidal (*Chem. Eur. J.*, 3(10):1691 (1997)), amine 1h can be reacted with oxaziridine 4a to give the Boc-protected hydrazine derivative. Deprotection with either TFA in dichloromethane or 4M HCl in dioxane affords hydrazine 4b. Condensation of hydrazine 4b and a suitably substituted hydroxy furanone 4c in methanol at elevated temperatures provides the pyridazinone 4d. Suitably substituted hydroxy furanone derivatives 4c can be prepared in two steps from styrene 4f according to a modified procedure described by van Niel (*J. Med. Chem.*, 48:6004 (2005)). Styrene 4f can be oxidized with lead tetraacetate in TFA to give the corresponding acetaldehyde derivative followed by condensation with glyoxylic acid in the presence of morpholine and hydrochloric acid at elevated temperatures will provide 4c.

Intermediates for preparation of compounds of the present invention wherein $R^2$ is —F can be prepared according to Scheme 5. Olefin 1g can be subjected to hydrofluorination, yielding as many as four isomeric alkyl fluorides. Following separation of the isomers, deprotection of the amine protecting group is accomplished by the action of either TFA or HCl, as previously shown in Scheme 1. The intermediate 5a can be elaborated to compounds of this invention according to the procedure described in Scheme 2.

Scheme 5

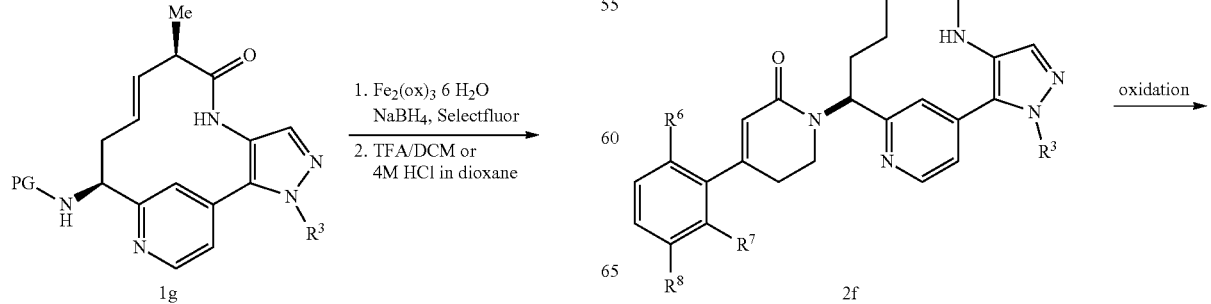

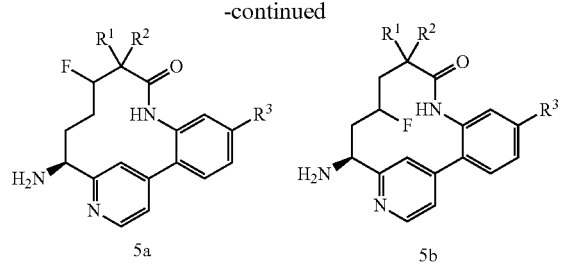

Intermediates for preparation of compounds of the present invention wherein $R^2$ is —F can be prepared according to Scheme 5. Olefin 1g can be subjected to hydrofluorination, yielding as many as four isomeric alkyl fluorides. Following separation of the isomers, deprotection of the amine protecting group is accomplished by the action of either TFA or HCl, as previously shown in Scheme 1. The intermediate 5a can be elaborated to compounds of this invention according to the procedure described in Scheme 2.

Compounds in this invention with pyridone connected to the macrocycle (6a) can be synthesized by oxidation of compounds 2f with various oxidations conditions such as CuI in DMSO, or cumene hydroperoxide/Pealman's catalyst as shown in Scheme 6.

Scheme 6

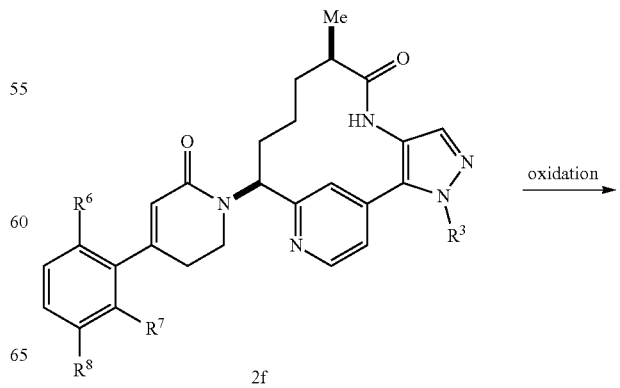

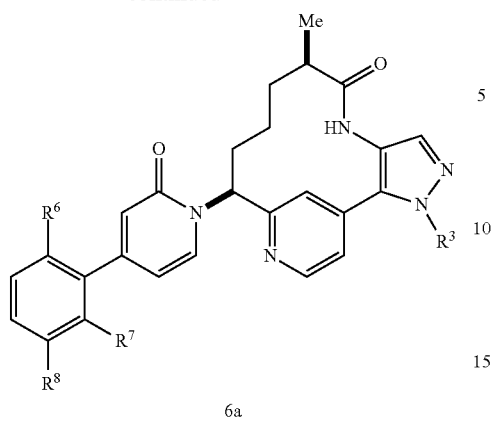

Alternatively, compounds in this invention (6a) with pyridone connected to the macrocycle can be synthesized as shown in Scheme 7. Treatment of 1-ethoxyprop-1-ene with malonyl dichloride followed by quenching with ethanol provides compound 7a, which can be hydrolyzed to 7b with KOH/EtOH. 7b can be subjected to concentrated H$_2$SO$_4$ at high temperature to provide 7c, which can react with 1h to give 7d. 7d can be converted to its triflate 7e, and upon Suzuki coupling with various boronic acid, compounds of this invention 6a can be prepared.

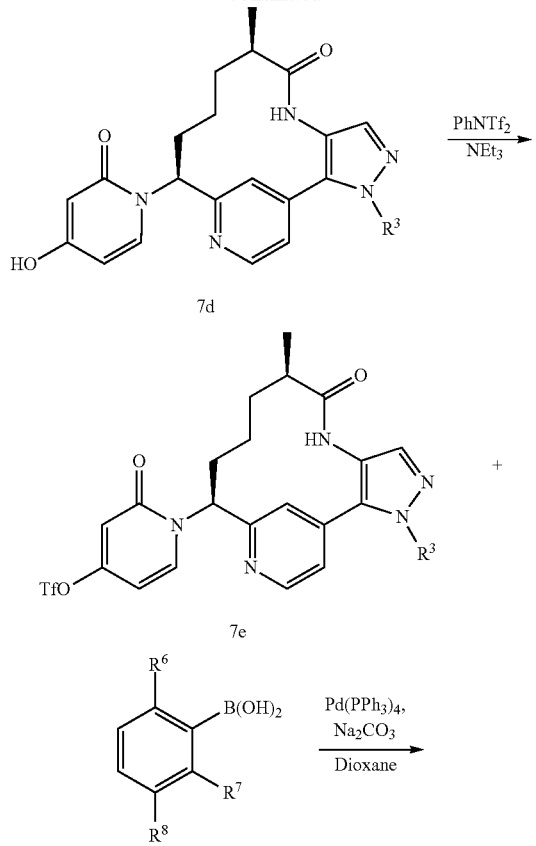

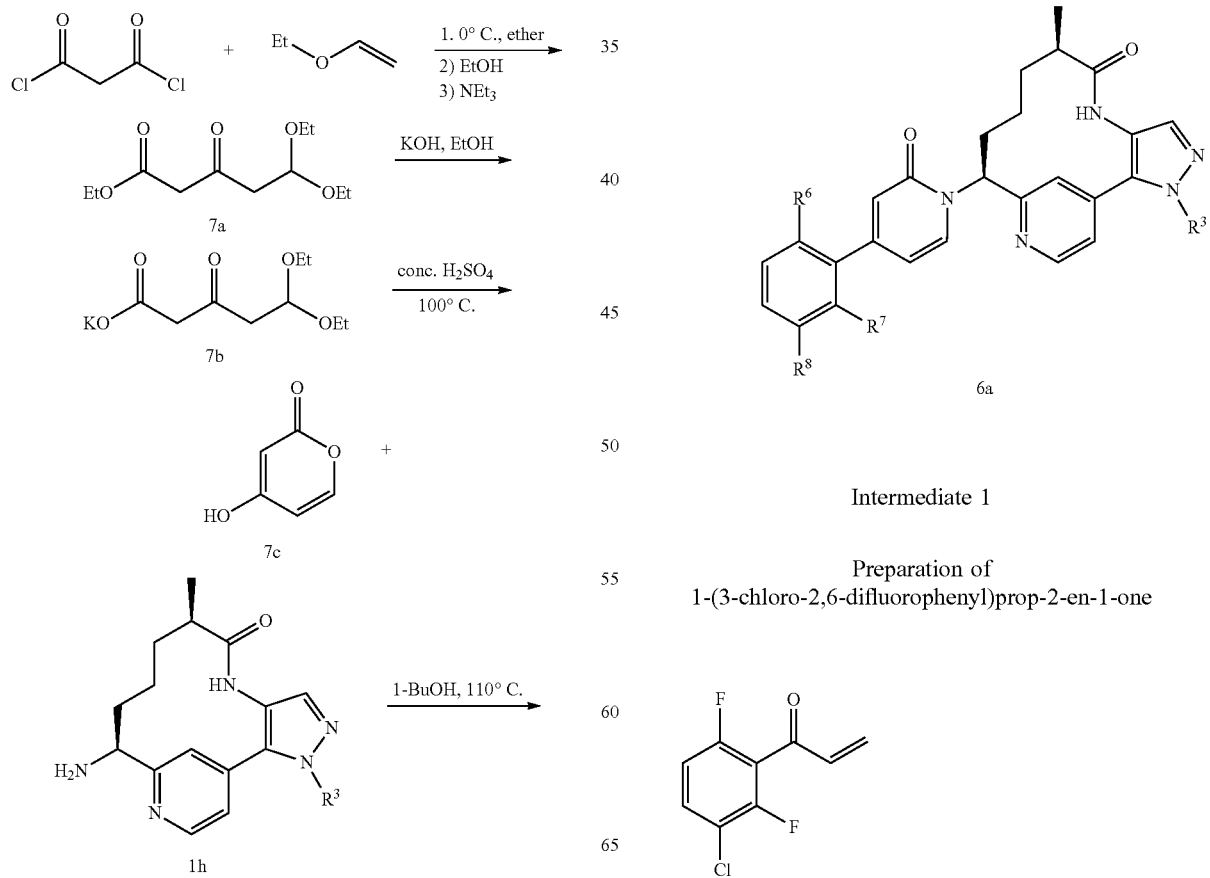

Intermediate 1

Preparation of
1-(3-chloro-2,6-difluorophenyl)prop-2-en-1-one

1A. Preparation of 1-(3-chloro-2,6-difluorophenyl)prop-2-en-1-ol

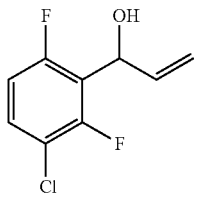

To a 100 mL dry RBF containing 1 M vinylmagnesium bromide in THF (24 mL, 24.0 mmol) under Ar at 0° C. was added 3-chloro-2,6-difluorobenzaldehyde (3.2 g, 18.13 mmol) in THF (10 mL) dropwise. The reaction was stirred for 1 h and quenched with 1 N HCl to pH 2. The mixture was extracted with Et$_2$O (3x). The combined organic layer was washed with brine, dried over MgSO$_4$, filtered, and concentrated to yield 1-(3-chloro-2,6-difluorophenyl)prop-2-en-1-ol (3.71 g, 100%) as a pale yellow oil. $^1$H NMR (500 MHz, CDCl$_3$) δ 7.34 (ddd, J=8.9, 8.1, 5.8 Hz, 1H), 6.90 (td, J=9.2, 1.7 Hz, 1H), 6.23 (dddt, J=17.2, 10.4, 5.8, 1.2 Hz, 1H), 5.60 (dd, J=7.6, 6.7 Hz, 1H), 5.40-5.31 (m, 1H), 5.28 (dt, J=10.2, 1.2 Hz, 1H), 2.38 (dt, J=8.3, 1.9 Hz, 1H).

1B. Preparation of 1-(3-chloro-2,6-difluorophenyl)prop-2-en-1-one

To a solution of 1-(3-chloro-2,6-difluorophenyl)prop-2-en-1-ol (3.7 g, 18.08 mmol) in acetone (90 mL) at 0° C. was added Jones reagent (8.77 ml, 23.51 mmol) dropwise. Upon finishing addition of Jones reagent, the reaction was quenched with iPrOH. The mixture was concentrated. The residue was suspended in water and extracted with DCM (3x). The combined organic layer was washed with brine, dried over MgSO$_4$, filtered, and concentrated. The residue was purified by silica gel chromatography to yield 1-(3-chloro-2,6-difluorophenyl)prop-2-en-1-one as a yellow oil (3.45 g, 94%) which solidified in freezer. $^1$H NMR (500 MHz, CDCl$_3$) δ 7.48 (ddd, J=9.0, 8.0, 5.5 Hz, 1H), 7.05-6.91 (m, 1H), 6.70 (ddt, J=17.5, 10.5, 1.1 Hz, 1H), 6.29-6.11 (m, 2H).

Intermediate 2

Preparation of 1-(3-chloro-2-fluoro-6-(trifluoromethyl)phenyl)prop-2-en-1-one

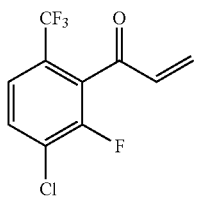 [SMILES: C=CC(=O)c1c(C(F)(F)F)ccc(Cl)c1F]

1-(3-Chloro-2-fluoro-6-(trifluoromethyl)phenyl)prop-2-en-1-one was prepared using a procedure analogous to that used for the preparation of Intermediate 1 by replacing 3-chloro-2,6-difluorobenzaldehyde with 3-chloro-2-fluoro-6-(trifluoromethyl) benzaldehyde. $^1$H NMR (500 MHz, CDCl$_3$) δ 7.64 (ddd, J=8.0, 7.4, 0.8 Hz, 1H), 7.50 (dd, J=8.5, 0.6 Hz, 1H), 6.69 (dd, J=17.6, 10.7 Hz, 1H), 6.27 (d, J=10.7 Hz, 1H), 6.01 (dd, J=17.7, 0.7 Hz, 1H).

Intermediate 3

Preparation of 1-(5-chloro-2-(1H-1,2,3-triazol-1-yl)phenyl)prop-2-en-1-one

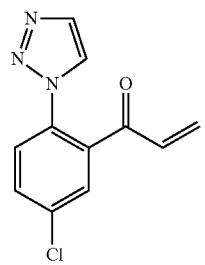 [SMILES: C=CC(=O)c1cc(Cl)ccc1-n1ccnn1]

3A. Preparation of 5-chloro-2-(1H-1,2,3-triazol-1-yl)benzaldehyde

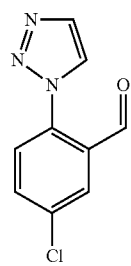 [SMILES: O=Cc1cc(Cl)ccc1-n1ccnn1]

A septum cap-sealed vial was charged with 5-chloro-2-fluorobenzaldehyde (1.0 g, 6.31 mmol), 1H-1,2,3-triazole (3.0 g, 43.4 mmol), and Cs$_2$CO$_3$ (2.260 g, 6.94 mmol). The thick solution was heated at 90° C. for 1 h. Purification by silica gel chromatography yielded a mixture of the desired product and unreacted triazole starting material. Upon addition of ~5-10 mL water, the product precipitated. Filtration and drying in vacuo yielded 5-chloro-2-(1H-1,2,3-triazol-1-yl)benzaldehyde as a white solid (0.52 g, 40%). MS(ESI) m/z: 208.3 (M+H)$^+$. $^1$H NMR (500 MHz, CDCl$_3$) δ 9.85 (s, 1H), 8.09 (d, J=2.2 Hz, 1H), 7.97 (d, J=1.1 Hz, 1H), 7.94 (d, J=0.8 Hz, 1H), 7.73 (dd, J=8.4, 2.3 Hz, 1H), 7.49 (d, J=8.3 Hz, 1H).

3B. Preparation of 1-(5-chloro-2-(1H-1,2,3-triazol-1-yl)phenyl)prop-2-en-1-one 1-(5-Chloro-2-(1H-1,2,3-triazol-1-yl)phenyl)prop-2-en-1-one was prepared using a procedure analogous to that used for the preparation of Intermediate 1 by using 5-chloro-2-(1H-1,2,3-triazol-1-yl)benzaldehyde. MS(ESI) m/z: 234.3 (M+H)$^+$. $^1$H NMR (500 MHz, CDCl$_3$) δ 7.82-7.78 (m, 2H), 7.66-7.59 (m, 2H), 7.56-7.51 (m, 1H), 6.25 (dd, J=17.6, 10.7 Hz, 1H), 5.93 (dd, J=17.3, 0.6 Hz, 1H), 5.82 (dd, J=10.7, 0.6 Hz, 1H).

Intermediate 4

Preparation of 1-(5-chloro-2-(4-chloro-1H-1,2,3-triazol-1-yl)phenyl)prop-2-en-1-one

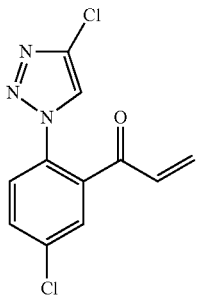 [SMILES: C=CC(=O)c1cc(Cl)ccc1-n1cc(Cl)nn1]

4A. Preparation of 2-azido-5-chlorobenzaldehyde

A solution of 5-chloro-2-fluorobenzaldehyde (1.38 g, 8.70 mmol) and NaN$_3$ (0.58 g, 8.92 mmol) in DMF (4 mL) was stirred at 55° C. for 8 h then cooled to rt. The reaction mixture was diluted with Et$_2$O and water which was then acidified with 1 N HCl to pH 4. The organic layer was washed with water (3×) followed by brine (3×), then dried over MgSO$_4$ and filtered. The organic layers were then concentrated to yield 1.47 g of 2-azido-5-chlorobenzaldehyde (93%) as pale yellow solid. $^1$H NMR (400 MHz, CDCl$_3$-d) δ 10.30 (s, 1H), 7.86 (d, J=2.6 Hz, 1H), 7.58 (dd, J=8.7, 2.5 Hz, 1H), 7.24 (d, J=8.6 Hz, 1H).

4B. Preparation of 5-chloro-2-(4-(tributylstannyl)-1H-1,2,3-triazol-1-yl)benzaldehyde A solution of 2-azido-5-chlorobenzaldehyde (386 mg, 2.126 mmol) and tributylstanylacetylene (0.646 mL, 2.126 mmol) in toluene (5 mL) was heated at 100° C. for 5 h then cooled to rt. After 5 h, the reaction mixture was concentrated and directly purified using normal phase chromatography to yield 495 mg of 5-chloro-2-(4-(tributylstannyl)-1H-1,2,3-triazol-1-yl)benzaldehyde (43%) as pale yellow oil. MS(ESI) m/z: 498.1 (M+H)$^+$.

4C. Preparation of 5-chloro-2-(4-chloro-1H-1,2,3-triazol-1-yl)benzaldehyde

To a solution of 5-chloro-2-(4-(tributylstannyl)-1H-1,2,3-triazol-1-yl)benzaldehyde (459 mg, 0.924 mmol) in ACN (5 mL) was added NCS (185 mg, 1.386 mmol) and the reaction was then heated at 60° C. for 15 h. After 15 h, the reaction mixture was concentrated and directly purified using normal phase chromatography to yield 117 mg of 5-chloro-2-(4-chloro-1H-1,2,3-triazol-1-yl)benzaldehyde (52%) as white solid. MS(ESI) m/z: 242.0 (M+H, chlorine isotope peak)$^+$.

4D. Preparation of 1-(5-chloro-2-(4-chloro-1H-1,2,3-triazol-1-yl)phenyl)prop-2-en-1-one 1-(5-Chloro-2-(4-chloro-1H-1,2,3-triazol-1-yl)phenyl) prop-2-en-1-one was prepared using a procedure analogous to that used for the preparation of Intermediate 1 by replacing 3-chloro-2,6-difluorobenzaldehyde with 5-chloro-2-(4-chloro-1H-1,2,3-triazol-1-yl)benzaldehyde. MS(ESI) m/z: 268.3 (M+H)$^+$. $^1$H NMR (400 MHz, CDCl$_3$) δ 7.71-7.66 (m, 1H), 7.62-7.52 (m, 2H), 7.44 (d, J=8.4 Hz, 1H), 6.29 (dd, J=17.6, 10.6 Hz, 1H), 5.98-5.79 (m, 2H).

Intermediate 5

Preparation of diethyl (2-chloro-2-oxoethyl)phosphonate

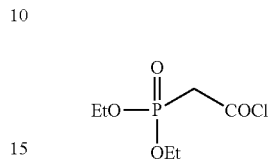

To a solution of 2-(diethoxyphosphoryl)acetic acid (0.1 mL, 0.622 mmol) in CH$_2$Cl$_2$ (1 mL) was added 2 M (CO)$_2$Cl$_2$ in DCM (0.6 mL, 1.24 mmol), followed by a drop of DMF. The reaction was stirred at rt for 2.5 h and concentrated in vacuo to yield diethyl (2-chloro-2-oxoethyl) phosphonate as yellow oil. $^1$H NMR (500 MHz, CDCl$_3$) δ 4.24 (dq, J=8.4, 7.1 Hz, 4H), 3.55-3.47 (d, J=21.46 Hz, 2H), 1.42-1.38 (t, J=7.4 Hz, 6H).

Intermediate 6

Preparation of (R)-2-methylbut-3-enoic Acid

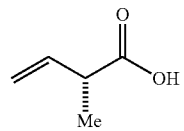

6A. Preparation of (R)-4-benzyl-3-((R)-2-methylbut-3-enoyl)oxazolidin-2-one To the solution of 2-methylbut-3-enoic acid (5.59 g, 55.9 mmol) and NMM (6.14 ml, 55.9 mmol) in THF (62 mL) at 0° C. was added pivaloyl chloride (6.87 ml, 55.9 mmol) dropwise. The reaction mixture was cooled to −78° C., and stirred for −2 h. In a separate flask: To the solution of (R)-4-benzyloxazolidin-2-one (8.25 g, 46.6 mmol) in THF (126 mL) at −78° C. was added 2.5 M nBuLi in hexane (20.49 mL, 51.2 mmol) dropwise. After 35 min, this reaction was transferred via cannula to the first reaction. The reaction mixture was stirred at −78° C. for 2 h, then the cold bath was removed, and the reaction was quenched with sat NH$_4$Cl. The reaction was diluted with water and extracted with EtOAc (3×). The combined organic layers were washed with brine, dried over Na$_2$SO$_4$, filtered, and concentrated to give a yellow oil (15 g). Purification by silica gel chromatography afforded (R)-4-benzyl-3-((R)-2-methylbut-3-enoyl)oxazolidin-2-one (6.59 g, 55%) as a colorless oil. MS(ESI) m/z: 282.1 (M+Na)$^+$. $^1$H NMR (500 MHz, CDCl$_3$) δ 7.36-7.19 (m, 5H), 6.03-5.93 (m, 1H), 5.23-5.10 (m, 2H), 4.69-4.63 (m, 1H), 4.51-4.43 (m, 1H), 4.23-4.15 (m, 2H), 3.29 (dd, J=13.5, 3.3 Hz, 1H), 2.79 (dd, J=13.5, 9.6 Hz, 1H), 1.35 (d, J=6.9 Hz, 3H) ppm. The other diastereomer (R)-4-benzyl-3-((S)-2-methylbut-3-enoyl)oxazolidin-2-one (4.6 g, 38%) also was obtained as a white solid. MS(ESI) m/z: 260.1 (M+H)$^+$.

6B. Preparation of (R)-2-methylbut-3-enoic Acid

To a clear colorless solution of (R)-4-benzyl-3-((R)-2-methylbut-3-enoyl) oxazolidin-2-one (6.05 g, 23.33 mmol) in THF (146 mL) at 0° C. was added with CHCl₃ (3×). The aqueous layer was acidified with conc. HCl to pH~3 and then it was extracted with EtOAc (3×). The EtOAc layers were combined, washed with brine, dried over MgSO₄, filtered and concentrated to afford (R)-2-methylbut-3-enoic acid (2.15 g, 92%) as a colorless oil. $^1$H NMR (500 MHz, CDCl₃) δ 10.84 (br. s., 1H), 5.94 (ddd, J=17.4, 10.1, 7.4 Hz, 1H), 5.22-5.13 (m, 2H), 3.23-3.15 (m, 1H), 1.31 (d, J=7.2 Hz, 3H).

Intermediate 7

Preparation of 1-cyclopropyl-4-nitro-1H-pyrazole

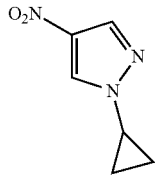 [SMILES: O=[N+]([O-])c1cnn(C2CC2)c1]

DCE (66 ml) was added to 4-nitro-1H-pyrazole (1.5 g, 13.3 mmol), cyclopropylboronic acid (2.28 g, 26.5 mmol), 2,2'-bipyridine (2.1 g, 13.3 mmol), and Na₂CO₃ (2.81 g, 26.5 mmol) in a 250 mL RBF. It was purged with Ar (3×). Cu(OAc)₂ (2.41 g, 13.3 mmol) was added followed purging with Ar. The reaction was then heated under Ar for 6 h. Upon the completion of reaction, the mixture was filtered through CELITE® and concentrated. Purification with silica gel chromatography yielded 1-cyclopropyl-4-nitro-1H-pyrazole (0.965 g, 47.5%) as a white solid.

Intermediate 8

Preparation of 1-ethyl-4-nitro-1H-pyrazole

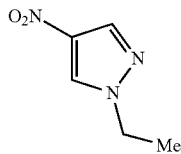

1-Ethyl-4-nitro-1H-pyrazole was prepared in the same manner as that used for the preparation of 1-methyl-4-nitro-1H-pyrazole described in Example 1D, by substituting EtI for MeI.

Intermediate 9

Preparation of 1-(2,2-difluoroethyl)-4-nitro-1H-pyrazole

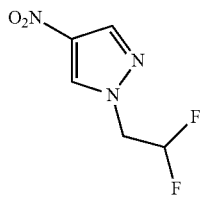 [SMILES: O=[N+]([O-])c1cnn(CC(F)F)c1]

1-(2,2-Difluoroethyl)-4-nitro-1H-pyrazole was prepared in the same manner as that used for the preparation of 1-methyl-4-nitro-1H-pyrazole described in Example 1D by substituting 2,2-difluoroethyl trifluoromethanesulfonate for MeI. $^1$H NMR (400 MHz, CDCl₃) δ 8.24 (s, 1H), 8.13 (s, 1H), 6.34-5.97 (m, 1H), 4.52 (td, J=13.5, 4.1 Hz, 2H).

Intermediate 10

Preparation of 4-nitro-1-(2,2,2-trifluoroethyl)-1H-pyrazole

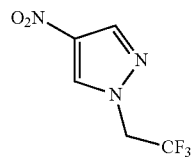 [SMILES: O=[N+]([O-])c1cnn(CC(F)(F)F)c1]

4-Nitro-1-(2,2,2-trifluoroethyl)-1H-pyrazole was prepared in the same manner as that used for the preparation of 1-methyl-4-nitro-1H-pyrazole described in Example 1D by replacing 1,1,1-trifluoro-3-iodopropane for MeI. $^1$H NMR (400 MHz, CDCl₃) δ 8.30 (s, 1H), 8.16 (s, 1H), 4.77 (q, J=8.1 Hz, 2H).

Intermediate 11

Preparation of 4-nitro-1-((2-(trimethylsilyl)ethoxy)methyl)-1H-pyrazole

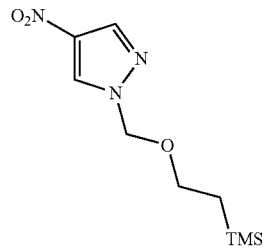 [SMILES: C[Si](C)(C)CCOCn1cc([N+](=O)[O-])cn1]

4-Nitro-1-((2-(trimethylsilyl)ethoxy)methyl)-1H-pyrazole was prepared in the same manner as that used for the preparation of 1-methyl-4-nitro-1H-pyrazole described in Example 1D by substituting SEM-Cl for MeI. $^1$H NMR (400 MHz, CDCl₃) δ 8.30 (s, 1H), 8.10 (s, 1H), 5.45 (s, 2H), 3.63 (dd, J=8.9, 7.8 Hz, 3H), 0.98-0.90 (m, 3H), 0.02--0.02 (m, 10H).

Intermediate 12

Preparation of 1-(6-bromo-3-chloro-2-fluorophenyl)prop-2-en-1-one

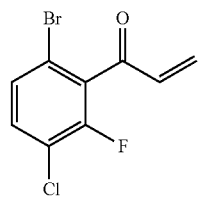

1-(6-Bromo-3-chloro-2-fluorophenyl)prop-2-en-1-one was prepared using a procedure analogous to intermediate 1 by replacing 3-chloro-2,6-difluorobenzaldehyde with 6-bromo-3-chloro-2-fluorobenzaldehyde. $^1$H NMR (500 MHz, CDCl$_3$) δ 7.33-7.41 (m, 2H), 6.64 (dd, J=17.6, 10.2 Hz, 1H), 6.25 (d, J=10.7 Hz, 1H), 6.07 (d, J=17.6 Hz, 1H).

Intermediate 13

Preparation of 1-(2-bromo-5-chlorophenyl)prop-2-en-1-one

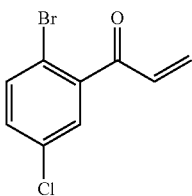

Intermediate 13 was prepared from 2-bromo-5-chlorobenzaldehyde using methods described for the synthesis of Intermediate 1 from 3-chloro-2,6-difluorobenzaldehyde to yield 1-(2-bromo-5-chlorophenyl)prop-2-en-1-one (1.4 g, 97%) as a clear, colorless oil. $^1$H NMR (500 MHz, CDCl$_3$) δ 7.97 (dd, J=8.5, 1.4 Hz, 1H), 7.79-7.65 (m, 2H), 7.19-7.06 (m, 1H), 6.61-6.48 (m, 2H).

Intermediate 14

Preparation of 1-(difluoromethyl)-4-nitro-1H-pyrazole

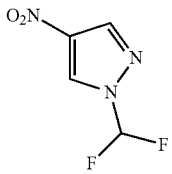 [SMILES: O=[N+]([O-])c1cnn(C(F)F)c1]

Cs$_2$CO$_3$ (14.41 g, 44.2 mmol) was suspended in a solution of 4-nitro-1H-pyrazole (5.00 g, 44.2 mmol) and DMF (40 mL). After heating to 120° C. for 5 min, solid sodium 2-chloro-2,2-difluoroacetate (13.48 g, 88 mmol) was added in 10 equal portions over 20 min. The reaction was complete after 10 min of additional heating. The mixture was added to a separatory funnel containing 100 mL water and extracted with Et$_2$O (2×50 mL). The combined organic layers were concentrated. Purification by normal-phase chromatography eluting with a gradient of hexanes/EtOAc yielded 1-(difluoromethyl)-4-nitro-1H-pyrazole (6.99 g, 42.9 mmol, 97% yield) as a clear, colorless oil. $^1$H NMR (500 MHz, CDCl$_3$) δ 8.58 (s, 1H), 8.22 (s, 1H), 7.39-7.05 (t, J=60 Hz, 1H).

Intermediate 15

Preparation of 1-(2,2-difluorocyclopropyl)-4-nitro-1H-pyrazole

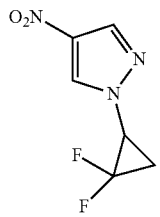 [SMILES: O=[N+]([O-])c1cnn(C2CC2(F)F)c1]

15A. Preparation of 4-nitro-1-vinyl-1H-pyrazole

4-Nitro-1H-pyrazole (1 g, 8.84 mmol) and BTEAC (0.20 g, 0.884 mmol) were added to a vial containing DCE (5 mL) and 50% aq NaOH (3.5 g, 44.2 mmol). The reaction was heated to 80° C. for 6 h. The reaction was filtered, the filtrate was concentrated to dryness in vacuo, and the residue was purified with normal phase chromatography (hexanes-EtOAc gradient). 4-Nitro-1-vinyl-1H-pyrazole (0.87 g, 71% yield) was isolated as a white solid. $^1$H NMR (400 MHz, CDCl$_3$) δ 8.31 (s, 1H), 8.16 (s, 1H), 7.02 (dd, J=15.6, 8.8 Hz, 1H), 5.80 (dd, J=15.5, 1.9 Hz, 1H), 5.17 (dd, J=8.8, 2.0 Hz, 1H).

15B. Preparation of 1-(2,2-difluorocyclopropyl)-4-nitro-1H-pyrazole

Trimethylsilyl 2,2-difluoro-2-(fluorosulfonyl)acetate (0.57 mL, 2.88 mmol) was slowly dropped (over 20 min) into a mixture of 4-nitro-1-vinyl-1H-pyrazole (0.2 g, 1.44 mmol) and NaF (6 mg, 0.144 mmol) in methyl benzoate (1 mL), and the solution was heated to 105° C. Upon completion of the addition, the reaction was complete. The mixture was cooled to rt and subjected directly to normal phase chromatography (hexanes-EtOAc gradient) to yield 1-(2,2-difluorocyclopropyl)-4-nitro-1H-pyrazole (0.084 g, 30.9% yield) as a yellow, crystalline solid. $^1$H NMR (400 MHz, CDCl$_3$) δ 8.26 (s, 1H), 8.12 (s, 1H), 4.18 (dddd, J=10.4, 8.4, 6.2, 2.3 Hz, 1H), 2.40-2.10 (m, 2H).

Intermediate 16

Preparation of 1-(3-chloro-6-(difluoromethoxy)-2-fluorophenyl)prop-2-en-1-one

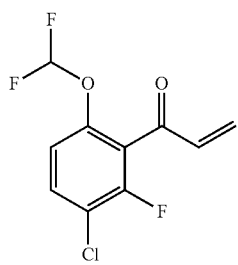 [SMILES: C=CC(=O)c1c(OC(F)F)ccc(Cl)c1F]

16A. Preparation of 3-chloro-6-(difluoromethoxy)-2-fluorobenzaldehyde

To a solution of 1-chloro-4-(difluoromethoxy)-2-fluorobenzene (400 mg, 2.04 mmol) in THF (8 mL) at −78° C. was added LDA in THF/heptane/ethylbenzene (1.4 mL, 2.4 mmol) dropwise. After continuing to stir at the same temp for 20 min, DMF (0.2 mL, 2.44 mmol) was added in one portion and stirring was continued at the same temperature for 10 min. HOAc (0.47 mL, 8.14 mmol) was added followed by water (30 mL). The aqueous layer was then extracted with EtOAc. The combined organic layers were dried over MgSO$_4$ and concentrated in vacuo. The crude product was purified by normal phase chromatography to yield 3-chloro-6-(difluoromethoxy)-2-fluorobenzaldehyde (120 mg, 21%) as a clear, colorless oil. $^1$H NMR (400 MHz, CDCl$_3$) δ 10.35 (d, J=0.9 Hz, 1H), 7.63 (dd, J=8.9, 8.0 Hz, 1H), 7.07 (dd, J=8.9, 1.2 Hz, 1H), 6.87-6.39 (t, J=72 Hz, 1H).

16B. Preparation of 1-(3-chloro-6-(difluoromethoxy)-2-fluorophenyl)prop-2-en-1-one 1-(3-Chloro-6-(difluoromethoxy)-2-fluorophenyl)prop-2-en-1-one was prepared from 3-chloro-6-(difluoromethoxy)-2-fluorobenzaldehyde using methods described for the synthesis of Intermediate 1 from 3-chloro-2,6-difluorobenzaldehyde to yield 3-chloro-6-(difluoromethoxy)-2-fluorobenzaldehyde (0.04 g, 67% yield) as a clear, colorless oil. $^1$H NMR (500 MHz, CDCl$_3$) δ 7.48 (dd, J=8.9, 8.1 Hz, 1H), 7.08-7.01 (m, 1H), 6.69-6.63 (m, 1H), 6.63-6.30 (t, J=73 Hz, 1H), 6.18 (d, J=10.5 Hz, 1H), 6.10 (d, J=17.6 Hz, 1H).

Intermediate 17

Preparation of 13-{4-[5-chloro-2-(1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one

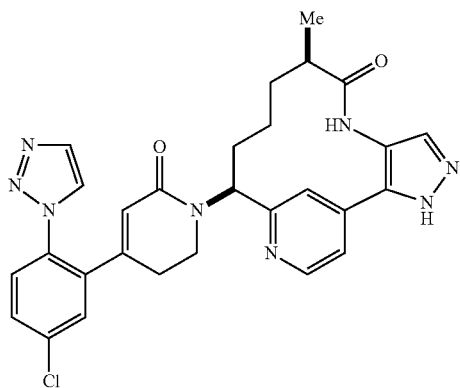

17A. Preparation of 13-{4-[5-chloro-2-(1H-1,2,3-triazol-1-yl)phenyl]-6-oxo-1,2,3,6-tetrahydropyridin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one

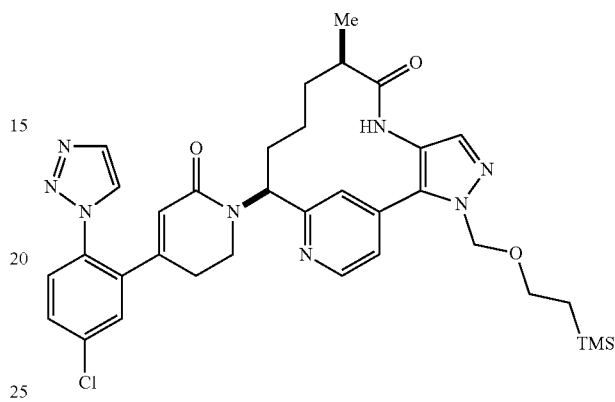

13-{4-[5-Chloro-2-(1H-1,2,3-triazol-1-yl)phenyl]-6-oxo-1,2,3,6-tetrahydropyridin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one was prepared according to the procedures described in Example 1 by substituting 1-methyl-4-nitro-1H-pyrazole with 4-nitro-1-((2-(trimethylsilyl)ethoxy)methyl)-1H-pyrazole, Intermediate 11.

17B. Preparation of 13-{4-[5-chloro-2-(1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one 13-{4-[5-Chloro-2-(1H-1,2,3-triazol-1-yl)phenyl]-6-oxo-1,2,3,6-tetrahydropyridin-1-yl}-9-methyl-3-{[2-(trimethylsilyl)ethoxy]methyl}-3,4,7,15-tetraazatricyclo[12.3.1.0$^{2,6}$]octadeca-1(18),2(6),4,14,16-pentaen-8-one was immediately treated with HCl to yield 13-{4-[5-chloro-2-(1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one. $^1$H NMR (500 MHz, CD$_3$OD) δ 8.69-8.64 (m, 1H), 8.36-8.32 (m, 1H), 7.94-7.90 (m, 2H), 7.82-7.77 (m, 2H), 7.65 (s, 2H), 7.62-7.58 (m, 1H), 5.87-5.82 (m, 1H), 5.56-5.50 (m, 1H), 3.44-3.39 (m, 2H), 2.69-2.60 (m, 1H), 2.30-2.11 (m, 3H), 2.10-1.93 (m, 2H), 1.74-1.65 (m, 1H), 1.42-1.28 (m, 2H), 1.20-1.14 (m, 3H). MS(ESI) m/z: 543.6 (M+H)$^+$. Analytical HPLC (Method A): RT=4.71 min, purity=>99.5%.

Intermediate 18

Preparation of (9R,13S)-13-[4-(3-chloro-2,6-difluorophenyl)-6-oxo-1,2,3,6-tetrahydropyridin-1-yl]-9-methyl-3,4,7,15-tetraazatricyclo[12.3.1.0²,⁶]octadeca-1(18),2(6),4,14,16-pentaen-8-one

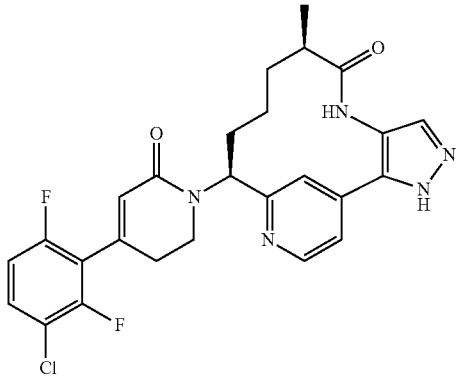 [SMILES: C[C@@H]1CCC[C@H](N2CCC(c3c(F)ccc(Cl)c3F)=CC2=O)c2cc(ccn2)-c2[nH]ncc2NC1=O]

(9R,13S)-13-[4-(3-Chloro-2,6-difluorophenyl)-6-oxo-1,2,3,6-tetrahydropyridin-1-yl]-9-methyl-3,4,7,15-tetraazatricyclo[12.3.1.0²,⁶]octadeca-1(18),2(6),4,14,16-pentaen-8-one was prepared in a manner similar to 13-{4-[5-chloro-2-(1H-1,2,3-triazol-1-yl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one, Intermediate 17, by substituting 1-(5-chloro-2-(1H-1,2,3-triazol-1-yl)phenyl)prop-2-en-1-one with 1-(3-chloro-2,6-difluorophenyl)prop-2-en-1-one to yield (0.5 mg, 11%) MS(ESI) m/z: 512.1 [M+H]⁺. ¹H NMR (500 MHz, CD₃OD) δ 8.68-8.59 (m, 1H), 7.82 (s, 1H), 7.78-7.70 (m, 1H), 7.59-7.50 (m, 2H), 7.18-7.05 (m, 1H), 6.19-6.09 (m, 1H), 5.75-5.61 (m, 1H), 3.83-3.73 (m, 1H), 3.73-3.56 (m, 2H), 2.82-2.59 (m, 3H), 2.26-2.14 (m, 1H), 2.13-2.03 (m, 1H), 2.03-1.93 (m, 1H), 1.76-1.63 (m, 1H), 1.45-1.26 (m, 2H), 1.25-1.18 (m, 2H), 1.14 (d, J=6.9 Hz, 5H). Analytical HPLC (Method A): RT=5.67 min, purity=100%.

Intermediate 19

Preparation of (9R,13S)-13-amino-3-(difluoromethyl)-9-methyl-3,4,7,15-tetraazatricyclo[12.3.1.0²,⁶]octadeca-1(18),2(6),4,14,16-pentaen-8-one

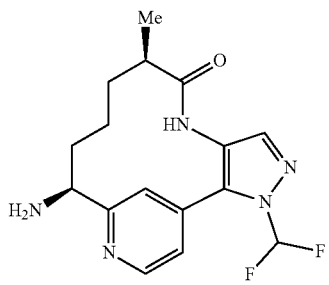 [SMILES: C[C@@H]1CCC[C@H](N)c2cc(ccn2)-c2c(cnn2C(F)F)NC1=O]

19A. Preparation of 1-(difluoromethyl)-4-nitro-1H-pyrazole

Cs₂CO₃ (14.41 g, 44.2 mmol) was suspended in a solution of 4-nitro-1H-pyrazole (5.00 g, 44.2 mmol) and DMF (40 mL). After heating to 120° C. for 5 min, solid sodium 2-chloro-2,2-difluoroacetate (13.48 g, 88 mmol) was added in 10 equal portions over 20 min. The reaction was complete after 10 min of additional heating. The mixture was added to a separatory funnel containing 100 mL water and extracted with Et₂O (2×50 mL). The combined organic layers were concentrated. Purification by normal-phase chromatography eluting with a gradient of hexanes/EtOAc yielded 1-(difluoromethyl)-4-nitro-1H-pyrazole (6.99 g, 42.9 mmol, 97% yield) as a clear, colorless oil. ¹H NMR (500 MHz, CDCl₃) δ 8.58 (s, 1H), 8.22 (s, 1H), 7.39-7.05 (t, J=60 Hz, 1H).

19B. Preparation of (S)-tert-butyl (1-(4-(1-(difluoromethyl)-4-nitro-1H-pyrazol-5-yl)pyridin-2-yl)but-3-en-1-yl)carbamate To a N₂ flushed, 500 mL RBF was added (S)-tert-butyl (1-(4-chloropyridin-2-yl)but-3-en-1-yl)carbamate, prepared as described in Example 1C, (10 g, 35.4 mmol), 1-(difluoromethyl)-4-nitro-1H-pyrazole, Intermediate 14, (6.34 g, 38.9 mmol) and dioxane (100 mL). The solution was bubbled with N₂ for 5 min. and Pd(OAc)₂ (0.40 g, 1.7 mmol), di(adamantan-1-yl)(butyl)phosphine (1.27 g, 3.5 mmol), K₂CO₃ (14.7 g, 106 mmol) and PvOH (1.08 g, 10.61 mmol) were added. The reaction mixture was bubbled with N₂ for 5 min. It was then heated to 100° C. for 3 h. Water (200 mL) was added. The reaction mixture was then extracted with EtOAc (2×200 mL). The combined organic extracts were washed with water (200 mL), brine (200 mL), dried over Na₂SO₄, filtered and concentrated in vacuo. Purification by normal phase chromatography eluting with a gradient of hexanes/EtOAc afforded (S)-tert-butyl (1-(4-(1-(difluoromethyl)-4-nitro-1H-pyrazol-5-yl)pyridin-2-yl)but-3-en-1-yl)carbamate (12.91 g, 31.5 mmol, 89% yield) as a slightly yellow oil. MS(ESI) m/z: 410.4 [M+H]⁺. ¹H NMR (400 MHz, CDCl₃) δ 8.80 (dd, J=5.1, 0.7 Hz, 1H), 8.36 (s, 1H), 7.34 (s, 1H), 7.31 (dd, J=5.1, 1.5 Hz, 1H), 7.27-6.91 (t, J=58 Hz, 1H), 5.79-5.63 (m, 1H), 5.16-5.03 (m, 2H), 4.92 (d, J=5.9 Hz, 1H), 2.67 (t, J=6.4 Hz, 2H), 1.46 (br. s., 9H).

19C. Preparation of (S)-tert-butyl (1-(4-(4-amino-1-(difluoromethyl)-1H-pyrazol-5-yl)pyridin-2-yl)but-3-en-1-yl)carbamate To a 100 mL, 3-necked RBF was added a solution of (S)-tert-butyl (1-(4-(1-(difluoromethyl)-4-nitro-1H-pyrazol-5-yl)pyridin-2-yl)but-3-en-1-yl)carbamate (0.78 g, 1.90 mmol) in MeOH (12 mL) and a solution of NH₄Cl (1.02 g, 19 mmol) in water (3 mL). To the solution was added Fe (0.53 g, 9.49 mmol). The reaction mixture was heated to 65° C. for 3 h. Water (50 mL) was added. After cooling to rt, the mixture was filtered through a CELITE® pad and rinsed with MeOH (200 mL). The filtrate was concentrated in vacuo. The residue was partitioned between EtOAc (100 mL) and water (100 mL). The organic phase was separated, washed with water (100 mL), brine (100 mL), dried over Na₂SO₄, filtered and concentrated in vacuo. Purification by normal phase chromatography eluting with a gradient of DCM/MeOH yielded (S)-tert-butyl (1-(4-(4-amino-1-(difluoromethyl)-1H-pyrazol-5-yl)pyridin-2-yl)but-3-en-1-yl)carbamate (0.585 g, 1.54 mmol, 81% yield) as an oil. MS(ESI) m/z: 380.1 [M+H]⁺. ¹H NMR (400 MHz, CDCl₃) δ 8.70 (dd, J=5.0, 0.7 Hz, 1H), 7.43 (s, 1H), 7.36 (s, 1H), 7.32 (dd, J=5.1, 1.5 Hz, 1H), 7.28-6.97 (t, J=58 Hz, 1H), 5.80-5.66 (m, 1H), 5.65-5.53 (m, 1H), 5.13-5.03 (m, 2H), 4.87 (br. s., 1H), 3.22 (br. s., 2H), 2.65 (t, J=6.5 Hz, 2H), 1.52-1.37 (m, 9H).

19D. Preparation of tert-butyl ((S)-1-(4-(1-(difluoromethyl)-4-((R)-2-methylbut-3-enamido)-1H-pyrazol-5-yl)pyridin-2-yl)but-3-en-1-yl)carbamate To a $N_2$ flushed, 3-necked, 250 mL RBF was added a solution of (S)-tert-butyl (1-(4-(4-amino-1-(difluoromethyl)-1H-pyrazol-5-yl)pyridin-2-yl)but-3-en-1-yl)carbamate (5 g, 13.18 mmol) and EtOAc (50 mL). The solution was cooled to −10° C. and (R)-2-methylbut-3-enoic acid, Intermediate 6, (1.72 g, 17.13 mmol), pyridine (4.26 mL, 52.7 mmol) and T3P® (23.54 mL, 39.5 mmol) were added. The cooling bath was removed and the solution was allowed to warm to rt and then stir over a period of 20 h. Water (30 mL) and EtOAc (30 mL) were added and the mixture was stirred for 30 min. The organic phase was separated and the aqueous layer was extracted with EtOAc (30 mL). The combined organic extracts were washed with brine (50 mL), dried over $Na_2SO_4$, filtered and concentrated in vacuo. Purification by normal phase chromatography eluting with a gradient of hexanes/EtOAc gave tert-butyl ((S)-1-(4-(1-(difluoromethyl)-4-((R)-2-methylbut-3-enamido)-1H-pyrazol-5-yl)pyridin-2-yl)but-3-en-1-yl)carbamate (5.69 g, 12.33 mmol, 94% yield). MS(ESI) m/z: 462.2 [M+H]$^+$. $^1$H NMR (400 MHz, CDCl$_3$) δ 8.75 (dd, J=5.0, 0.6 Hz, 1H), 8.37 (s, 1H), 7.32 (t, J=59 Hz, 1H), 7.28 (br. s., 1H), 7.20 (s, 1H), 5.97-5.85 (m, 1H), 5.78-5.65 (m, 1H), 5.56-5.44 (m, 1H), 5.28-5.19 (m, 2H), 5.12 (d, J=2.0 Hz, 2H), 4.91-4.82 (m, 1H), 3.20-3.11 (m, 1H), 2.72-2.62 (m, 2H), 1.48-1.43 (s, 9H), 1.33 (d, J=6.8 Hz, 3H).

19E. Preparation of tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate To a $N_2$ flushed, 2 L, 3-necked, RBF was added a solution of tert-butyl ((S)-1-(4-(1-(difluoromethyl)-4-((R)-2-methylbut-3-enamido)-1H-pyrazol-5-yl)pyridin-2-yl)but-3-en-1-yl)carbamate (3 g, 6.50 mmol) in EtOAc (1300 mL). The solution was sparged with Ar for 15 mi. Second Generation Grubbs Catalyst (1.38 g, 1.63 mmol) was added in one portion. The reaction mixture was heated to reflux for 24 h. After cooling to rt, the solvent was removed and the residue was purified by normal phase chromatography eluting with a gradient of DCM/MeOH to yield tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (2.13 g, 4.91 mmol, 76% yield) as a tan solid. MS(ESI) m/z: 434.4 [M+H]$^+$. $^1$H NMR (400 MHz, CDCl$_3$) δ 8.71 (d, J=5.1 Hz, 1H), 7.78 (s, 1H), 7.44-7.40 (m, 1H), 7.36 (br. s., 1H), 7.27 (t, J=58 Hz, 1H), 6.87 (s, 1H), 6.49-6.39 (m, 1H), 5.78 (s, 1H), 4.80 (br. s., 2H), 3.18-3.08 (m, 1H), 3.08-2.98 (m, 1H), 2.06-1.93 (m, 1H), 1.51 (s, 9H), 1.19 (d, J=6.6 Hz, 3H).

19F. Preparation of tert-butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate Pd on carbon (0.60 g, 0.570 mmol) was added to a 250 mL Parr hydrogenation flask containing a solution of tert-butyl N-[(9R,10E,13S)-3-(difluoromethyl)-9-methyl-8-oxo-3,4,7,15-tetraazatricyclo[12.3.1.0$^{2,6}$]octadeca-1(18),2(6),4,10,14,16-hexaen-13-yl]carbamate (2.46 g, 5.68 mmol) in EtOH (100 mL). The flask was purged with $N_2$ and pressurized to 55 psi of $H_2$ allowed to stir for 18 h. The reaction was filtered through CELITE® and concentrated to yield tert-butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (2.17 g, 88% yield) as a tan solid. MS(ESI) m/z: 436.3 [M+H]$^+$. $^1$H NMR (400 MHz, DMSO-d$_6$) δ 9.32 (s, 1H), 8.71 (d, J=5.0 Hz, 1H), 7.96 (t, J=58 Hz, 1H), 7.43 (s, 1H), 7.32 (d, J=4.8 Hz, 1H), 7.22 (d, J=7.3 Hz, 1H), 4.66 (d, J=8.3 Hz, 1H), 2.62 (br. s., 1H), 1.88 (d, J=12.8 Hz, 1H), 1.77-1.59 (m, 2H), 1.42-1.28 (m, 9H), 1.15 (d, J=18.2 Hz, 2H), 0.83 (d, J=7.0 Hz, 3H).

19G. Preparation of (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one 4 N HCl in dioxane (3.88 mL, 15.5 mmol) was added to a solution of tert-butyl N-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]carbamate (2.25 g, 5.2 mmol) in MeOH (10 mL). The reaction was allowed to stir at rt for 2 h. The reaction was cooled in an ice bath, and 7 N NH$_3$ in MeOH (13.3 mL, 93.0 mmol) was added. After 5 min, the reaction was diluted with CH$_2$Cl$_2$ (80 mL) and the solid that formed was filtered. The filtrate was concentrated to yield (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (1.3 g, 3.88 mmol, 75% yield). MS(ESI) m/z: 336.3 [M+H]$^+$. $^1$H NMR (400 MHz, DMSO-d$_6$) δ 9.33 (s, 1H), 8.71 (d, J=5.0 Hz, 1H), 7.94 (t, J=58 Hz, 1H), 7.85 (s, 1H), 7.40 (s, 1H), 7.32 (d, J=5.0 Hz, 1H), 4.01 (dd, J=10.2, 5.1 Hz, 1H), 2.63-2.53 (m, 1H), 1.90-1.69 (m, 2H), 1.53-1.36 (m, 2H), 1.16-1.00 (m, 1H), 0.85 (d, J=7.0 Hz, 3H).

Example 1

Preparation of (9R,13S)-13-{4-[5-chloro-2-(1H-1,2,3-triazol-1-yl)phenyl]-6-oxo-1,2,3,6-tetrahydropyridin-1-yl}-3,9-dimethyl-3,4,7,15-tetraazatricyclo[12.3.1.0$^{2,6}$]octadeca-1(18),2(6),4,14,16-pentaen-8-one trifluoroacetate

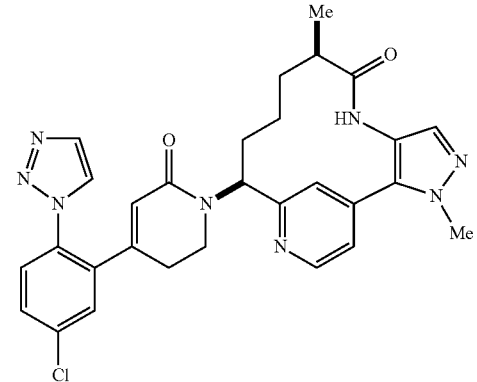

1A. Preparation of (S,E)-N-((4-chloropyridin-2-yl)methylene)-2-methylpropane-2-sulfinamide To a solution of S-(−)-t-butyl-sulfinamide (0.856 g, 7.06 mmol) in DCM (14.13 mL) was added sequentially CuSO$_4$ (2.481 g, 15.54 mmol) and 4-chloropicolinaldehyde (1.0 g, 7.06 mmol) The white suspension was stirred at rt. After 3 h, the brown suspension was filtered through CELITE®, eluting with DCM, to give a clear brown filtrate. Concentration gave a brown oil weighing 1.85 g. Purification by normal phase chromatography gave 1.31 g of (S,E)-N-((4-chloropyridin-2-yl)methylene)-2-methylpropane-2-sulfinamide as a clear, yellow oil. MS(ESI) m/z: 245.0 (M+H)$^+$.

1B. Preparation of (S)—N—((S)-1-(4-chloropyridin-2-yl)but-3-enyl)-2-methylpropane-2-sulfinamide To a cooled (0-5° C.) mixture of InCl$_3$ (13.56 g, 61.3 mmol) in THF (170 mL) was added dropwise over 30 min a solution of 1 M allylmagnesium bromide in Et$_2$O (62 mL, 61.3 mmol). The reaction was allowed to warm to rt. After 1 h at rt, a solution of (S,E)-N-((4-chloropyridin-2-yl)methylene)-2-methylpropane-2-sulfinamide (10 g, 40.9 mmol) in EtOH (170 mL) was added. After 2-3 h, the reaction was concentrated under vacuum at 50-55° C. The crude material was partitioned between EtOAc (200 ml) and water (50 ml) and the layers were separated. The aqueous layer was extracted with EtOAc (2×50 ml). The organic layers were combined and washed with brine (100 ml), dried over Na$_2$SO$_4$, filtered and concentrated to give (S)—N—((S)-1-(4-chloropyridin-2-yl)but-3-enyl)-2-methylpropane-2-sulfinamide (13.5 g, 106%) as a yellow oil. MS(ESI) m/z: 287.2 (M+H)$^+$.

1C. Preparation of (S)-tert-butyl 1-(4-chloropyridin-2-yl)but-3-enylcarbamate (S)—N—((S)-1-(4-Chloropyridin-2-yl)but-3-enyl)-2-methylpropane-2-sulfinamide (75 g, 261 mmol) was dissolved in MeOH (1500 mL). Aq 6 N HCl (750 ml, 4.5 mol) was added. The reaction was stirred at rt for 2-3 h and then was concentrated. The residue was diluted with water (2 L), washed with EtOAc (500 ml). The aqueous layer was basified with sat NaHCO$_3$, extracted into EtOAc (3×1 L). The combined organic layers were washed with water (1 L) and brine (1 L), dried over Na$_2$SO$_4$, filtered and concentrated under vacuum at 50-55° C. to give crude product (43 g, 90%). MS(ESI) m/z: 183.2 (M+H)$^+$. The crude product (42 g, 230 mmol) was dissolved in DCM (420 mL), and Et$_3$N (32.1 mL, 230 mmol) was added followed by dropwise addition of BOC$_2$O (53.4 mL, 230 mmol). The reaction was stirred at rt for 2-3 h. The reaction was diluted with excess DCM (1 L), washed with water (500 ml) and brine (500 ml). The organic layer was dried over Na$_2$SO$_4$, filtered, and concentrated. The crude product was then purified using silica gel chromatography to give (S)-tert-butyl 1-(4-chloropyridin-2-yl)but-3-enylcarbamate (61 g, 86%) as a pale yellow solid. MS(ESI) m/z: 283.2 (M+H)$^+$.

1D. Preparation of 1-methyl-4-nitro-1H-pyrazole

To a solution of 4-nitro-1H-pyrazole (2.5 g, 22.11 mmol) in THF (50 mL) was added NaH (0.973 g, 24.32 mmol) and the mixture was stirred at rt for 5 min. To this suspension was then added MeI (1.382 mL, 22.11 mmol) and stirred at rt overnight. The reaction mixture was then diluted with EtOAc and washed with brine. The organic layer was concentrated, followed by purification using normal phase chromatography to yield 1-methyl-4-nitro-1H-pyrazole a as white solid (1.9 g, 80%). $^1$H NMR (400 MHz, CDCl$_3$) δ ppm 8.12 (s, 1H), 8.06 (s, 1H), 3.97 (s, 3H).

1E. Preparation of (S)-tert-butyl (1-(4-(1-methyl-4-nitro-1H-pyrazol-5-yl)pyridin-2-yl)but-3-en-1-yl)carbamate To a pressure vial was added (S)-tert-butyl 1-(4-chloropyridin-2-yl)but-3-enylcarbamate (3.0 g, 10.61 mmol), 1-methyl-4-nitro-1H-pyrazole, (1.348 g, 10.61 mmol), di(adamant-1-yl)(butyl)phosphine (1.141 g, 3.18 mmol), pivalic acid (0.369 ml, 3.18 mmol) and K$_2$CO$_3$ (4.40 g, 31.8 mmol). To the reaction mixture was then added DMF (21 mL) and the vial was purged with Ar (3×). To this mixture was then added Pd(OAc)$_2$ (0.476 g, 2.122 mmol). The vial was sealed and heated in oil bath at 120° C. overnight. The reaction mixture was filtered and partitioned between aq 10% LiCl (15 mL) and EtOAc (30 mL). The aqueous layer was extracted with EtOAc (2×20 mL) and the combined organic layers were washed with brine (15 mL) and dried over MgSO$_4$, filtered and concentrated. The crude product was then purified using normal phase chromatography to yield 1.2 g of (S)-tert-butyl (1-(4-(1-methyl-4-nitro-1H-pyrazol-5-yl)pyridin-2-yl)but-3-en-1-yl)carbamate (29%) as a brown oil. MS(ESI) m/z: 374.4 (M+H)$^+$.

1F. Preparation of (S)-tert-butyl (1-(4-(4-amino-1-methyl-1H-pyrazol-5-yl)pyridin-2-yl)but-3-en-1-yl) carbamate A solution of (S)-tert-butyl (1-(4-(1-methyl-4-nitro-1H-pyrazol-5-yl)pyridin-2-yl)but-3-en-1-yl)carbamate (1.2 g, 3.21 mmol) in MeOH (10 mL) and AcOH (1 mL) was heated in oil bath to 60° C. To the above clear solution was then slowly added Zn (0.420 g, 6.43 mmol) and allowed to stir at the same temperature for 15 min. The reaction mixture was then filtered through CELITE® and concentrated to yield the crude product. The crude product was then purified using normal phase chromatography to yield 0.88 g of (S)-tert-butyl (1-(4-(4-amino-1-methyl-1H-pyrazol-5-yl)pyridin-2-yl)but-3-en-1-yl)carbamate (76%) as pale brown oil. MS(ESI) m/z: 344.4 (M+H)$^+$.

1G. Preparation of tert-butyl ((S)-1-(4-(1-methyl-4-((R)-2-methylbut-3-enamido)-1H-pyrazol-5-yl)pyridin-2-yl)but-3-en-1-yl)carbamate To a solution of (R)-2-methylbut-3-enoic acid, Intermediate 6, (385 mg, 3.84 mmol), (S)-tert-butyl (1-(4-(4-amino-1-methyl-1H-pyrazol-5-yl)pyridin-2-yl)but-3-en-1-yl)carbamate (880 mg, 2.56 mmol) and pyridine (0.620 mL, 7.69 mmol) in EtOAc (40 mL) at −10° C. under Ar was added T3P® (50% wt in EtOAc) (3.05 mL, 5.12 mmol) dropwise. The reaction mixture was stirred at −10° C. which was allowed to gradually warm up to rt. The reaction mixture was then allowed to stir at rt for 2 h. The reaction mixture was then diluted with EtOAc followed by washing with aq sat NaHCO$_3$ and brine. The organic layers were pooled together, dried over MgSO$_4$, filtered and concentrated. The crude product was then purified using normal phase chromatography to yield 0.6 g of tert-butyl ((S)-1-(4-(1-methyl-4-((R)-2-methylbut-3-enamido)-1H-pyrazol-5-yl)pyridin-2-yl)but-3-en-1-yl)carbamate (52%) as yellow oil. MS(ESI) m/z: 426.5 (M+H)$^+$.

1H. Preparation of tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate A solution of tert-butyl ((S)-1-(4-(1-methyl-4-((R)-2-methylbut-3-enamido)-1H-pyrazol-5-yl)pyridin-2-yl)but-3- en-1-yl)carbamate (600 mg, 1.410 mmol) in DCE (18 mL) was purged by bubbling Ar into the reaction mixture. Second Generation Grubbs Catalyst (480 mg, 0.564 mmol) was then added. The reaction mixture was purged with Ar and evacuated again (3×). The reaction mixture was then heated at 120° C. in a microwave vial for 30 min. The reaction mixture was then concentrated and the crude residue was purified using normal phase chromatography to yield 118 mg of tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (20%) as brown oil. MS(ESI) m/z: 398.5 (M+H)$^+$.

1I. Preparation of tert-butyl N-[(9R,13S)-3,9-dimethyl-8-oxo-3,4,7,15-tetraazatricyclo[12.3.1.0$^{2,6}$] octadeca-1(18),2(6),4,14,16-pentaen-13-yl]carbamate To a degassed solution of tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (118 mg, 0.297 mmol) in EtOH (12 mL) was added Pd on carbon (31.6 mg, 0.030 mmol) and the reaction mixture was then stirred under H$_2$ at 55 psi for 5 h. The reaction mixture was then filtered though CELITE® and concentrated to yield tert-butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate (92 mg, 72%) as brown oil. MS(ESI) m/z: 400.4 (M+H)$^+$.

1J. Preparation of (9R,13S)-13-amino-3,9-dimethyl-3,4,7,15-tetraazatricyclo [12.3.1.0$^{2,6}$]octadeca-1(18),2(6),4,14,16-pentaen-8-one To a solution of tert-butyl N-[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamate (92 mg, 0.230 mmol) in MeOH (3 mL) was added 4 M HCl in dioxane (3 mL, 12.00 mmol) and the reaction was stirred at rt for 1.5 h. The reaction mixture was then concentrated in vacuo to yield 86 mg of (9R,13S)-13-amino-3,9-dimethyl-3,4,7,15-tetraazatricyclo [12.3.1.0$^{2,6}$]octadeca-1(18),2(6),4,14,16-pentaen-8-one as yellow solid. MS(ESI) m/z: 300.4 (M+H)$^+$.

1K. Preparation of (9R,13S)-13-({3-[5-chloro-2-(1H-1,2,3-triazol-1-yl)phenyl]-3-oxopropyl}amino)-3,9-dimethyl-3,4,7,15-tetraazatricyclo[12.3.1.0$^{2,6}$] octadeca-1(18),2(6),4,14,16-pentaen-8-one To a solution of (9R,13S)-13-amino-3,9-dimethyl-3,4,7,15-tetraazatricyclo[12.3.1.0$^{2,6}$]octadeca-1(18),2(6),4,14,16-pentaen-8-one (34 mg, 0.091 mmol) and 1-(5-chloro-2-(1H-1,2,3-triazol-1-yl)phenyl)prop-2-en-1-one (21.34 mg, 0.091 mmol) in DCM (2 mL) was added DIEA (16 µL, 0.092 mmol). The reaction was then stirred at rt for 15 min. At the end of 15 min, the crude reaction mixture was used in the next step. MS(ESI) m/z: 533.4 (M+H)$^+$.

1L. Preparation of [({3-[5-chloro-2-(1H-1,2,3-triazol-1-yl)phenyl]-3-oxopropyl}[(9R,13S)-3,9-dimethyl-8-oxo-3,4,7,15-tetraazatricyclo[12.3.1.0$^{2,6}$] octadeca-1(18),2(6),4,14,16-pentaen-13-yl] carbamoyl)methyl]phosphonate To the crude reaction mixture, (9R,13S)-13-({3-[5-chloro-2-(1H-1,2,3-triazol-1-yl)phenyl]-3-oxopropyl}amino)-3,9-dimethyl-3,4,7,15-tetraazatricyclo [12.3.1.0$^{2,6}$]octadeca-1(18),2(6),4,14,16-pentaen-8-one (49 mg, 0.092 mmol) at 0° C. was added diethyl (2-chloro-2-oxoethyl)phosphonate (276 µl, 0.276 mmol) and the reaction mixture was gradually warmed to rt and was stirred at rt for 30 min. The reaction mixture was then quenched using 0.2 mL H$_2$O followed by purification using reverse phase HPLC. The desired fractions are then concentrated using a BIOTAGE® V10 to give 43 mg of [({3-[5-chloro-2-(1H-1,2,3-triazol-1-yl)phenyl]-3-oxopropyl}[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamoyl)methyl] phosphonate as clear oil. MS(ESI) m/z: 711.4 (M+H)$^+$.

1M. Preparation of (9R,13S)-13-{4-[5-chloro-2-(1H-1,2,3-triazol-1-yl)phenyl]-6-oxo-1,2,3,6-tetrahydropyridin-1-yl)}-3,9-dimethyl-3,4,7,15-tetraazatricyclo[12.3.1.0$^{2,6}$]octadeca-1(18),2(6),4,14,16-pentaen-8-one trifluoroacetate To a solution of [({3-[5-chloro-2-(1H-1,2,3-triazol-1-yl)phenyl]-3-oxopropyl}[(9R,13S)-3,9-dimethyl-8-oxo-3,4,7,15-tetraazatricyclo[12.3.1.0$^{2,6}$]octadeca-1(18),2(6),4,14,16-pentaen-13-yl]carbamoyl)methyl]phosphonate (43 mg, 0.060 mmol) in MeOH (1.5 mL) at 0° C. was added NaOMe (52.3 mg, 0.242 mmol). The ice bath was removed and stirring was continued at rt for 10 min. The reaction mixture was then quenched with 1 N HCl (0.05 mL) and concentrated to give the crude product. The crude product was then purified using reverse phase HPLC to afford 21 mg of (9R,13S)-13-{4-[5-chloro-2-(1H-1,2,3-triazol-1-yl)phenyl]-6-oxo-1,2,3,6-tetrahydropyridin-1-yl}-3,9-dimethyl-3,4,7,15-tetraazatricyclo[12.3.1.0$^{2,6}$]octadeca-1(18),2(6),4,14,16-pentaen-8-one trifluoroacetate as a pale yellow solid. $^1$H NMR (400 MHz, CD$_3$OD-d$_4$) δ 8.76 (d, J=6.4 Hz, 1H), 8.27 (d, J=0.9 Hz, 1H), 7.85 (d, J=1.1 Hz, 1H), 7.81-7.77 (m, 2H), 7.62-7.48 (m, 4H), 5.77 (s, 1H), 5.39 (dd, J=12.5, 3.7 Hz, 1H), 4.05 (s, 3H), 3.42 (t, J=6.9 Hz, 2H), 2.57-2.45 (m, 1H), 2.23-2.06 (m, 3H), 1.95-1.82 (m, 2H), 1.61-1.48 (m, 1H), 1.34-1.24 (m, 1H), 1.13 (d, J=6.8 Hz, 2H), 1.07-1.02 (m, 3H). MS(ESI) m/z: 557.4 (M+H). Analytical HPLC (Method A): RT=5.82 min, purity=>95%; Factor XIa Ki=1.8 nM, Plasma Kallikrein Ki=24 nM.

Example 2

Preparation of (9R,13S)-13-[4-(3-chloro-2,6-difluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one

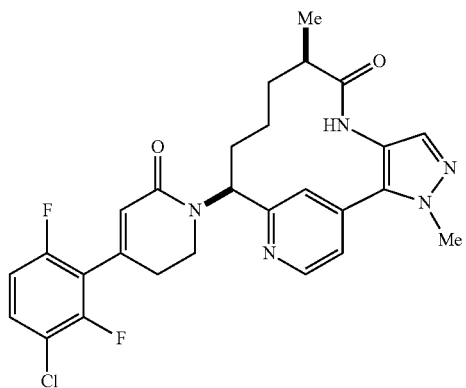

(9R,13S)-13-[4-(3-Chloro-2,6-difluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one was prepared according to the procedures described in Example 1 by substituting, 1-(5-chloro-2-(1H-1,2,3-triazol-1-yl)phenyl)prop-2-en-1-one with 1-(3-chloro-2,6-difluorophenyl)prop-2-en-1-one, Intermediate 1. $^1$H NMR (400 MHz, CD$_3$OD) δ 8.80 (d, J=5.5 Hz, 1H), 7.84-7.73 (m, 2H), 7.59-7.48 (m, 2H), 7.10 (td, J=9.2, 2.0 Hz, 1H), 6.12 (s, 1H), 5.56 (dd, J=12.5, 3.7 Hz, 1H), 4.09 (s, 3H), 3.70 (t, J=6.8 Hz, 2H), 2.79-2.68 (m, 2H), 2.65-2.53 (m, 1H), 2.33-2.19 (m, 1H), 2.07-1.90 (m, 2H), 1.69-1.56 (m, 1H), 1.21 (br. s., 2H), 1.10 (d, J=6.8 Hz, 3H). MS(ESI) m/z: 526.4 (M+H). Analytical HPLC (Method A): RT=6.97 min, purity=>95%; Factor XIa Ki=10 nM, Plasma Kallikrein Ki=30 nM.

Example 3

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7,15-tetraazatricyclo [12.3.1.0$^{2,6}$]octadeca-1(18),2(6),4,14,16-pentaen-8-one

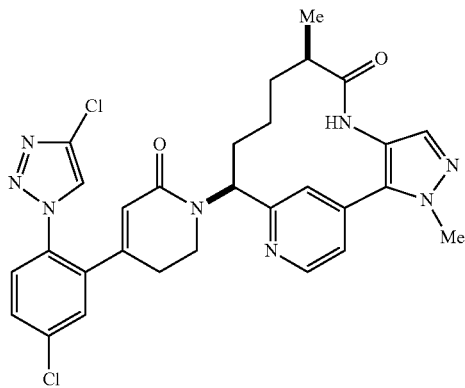

(9R,13S)-13-{4-[5-Chloro-2-(4-chloro-1H-1,2,3-triazol-1-yl)phenyl]-6-oxo-1,2,3,6-tetrahydropyridin-1-yl}-3,9-dimethyl-3,4,7,15-tetraazatricyclo[12.3.1.0$^{2,6}$]octadeca-1(18),2(6),4,14,16-pentaen-8-one was prepared according to the procedures described in Example 1 by substituting 1-(5-chloro-2-(1H-1,2,3-triazol-1-yl)phenyl)prop-2-en-1-one, with 1-(5-chloro-2-(4-chloro-1H-1,2,3-triazol-1-yl)phenyl)prop-2-en-1-one, Intermediate 4. $^1$H NMR (400 MHz, CD$_3$OD) δ 8.77 (d, J=5.3 Hz, 1H), 8.48 (s, 1H), 7.71-7.57 (m, 4H), 7.54 (s, 1H), 5.86 (s, 1H), 5.55 (dd, J=12.8, 3.7 Hz, 1H), 4.09 (s, 3H), 3.60-3.49 (m, 2H), 2.60 (d, J=5.7 Hz, 1H), 2.26 (t, J=6.8 Hz, 2H), 2.18 (d, J=1.2 Hz, 1H), 2.04-1.84 (m, 2H), 1.68-1.52 (m, 1H), 1.45-1.31 (m, 2H), 1.20 (d, J=6.6 Hz, 2H), 1.13-1.08 (m, 3H). MS(ESI) m/z: 591.3 (M+H). Analytical HPLC (Method A): RT=6.69 min, purity=>95%; Factor XIa Ki=0.12 nM, Plasma Kallikrein Ki=6 nM.

Example 4

Preparation of 4-chloro-2-{1-[(9R,13S)-3-(difluoromethyl)-9-methyl-8-oxo-3,4,7,15-tetraazatricyclo [12.3.1.0$^{2,6}$]octadeca-1(18),2(6),4,14,16-pentaen-13-yl]-2-oxo-1,2-dihydropyridin-4-yl}benzonitrile

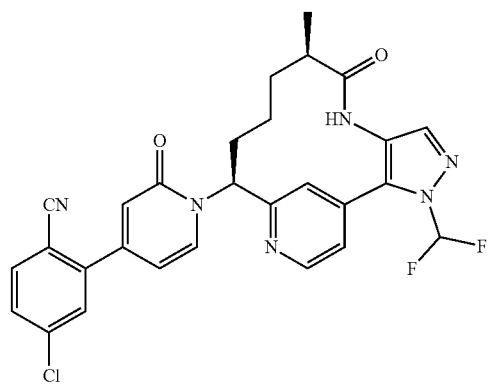 [SMILES: C[C@@H]1CCC[C@H](n2ccc(-c3cc(Cl)ccc3C#N)cc2=O)c2cc(ccn2)-c2c(cnn2C(F)F)NC1=O]

4A. Preparation of (9R,13S)-3-(difluoromethyl)-13-(4-hydroxy-2-oxo-1,2-dihydropyridin-1-yl)-9-methyl-3,4,7,15-tetraazatricyclo[12.3.1.0$^{2,6}$]octadeca-1(18),2(6),4,14,16-pentaen-8-one

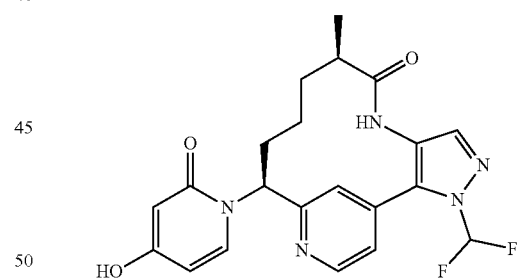

To a solution of (9R,13S)-13-amino-3-(difluoromethyl)-9-methyl-3,4,7,15-tetraazatricyclo[12.3.1.0$^{2,6}$]octadeca-1(18),2(6),4,14,16-pentaen-8-one (0.060 g, 0.178 mmol), Intermediate 19, 4-hydroxy-2H-pyran-2-one, in a vial was added nBuOH (0.8 mL) and water (0.2 mL). The vessel was capped and heated at 110° C. for 15 h then cooled to rt. The reaction mixture was concentrated and purified by normal phase chromatography to give (9R,13S)-3-(difluoromethyl)-13-(4-hydroxy-2-oxo-1,2-dihydropyridin-1-yl)-9-methyl-3,4,7,15-tetraazatricyclo[12.3.1.0$^{2,6}$]octadeca-1(18),2(6),4,14,16-pentaen-8-one (0.0055 g, 7.2%) as a yellow solid. MS(ESI) m/z: 430.0 (M+H).

4B. Preparation of 1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-2-oxo-1,2-dihydropyridin-4-yl trifluoromethanesulfonate

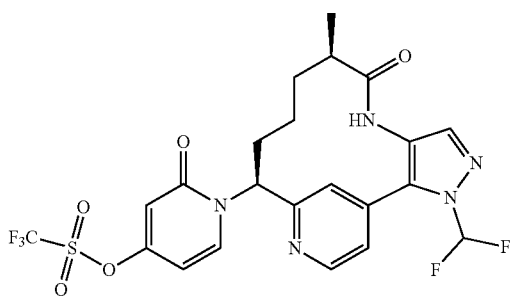 [SMILES: C[C@@H]1CCC[C@H](n2ccc(OS(=O)(=O)C(F)(F)F)cc2=O)c2cc(ccn2)-c2c(cnn2C(F)F)NC1=O]

To a vial containing (9R,13S)-3-(difluoromethyl)-13-(4-hydroxy-2-oxo-1,2-dihydropyridin-1-yl)-9-methyl-3,4,7,15-tetraazatricyclo[12.3.1.0²,⁶]octadeca-1(18),2(6),4,14,16-pentaen-8-one (5.5 mg, 0.013 mmol), 1,1,1-trifluoro-N-phenyl-N-((trifluoromethyl)sulfonyl)methanesulfonamide (5.49 mg, 0.015 mmol) was added Et₃N (5.36 µl, 0.038 mmol) in DMF (0.3 mL). After 1 h at rt, the reaction mixture was concentrated and purified by normal phase chromatography to give 1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-2-oxo-1,2-dihydropyridin-4-yl trifluoromethanesulfonate (1.8 mg, 25.03% yield) as a yellow solid. MS(ESI) m/z: 562.08 (M+H).

4C. Preparation of 4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-2-oxo-1,2-dihydropyridin-4-yl}benzonitrile trifluoroacetate To a dioxane (0.15 mL) solution of 1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-2-oxo-1,2-dihydropyridin-4-yl trifluoromethanesulfonate (1.8 mg, 3.21 µmol), (5-chloro-2-cyanophenyl)boronic acid (0.698 mg, 3.85 µmol) was added aq 2 M Na₂CO₃ (3.21 µl, 6.41 µmol). The solution was purged with Ar, and Pd(PPh₃)₄ (0.370 mg, 0.321 µmol) was added. The reaction was purged with Ar for several min then was capped and heated at 100° C. for 3 h, then cooled to rt. The reaction mixture was concentrated and the residue purified by reverse phase HPLC to give 4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-2-oxo-1,2-dihydropyridin-4-yl}benzonitrile trifluoroacetate (1.62 mg, 2.370 µmol, 73.9% yield) as an white solid. MS(ESI) m/z: 549.4 (M+H). ¹H NMR (500 MHz, CDCl₃) δ 8.74 (d, J=5.0 Hz, 1H), 8.36 (d, J=6.9 Hz, 1H), 7.87 (d, J=8.3 Hz, 1H), 7.79-7.72 (m, 1H), 7.71 (d, J=1.9 Hz, 1H), 7.68-7.64 (m, 2H), 7.52 (d, J=4.1 Hz, 1H), 6.73 (d, J=1.9 Hz, 1H), 6.64 (dd, J=7.3, 2.1 Hz, 1H), 6.19 (dd, J=13.1, 4.3 Hz, 1H), 2.76-2.67 (m, 1H), 2.38-2.27 (m, 1H), 2.13-1.98 (m, 2H), 1.70-1.57 (m, 1H), 1.55-1.41 (m, 1H), 1.38-1.29 (m, 1H), 1.02 (d, J=6.9 Hz, 3H), 0.70 (br. s., 1H). Analytical HPLC (Method A): RT=8.66 min, purity=>99%; Factor XIa Ki=3.2 nM, Plasma Kallikrein Ki=19 nM.

Example 5

Preparation of 13-{4-[5-chloro-2-(1H-1,2,3-triazol-1-yl)phenyl]-6-oxo-1,2,3,6-tetrahydropyridin-1-yl}-3-cyclopropyl-9-methyl-3,4,7,15-tetraazatricyclo[12.3.1.0²,⁶]octadeca-1(18),2(6),4,14,16-pentaen-8-one

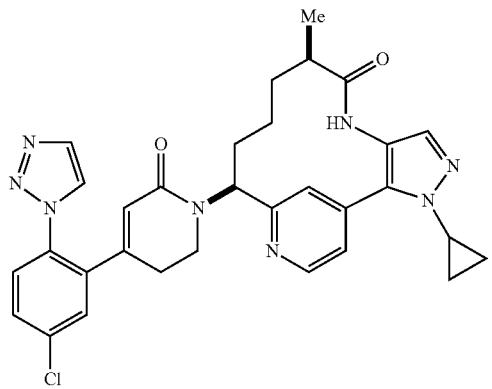

13-{4-[5-Chloro-2-(1H-1,2,3-triazol-1-yl)phenyl]-6-oxo-1,2,3,6-tetrahydropyridin-1-yl}-3-cyclopropyl-9-methyl-3,4,7,15-tetraazatricyclo[12.3.1.0²,⁶]octadeca-1(18),2(6),4,14,16-pentaen-8-one was prepared according to the procedures described in Example 1 by substituting 1-methyl-4-nitro-1H-pyrazole, Example 1D, with 1-cyclopropyl-4-nitro-1H-pyrazole, Intermediate 7. ¹H NMR (500 MHz, CD₃OD) δ 8.75 (d, J=5.5 Hz, 1H), 8.33 (d, J=1.1 Hz, 1H), 7.92 (d, J=1.1 Hz, 1H), 7.89-7.85 (m, 1H), 7.70-7.63 (m, 3H), 7.59 (dd, J=8.1, 0.7 Hz, 1H), 7.49 (s, 1H), 5.84 (t, J=1.2 Hz, 1H), 5.56-5.48 (m, 1H), 3.98-3.88 (m, 1H), 3.64-3.55 (m, 1H), 3.55-3.46 (m, 1H), 2.65-2.54 (m, 1H), 2.27-2.11 (m, 3H), 2.03-1.94 (m, 1H), 1.93-1.82 (m, 1H), 1.67-1.53 (m, 1H), 1.39-1.28 (m, 1H), 1.28-1.18 (m, 1H), 1.16-1.03 (m, 8H). MS(ESI) m/z: 583.5 (M+H)⁺. Analytical HPLC (Method A): RT=6.11 min, purity=98%; Factor XIa Ki=1.4 nM, Plasma Kallikrein Ki=52 nM.

Example 6

Preparation of (9R,13S)-13-{4-[3-chloro-2-fluoro-6-trifluoromethyl)phenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one

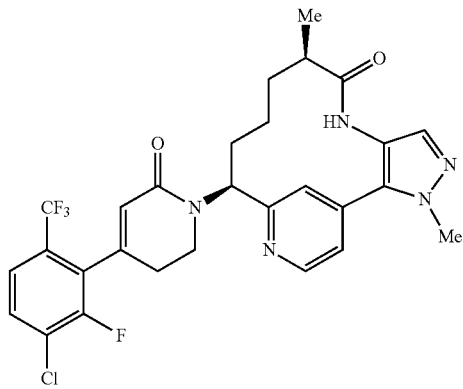 [SMILES: C[C@@H]1CCC[C@H](N2CCC(c3c(C(F)(F)F)ccc(Cl)c3F)=CC2=O)c2cc(ccn2)-c2c(cnn2C)NC1=O]

(9R,13S)-13-{4-[3-Chloro-2-fluoro-6-trifluoromethyl)phenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one was prepared according to the procedures described in Example 1 by substituting, 1-(5-chloro-2-(1H-1,2,3-triazol-1-yl)phenyl)prop-2-en-1-one with 1-(3-chloro-2-fluoro-6-(trifluoromethyl)phenyl)prop-2-en-1-one, Intermediate 2. $^1$H NMR (400 MHz, CD$_3$OD-d$_4$) δ 8.74 (d, J=5.5 Hz, 1H), 7.76 (s, 1H), 7.72 (dd, J=5.6, 1.2 Hz, 1H), 7.67-7.61 (m, 1H), 7.56-7.51 (m, 1H), 7.47 (s, 1H), 5.87 (s, 1H), 5.47 (dd, J=12.5, 3.7 Hz, 1H), 4.01 (s, 3H), 3.65 (br. s., 2H), 2.55-2.44 (m, 2H), 2.25-2.12 (m, 1H), 1.98-1.84 (m, 2H), 1.60-1.48 (m, 1H), 1.13 (br. s., 2H), 1.02 (d, J=6.8 Hz, 3H). MS(ESI) m/z: 576.1 (M+H). Analytical HPLC (Method A): RT=8.27 min, purity=97%; Factor XIa Ki=1.7 nM, Plasma Kallikrein Ki=7 nM.

Example 7

Preparation of 13-{4-[5-chloro-2-(1H-1,2,3-triazol-1-yl)phenyl]-6-oxo-1,2,3,6-tetrahydropyridin-1-yl}-3-ethyl-9-methyl-3,4,7,15-tetraazatricyclo[12.3.1.0²,⁶]octadeca-1(18),2(6),4,14,16-pentaen-8-one

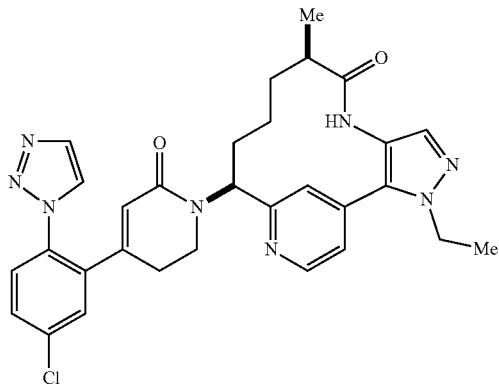

13-{4-[5-Chloro-2-(1H-1,2,3-triazol-1-yl)phenyl]-6-oxo-1,2,3,6-tetrahydropyridin-1-yl}-3-ethyl-9-methyl-3,4,7,15-tetraazatricyclo[12.3.1.0²,⁶]octadeca-1(18),2(6),4,14,16-pentaen-8-one was prepared according to the procedures described in Example 1 by substituting 1-methyl-4-nitro-1H-pyrazole with 1-ethyl-4-nitro-1H-pyrazole, Intermediate 8. $^1$H NMR (400 MHz, CD$_3$OD) δ 8.80 (d, J=5.5 Hz, 1H), 8.35 (d, J=1.1 Hz, 1H), 7.92 (d, J=1.1 Hz, 1H), 7.79 (s, 1H), 7.73 (dd, J=5.5, 1.5 Hz, 1H), 7.69-7.63 (m, 2H), 7.62-7.55 (m, 2H), 5.84 (s, 1H), 5.48 (dd, J=12.5, 3.7 Hz, 1H), 4.42 (q, J=7.0 Hz, 2H), 3.51 (dd, J=7.9, 6.2 Hz, 2H), 2.66-2.51 (m, 1H), 2.30-2.10 (m, 3H), 2.02-1.83 (m, 2H), 1.68-1.54 (m, 1H), 1.52 (t, J=7.3 Hz, 3H), 1.17 (br. s., 2H), 1.10 (d, J=6.8 Hz, 3H). MS(ESI) m/z: 571.2 (M+H). Analytical HPLC (Method A): RT=9.150 min, purity=97%; Factor XIa Ki=1.3 nM, Plasma Kallikrein Ki=41 nM.

Example 8

Preparation of 13-{4-[5-chloro-2-(1H-1,2,3-triazol-1-yl)phenyl]-6-oxo-1,2,3,6-tetrahydropyridin-1-yl}-3-(2,2-difluoroethyl)-9-methyl-3,4,7,15-tetraazatricyclo[12.3.1.0²,⁶]octadeca-1(18),2(6),4,14,16-pentaen-8-one

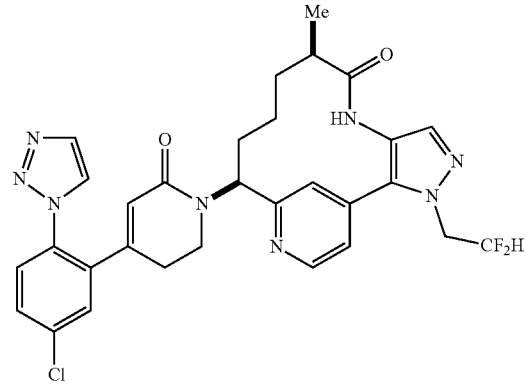

13-{4-[5-Chloro-2-(1H-1,2,3-triazol-1-yl)phenyl]-6-oxo-1,2,3,6-tetrahydropyridin-1-yl}-3-(2,2-difluoroethyl)-9-methyl-3,4,7,15-tetraazatricyclo[12.3.1.0²,⁶]octadeca-1(18),2(6),4,14,16-pentaen-8-one was prepared according to the procedures described in Example 1 by substituting 1-methyl-4-nitro-1H-pyrazole with 1-(2,2-difluoroethyl)-4-nitro-1H-pyrazole, Intermediate 9. $^1$H NMR (400 MHz, CD$_3$OD) δ 8.82 (d, J=5.5 Hz, 1H), 8.33 (d, J=0.9 Hz, 1H), 7.91 (d, J=1.1 Hz, 1H), 7.78 (s, 1H), 7.73 (dd, J=5.5, 1.3 Hz, 1H), 7.68-7.63 (m, 3H), 7.61-7.56 (m, 1H), 6.48-6.15 (m, 1H), 5.84 (s, 1H), 5.49 (dd, J=12.5, 4.0 Hz, 1H), 4.85-4.72 (m, 2H), 3.59-3.45 (m, 2H), 2.64-2.52 (m, 1H), 2.26-2.12 (m, 3H), 1.99-1.84 (m, 2H), 1.59 (td, J=13.8, 8.3 Hz, 1H), 1.43-1.31 (m, 1H), 1.23-1.14 (m, 1H), 1.09 (d, J=7.0 Hz, 3H). MS(ESI) m/z: 607.2 (M+H). Analytical HPLC (Method A): RT=6.521 min, purity=97%; Factor XIa Ki=11 nM, Plasma Kallikrein Ki=90 nM.

Example 9

Preparation of (9R,13S)-13-[4-(3-chloro-2,6-difluorophenyl)-6-oxo-1,2,3,6-tetrahydropyridin-1-yl]-4-(2-hydroxypyridin-4-yl)-9-methyl-3,4,7,15-tetraazatricyclo[12.3.1.0²,⁶]octadeca-1(18),2,5,14,16-pentaen-8-one

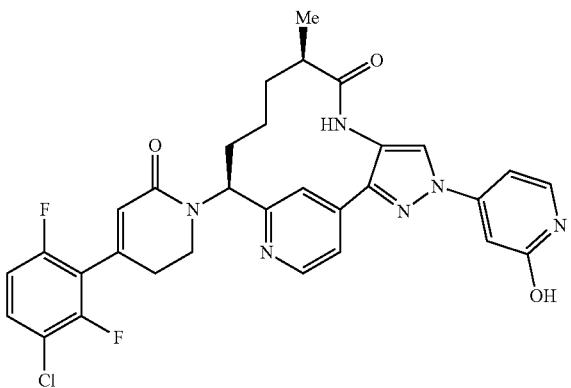 [SMILES: C[C@@H]1CCC[C@H](N2CCC(c3c(F)ccc(Cl)c3F)=CC2=O)c2cc(ccn2)-c2nn(-c3ccnc(O)c3)cc2NC1=O]

9A. Preparation of (9R,13S)-13-[4-(3-chloro-2,6-difluorophenyl)-6-oxo-1,2,3,6-tetrahydropyridin-1-yl]-4-(2-methoxypyridin-4-yl)-9-methyl-3,4,7,15-tetraazatricyclo [12.3.1.0$^{2,6}$]octadeca-1(18),2,5,14,16-pentaen-8-one (9R,13S)-13-[4-(3-Chloro-2,6-difluorophenyl)-6-oxo-1,2,3,6-tetrahydropyridin-1-yl]-9-methyl-3,4,7,15-tetraazatricyclo[12.3.1.0$^{2,6}$]octadeca-1(18),2(6),4,14,16-pentaen-8-one (0.045 g, 0.088 mmol), (1R,2R)—N1,N2-dimethylcyclohexane-1,2-diamine (0.013 g, 0.088 mmol), 4-iodo-2-methoxypyridine (0.041 g, 0.176 mmol), CuI (3.4 mg, 0.018 mmol), Cs$_2$CO$_3$ (0.057 g, 0.176 mmol), and DMF (2 mL) were added to a microwave vial. The mixture was then degassed and back-filled with Ar (3×). Upon sealing the microwave cap, the reaction was then heated to 125° C. for 30 min in microwave. The mixture was purified by reverse phase chromatography to yield (9R,13S)-13-[4-(3-chloro-2,6-difluorophenyl)-6-oxo-1,2,3,6-tetrahydropyridin-1-yl]-4-(2-methoxypyridin-4-yl)-9-methyl-3,4,7,15-tetraazatricyclo [12.3.1.0$^{2,6}$]octadeca-1(18),2,5,14,16-pentaen-8-one (5.9 mg, 11%). MS(ESI) m/z: 619.4 (M+H). $^1$H NMR (500 MHz, DMSO-d$_6$) δ 8.83 (s, 1H), 8.68 (d, J=4.9 Hz, 1H), 8.29 (d, J=5.8 Hz, 1H), 7.75 (s, 1H), 7.68 (d, J=5.8 Hz, 1H), 7.59 (d, J=4.9 Hz, 2H), 7.34 (s, 1H), 7.27 (s, 1H), 6.08 (s, 1H), 5.74-5.62 (m, 1H), 3.93 (s, 4H), 2.77-2.61 (m, 3H), 2.20-1.98 (m, 2H), 1.83-1.71 (m, 1H), 1.64-1.50 (m, 1H), 1.42-1.27 (m, 1H), 0.98 (d, J=6.7 Hz, 3H), 0.85-0.65 (m, 1H). Analytical HPLC (Method C): RT=1.64 min, purity=100%.

9B. Preparation of (9R,13S)-13-[4-(3-chloro-2,6-difluorophenyl)-6-oxo-1,2,3,6-tetrahydropyridin-1-yl]-4-(2-hydroxypyridin-4-yl)-9-methyl-3,4,7,15-tetraazatricyclo[12.3.1.0$^{2,6}$]octadeca-1(18),2,5,14,16-pentaen-8-one (9R,13S)-13-[4-(3-Chloro-2,6-difluorophenyl)-6-oxo-1,2,3,6-tetrahydropyridin-1-yl]-4-(2-methoxypyridin-4-yl)-9-methyl-3,4,7,15-tetraazatricyclo[12.3.1.0$^{2,6}$]octadeca-1(18),2,5,14,16-pentaen-8-one (30 mg, 0.048 mmol) was dissolved in THF (2 mL) and conc. HCl (500 µl, 6.00 mmol) was added. The solution was heated to 70° C. for 8 h. The reaction was then cooled to rt and concentrated to dryness in vacuo. The residue was purified by reverse phase chromatography to yield (9R,13S)-13-[4-(3-chloro-2,6-difluorophenyl)-6-oxo-1,2,3,6-tetrahydropyridin-1-yl]-4-(2-hydroxypyridin-4-yl)-9-methyl-3,4,7,15-tetraazatricyclo [12.3.1.0$^{2,6}$]octadeca-1(18),2,5,14,16-pentaen-8-one (12 mg, 32%). MS(ESI) m/z: 605.4 (M+H). $^1$H NMR (500 MHz, CD$_3$OD) δ 8.80-8.71 (m, 1H), 8.63 (s, 1H), 8.09-8.03 (m, 1H), 8.01-7.95 (m, 1H), 7.69-7.62 (m, 1H), 7.61-7.52 (m, 1H), 7.17-7.08 (m, 2H), 7.05-6.99 (m, 1H), 6.18-6.12 (m, 1H), 5.68-5.60 (m, 1H), 3.79-3.65 (m, 2H), 2.89-2.79 (m, 1H), 2.79-2.67 (m, 2H), 2.33-2.21 (m, 1H), 2.19-2.05 (m, 2H), 1.83-1.69 (m, 1H), 1.50-1.29 (m, 3H), 1.19 (d, J=6.9 Hz, 3H). Analytical HPLC (Method A): RT=6.22 min, purity=96%. Factor XIa Ki=14 nM, Plasma Kallikrein Ki=14 nM.

Example 10

Preparation of (9R,13S)-13-[4-(3-chloro-2,6-difluorophenyl)-6-oxo-1,2,3,6-tetrahydropyridin-1-yl]-3-ethyl-9-methyl-3,4,7,15-tetraazatricyclo[12.3.1.0$^{2,6}$] octadeca-1(18),2(6),4,14,16-pentaen-8-one

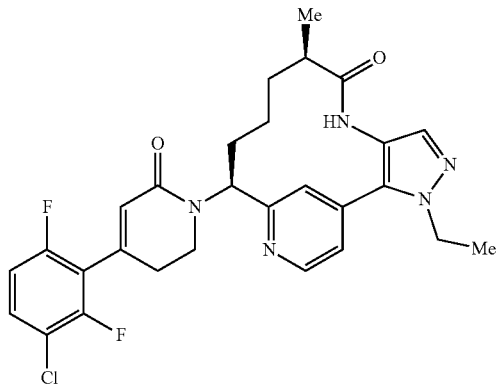 [SMILES: CCn1ncc2c1-c1ccnc(c1)[C@@H](N1CCC(c3c(F)ccc(Cl)c3F)=CC1=O)CCC[C@@H](C)C(=O)N2]

(9R,13S)-13-[4-(3-Chloro-2,6-difluorophenyl)-6-oxo-1,2,3,6-tetrahydropyridin-1-yl]-3-ethyl-9-methyl-3,4,7,15-tetraazatricyclo[12.3.1.0$^{2,6}$]octadeca-1(18),2(6),4,14,16-pentaen-8-one was prepared according to the procedures described in Example 1 by substituting 1-(5-chloro-2-(1H-1,2,3-triazol-1-yl)phenyl)prop-2-en-1-one with 1-(3-chloro-2,6-difluorophenyl)prop-2-en-1-one, Intermediate 1, and by substituting 1-methyl-4-nitro-1H-pyrazole with 1-ethyl-4-nitro-1H-pyrazole, Intermediate 8. $^1$H NMR (400 MHz, CD$_3$OD) δ 8.84 (d, J=5.5 Hz, 1H), 7.86 (s, 1H), 7.76 (dd, J=5.7, 1.5 Hz, 1H), 7.61 (s, 1H), 7.56 (td, J=8.7, 5.5 Hz, 1H), 7.12 (td, J=9.2, 1.8 Hz, 1H), 6.13 (s, 1H), 5.56 (dd, J=12.5, 4.0 Hz, 1H), 4.43 (q, J=7.1 Hz, 2H), 3.74 (t, J=6.8 Hz, 2H), 2.85-2.69 (m, 2H), 2.65-2.54 (m, 1H), 2.38-2.20 (m, 1H), 2.10-1.88 (m, 2H), 1.71-1.58 (m, 1H), 1.53 (t, J=7.3 Hz, 3H), 1.22 (br. s., 2H), 1.12 (d, J=6.8 Hz, 3H). MS(ESI) m/z: 540.2 (M+H)$^+$. Analytical HPLC (Method A): RT=11.04 min, purity=97%. Factor XIa Ki=14 nM, Plasma Kallikrein Ki=50 nM.

Example 11

Preparation of 13-{4-[5-chloro-2-(1H-1,2,3-triazol-1-yl)phenyl]-6-oxo-1,2,3,6-tetrahydropyridin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one

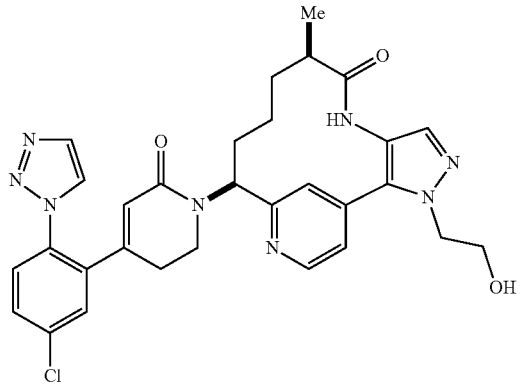

11A. Preparation of 3-{2-[(tert-butyldimethylsilyl)oxy]ethyl}-13-{4-[5-chloro-2-(1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one

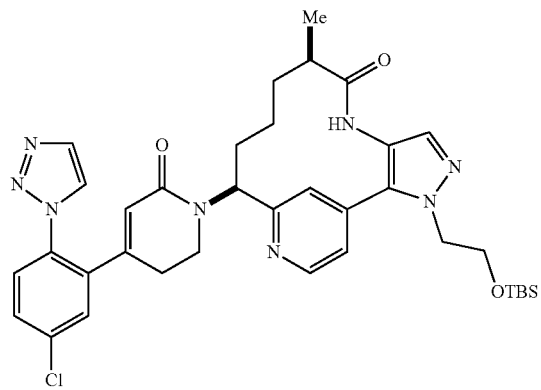

DMF (0.7 ml) was added to a vial containing 4-nitro-1-(2,2,2-trifluoroethyl)-1H-pyrazole, 4-nitro-1-(2,2,2-trifluoroethyl)-1H-pyrazole, Intermediate 10, (0.02 g, 0.037 mmol), Cs$_2$CO$_3$ (0.024 g, 0.074 mmol), and (2-bromoethoxy)(tert-butyl)dimethylsilane (0.026 g, 0.110 mmol). The suspension was heated to 75° C. for 25 min then concentrated at rt. The crude product was used in the subsequent step.

11B. Preparation of 13-{4-[5-chloro-2-(1H-1,2,3-triazol-1-yl)phenyl]-6-oxo-1,2,3,6-tetrahydropyridin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one To 3-{2-[(tert-butyldimethylsilyl)oxy]ethyl}-13-{4-[5-chloro-2-(1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one was added MeOH (0.7 ml) and conc. HCl (0.05 ml, 0.60 mmol) and the reaction was stirred for 10 min. The crude product was purified by reverse phase preparative HPLC to yield 13-{4-[5-chloro-2-(1H-1,2,3-triazol-1-yl)phenyl]-6-oxo-1,2,3,6-tetrahydropyridin-1-yl}-3-(2-hydroxyethyl)-9-methyl-3,4,7,15-tetraazatricyclo[12.3.1.0$^{2,6}$]octadeca-1(18),2(6),4,14,16-pentaen-8-one as a white solid (6 mg, 8.22 μmol, 22.2% yield). $^1$H NMR (500 MHz, CD$_3$OD) δ 8.76-8.70 (m, 1H), 8.34-8.30 (m, 1H), 7.93-7.88 (m, 1H), 7.84-7.78 (m, 1H), 7.68-7.62 (m, 3H), 7.60 (s, 3H), 5.89-5.81 (m, 1H), 5.59-5.50 (m, 1H), 4.44-4.38 (m, 2H), 4.05-3.97 (m, 3H), 3.51-3.45 (m, 2H), 2.61-2.51 (m, 1H), 2.23-2.09 (m, 3H), 1.99-1.81 (m, 2H), 1.65-1.53 (m, 1H), 1.39-1.28 (m, 2H), 1.19-1.12 (m, 2H), 1.12-1.08 (m, 3H). MS(ESI) m/z: 587.5 (M+H)$^+$. Analytical HPLC (Method A): RT=5.33 min, purity=96%; Factor XIa Ki=5.5 nM, Plasma Kallikrein Ki=140 nM.

Example 12

Preparation of 2-(13-{4-[5-chloro-2-(1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0$^{2,6}$]octadeca-1(18),2,5,14,16-pentaen-4-yl) acetic Acid

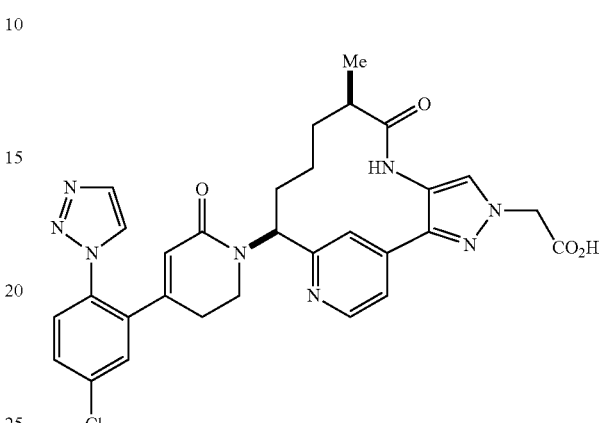

12A. Preparation of 2-(13-{4-[5-chloro-2-(1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0$^{2,6}$]octadeca-1(18),2,5,14,16-pentaen-4-yl) acetate

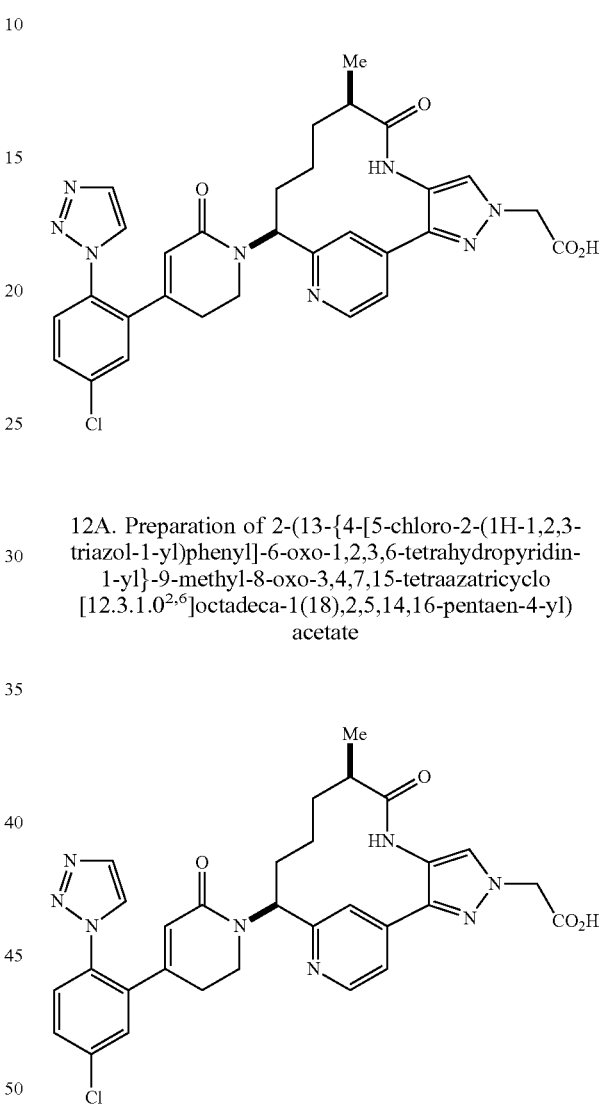

2-(13-{4-[5-Chloro-2-(1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0$^{2,6}$]octadeca-1(18),2,5,14,16-pentaen-4-yl)acetate was prepared according to the procedures described in Example 11 by substituting (2-bromoethoxy)(tert-butyl)dimethylsilane with ethyl 2-bromoacetate. $^1$H NMR (400 MHz, CD$_3$OD) δ 8.69-8.62 (m, 1H), 8.37-8.34 (m, 1H), 8.31-8.26 (m, 1H), 8.03-7.98 (m, 1H), 7.96-7.91 (m, 1H), 7.89-7.84 (m, 1H), 7.70-7.64 (m, 2H), 7.63-7.58 (m, 1H), 5.89-5.82 (m, 1H), 5.48-5.38 (m, 1H), 5.17-5.13 (m, 2H), 4.34-4.23 (m, 2H), 2.92-2.83 (m, 1H), 2.41-2.28 (m, 1H), 2.25-2.16 (m, 2H), 2.03-1.87 (m, 2H), 1.76-1.64 (m, 1H), 1.61-1.49 (m, 1H), 1.32 (s, 4H), 1.26-1.20 (m, 3H). MS(ESI) m/z: 629.4 (M+H)$^+$. Analytical HPLC (Method A): RT=5.33 min, purity=96%.

12B. Preparation of 2-(13-{4-[5-chloro-2-(1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0$^{2,6}$]octadeca-1(18),2,5,14,16-pentaen-4-yl) acetic Acid To a solution of 2-(13-{4-[5-chloro-2-(1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0$^{2,6}$]octadeca-1(18),2,5,14,16-pentaen-4-yl)acetate (16 mg, 0.025 mmol) in THF (1 mL) was added LiOH (0.216 mL, 0.432 mmol) and the reaction was stirred at rt for 1 h. After 1 h, the reaction mixture was concentrated and the residue purified by reverse phase HPLC purification to afford 9.5 mg of 2-(13-{4-[5-chloro-2-(1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0$^{2,6}$]octadeca-1(18),2,5,14,16-pentaen-4-yl)acetic acid (50%) as white solid. $^1$H NMR (400 MHz, CD$_3$OD) δ 8.71 (d, J=6.2 Hz, 1H), 8.34 (d, J=1.1 Hz, 1H), 8.15 (s, 1H), 8.09 (dd, J=5.9, 1.5 Hz, 1H), 7.92 (d, J=1.1 Hz, 1H), 7.90-7.89 (m, 1H), 7.69-7.56 (m, 3H), 5.82 (s, 1H), 5.42 (dd, J=11.2, 3.3 Hz, 1H), 5.11 (d, J=0.9 Hz, 2H), 3.49-3.39 (m, 1H), 3.42-3.40 (m, 1H), 2.67-2.54 (m, 1H), 2.34-1.94 (m, 5H), 1.79-1.64 (m, 1H), 1.63-1.49 (m, 1H), 1.31 (d, J=7.0 Hz, 1H), 1.19 (d, J=7.0 Hz, 3H). MS(ESI) m/z: 601.4 (M+H). Analytical HPLC (Method A): RT=4.99 min, purity=>95%; Factor XIa Ki=14 nM, Plasma Kallikrein Ki=480 nM.

Example 13

Preparation of (9S,13S)-13-{4-[5-chloro-2-(4-chloro-1H-1,2,3-triazol-1-yl)phenyl]-6-oxo-1,2,3,6-tetrahydropyridin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate, isomer A

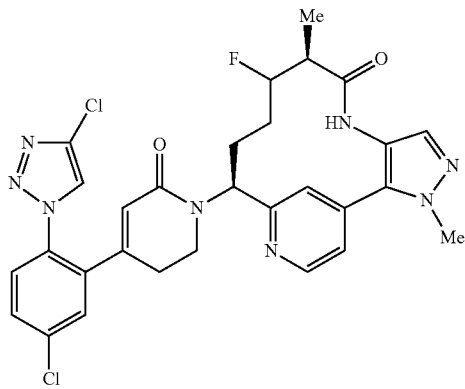 [SMILES: C[C@H]1C(=O)Nc2cnn(C)c2-c2ccnc(c2)[C@@H](N2CCC(c3cc(Cl)ccc3-n3cc(Cl)nn3)=CC2=O)CCC1F]

13A. Preparation of tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate In a 250 ml RBF, Fe$_2$(C$_2$O$_4$)$_3$·6H$_2$O (449 mg, 0.928 mmol) in water (20 mL) was stirred in a warm water bath until dissolved into a clear yellow solution. SELECTFLUOR® (329 mg, 0.928 mmol) was added, followed by adding tert-butyl N-[(9R,10E,13S)-3,9-dimethyl-8-oxo-3,4,7,15-tetraazatricyclo[12.3.1.0$^{2,6}$]octadeca-1(18),2(6),4,10,14,16-hexaen-13-yl]carbamate (123 mg, 0.309 mmol), which was prepared as in Example 1, in ACN (20 mL), followed by adding NaBH$_4$ (94 mg, 2.476 mmol) portionwise and stirred at rt for 1 h. The reaction mixture was quenched with 28%-30% aq NH$_4$OH (10 ml), extracted with 10% MeOH in DCM (200 ml, 3×). The combined organic phase was washed with brine, dried over MgSO$_4$, filtered and concentrated. Purification by reverse phase chromatography, followed by neutralization gave tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate (35.4 mg, 27%), as a white solid and as a mixture of stereo- and regio-diastereomers. MS(ESI) m/z: 418.1 (M+H).

13B1 and 13B2. Preparation of tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate, isomer A (13B1), and tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate, isomer B (13B2)

tert-Butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate (35.4 mg), a mixture of diastereomers, was resolved by chiral SFC separation. Column: Lux 5μ Cellulose-4, 21×250 mm, 5μ. Mobile Phase: 15% MeOH-0.1% DEA/85% CO$_2$, Flow Conditions: 45 mL/min, 150 Bar, 40° C. 1st peak fraction gave 20 mg of 13B1 as a white solid which was labeled as single isomer A; and the 2nd peak fraction was concentrated to give 10 mg of 13B2 as a white solid which was labeled as single isomer B.

13C. Preparation of (9S,13S)-13-{4-[5-chloro-2-(4-chloro-1H-1,2,3-triazol-1-yl)phenyl]-6-oxo-1,2,3,6-tetrahydropyridin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate, isomer A (9S,13S)-13-{4-[5-Chloro-2-(4-chloro-1H-1,2,3-triazol-1-yl)phenyl]-6-oxo-1,2,3,6-tetrahydropyridin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate, isomer A (0.0150 g, 61%) was prepared according to the procedures described in Example 1, by using 1-(5-chloro-2-(4-chloro-1H-1,2,3-triazol-1-yl)phenyl)prop-2-en-1-one and tert-butyl N-[(9S,13S)-10-fluoro-3,9-dimethyl-8-oxo-3,4,7,15-tetraazatricyclo[12.3.1.0$^{2,6}$]octadeca-1(18),2(6),4,14,16-pentaen-13-yl]carbamate. MS(ESI) m/z: 609.1 (M+H). $^1$H NMR (400 MHz, CD$_3$OD) δ 8.72 (d, J=5.3 Hz, 1H), 8.44 (s, 1H), 7.63-7.59 (m, 2H), 7.57-7.50 (m, 2H), 7.47-7.44 (m, 2H), 5.78 (s, 1H), 5.67 (dd, J=12.7, 5.4 Hz, 1H), 5.27-5.09 (m, 1H), 4.22-4.14 (m, 1H), 4.01 (s, 3H), 3.70 (ddd, J=12.5, 9.7, 5.1 Hz, 1H), 3.12-3.01 (m, 1H), 2.43-2.32 (m, 1H), 2.31-2.21 (m, 1H), 2.20-2.10 (m, 1H), 2.03-1.92 (m, 1H), 1.71-1.55 (m, 1H), 0.93 (d, J=6.8 Hz, 3H), 0.62-0.40 (m, 1H). Analytical HPLC (Method A): RT=8.16 min, purity=>99%; Factor XIa Ki=0.1 nM, Plasma Kallikrein Ki=6 nM.

Example 14

Preparation of (9R,13S)-13-{4-[3-chloro-2-fluoro-6-(trifluoromethyl)phenyl]-6-oxo-1,2,3,6-tetrahydropyridin-1-yl}-3-(difluoromethyl)-9-methyl-3,4,7,15-tetraazatricyclo[12.3.1.0²,⁶]octadeca-1(18),2(6),4,14,16-pentaen-8-one

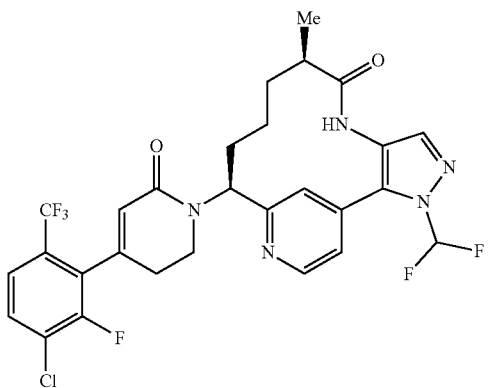 [SMILES: C[C@@H]1CCC[C@H](N2CCC(c3c(C(F)(F)F)ccc(Cl)c3F)=CC2=O)c2cc(ccn2)-c2c(cnn2C(F)F)NC1=O]

(9R,13S)-13-{4-[3-Chloro-2-fluoro-6-(trifluoromethyl)phenyl]-6-oxo-1,2,3,6-tetrahydropyridin-1-yl}-3-(difluoromethyl)-9-methyl-3,4,7,15-tetraazatricyclo[12.3.1.0²,⁶]octadeca-1(18),2(6),4,14,16-pentaen-8-one (25 mg, 53%). was prepared in a similar manner to Example 1 by using 1-(difluoromethyl)-4-nitro-1H-pyrazole, Intermediate 14, and -(3-chloro-2-fluoro-6-(trifluoromethyl)phenyl)prop-2-en-1-one, Intermediate 2. MS(ESI) m/z: 612.3 (M+H). $^1$H NMR (400 MHz, CD$_3$CN) δ 8.87-8.73 (m, 1H), 7.82-7.36 (m, 7H), 5.93 (s, 1H), 5.66-5.52 (m, 1H), 4.23-4.03 (m, 1H), 3.97-3.83 (m, 1H), 3.82-3.66 (m, 1H), 2.73-2.46 (m, 3H), 2.34-2.17 (m, 1H), 1.66-1.48 (m, 2H), 1.38-1.18 (m, 3H), 1.01 (d, J=6.8 Hz, 4H), 0.85-0.71 (m, 1H). Analytical HPLC (Method A): RT=9.88 min, purity=94%; Factor XIa Ki=1 nM, Plasma Kallikrein Ki=110 nM.

Example 15

Preparation of (9S,13S)-13-{4-[5-chloro-2-(4-chloro-1H-1,2,3-triazol-1-yl)phenyl]-6-oxo-1,2,3,6-tetrahydropyridin-1-yl}-10-fluoro-3,9-dimethyl-3,4,7,15-tetraazatricyclo[12.3.1.0²,⁶]octadeca-1(18),2(6),4,14,16-pentaen-8-one trifluoroacetate, isomer B

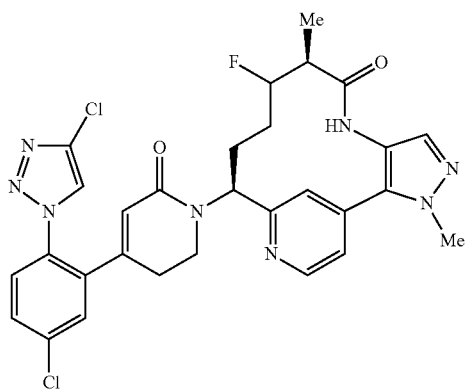 [SMILES: C[C@H]1C(=O)Nc2cnn(C)c2-c2ccnc(c2)[C@@H](N2CCC(c3cc(Cl)ccc3-n3cc(Cl)nn3)=CC2=O)CCC1F]

(9S,13S)-13-{4-[5-Chloro-2-(4-chloro-1H-1,2,3-triazol-1-yl)phenyl]-6-oxo-1,2,3,6-tetrahydropyridin-1-yl}-10-fluoro-3,9-dimethyl-3,4,7,15-tetraazatricyclo[12.3.1.0²,⁶]octadeca-1(18),2(6),4,14,16-pentaen-8-one trifluoroacetate, isomer B (0.0081 g, 62%) was prepared according to the procedures described in Example 13, by replacing tert-butyl N-[(9S,13S)-10-fluoro-3,9-dimethyl-8-oxo-3,4,7,15-tetraazatricyclo[12.3.1.0²,⁶]octadeca-1(18),2(6),4,14,16-pentaen-13-yl]carbamate with tert-butyl N-[(9S,13S)-10-fluoro-3,9-dimethyl-8-oxo-3,4,7,15-tetraazatricyclo[12.3.1.0²,⁶]octadeca-1(18),2(6),4,14,16-pentaen-13-yl]carbamate, isomer B, prepared as intermediate 13B2. MS(ESI) m/z: 609.1 (M+H). $^1$H NMR (500 MHz, methanol-d$_4$) δ 8.80 (d, J=5.5 Hz, 1H), 8.45 (s, 1H), 7.72 (dd, J=5.5, 1.4 Hz, 1H), 7.65-7.61 (m, 2H), 7.59-7.57 (m, 2H), 7.56-7.54 (m, 2H), 5.84 (d, J=1.4 Hz, 1H), 5.67 (dd, J=12.9, 2.8 Hz, 1H), 4.50-4.30 (m, 1H), 4.06 (s, 3H), 3.47-3.36 (m, 1H), 3.20-3.05 (m, 1H), 2.82-2.53 (m, 2H), 2.33-1.86 (m, 4H), 1.22 (d, J=6.6 Hz, 3H) Analytical HPLC (Method A): RT=7.29 min, purity=>95%; Factor XIa Ki=19 nM, Plasma Kallikrein Ki=450 nM.

Example 16

Preparation of 2-[(9R,13S)-13-{4-[5-chloro-2-(4-chloro-1H-1,2,3-triazol-1-yl)phenyl]-6-oxo-1,2,3,6-tetrahydropyridin-1-yl}-9-methyl-8-oxo-3,4,7,15-tetraazatricyclo [12.3.1.0²,⁶]octadeca-1(18),2(6),4,14,16-pentaen-3-yl]acetic acid

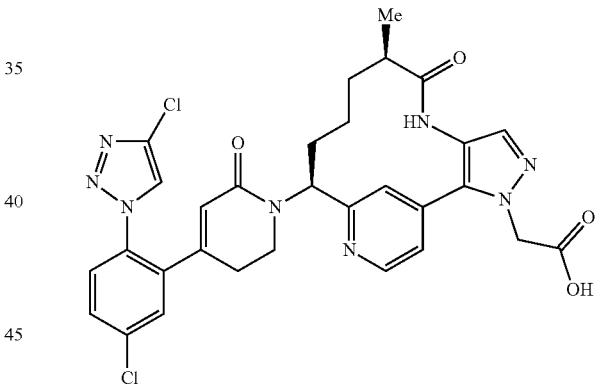

A solution of (9R,13S)-13-{4-[5-chloro-2-(4-chloro-1H-1,2,3-triazol-1-yl)phenyl]-6-oxo-1,2,3,6-tetrahydropyridin-1-yl}-3-(2-hydroxyethyl)-9-methyl-3,4,7,15-tetraazatricyclo[12.3.1.0²,⁶]octadeca-1(18),2(6),4,14,16-pentaen-8-one trifluoroacetate (0.025 g, 0.040 mmol), prepared as described in Example 35, in acetone (2 mL) was cooled to 0° C. To this cooled mixture was then added 2.86 molar solution of Jones reagent (0.028 mL, 0.080 mmol) and the resulting reaction mixture was allowed to warm to rt over a period of 2 h. The reaction mixture was then quenched with 0.5 mL of IPA and concentrated. The resulting residue was purified by prep HPLC purification to afford 2-[(9R,13S)-13-{4-[5-chloro-2-(4-chloro-1H-1,2,3-triazol-1-yl)phenyl]-6-oxo-1,2,3,6-tetrahydropyridin-1-yl}-9-methyl-8-oxo-3,4,7,15-tetraazatricyclo[12.3.1.0²,⁶]octadeca-1(18),2(6),4,14,16-pentaen-3-yl]acetic acid trifluoroacetate (4.5 mg, 5.70 μmol, 14% yield) as a white solid. $^1$H NMR (400 MHz, CD$_3$OD) δ 8.74-8.65 (m, 1H), 8.47-8.44 (m, 1H), 7.68-7.47 (m, 6H), 5.82 (s, 1H), 5.54 (dd, J=12.8, 3.7 Hz, 1H), 5.20-5.06 (m, 2H), 4.21-4.07 (m, 1H), 3.61-3.43 (m, 2H), 2.62-2.49 (m, 2H), 2.30-2.05 (m, 3H), 1.99-1.77 (m, 2H), 1.66-1.50 (m, 1H), 1.43-1.16 (m, 3H). MS(ESI) m/z: 635.4 [M+H]$^+$. Analytical HPLC (Method A): RT=6.74 min, purity=>95.0%; Factor XIa Ki=0.19 nM, Plasma Kallikrein Ki=17 nM.

Example 17

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one

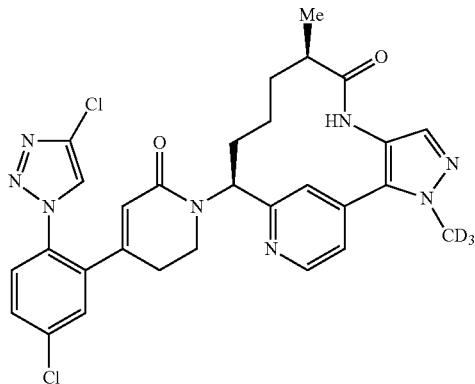 [SMILES: [2H]C([2H])([2H])n1ncc2c1-c1ccnc(c1)[C@@H](N1CCC(c3cc(Cl)ccc3-n3cc(Cl)nn3)=CC1=O)CCC[C@@H](C)C(=O)N2]

17A. Preparation of 1-($^2$H$_3$)methyl-4-nitro-1H-pyrazole

DIAD (5.59 mL, 28.7 mmol) was added to a solution of 4-nitro-1H-pyrazole (2.5 g, 22.11 mmol), CD$_3$OD (0.898 mL, 22.11 mmol), and Ph$_3$P (resin bound) (8.84 g, 26.5 mmol) in THF (40 mL) and stirred overnight. The reaction was quenched with water, extracted with EtOAc, washed with brine, dried over Na$_2$SO$_4$, filtered, and concentrated. The crude product was purified by normal phase chromatography eluting with a gradient of DCM/MeOH to afford 1-($^2$H$_3$)methyl-4-nitro-1H-pyrazole (1.92 g, 14.76 mmol, 66.7% yield) as a white solid. MS(ESI) m/z: 131.0 (M+H)$^+$. $^1$H NMR (400 MHz, CDCl$_3$) δ 8.13 (d, J=0.4 Hz, 1H), 8.05 (s, 1H).

17B. Preparation of tert-butyl N-[(1S)-1-{4-[1-($^2$H$_3$)methyl-4-nitro-1H-pyrazol-5-yl]pyridin-2-yl}but-3-en-1-yl]carbamate To a large microwave vial were added (S)-tert-butyl (1-(4-chloropyridin-2-yl)but-3-en-1-yl)carbamate (2.61 g, 9.22 mmol), 1-($^2$H$_3$)methyl-4-nitro-1H-pyrazole (1.0 g, 7.69 mmol), di(adamantan-1-yl)(butyl)phosphine (0.413 g, 1.15 mmol), K$_2$CO$_3$ (3.19 g, 23.06 mmol), pivalic acid (0.268 ml, 2.306 mmol) and DMF (15.37 ml). The reaction was purged with Ar for 10 min, then Pd(OAc)$_2$ (0.173 g, 0.769 mmol) was added, the vial sealed, and stirred at 115° C. overnight. The reaction was then partitioned between EtOAc and H$_2$O. The aqueous layer was extracted with EtOAc (2×). The combined organic layer was washed with brine, dried over MgSO$_4$, filtered and concentrated. The residue was purified by normal phase chromatography eluting with a gradient of hexanes/EtOAc to give tert-butyl N-[(1S)-1-{4-[1-($^2$H$_3$)methyl-4-nitro-1H-pyrazol-5-yl]pyridin-2-yl}but-3-en-1-yl]carbamate (1.49 g, 3.96 mmol, 51.5% yield) as a lavender foam. MS(ESI) m/z: 377.0 (M+H)$^+$. $^1$H NMR (400 MHz, CDCl$_3$) δ 8.77 (d, J=4.8 Hz, 1H), 8.21 (s, 1H), 7.26 (s, 1H), 7.23 (dd, J=5.1, 1.5 Hz, 1H), 5.78-5.65 (m, 1H), 5.55 (d, J=6.8 Hz, 1H), 5.14-5.03 (m, 2H), 4.89 (d, J=6.8 Hz, 1H), 2.66 (t, J=6.6 Hz, 2H), 1.44 (s, 9H).

17C. Preparation of tert-butyl N-[(1S)-1-{4-[4-amino-1-($^2$H$_3$)methyl-1H-pyrazol-5-yl]pyridin-2-yl}but-3-en-1-yl]carbamate tert-Butyl N-[(1S)-1-{4-[1-($^2$H$_3$)methyl-4-nitro-1H-pyrazol-5-yl]pyridin-2-yl}but-3-en-1-yl]carbamate (1.45 g, 3.85 mmol) was dissolved in acetone (15 mL)/water (3 mL), cooled to 0° C., and NH$_4$Cl (1.030 g, 19.26 mmol) and Zn (2.52 g, 38.5 mmol) were added and the reaction was allowed to warm to rt. After 1 h, the reaction was filtered and filtrate partitioned with water (30 mL) and EtOAc (50 ml). The aqueous layer was extracted with EtOAc (2×50 mL). The combined organic layer was washed with brine (20 ml), dried (MgSO$_4$), filtered, and concentrated. The residue was purified by normal phase chromatography eluting with a DCM/MeOH gradient to afford tert-butyl N-[(1S)-1-{4-[4-amino-1-($^2$H$_3$)methyl-1H-pyrazol-5-yl]pyridin-2-yl}but-3-en-1-yl]carbamate (0.62 g, 46.5%). MS(ESI) m/z: 347.2 (M+H)$^+$. $^1$H NMR (400 MHz, CDCl$_3$) δ 8.67 (dd, J=5.1, 0.7 Hz, 1H), 7.26-7.23 (m, 2H), 7.21 (dd, J=5.1, 1.5 Hz, 1H), 5.79-5.66 (m, 1H), 5.58 (d, J=7.3 Hz, 1H), 5.11-5.05 (m, 2H), 4.86 (q, J=6.6 Hz, 1H), 2.64 (t, J=6.7 Hz, 2H), 1.44 (s, 9H).

17D. Preparation of tert-butyl N-[(1S)-1-{4-[1-($^2$H$_3$)methyl-4-[(2R)-2-methylbut-3-enamido]-1H-pyrazol-5-yl]pyridin-2-yl}but-3-en-1-yl]carbamate (R)-2-Methylbut-3-enoic acid (233 mg, 2.327 mmol), tert-butyl N-[(1S)-1-{4-[4-amino-1-($^2$H$_3$)methyl-1H-pyrazol-5-yl]pyridin-2-yl}but-3-en-1-yl]carbamate (620 mg, 1.79 mmol), pyridine (0.433 ml, 5.37 mmol) in EtOAc (17.900 mL) was cooled to −10° C. under Ar followed by dropwise addition of T3P® (50% wt in EtOAc) (2.131 ml, 3.58 mmol and then the reaction mixture was gradually warmed up to rt. After 3.5 h, the reaction mixture was diluted with EtOAc, washed with 1.5 M K$_2$HPO$_4$ followed by brine, dried over Na$_2$SO$_4$, filtered, and concentrated. The crude product was then purified by normal phase chromatography eluting with a gradient of hexanes/EtOAc to give tert-butyl N-[(1S)-1-{4-[1-($^2$H$_3$)methyl-4-[(2R)-2-methylbut-3-enamido]-1H-pyrazol-5-yl]pyridin-2-yl}but-3-en-1-yl]carbamate. (529 mg, 1.234 mmol, 69.0% yield) as a yellow foam. MS(ESI) m/z: 429.2 (M+H)$^+$.

17E. Preparation of tert-butyl N-[(9R,10E,13S)-3-($^2$H$_3$)methyl-9-methyl-8-oxo-3,4,7,15-tetraazatricyclo[12.3.1.0$^{2,6}$]octadeca-1 (18),2(6),4,10,14,16-hexaen-13-yl]carbamate Five large microwave vials were charged in equal amounts with the following: tert-butyl N-[(1S)-1-{4-[1-($^2$H$_3$)methyl-4-[(2R)-2-methylbut-3-enamido]-1H-pyrazol-5-yl]pyridin-2-yl}but-3-en-1-yl]carbamate (0.51 g, 1.190 mmol) in degassed DCE (90 mL) was irradiated 120° C. for 30 min in the presence of Second Generation Grubbs Catalyst (0.404 g, 0.476 mmol). The reactions were combined, concentrated, and the residue purified by normal phase column chromatography eluting with a gradient of hexanes/EtOAc to give tert-butyl N-[(9R,10E,13S)-3-($^2$H$_3$)methyl-9-methyl-8-oxo-3,4,7,15-tetraazatricyclo[12.3.1.0$^{2,6}$]octadeca-1(18),2(6),4,10,14,16-hexaen-13-yl]carbamate (0.124 g, 26.0%) as a brown solid. MS(ESI) m/z: 401.2 (M+H)$^+$. $^1$H NMR (400 MHz, CDCl$_3$) δ 8.66 (d, J=5.1 Hz, 1H), 7.52 (s, 1H), 7.19 (d, J=4.8 Hz, 1H), 6.80 (s, 1H), 6.37 (d, J=7.5 Hz, 1H), 5.68 (t, J=11.2 Hz, 1H), 4.82-4.63 (m, 2H), 3.12-2.93 (m, 2H), 1.93 (q, J=11.1 Hz, 1H), 1.48 (s, 9H), 1.15 (d, J=5.9 Hz, 3H).

17F. Preparation of tert-butyl N-[(9R,13S)-3-($^2$H$_3$)methyl-9-methyl-8-oxo-3,4,7,15-tetraazatricyclo[12.3.1.0$^{2,6}$]octadeca-1(18),2(6),4,14,16-pentaen-13-yl]carbamate PtO$_2$ (6.80 mg, 0.030 mmol) was added to a stirring solution of tert-butyl N-[(9R,10E,13S)-3-($^2$H$_3$)methyl-9-methyl-8-oxo-3,4,7,15-tetraazatricyclo[12.3.1.0$^{2,6}$]octadeca-1(18),2(6),4,10,14,16-hexaen-13-yl]carbamate (0.120 g, 0.300 mmol) in EtOH (10 mL). The suspension was subjected to a H$_2$ atmosphere (55 psi) for 1 h. The catalyst was filtered off through a plug of CELITE® and the filtrate concentrated. The product (0.104 g, 86%) was carried forward to the next reaction as is without further purification. MS(ESI) m/z: 403.2 (M+H)$^+$.

17G. Preparation of (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one 4 M HCl in dioxane (1.6 ml) was added to a stirring solution of tert-butyl N-[(9R,13S)-3-($^2$H$_3$)methyl-9-methyl-8-oxo-3,4,7,15-tetraazatricyclo[12.3.1.0$^{2,6}$]octadeca-1(18),2(6),4,14,16-pentaen-13-yl]carbamate (0.100 g, 0.248 mmol) in MeOH (3 mL). After stirring overnight, the reaction mixture was concentrated to dryness and placed under high vacuum. The hydrogen chloride salt was free based by dissolution in MeOH, passing through a resin bound NaHCO$_3$ cartridge (StratoSpheres SPE; 500 mg, 0.90 mmol loading) and the filtrate concentrated. The material was carried forward as is to next reaction. MS(ESI) m/z: 303.4 (M+H)$^+$.

17H. Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate (9R,13S)-13-{4-[5-Chloro-2-(4-chloro-1H-1,2,3-triazol-1-yl)phenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate (14 mg, 33% yield) was prepared according to the procedures described in Example 1 by using (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one and 1-(5-chloro-2-(4-chloro-1H-1,2,3-triazol-1-yl)phenyl)prop-2-en-1-one, Intermediate 4. MS(ESI) m/z: 594.1 (M+H)$^+$. $^1$H NMR: (500 MHz, methanol-d$_4$) δ 8.78 (br. s., 1H), 8.48 (s, 1H), 7.73-7.52 (m, 7H), 5.85 (s, 1H), 5.60-5.55 (m, 1H), 3.58-3.51 (m, 2H), 2.61-2.56 (m, 1H), 2.25 (t, J=6.7 Hz, 2H), 2.20-2.15 (m, 1H), 2.00-1.86 (m, 3H), 1.61 (dd, J=13.3, 5.9 Hz, 1H), 1.23-1.19 (m, 1H), 1.10 (d, J=6.9 Hz, 3H). Analytical HPLC (Method A): RT=5.94 min, purity=92%; Factor XIa Ki=0.15 nM, Plasma Kallikrein Ki=10 nM.

Example 18

Preparation of (9R,13S)-13-{4-[3-chloro-2-fluoro-6-(trifluoromethyl)phenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one

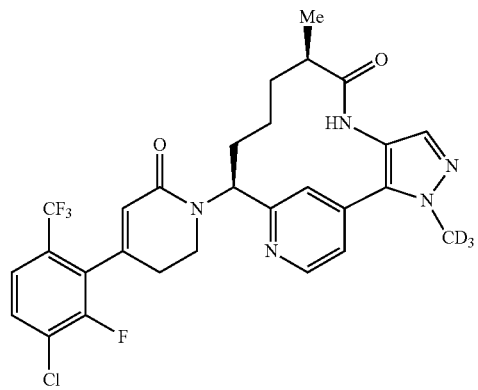 [SMILES: [2H]C([2H])([2H])n1ncc2c1-c1ccnc(c1)[C@@H](N1CCC(c3c(C(F)(F)F)ccc(Cl)c3F)=CC1=O)CCC[C@@H](C)C(=O)N2]

(9R,13S)-13-{4-[3-Chloro-2-fluoro-6-(trifluoromethyl)phenyl]-6-oxo-1,2,3,6-tetrahydropyridin-1-yl}-3-($^2$H$_3$)methyl-9-methyl-3,4,7,15-tetraazatricyclo-[12.3.1.0$^{2,6}$]octadeca-1(18),2(6),4,14,16-pentaen-8-one trifluoroacetate (17.6 mg, 39%) was prepared similar to procedures described in Example 1 by using (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one, prepared as described for Example 17G and 1-(3-chloro-2-fluoro-6-(trifluoromethyl)phenyl)prop-2-en-1-one, Intermediate 2. MS(ESI) m/z: 579.1 (M+H)$^+$. $^1$H NMR: (500 MHz, CD$_3$OD) δ 8.78 (br. s., 1H), 8.48 (s, 1H), 7.73-7.52 (m, 7H), 5.85 (s, 1H), 5.60-5.55 (m, 1H), 3.58-3.51 (m, 2H), 2.61-2.56 (m, 1H), 2.25 (t, J=6.7 Hz, 2H), 2.20-2.15 (m, 1H), 2.00-1.86 (m, 3H), 1.61 (dd, J=13.3, 5.9 Hz, 1H), 1.23-1.19 (m, 1H), 1.10 (d, J=6.9 Hz, 3H). Analytical HPLC (Method A): RT=7.26 min, purity=95%; Factor XIa Ki=2.8 nM, Plasma Kallikrein Ki=30 nM.

Example 19

Preparation of 4-chloro-2-{1-[(9R,13S)-3-(difluoromethyl)-9-methyl-8-oxo-3,4,7,15-tetraazatricyclo[12.3.1.0$^{2,6}$]octadeca-1(18),2(6),4,14,16-pentaen-13-yl]-6-oxo-1,2,3,6-tetrahydropyridin-4-yl}benzonitrile

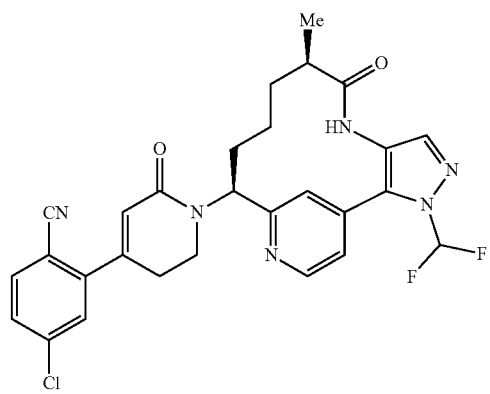 [SMILES: C[C@@H]1CCC[C@H](N2CCC(c3cc(Cl)ccc3C#N)=CC2=O)c2cc(ccn2)-c2c(cnn2C(F)F)NC1=O]

19A. Preparation of (9R,13S)-13-[4-(2-bromo-5-chlorophenyl)-6-oxo-1,2,3,6-tetrahydropyridin-1-yl]-3-(difluoromethyl)-9-methyl-3,4,7,15-tetraazatricyclo[12.3.1.0²,⁶]octadeca-1(18),2(6),4,14,16-pentaen-8-one (9R,13S)-13-[4-(2-Bromo-5-chlorophenyl)-6-oxo-1,2,3,6-tetrahydropyridin-1-yl]-3-(difluoromethyl)-9-methyl-3,4,7,15-tetraazatricyclo[12.3.1.0²,⁶]octadeca-1(18),2(6),4,14,16-pentaen-8-one (35 mg, 47%) was prepared in a similar manner to Example 1 by using 1-(6-bromo-3-chloro-2-fluorophenyl)prop-2-en-1-one and 1-(difluoromethyl)-4-nitro-1H-pyrazole. MS(ESI) m/z: 604.2 (M+H) and 606.2 (M+2+H).

19B. Preparation of 4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,2,3,6-tetrahydropyridin-4-yl}benzonitrile 4-Chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,2,3,6-tetrahydropyridin-4-yl}benzonitrile was prepared from (9R,13S)-13-[4-(2-bromo-5-chlorophenyl)-6-oxo-1,2,3,6-tetrahydropyridin-1-yl]-3-(difluoromethyl)-9-methyl-3,4,7,15-tetraazatricyclo[12.3.1.0²,⁶]octadeca-1(18),2(6),4,14,16-pentaen-8-one in a similar manner to the procedures described in Example 1 to yield 4-chloro-2-{1-[(9R,13S)-3-(difluoromethyl)-9-methyl-8-oxo-3,4,7,15-tetraazatricyclo[12.3.1.0²,⁶]octadeca-1(18),2(6),4,14,16-pentaen-13-yl]-6-oxo-1,2,3,6-tetrahydropyridin-4-yl}benzonitrile (9 mg, 26%). MS(ESI) m/z: 551.3 (M+H). ¹H NMR (400 MHz, CD₃CN) δ 8.80 (d, J=5.5 Hz, 1H), 7.85-7.71 (m, 4H), 7.71-7.36 (m, 4H), 6.20 (s, 1H), 5.53 (dd, J=12.7, 4.3 Hz, 1H), 3.95-3.83 (m, 1H), 3.82-3.72 (m, 1H), 2.81 (t, J=6.6 Hz, 2H), 2.56 (td, J=7.2, 3.1 Hz, 1H), 2.28 (dd, J=6.4, 3.5 Hz, 1H), 1.95-1.85 (m, 2H), 1.65-1.51 (m, 1H), 1.41-1.21 (m, 2H), 1.06-0.98 (m, 3H), 0.96-0.74 (m, 2H). Analytical HPLC (Method A): RT=8.24 min, purity=96%; Factor XIa Ki=1.4 nM, Plasma Kallikrein Ki=10 nM.

Example 20

Preparation of (9S,13S)-13-{4-[3-chloro-2-fluoro-6-(trifluoromethyl)phenyl]-6-oxo-1,2,3,6-tetrahydropyridin-1-yl}-10-fluoro-3,9-dimethyl-3,4,7,15-tetraazatricyclo[12.3.1.0²,⁶]octadeca-1(18),2(6),4,14,16-pentaen-8-one

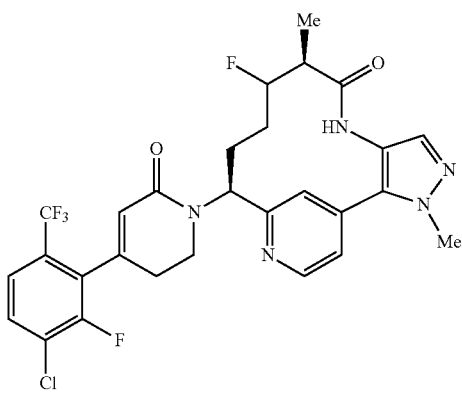

(9S,13S)-13-{4-[3-Chloro-2-fluoro-6-(trifluoromethyl)phenyl]-6-oxo-1,2,3,6-tetrahydropyridin-1-yl}-10-fluoro-3,9-dimethyl-3,4,7,15-tetraazatricyclo[12.3.1.0²,⁶]octadeca-1(18),2(6),4,14,16-pentaen-8-one trifluoroacetate (0.0144 g, 66%) was prepared according to the procedures described in Example 13, by replacing 1-(5-chloro-2-(4-chloro-1H-1,2,3-triazol-1-yl)phenyl)prop-2-en-1-one with 1-(3-chloro-2-fluoro-6-(trifluoromethyl)phenyl)prop-2-en-1-one, intermediate 2. MS(ESI) m/z: 594.2 (M+H). ¹H NMR (400 MHz, CD₃OD) δ 8.76 (d, J=5.3 Hz, 1H), 7.73-7.66 (m, 1H), 7.60 (d, J=8.6 Hz, 1H), 7.55-7.44 (m, 3H), 5.93 (s, 1H), 5.79 (dd, J=12.7, 5.4 Hz, 1H), 5.33-5.14 (m, 1H), 4.49-4.38 (m, 1H), 4.03 (s, 3H), 3.97-3.87 (m, 1H), 3.15-3.05 (m, 1H), 2.90-2.49 (m, 2H), 2.30-2.19 (m, 1H), 2.13-2.00 (m, 1H), 1.77-1.59 (m, 1H), 0.96 (d, J=6.8 Hz, 3H), 0.67-0.45 (m, 1H). Analytical HPLC (Method A): RT=8.39 min, purity=>98%; Factor XIa Ki=1.4 nM, Plasma Kallikrein Ki=40 nM.

Example 21

Preparation of (9R,13S)-13-{4-[3-chloro-6-(difluoromethoxy)-2-fluorophenyl]-6-oxo-1,2,3,6-tetrahydropyridin-1-yl}-3-(difluoromethyl)-9-methyl-3,4,7,15-tetraazatricyclo[12.3.1.0²,⁶]octadeca-1(18),2(6),4,14,16-pentaen-8-one

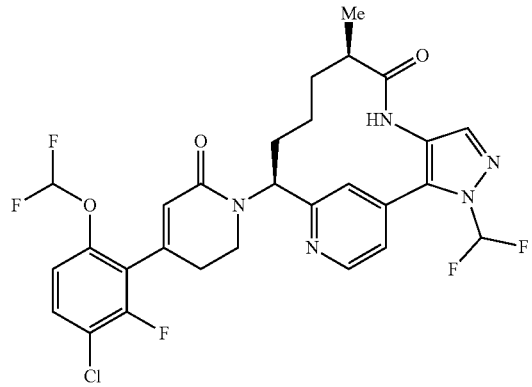 [SMILES: C[C@@H]1CCC[C@H](N2CCC(c3c(OC(F)F)ccc(Cl)c3F)=CC2=O)c2cc(ccn2)-c2c(cnn2C(F)F)NC1=O]

(9R,13S)-13-{4-[3-Chloro-6-(difluoromethoxy)-2-fluorophenyl]-6-oxo-1,2,3,6-tetrahydropyridin-1-yl}-3-(difluoromethyl)-9-methyl-3,4,7,15-tetraazatricyclo[12.3.1.0²,⁶]octadeca-1(18),2(6),4,14,16-pentaen-8-one (28 mg, 79%) was prepared in a similar manner to Example 1 by using 1-(difluoromethyl)-4-nitro-1H-pyrazole, Intermediate 14, and 1-(3-chloro-6-(difluoromethoxy)-2-fluorophenyl)prop-2-en-1-one, Intermediate 16. MS(ESI) m/z: 610.3 (M+H). ¹H NMR (500 MHz, CD₃OD) δ 8.85-8.74 (m, 1H), 7.79 (s, 1H), 7.69 (s, 2H), 7.65-7.51 (m, 2H), 7.16-7.09 (m, 1H), 6.92 (s, 1H), 6.03 (s, 1H), 5.69-5.60 (m, 1H), 3.93-3.81 (m, 1H), 3.80-3.69 (m, 1H), 2.75-2.57 (m, 3H), 2.33-2.16 (m, 1H), 2.06-1.87 (m, 2H), 1.72-1.53 (m, 1H), 1.41-1.19 (m, 2H), 1.09 (d, J=6.9 Hz, 3H), 0.95-0.83 (m, 1H). Analytical HPLC (Method A): RT=9.60 min, purity=99%; Factor XIa Ki=0.69 nM, Plasma Kallikrein Ki=40 nM.

Example 22

Preparation of (9R,13S)-13-[4-(3-chloro-2,6-difluorophenyl)-6-oxo-1,2,3,6-tetrahydropyridin-1-yl]-3-(difluoromethyl)-9-methyl-3,4,7,15-tetraazatricyclo[12.3.1.0$^{2,6}$]octadeca-1(18),2(6),4,14,16-pentaen-8-one

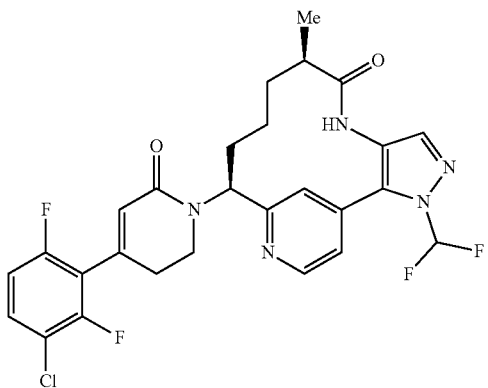 [SMILES: C[C@@H]1CCC[C@H](N2CCC(c3c(F)ccc(Cl)c3F)=CC2=O)c2cc(ccn2)-c2c(cnn2C(F)F)NC1=O]

(9R,13S)-13-[4-(3-Chloro-2,6-difluorophenyl)-6-oxo-1,2,3,6-tetrahydropyridin-1-yl]-3-(difluoromethyl)-9-methyl-3,4,7,15-tetraazatricyclo[12.3.1.0$^{2,6}$]octadeca-1(18),2(6),4,14,16-pentaen-8-one (22 mg, 54%). was prepared in a similar manner to Example 1 by using 1-(difluoromethyl)-4-nitro-1H-pyrazole, Intermediate 14, and 1-(3-chloro-2,6-difluorophenyl)prop-2-en-1-one, Intermediate 1. MS(ESI) m/z: 562.3 (M+H). $^1$H NMR (400 MHz, CD$_3$CN) δ 8.78 (d, J=5.3 Hz, 1H), 7.73 (s, 1H), 7.65 (s, 1H), 7.53 (s, 2H), 7.15-7.01 (m, 1H), 6.08 (s, 1H), 5.67-5.55 (m, 1H), 3.93-3.80 (m, 1H), 3.80-3.66 (m, 1H), 2.67 (s, 2H), 2.62-2.47 (m, 2H), 2.30-2.17 (m, 1H), 1.66-1.47 (m, 1H), 1.41-1.16 (m, 2H), 1.02 (d, J=6.8 Hz, 3H), 0.91-0.69 (m, 1H). Analytical HPLC (Method A): RT=9.03 min, purity=98%; Factor XIa Ki=8 nM, Plasma Kallikrein Ki=50 nM.

Example 23

Preparation of (9R,13S)-13-{4-[3-chloro-6-(difluoromethoxy)-2-fluorophenyl]-6-oxo-1,2,3,6-tetrahydropyridin-1-yl}-3,9-dimethyl-3,4,7,15-tetraazatricyclo[12.3.1.0$^{2,6}$]octadeca-1(18),2(6),4,14,16-pentaen-8-one

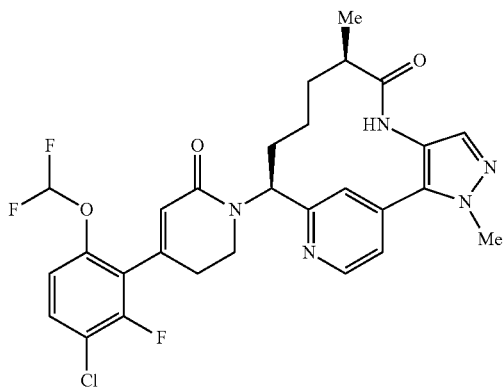 [SMILES: C[C@@H]1CCC[C@H](N2CCC(c3c(OC(F)F)ccc(Cl)c3F)=CC2=O)c2cc(ccn2)-c2c(cnn2C)NC1=O]

(9R,13S)-13-{4-[3-Chloro-6-(difluoromethoxy)-2-fluorophenyl]-6-oxo-1,2,3,6-tetrahydropyridin-1-yl}-3,9-dimethyl-3,4,7,15-tetraazatricyclo[12.3.1.0$^{2,6}$]octadeca-1(18),2(6),4,14,16-pentaen-8-one trifluoroacetate (21 mg, 0.025 mmol, 31% yield) was prepared according to the procedures described in Example 1 by substituting 1-(5-chloro-2-(1H-1,2,3-triazol-1-yl)phenyl)prop-2-en-1-one with 1-[3-chloro-6-(difluoromethoxy)-2-fluorophenyl]prop-2-en-1-one, Intermediate 16. $^1$H NMR (400 MHz, CD$_3$OD) δ 8.80 (d, J=5.5 Hz, 1H), 7.83 (s, 1H), 7.79 (dd, J=5.6, 1.4 Hz, 1H), 7.57-7.48 (m, 2H), 7.13-7.05 (m, 1H), 6.89 (s, 1H), 6.71 (s, 1H), 6.00 (s, 1H), 5.53 (dd, J=12.5, 3.7 Hz, 1H), 4.08 (s, 3H), 3.67 (t, J=6.9 Hz, 2H), 2.76-2.50 (m, 3H), 2.34-2.18 (m, 1H), 2.08-1.88 (m, 2H), 1.69-1.53 (m, 1H), 1.21 (br. s., 2H), 1.09 (d, J=6.8 Hz, 3H). MS(ESI) m/z: 574.3 [M+H]$^+$. Analytical HPLC (Method A): RT=7.63 min, purity=>95.0%; Factor XIa Ki=0.92 nM, Plasma Kallikrein Ki=7 nM.

Example 24

Preparation of (9R,13S)-13-[4-(3,6-dichloro-2-fluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one

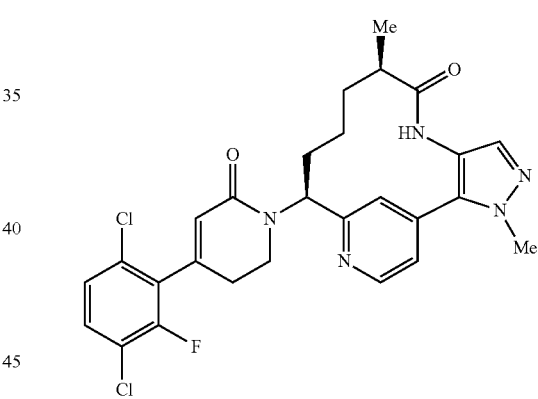

(9R,13S)-13-[4-(3,6-Dichloro-2-fluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one trifluoroacetate (0.016 g, 61% yield) was prepared in a similar manner as the procedure described in Example 2, by replacing 1-(3-chloro-2,6-difluorophenyl)prop-2-en-1-one with 1-(3,6-dichloro-2-fluorophenyl)prop-2-en-1-one (0.032 g, 0.039 mmol), prepared as described in Example 31A. MS(ESI) m/z: 542.2 (M+H)$^+$. $^1$H NMR (400 MHz, CD$_3$OD) d 8.79 (d, J=5.5 Hz, 1H), 7.77 (s, 1H), 7.71 (dd, J=5.4, 1.7 Hz, 1H), 7.54-7.47 (m, 2H), 7.34 (dd, J=8.7, 1.7 Hz, 1H), 5.98 (t, J=1.3 Hz, 1H), 5.58 (dd, J=12.5, 4.0 Hz, 1H), 4.08 (s, 3H), 3.74 (t, J=7.0 Hz, 2H), 2.73-2.53 (m, 3H), 2.31-2.19 (m, 1H), 2.04-1.91 (m, 2H), 1.67-1.55 (m, 1H), 1.28-1.14 (m, 2H), 1.09 (d, J=6.8 Hz, 3H). Analytical HPLC (Method A): RT=7.36 min, 99.5% purity; Factor XIa Ki=2.7 nM, Plasma Kallikrein Ki=6 nM.

Example 25

Preparation of (9S,13S)-13-{4-[5-chloro-2-(4-chloro-1H-1,2,3-triazol-1-yl)phenyl]-6-oxo-1,2,3,6-tetrahydropyridin-1-yl}-3-methyl-9-(propan-2-yl)-3,4,7,15-tetraazatricyclo[12.3.1.0$^{2,6}$]octadeca-1(18),2(6),4,14,16-pentaen-8-one

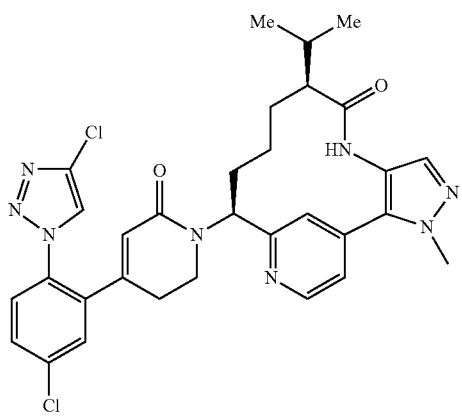 [SMILES: CC(C)[C@@H]1CCC[C@H](N2CCC(c3cc(Cl)ccc3-n3cc(Cl)nn3)=CC2=O)c2cc(ccn2)-c2c(cnn2C)NC1=O]

25A. Preparation of 2-isopropylbut-3-enoic Acid

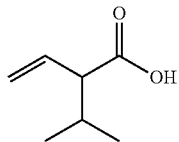

To a flame-dry RBF was added 2 M DIA in THF (3.64 ml, 25.6 mmol) and THF (58.1 ml). The reaction was cooled to −78° C. and 1.6 M nBuLi in hexanes (15.97 ml, 25.6 mmol) was added. The reaction was stirred at −78° C. for 30 min and but-3-enoic acid (0.990 ml, 11.62 mmol) was added and the reaction was stirred for additional 30 min. Then at −78° C. iPrI (1.739 ml, 17.42 mmol) was added and the reaction was slowly warmed to rt over 2 h and then stirred at rt overnight. The reaction was quenched with sat aq NH$_4$Cl (15 ml) and then the pH of the solution was adjusted to <4 using 1 N HCl. The reaction was extracted with EtOAc (3×30 mL). The combined EtOAc layer was washed with brine (40 mL) and dried over MgSO$_4$, filtered and concentrated. The residue was purified using ISCO system (0-50% EtOAc/Hex gradient) to give 2-isopropylbut-3-enoic acid (800 mg, 6.24 mmol, 53.7% yield) as a clear liquid. $^1$H NMR (400 MHz, CDCl$_3$) δ 5.98-5.65 (m, 1H), 5.33-5.05 (m, 2H), 2.73 (t, J=8.8 Hz, 1H), 2.08-1.95 (m, 1H), 1.09-0.74 (m, 6H).

25B. Preparation of tert-butyl ((1S-[1-(4-{1-methyl-4-[2-(propan-2-yl)but-3-enamido]-1H-pyrazol-5-yl}pyridin-2-yl)but-3-en-1-yl]carbamate

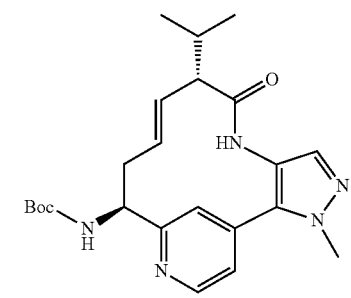

To a RBF was added (S)-tert-butyl (1-(4-(4-amino-1-methyl-1H-pyrazol-5-yl)pyridin-2-yl)but-3-en-1-yl)carbamate, prepared as described in Example 1F, (765 mg, 2.228 mmol), EtOAc (20 mL), 2-isopropylbut-3-enoic acid (286 mg, 2.228 mmol), and pyridine (0.540 mL, 6.68 mmol). The solution was cooled in a brine/ice bath and 50% T3PR (1.989 mL, 3.34 mmol) was added. The reaction was stirred at 0° C. for 10 min and then at rt for 60 min. The reaction was diluted with EtOAc (30 mL) and washed with sat NaHCO$_3$ (20 mL), water (30 mL) and brine (30 mL). The organic layer was separated, dried over MgSO$_4$, filtered and concentrated. The residue was purified using ISCO system (0-100% EtOAc/Hex gradient) to give tert-butyl ((1S)-1-(4-(4-(2-isopropylbut-3-enamido)-1-methyl-1H-pyrazol-5-yl)pyridin-2-yl)but-3-en-1-yl)carbamate (850 mg, 1.874 mmol, 84% yield) as diastereomer mixture as a yellow solid. MS(ESI) m/z: 454.2 (M+H)$^+$.

25C1 and 25C2. Preparation of tert-butyl N-[(9S,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate, and tert-Butyl N-[(9R,10E,13S)-3-methyl-8-oxo-9-(propan-2-yl)-3,4,7,15 tetraazatricyclo[12.3.1.0$^{2,6}$]octadeca-1(18),2(6),4,10,14,16-hexaen-13-yl]carbamate

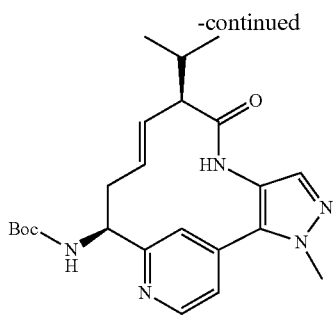

To a microwave vial was added tert-butyl ((1S)-1-(4-(4-(2-isopropylbut-3-enamido)-1-methyl-1H-pyrazol-5-yl)pyridin-2-yl)but-3-en-1-yl)carbamate (250 mg, 0.551 mmol) and DCE (15 mL). The reaction was purged with Ar for 1 min, then Second Generation Grubbs Catalyst (187 mg, 0.220 mmol) was added. The reaction was sealed and heated at microwave at 120° C. for 60 min. The reaction was then concentrated and the residue was purified using reverse phase preparative HPLC to give tert-butyl N-[(9S,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate trifluoroacetate, 25C1, (50 mg, 0.093 mmol, 16.8% yield), (ESI) m/z: 426.2 (M+H)$^+$, which has shorter retention time and tert-butyl N-[(9R,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen- 13-yl]carbamate trifluoroacetate 25C2, (50 mg, 0.093 mmol, 16.8% yield), MS(ESI) m/z: 426.2 (M+H)$^+$ which has longer retention time.

25D. Preparation of tert-butyl N-[(9S,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate

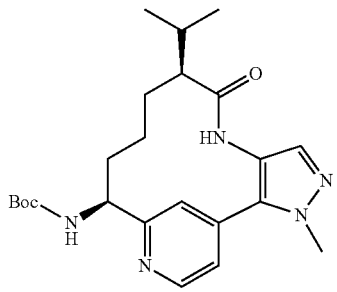 [SMILES: CC(C)[C@@H]1CCC[C@H](NC(=O)OC(C)(C)C)c2cc(ccn2)-c2c(cnn2C)NC1=O]

To a 3-neck RBF was added tert-butyl N-[(9R,10E,13S)-3-methyl-8-oxo-9-(propan-2-yl)-3,4,7,15-tetraazatricyclo[12.3.1.0$^{2,6}$]octadeca-1(18),2(6),4,10,14,16-hexaen-13-yl]carbamate trifluoroacetate (25C2) (15 mg, 0.028 mmol), EtOH (3 mL) and PtO$_2$ (3.16 mg, 0.014 mmol). The reaction was stirred under a H$_2$ atmosphere (balloon pressure) for 1 h. The reaction was filtered through CELITE® and the filtrate was concentrated to give tert-butyl N-[(9S,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate (10 mg, 0.023 mmol, 84% yield) as a brown solid. MS(ESI) m/z: 618.2 (M+H)$^+$.

25E. Preparation of (9S,13S)-13-amino-3-methyl-9-(propan-2-yl)-3,4,7,15-tetraazatricyclo[12.3.1.0$^{2,6}$]octadeca-1(18),2(6),4,14,16-pentaen-8-one

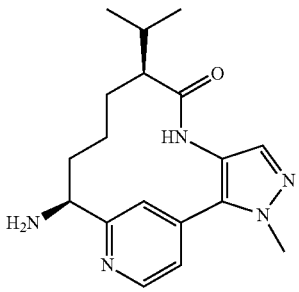 [SMILES: CC(C)[C@@H]1CCC[C@H](N)c2cc(ccn2)-c2c(cnn2C)NC1=O]

To a RBF was added tert-butyl N-[(9S,13S)-3-methyl-8-oxo-9-(propan-2-yl)-3,4,7,15-tetraazatricyclo[12.3.1.0$^{2,6}$]octadeca-1(18),2(6),4,14,16-pentaen-13-yl]carbamate (20 mg, 0.047 mmol), dioxane (3 mL), 4 N HCl in dioxane (0.142 mL, 4.68 mmol) and MeOH (0.5 mL). The reaction was stirred at rt for 5 min. The reaction was concentrated and the residue was purified using reverse phase preparative HPLC to give (9S,13S)-13-amino-3-methyl-9-(propan-2-yl)-3,4,7,15-tetraazatricyclo[12.3.1.0$^{2,6}$]octadeca-1(18),2(6),4,14,16-pentaen-8-one hydrochloride. The product was added to a pre-rinsed Agilent StratoSpheres SPE PL-HCO$_3$ MP Resin cartridge. Gravity filtration, eluting with MeOH, gave a clear, slightly brown filtrate. Concentration provided (9S,13S)-13-amino-3-methyl-9-(propan-2-yl)-3,4,7,15-tetraazatricyclo[12.3.1.0$^{2,6}$]octadeca-1(18),2(6),4,14,16-pentaen-8-one (1.5 mg, 3.43 μmol, 7.34% yield) as a beige solid. MS(ESI) m/z: 328.2 (M+H)$^+$.

25F. Preparation of (9S,13S)-13-{4-[5-chloro-2-(4-chloro-1H-1,2,3-triazol-1-yl)phenyl]-6-oxo-1,2,3,6-tetrahydropyridin-1-yl}-3-methyl-9-(propan-2-yl)-3,4,7,15-tetraazatricyclo[12.3.1.0$^{2,6}$]octadeca-1(18),2(6),4,14,16-pentaen-8-one (9S,13S)-13-{4-[5-Chloro-2-(4-chloro-1H-1,2,3-triazol-1-yl)phenyl]-6-oxo-1,2,3,6-tetrahydropyridin-1-yl}-3-methyl-9-(propan-2-yl)-3,4,7,15-tetraazatricyclo[12.3.1.0$^{2,6}$]octadeca-1(18),2(6),4,14,16-pentaen-8-one was prepared according to the procedures described in Example 1 by using 1-(5-chloro-2-(4-chloro-1H-1,2,3-triazol-1-yl)phenyl)prop-2-en-1-one, Intermediate 4, and (9R,13S)-13-amino-3-methyl-9-(propan-2-yl)-3,4,7,15-tetraazatricyclo[12.3.1.0$^{2,6}$]octadeca-1(18),2(6),4,14,16-pentaen-8-one. $^1$H NMR (400 MHz, CD$_3$OD) δ 8.79 (d, J=5.3 Hz, 1H), 8.47 (s, 1H), 7.78 (s, 1H), 7.74 (dd, J=5.4, 1.2 Hz, 1H), 7.68-7.57 (m, 3H), 7.53 (s, 1H), 5.85 (s, 1H), 5.50 (dd, J=12.5, 3.5 Hz, 1H), 4.10 (s, 3H), 3.55-3.40 (m, 2H), 2.30-2.13 (m, 3H), 2.10-1.90 (m, 3H), 1.79 (dt, J=9.2, 6.6 Hz, 1H), 1.61 (d, J=6.6 Hz, 1H), 1.35 (d, J=3.1 Hz, 1H), 1.19-1.09 (m, 1H), 0.99 (dd, J=6.6, 4.2 Hz, 6H). MS(ESI) m/z: 619.2 (M+H). Analytical HPLC (Method A): RT=6.67 min, purity=98%; Factor XIa Ki=0.47 nM, Plasma Kallikrein Ki=16 nM.

Example 26

Preparation of (9R,13S)-13-{4-[3-chloro-6-(difluoromethyl)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one

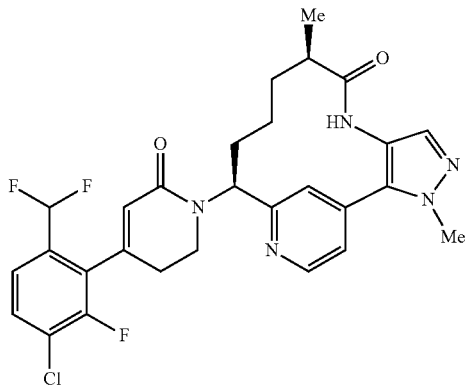 [SMILES: C[C@@H]1CCC[C@H](N2CCC(c3c(C(F)F)ccc(Cl)c3F)=CC2=O)c2cc(ccn2)-c2c(cnn2C)NC1=O]

26A. Preparation of 3-chloro-6-(difluoromethyl)-2-fluorobenzaldehyde

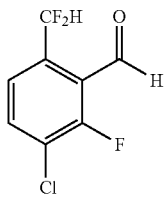

To a solution of 1-chloro-4-(difluoromethyl)-2-fluorobenzene (373 mg, 2.066 mmol) in THF (6 mL) at −78° C. was added LDA in THF/heptane/ethylbenzene (1.240 mL, 2.479 mmol) dropwise. After continuing to stir at the same temp for 20 min, DMF (0.191 mL, 2.479 mmol) was added and stirred at the same temperature for 10 min. AcOH (0.473 mL, 8.26 mmol) was added followed by water (30 mL). The reaction was extracted with EtOAc (30 ml). The EtOAc layer was washed with water (15 ml) and brine (15 ml), dried over MgSO₄, filtered and concentrated. The residue was purified using ISCO system (0-30% EtOAc/Hex gradient) to give 3-chloro-6-(difluoromethyl)-2-fluorobenzaldehyde (400 mg, 1.918 mmol, 93% yield) as a light yellow liquid. ¹H NMR (400 MHz, CD₃OD) δ 10.48 (s, 1H), 7.80-7.72 (m, 1H), 7.62 (d, J=8.4 Hz, 1H), 7.56-7.27 (t, 1H).

26B. Preparation of 1-(3-chloro-6-(difluoromethyl)-2-fluorophenyl)prop-2-en-1-one

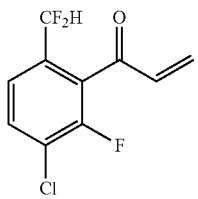

1-(3-Chloro-6-(difluoromethyl)-2-fluorophenyl)prop-2-en-1-one was prepared using a procedure analogous to that used for the preparation of Intermediate 1 by replacing 3-chloro-2,6-difluorobenzaldehyde with 3-chloro-6-(difluoromethyl)-2-fluorobenzaldehyde. ¹H NMR (400 MHz, CDCl₃) δ 7.64-7.55 (m, 1H), 7.47 (d, J=8.4 Hz, 1H), 6.95-6.57 (m, 2H), 6.24-6.05 (m, 2H).

26C. Preparation of (9R,13S)-13-{4-[3-chloro-6-(difluoromethyl)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one (9R,13S)-13-{4-[3-Chloro-6-(difluoromethyl)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one was prepared according to the procedures described in Example 1 by substituting, 1-(5-chloro-2-(1H-1,2,3-triazol-1-yl)phenyl)prop-2-en-1-one with 1-(3-chloro-6-(difluoromethyl)-2-fluorophenyl)prop-2-en-1-one. ¹H NMR (400 MHz, CD₃OD-d₄) δ 8.81 (d, J=5.3 Hz, 1H), 7.77 (s, 1H), 7.72 (dd, J=5.3, 1.5 Hz, 1H), 7.68 (t, J=7.8 Hz, 1H), 7.57-7.49 (m, 2H), 7.03-6.70 (m, 1H), 5.99 (s, 1H), 5.61 (dd, J=12.7, 3.9 Hz, 1H), 4.10 (s, 3H), 3.75 (t, J=6.8 Hz, 2H), 2.72-2.54 (m, 3H), 2.32-2.19 (m, 1H), 2.08-1.92 (m, 2H), 1.64 (dd, J=14.5, 8.8 Hz, 1H), 1.23 (br. s., 2H), 1.12 (d, J=6.8 Hz, 3H). MS(ESI) m/z: 558.1 (M+H). Analytical HPLC (Method A): RT=7.13 min, purity=98%; Factor XIa Ki=0.48 nM, Plasma Kallikrein Ki=5 nM.

Example 27

Preparation of (9R,13S)-13-{4-[3-chloro-6-(difluoromethoxy)-2-fluorophenyl]-2-oxo-1,2-dihydropyridin-1-yl}-3,9-dimethyl-3,4,7,15-tetraazatricyclo[12.3.1.0²,⁶]octadeca-1(18),2(6),4,14,16-pentaen-8-one trifluoroacetate

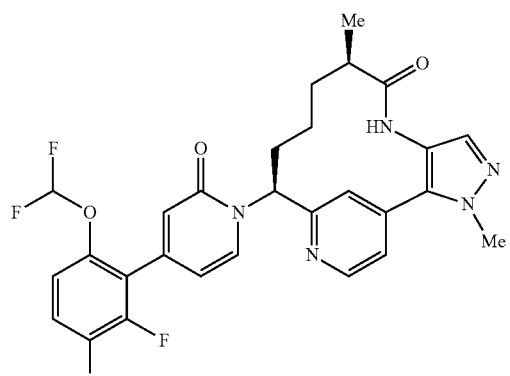

To a sealed tube containing (9R,13S)-13-{4-[3-chloro-6-(difluoromethoxy)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one, prepared as described in Example 23, (21 mg, 0.037 mmol), CuI (6.97 mg, 0.037 mmol) in DMSO (1 mL) was added 3-iodopyridine (15.00 mg, 0.073 mmol) and Cs₂CO₃ (47.7 mg, 0.146 mmol). The reaction mixture was purged with Ar (3×), then stirred at 95° C. overnight. The reaction mixture was concentrated and purified using prep-HPLC to give (9R,13S)-13-{4-[3-chloro-6-(difluoromethoxy)-2-fluorophenyl]-2-oxo-1,2-dihydropyridin-1-yl}-3,9-dimethyl-3,4, 7,15-tetraazatricyclo[12.3.1.0$^{2,6}$]octadeca-1(18),2(6),4,14,16-pentaen-8-one trifluoroacetate (1.4 mg, 1.898 μmol, 5.19% yield) as a clear film. $^1$H NMR (400 MHz, CD$_3$OD) δ 8.75 (d, J=5.1 Hz, 1H), 7.76 (s, 1H), 7.67-7.59 (m, 1H), 7.56-7.52 (m, 2H), 7.50 (dd, J=8.4, 2.2 Hz, 1H), 7.19 (d, J=9.0 Hz, 1H), 7.09-6.68 (m, 1H), 6.61 (s, 1H), 6.48 (d, J=7.7 Hz, 1H), 6.18 (dd, J=12.9, 4.3 Hz, 1H), 4.08 (s, 3H), 2.79-2.66 (m, 1H), 2.39-2.28 (m, 1H), 2.18-2.01 (m, 2H), 1.71-1.60 (m, 1H), 1.47 (br. s., 1H), 1.06 (d, J=6.8 Hz, 3H), 0.83 (br. s., 1H). MS(ESI) m/z: 572.2 (M+H)$^+$. Analytical HPLC (Method A): RT=11.21 min, purity=93%; Factor XIa Ki=4.9 nM, Plasma Kallikrein Ki=40 nM.

Example 28

Preparation of (9S,13S)-13-{4-[3-chloro-2-fluoro-6-(trifluoromethyl)phenyl]-2-oxo-1,2-dihydropyridin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate

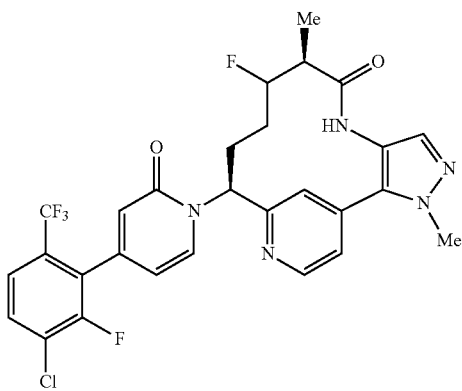 [SMILES: C[C@H]1C(=O)Nc2cnn(C)c2-c2ccnc(c2)[C@@H](n2ccc(-c3c(C(F)(F)F)ccc(Cl)c3F)cc2=O)CCC1F]

A reaction vial containing (9S,13S)-13-{4-[3-chloro-2-fluoro-6-(trifluoromethyl)phenyl]-6-oxo-1,2,3,6-tetrahydropyridin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate, prepared as described in Example 20, (0.010 g, 0.014 mmol), 3-iodopyridine (0.020 g, 0.098 mmol), CuI (0.008 g, 0.042 mmol), Cs$_2$CO$_3$ (0.023 g, 0.071 mmol) in DMSO (2 mL) was capped and heated at 100° C. for 16 h. After this time, the reaction was cooled to rt. The reaction mixture was filtered, and concentrated. Purification by reverse phase chromatography afforded (9S,13S)-13-{4-[3-chloro-2-fluoro-6-(trifluoromethyl)phenyl]-2-oxo-1,2-dihydropyridin-1-yl}-10-fluoro-3,9-dimethyl-3,4,7,15-tetraazatricyclo[12.3.1.0$^{2,6}$]octadeca-1(18),2(6),4,14,16-pentaen-8-one trifluoroacetate (0.0012 g, 11%) as a beige solid. MS(ESI) m/z: 592.4 (M+H). $^1$H NMR (400 MHz, CD$_3$OD) δ 8.81 (d, J=5.1 Hz, 1H), 8.66 (br. s., 1H), 7.85-7.77 (m, 1H), 7.70 (d, J=8.8 Hz, 1H), 7.59 (s, 1H), 7.53 (s, 1H), 7.50 (dd, J=5.1, 1.5 Hz, 1H), 6.56 (s, 1H), 6.51 (d, J=7.3 Hz, 1H), 5.49-5.29 (m, 1H), 4.07 (s, 3H), 3.25-3.13 (m, 1H), 2.44-2.19 (m, 2H), 1.91-1.70 (m, 1H), 1.43-1.28 (m, 1H), 1.02 (d, J=7.0 Hz, 3H), 0.76-0.52 (m, 1H). Analytical HPLC (Method A): RT=8.26 min, purity=>92%; Factor XIa Ki=3 nM, Plasma Kallikrein Ki=25 nM.

Example 29

Preparation of (9R,13S)-13-{4-[3-chloro-6-(difluoromethyl)-2-fluorophenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one

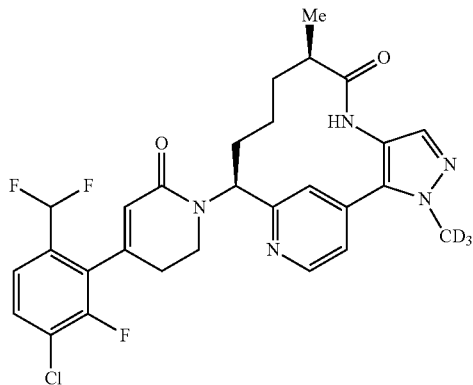 [SMILES: [2H]C([2H])([2H])n1ncc2c1-c1ccnc(c1)[C@@H](N1CCC(c3c(C(F)F)ccc(Cl)c3F)=CC1=O)CCC[C@@H](C)C(=O)N2]

(9R,13S)-13-{4-[3-Chloro-6-(difluoromethyl)-2-fluorophenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate (18 mg, 43%) was prepared similar to procedures described in Example 1 by using (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one, prepared as described in Example 17G and 1-(3-chloro-6-(difluoromethyl)-2-fluorophenyl)prop-2-en-1-one, prepared as described for Example 26. MS(ESI) m/z: 561.2 (M+H)$^+$. $^1$H NMR (400 MHz, CD$_3$OD) δ 8.82 (br. s., 1H), 7.76 (br. s., 1H), 7.71-7.66 (m, 2H), 7.56-7.52 (m, 2H), 7.04-6.82 (m, 1H), 6.00 (s, 1H), 5.63 (d, J=10.3 Hz, 1H), 3.76 (t, J=6.9 Hz, 2H), 2.69-2.59 (m, 3H), 2.29-2.22 (m, 1H), 2.03-1.97 (m, 2H), 1.69-1.61 (m, 1H), 1.24 (d, J=4.2 Hz, 1H), 1.12 (d, J=6.8 Hz, 3H). Analytical HPLC (Method A): RT=6.93 min, purity=95%; Factor XIa Ki=0.6 nM, Plasma Kallikrein Ki=6 nM.

Example 30

Preparation of (9R,13S)-13-{4-[3-chloro-6-(difluoromethoxy)-2-fluorophenyl]-6-oxo-1,2,3,6-tetrahydropyridin-1-yl}-3-($^2$H$_3$)methyl-9-methyl-3,4,7,15-tetraazatricyclo[12.3.1.0$^{2,6}$]octadeca-1(18),2(6),4,14,16-pentaen-8-one

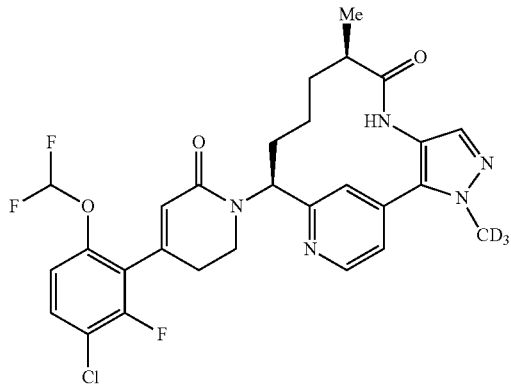 [SMILES: [2H]C([2H])([2H])n1ncc2c1-c1ccnc(c1)[C@@H](N1CCC(c3c(OC(F)F)ccc(Cl)c3F)=CC1=O)CCC[C@@H](C)C(=O)N2]

(9R,13S)-13-{4-[3-Chloro-6-(difluoromethoxy)-2-fluorophenyl]-6-oxo-1,2,3,6-tetrahydropyridin-1-yl}-3-($^2H_3$)methyl-9-methyl-3,4,7,15-tetraazatricyclo[12.3.1.0$^{2,6}$]octadeca-1(18),2(6),4,14,16-pentaen-8-one trifluoroacetate (2.1 mg, 18%) was prepared similar to procedures described in Example 1 by using (9R,13S)-13-amino-3-($^2H_3$)methyl-9-methyl-3,4,7,15-tetraazatricyclo[12.3.1.0$^{2,6}$]octadeca-1(18),2(6),4,14,16-pentaen-8-one, prepared as described for Example 17G and 1-(3-chloro-6-(difluoromethoxy)-2-fluorophenyl)prop-2-en-1-one, Intermediate 16. MS(ESI) m/z: 577.3 (M+H)$^+$. $^1$H NMR (500 MHz, CD$_3$OD) d 7.61-7.54 (m, 2H), 7.15 (d, J=9.1 Hz, 1H), 7.10-6.78 (m, 2H), 6.06 (s, 1H), 5.71 (br. s., 1H), 3.85-3.73 (m, 2H), 2.71-2.60 (m, 3H), 2.27-2.21 (m, 1H), 2.04-1.95 (m, 2H), 1.65 (td, J=13.5, 8.3 Hz, 1H), 1.28 (d, J=9.9 Hz, 1H), 1.22-1.15 (m, 1H), 1.16-1.07 (m, 3H). Analytical HPLC (Method A): RT=9.98 min, purity=95%; Factor XIa Ki=1 nM, Plasma Kallikrein Ki=7 nM.

Example 31

Preparation of (9R,13S)-13-[4-(3,6-dichloro-2-fluorophenyl)-6-oxo-1,2,3,6-tetrahydropyridin-1-yl]-3-(difluoromethyl)-9-methyl-3,4,7,15-tetraazatricyclo[12.3.1.0$^{2,6}$]octadeca-1(18),2(6),4,14,16-pentaen-8-one

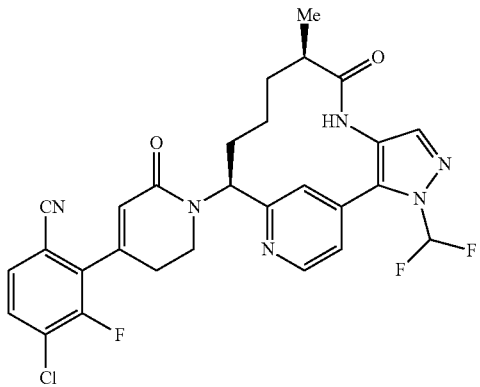 [SMILES: C[C@@H]1CCC[C@H](N2CCC(c3c(C#N)ccc(Cl)c3F)=CC2=O)c2cc(ccn2)-c2c(cnn2C(F)F)NC1=O]

31A. Preparation of 1-(3,6-dichloro-2-fluorophenyl)prop-2-en-1-one 1-(3,6-Dichloro-2-fluorophenyl)prop-2-en-1-one was prepared in a similar manner as the procedure described for the preparation of 1-(3-chloro-2,6-difluorophenyl) prop-2-en-1-one, Intermediate 1, by replacing 3-chloro-2,6-difluorobenzaldehyde, with 3,6-dichloro-2-fluorobenzaldehyde. MS(ESI) m/z: 219.0 (M+H)$^+$. $^1$H NMR (400 MHz, CDCl$_3$) δ 7.42 (t, J=8.1 Hz, 1H), 7.20 (dd, J=8.7, 1.4 Hz, 1H), 6.63 (dd, J=17.6, 10.6 Hz, 1H), 6.23 (d, J=10.3 Hz, 1H), 6.06 (d, J=17.6 Hz, 1H).

31B. Preparation of (9R,13S)-13-[4-(3,6-dichloro-2-fluorophenyl)-6-oxo-1,2,3,6-tetrahydropyridin-1-yl]-3-(difluoromethyl)-9-methyl-3,4,7,15-tetraazatricyclo[12.3.1.0$^{2,6}$]octadeca-1(18),2(6),4,14,16-pentaen-8-one trifluoroacetate (9R,13S)-13-[4-(3,6-Dichloro-2-fluorophenyl)-6-oxo-1,2,3,6-tetrahydropyridin-1-yl]-3-(difluoromethyl)-9-methyl-3,4,7,15-tetraazatricyclo[12.3.1.0$^{2,6}$]octadeca-1(18),2(6),4,14,16-pentaen-8-one (0.014 g, 81% yield) was prepared in a similar manner as the procedure described in Example 22, by replacing 1-(3-chloro-2,6-difluorophenyl) prop-2-en-1-one with 1-(3,6-dichloro-2-fluorophenyl)prop-2-en-1-one (8.94 mg, 0.041 mmol). MS(ESI) m/z: 578.1 (M+H)$^+$. $^1$H NMR (400 MHz, CD$_3$OD) δ 8.79 (d, J=5.1 Hz, 1H), 7.83-7.67 (m, 3H), 7.61 (d, J=4.8 Hz, 1H), 7.55-7.46 (m, 1H), 7.34 (dd, J=8.7, 1.7 Hz, 1H), 5.97 (s, 1H), 5.62 (dd, J=12.7, 3.9 Hz, 1H), 3.93-3.73 (m, 2H), 2.73-2.54 (m, 3H), 2.30-2.18 (m, 1H), 2.01-1.87 (m, 2H), 1.66-1.54 (m, 1H), 1.30-1.18 (m, 1H), 1.10-0.94 (m, 4H). Analytical HPLC (Method A): RT=8.75 min, 100% purity; Factor XIa Ki=1.9 nM, Plasma Kallikrein Ki=11 nM.

Example 32

Preparation of 4-chloro-2-{1-[(9R,13S)-3-($^2H_3$)methyl-9-methyl-8-oxo-3,4,7,15-tetraazatricyclo[12.3.1.0$^{2,6}$]octadeca-1(18),2(6),4,14,16-pentaen-13-yl]-6-oxo-1,2,3,6-tetrahydropyridin-4-yl}benzonitrile

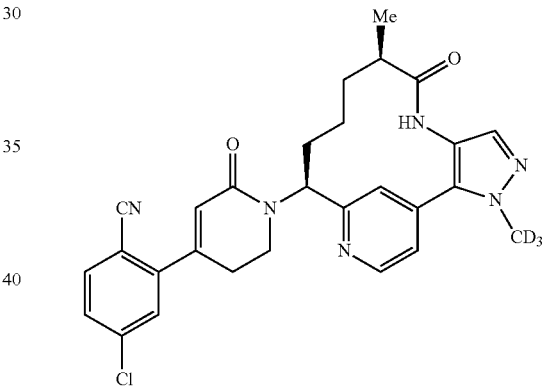

4-Chloro-2-{1-[(9R,13S)-3-($^2H_3$)methyl-9-methyl-8-oxo-3,4,7,15-tetraazatricyclo[12.3.1.0$^{2,6}$]octadeca-1(18),2(6),4,14,16-pentaen-13-yl]-6-oxo-1,2,3,6-tetrahydropyridin-4-yl}benzonitrile trifluoroacetate (2.1 mg, 18%) was prepared similar to procedures described in Example 1 by using (9R,13S)-13-amino-3-($^2H_3$)methyl-9-methyl-3,4,7,15-tetraazatricyclo[12.3.1.0$^{2,6}$]octadeca-1(18),2(6),4,14,16-pentaen-8-one, prepared as described in Example 17G, and 2-acryloyl-4-chlorobenzonitrile, prepared as describe in Example 19. MS(ESI) m/z: 518 (M+H)$^+$. $^1$H NMR: (400 MHz, CD$_3$OD) δ 8.80 (br. s., 1H), 7.84 (d, J=8.4 Hz, 1H), 7.76 (s, 1H), 7.71-7.66 (m, 2H), 7.62 (dd, J=8.3, 2.1 Hz, 1H), 7.56 (s, 1H), 6.25 (s, 1H), 5.63 (dd, J=12.4, 3.2 Hz, 1H), 3.84-3.74 (m, 2H), 2.89-2.82 (m, 2H), 2.65-2.57 (m, 1H), 2.32-2.21 (m, 1H), 2.06-1.96 (m, 2H), 1.69-1.60 (m, 1H), 1.12 (d, J=6.8 Hz, 3H). Analytical HPLC (Method A): RT=6.22 min, purity=98%; Factor XIa Ki=2.4 nM, Plasma Kallikrein Ki=4 nM.

Example 33

Preparation of (9R,13S)-13-{4-[3-chloro-6-(1,1-difluoroethyl)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one

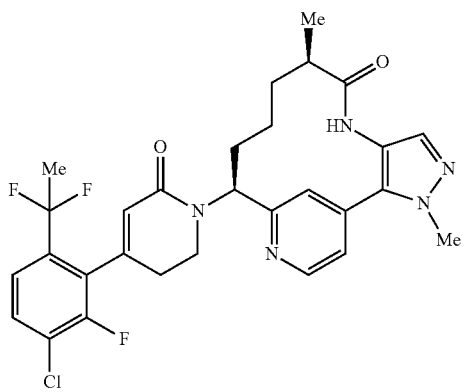 [SMILES: C[C@@H]1CCC[C@H](N2CCC(c3c(C(C)(F)F)ccc(Cl)c3F)=CC2=O)c2cc(ccn2)-c2c(cnn2C)NC1=O]

33A. Preparation of 1-chloro-4-(1,1-difluoroethyl)-2-fluorobenzene

To a tube was added 1-(4-chloro-3-fluorophenyl)ethanone (1 g, 5.79 mmol), $CH_2Cl_2$ (10 mL) and DAST (2.297 mL, 17.38 mmol). The reaction was then sealed and stirred at 45° C. for 8 h. The reaction was carefully quenched with cold sat aq $NaHCO_3$ over 30 min until the pH was >7. The organic layer was separated, washed with water (10 ml), dried over $MgSO_4$, filtered and concentrated. The residue was purified using ISCO system (0-10% EtOAC/Hex gradient) to give 1-chloro-4-(1,1-difluoroethyl)-2-fluorobenzene (30 mg, 0.154 mmol, 2.66% yield) as light brown liquid. $^1H$ NMR (400 MHz, $CDCl_3$) δ 7.49-7.42 (m, 1H), 7.32-7.27 (m, 1H), 7.25-7.20 (m, 1H), 1.90 (t, J=18.2 Hz, 3H).

33B. Preparation of 3-chloro-6-(1,1-difluoroethyl)-2-fluorobenzaldehyde

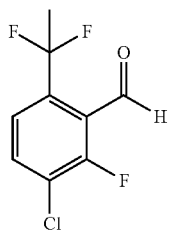

To a solution of 1-chloro-4-(1,1-difluoroethyl)-2-fluorobenzene (110 mg, 0.565 mmol) in THF (2 mL) at −78° C. was added LDA in THF/heptane/ethylbenzene (0.339 mL, 0.678 mmol) dropwise. The solution turned dark. After continuing to stir at the same temp for 20 min, DMF (0.052 mL, 0.678 mmol) was added and then the reaction was stirred at the same temperature for 10 min. AcOH (0.129 mL, 2.261 mmol) was added followed by water (30 mL). The reaction was extracted with EtOAc (30 ml). The EtOAc layer was washed with water (15 ml) and brine (15 ml), dried over $MgSO_4$, filtered and concentrated. The residue was purified using ISCO system (0-30% EtOAc/Hex) to give 3-chloro-6-(1,1-difluoroethyl)-2-fluorobenzaldehyde (100 mg, 0.449 mmol, 79% yield) as a light yellow liquid. $^1H$ NMR (400 MHz, $CDCl_3$) δ 10.45 (s, 1H), 7.63 (t, J=7.7 Hz, 1H), 7.45-7.31 (m, 1H), 2.08-2.00 (m, 3H).

33C. Preparation of 1-(3-chloro-6-(1,1-difluoroethyl)-2-fluorophenyl)prop-2-en-1-one

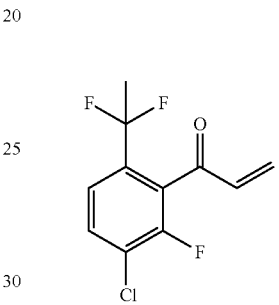

1-(3-Chloro-6-(1,1-difluoroethyl)-2-fluorophenyl)prop-2-en-1-one was prepared using a procedure analogous to that used for the preparation of Intermediate 1 by replacing 3-chloro-2,6-difluorobenzaldehyde with 3-chloro-6-(1,1-difluoroethyl)-2-fluorobenzaldehyde. $^1H$ NMR (400 MHz, $CDCl_3$) δ 7.52 (t, J=7.8 Hz, 1H), 7.29 (dd, J=8.4, 0.7 Hz, 1H), 6.64 (dd, J=17.6, 10.6 Hz, 1H), 6.22-6.16 (m, 1H), 6.03-5.94 (m, 1H), 1.91 (t, J=18.5 Hz, 3H).

33D. Preparation of (9R,13S)-13-{4-[3-chloro-6-(1,1-difluoroethyl)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one (9R,13S)-13-{4-[3-Chloro-6-(1,1-difluoroethyl)-2-fluorophenyl]-6-oxo-1,2,3,6-tetrahydropyridin-1-yl}-3,9-dimethyl-3,4,7,15-tetraazatricyclo[12.3.1.0²,⁶]octadeca-1(18),2(6),4,14,16-pentaen-8-one was prepared according to the procedures described in Example 1 by substituting 1-(5-chloro-2-(1H-1,2,3-triazol-1-yl)phenyl)prop-2-en-1-one with 1-(3-chloro-6-(1,1-difluoroethyl)-2-fluorophenyl)prop-2-en-1-one. $^1H$ NMR (400 MHz, $CD_3OD$-$d_4$) 8.81 (d, J=5.3 Hz, 1H), 7.77 (s, 1H), 7.71 (br. s., 1H), 7.65-7.58 (m, 1H), 7.57-7.52 (m, 1H), 7.45 (d, J=8.6 Hz, 1H), 5.92 (s, 1H), 5.61 (d, J=9.5 Hz, 1H), 4.10 (s, 3H), 3.79-3.67 (m, 2H), 2.71-2.58 (m, 3H), 2.25 (br. s., 1H), 2.06-1.87 (m, 5H), 1.71-1.56 (m, 1H), 1.22 (br. s., 2H), 1.12 (d, J=6.8 Hz, 3H). MS(ESI) m/z: 572.2 (M+H). Analytical HPLC (Method A): RT=10.48 min, purity=96%; Factor XIa Ki=5.7 nM, Plasma Kallikrein Ki=50 nM.

Example 34

Preparation of (9R,13S)-3-[2-(tert-butoxy)ethyl]-13-{4-[5-chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one

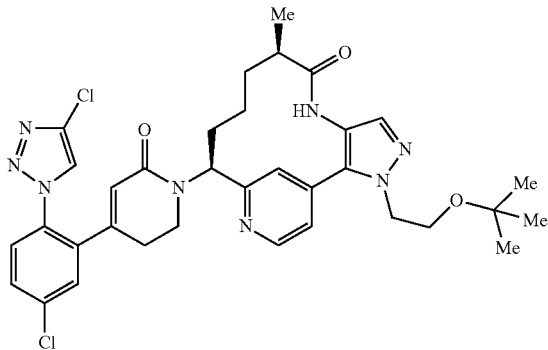 [SMILES: C[C@@H]1CCC[C@H](N2CCC(c3cc(Cl)ccc3-n3cc(Cl)nn3)=CC2=O)c2cc(ccn2)-c2c(cnn2CCOC(C)(C)C)NC1=O]

34A. Preparation of 1-(2-(tert-butoxy)ethyl)-4-nitro-1H-pyrazole

DIAD (8.60 mL, 44.2 mmol) was added to a solution of 4-nitro-1H-pyrazole (5 g, 44.2 mmol), 2-(tert-butoxy)ethanol (5.23 g, 44.2 mmol), and PPh$_3$ (11.60 g, 44.2 mmol) in THF (40 mL) and stirred at rt for 2 h. The reaction mixture was then quenched with water and purified using silica gel chromatography to yield 1-(2-(tert-butoxy)ethyl)-4-nitro-1H-pyrazole (10.45 g, 44.1 mmol, 95% yield). $^1$H NMR (400 MHz, CDCl$_3$) δ 8.24 (s, 1H), 8.05 (s, 1H), 4.26 (t, J=5.1 Hz, 2H), 3.76-3.63 (m, 2H), 1.10 (s, 9H).

34B. Preparation of (S)-benzyl (1-(4-(1-(2-(tert-butoxy)ethyl)-4-nitro-1H-pyrazol-5-yl)pyridin-2-yl)but-3-en-1-yl)carbamate To a N$_2$ flushed pressure vial was added (S)-benzyl (1-(4-chloropyridin-2-yl)but-3-en-1-yl)carbamate (3.0 g, 9.47 mmol) prepared as (S)-tert-butyl (1-(4-chloropyridin-2-yl)but-3-en-1-yl)carbamate, described in Example 1C, by replacing Boc$_2$O with Cbz-Cl, and 1-(2-(tert-butoxy)ethyl)-4-nitro-1H-pyrazole (1.34 g, 6.31 mmol), di(adamant-1-yl)(butyl)phosphine (0.679 g, 1.894 mmol), PvOH (0.193 ml, 1.894 mmol) and K$_2$CO$_3$ (2.62 g, 18.94 mmol). To the reaction mixture was then added DMF (18 mL) and the vial was purged with N$_2$ for 5 min. To this mixture was then added Pd(OAc)$_2$ (0.283 g, 1.263 mmol). The reaction mixture was again briefly purged with N$_2$. The vial was sealed and heated in oil bath at 120° C. for 4 h. The reaction mixture was cooled to rt and partitioned between 10% aqueous LiCl (15 mL) and EtOAc (30 mL). The aqueous layer was extracted with EtOAc (2×20 mL) and the combined organic layers were washed with brine (15 mL), dried over MgSO$_4$, filtered and concentrated. The crude product was then purified using normal phase chromatography to yield (S)-benzyl (1-(4-(1-(2-(tert-butoxy)ethyl)-4-nitro-1H-pyrazol-5-yl)pyridin-2-yl)but-3-en-1-yl)carbamate (2.2 g, 4.23 mmol, 67% yield) as a brown oil. MS(ESI) m/z: 494.2 (M+H)$^+$.

34C. Preparation of (S)-benzyl (1-(4-(4-amino-1-(2-(tert-butoxy)ethyl)-1H-pyrazol-5-yl)pyridin-2-yl)but-3-en-1-yl)carbamate A solution of (S)-benzyl (1-(4-(1-(2-(tert-butoxy)ethyl)-4-nitro-1H-pyrazol-5-yl)pyridin-2-yl)but-3-en-1-yl)carbamate (0.95 g, 1.925 mmol) in MeOH (10 mL) and AcOH (1.0 mL) was heated in oil bath to 40° C. To the above clear solution was then slowly added Zn (0.252 g, 3.85 mmol, in 3 portions (50:25:25%) and allowed to stir at the same temperature for 5 min. The reaction mixture was monitored by LCMS and once reaction was completed, to the cooled reaction mixture was then added 1.0 g of K$_2$CO$_3$ (1 g for 1 mL AcOH) and 1.0 mL water, and was then stirred for 5 min. The reaction mixture was then filtered over a pad of CELITE® and concentrated in vacuo to yield the crude product. The crude product was partitioned between EtOAc (40 mL) and sat aq NaHCO$_3$ (20 mL). The organic layer was separated, dried over MgSO$_4$, filtered and concentrated. The crude product was then purified using normal phase chromatography to yield (S)-benzyl (1-(4-(4-amino-1-(2-(tert-butoxy)ethyl)-1H-pyrazol-5-yl)pyridin-2-yl)but-3-en-1-yl)carbamate (0.49 g, 1.004 mmol, 52% yield) as pale brown oil. MS(ESI) m/z: 464.5 (M+H)$^+$.

34D. Preparation of benzyl ((S)-1-(4-(1-(2-(tert-butoxy)ethyl)-4-((R)-2-methylbut-3-enamido)-1H-pyrazol-5-yl)pyridin-2-yl)but-3-en-1-yl)carbamate To a N$_2$ flushed, 3-necked, 250 mL RBF was added (S)-benzyl (1-(4-(4-amino-1-(2-(tert-butoxy)ethyl)-1H-pyrazol-5-yl)pyridin-2-yl)but-3-en-1-yl)carbamate (0.49 g, 1.057 mmol) and EtOAc (15 mL). The solution was cooled to −10° C. and (R)-2-methylbut-3-enoic acid, as prepared in Intermediate 6 (106 mg, 1.057 mmol), pyridine (0.171 mL, 2.114 mmol) and T3P® (0.944 mL, 1.586 mmol) were added. The cooling bath was removed and the solution was allowed to warm to rt and then stir over a period of 20 h. Water (20 mL) and EtOAc (20 mL) were added and the mixture was stirred for 30 min. The organic phase was separated and the aqueous layer was extracted with EtOAc (20 mL). The combined organic extracts was washed with brine (15 mL), dried over Na$_2$SO$_4$, filtered and concentrated in vacuo. Purification by normal phase chromatography eluting with a gradient of hexanes/EtOAc gave benzyl ((S)-1-(4-(1-(2-(tert-butoxy)ethyl)-4-((R)-2-methylbut-3-enamido)-1H-pyrazol-5-yl)pyridin-2-yl)but-3-en-1-yl)carbamate (0.35 g, 0.609 mmol, 58% yield). MS(ESI) m/z: 546.6 [M+H]$^+$.

34E. Preparation of benzyl N-[(9R,10E,13S)-3-[2-(tert-butoxy)ethyl]-9-methyl-8-oxo-3,4,7,15-tetraazatricyclo[12.3.1.0²,⁶]octadeca-1(18),2(6),4,10,14,16-hexaen-13-yl]carbamate To a N₂ flushed, 250 mL, 3-necked, RBF was added a solution of benzyl ((S)-1-(4-(1-(2-(tert-butoxy)ethyl)-4-((R)-2-methylbut-3-enamido)-1H-pyrazol-5-yl)pyridin-2-yl)but-3-en-1-yl)carbamate (350 mg, 0.641 mmol) in DCE (18 mL). The solution was sparged with Ar for 15 min. Second Generation Grubbs Catalyst (218 mg, 0.257 mmol) was added in one portion. The reaction mixture was heated in a microwave to 120° C. for 30 min. After cooling to rt, the solvent was removed and the residue was purified by normal phase chromatography eluting with a gradient of DCM/MeOH to yield benzyl N-[(9R,10E,13S)-3-[2-(tert-butoxy)ethyl]-9-methyl-8-oxo-3,4,7,15-tetraazatricyclo[12.3.1.0²,⁶]octadeca-1(18),2(6),4,10,14,16-hexaen-13-yl]carbamate (140 mg, 0.243 mmol, 38% yield) as a tan solid. MS(ESI) m/z: 518.5 [M+H]⁺.

34F. Preparation of (9R,13S)-13-amino-3-[2-(tert-butoxy)ethyl]-9-methyl-3,4,7,15-tetraazatricyclo[12.3.1.0²,⁶]octadeca-1(18),2(6),4,14,16-pentaen-8-one Pd on carbon (0.033 g, 0.031 mmol) was added to a 250 mL Parr hydrogenation flask containing a solution of benzyl N-[(9R,10E,13S)-3-[2-(tert-butoxy)ethyl]-9-methyl-8-oxo-3,4,7,15-tetraazatricyclo[12.3.1.0²,⁶]octadeca-1(18),2(6),4,10,14,16-hexaen-13-yl]carbamate (160 mg, 0.309 mmol) in EtOH (10 mL). The flask was purged with N₂ and pressurized to 55 psi of H₂ and allowed to stir for 4 h. The reaction was filtered through a pad of CELITE® and concentrated to yield (9R,13S)-13-amino-3-[2-(tert-butoxy)ethyl]-9-methyl-3,4,7,15-tetraazatricyclo[12.3.1.0²,⁶]octadeca-1(18),2(6),4,14,16-pentaen-8-one (81 mg, 0.210 mmol, 68% yield) as a tan solid. MS(ESI) m/z: 386.5 [M+H]⁺.

34G. Preparation of (9R,13S)-3-[2-(tert-Butoxy)ethyl]-13-{4-[5-chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one trifluoroacetate (9R,13S)-3-[2-(tert-Butoxy)ethyl]-13-{4-[5-chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one trifluoroacetate was prepared according to the procedures described in Example 1 by substituting 1-(5-chloro-2-(1H-1,2,3-triazol-1-yl)phenyl)prop-2-en-1-one with 1-(5-chloro-2-(4-chloro-1H-1,2,3-triazol-1-yl)phenyl)prop-2-en-1-one, Intermediate 4, to yield (9R,13S)-3-[2-(tert-butoxy)ethyl]-13-{4-[5-chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one trifluoroacetate (48 mg, 0.058 mmol, 27% yield). ¹H NMR (400 MHz, CD₃OD) δ 8.80 (d, J=5.5 Hz, 1H), 8.49-8.44 (m, 1H), 8.23 (d, J=5.5 Hz, 1H), 7.82 (s, 1H), 7.68-7.53 (m, 4H), 5.86-5.79 (m, 1H), 5.48 (dd, J=12.8, 3.5 Hz, 1H), 4.51-4.33 (m, 2H), 3.94-3.78 (m, 2H), 3.53-3.34 (m, 2H), 2.58-2.46 (m, 1H), 2.26-2.14 (m, 3H), 2.02-1.83 (m, 2H), 1.66-1.51 (m, 1H), 1.30 (br. s., 1H), 1.10 (d, J=6.8 Hz, 3H), 1.08-1.03 (m, 9H). MS(ESI) m/z: 677.5 [M+H]⁺. Analytical HPLC (Method A): RT=7.93 min, purity=>95.0%; Factor XIa Ki=1.1 nM, Plasma Kallikrein Ki=50 nM.

Example 35

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-(2-hydroxyethyl)-9-methyl-3,4,7,15-tetraazatricyclo[12.3.1.0²,⁶]octadeca-1(18),2(6),4,14,16-pentaen-8-one

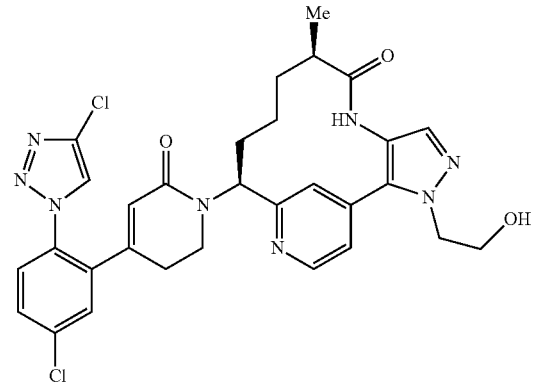 [SMILES: C[C@@H]1CCC[C@H](N2CCC(c3cc(Cl)ccc3-n3cc(Cl)nn3)=CC2=O)c2cc(ccn2)-c2c(cnn2CCO)NC1=O]

To a solution of (9R,13S)-3-[2-(tert-butoxy)ethyl]-13-{4-[5-chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one trifluoroacetate (32 mg, 0.047 mmol)) in DCM was added TFA (2 mL) and the reaction stirred at rt for 1 h. The reaction mixture was then concentrated in vacuo and purified using prep HPLC purification to yield (9R,13S)-13-{4-[5-chloro-2-(4-chloro-1H-1,2,3-triazol-1-yl)phenyl]-6-oxo-1,2,3,6-tetrahydropyridin-1-yl}-3-(2-hydroxyethyl)-9-methyl-3,4,7,15-tetraazatricyclo[12.3.1.0²,⁶]octadeca-1(18),2(6),4,14,16-pentaen-8-one trifluoroacetate (28.4 mg, 0.037 mmol, 78% yield). ¹H NMR (400 MHz, CD₃OD) δ 8.77 (d, J=5.3 Hz, 1H), 8.48 (s, 1H), 7.89 (dd, J=5.3, 1.3 Hz, 1H), 7.70-7.58 (m, 6H), 5.86 (s, 1H), 5.56 (dd, J=12.8, 3.5 Hz, 1H), 4.47-4.40 (m, 2H), 4.07-3.98 (m, 3H), 3.52 (t, J=6.8 Hz, 2H), 2.65-2.52 (m, 1H), 2.49-2.36 (m, 1H), 2.34-2.11 (m, 2H), 2.01-1.82 (m, 2H), 1.69-1.52 (m, 1H), 1.18 (br. s., 1H), 1.12 (d, J=7.0 Hz, 3H). MS(ESI) m/z: 621.5 [M+H]⁺. Analytical HPLC (Method A): RT=6.42 min, purity=>95.0%; Factor XIa Ki=0.82 nM, Plasma Kallikrein Ki=32 nM.

Example 36

Preparation of (9R,13S)-13-[4-(6-bromo-3-chloro-2-fluorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one

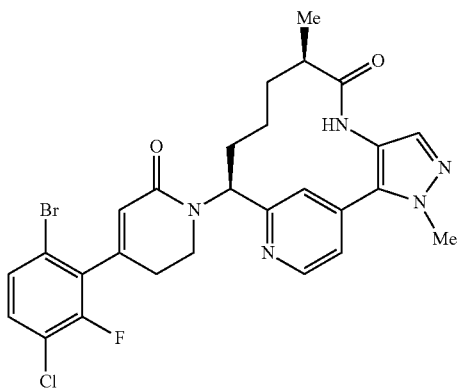 [SMILES: C[C@@H]1CCC[C@H](N2CCC(c3c(Br)ccc(Cl)c3F)=CC2=O)c2cc(ccn2)-c2c(cnn2C)NC1=O]

(9R,13S)-13-[4-(6-Bromo-3-chloro-2-fluorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one was prepared according to the procedures described in Example 1 by substituting, 1-(5-chloro-2-(1H-1,2,3-triazol-1-yl)phenyl)prop-2-en-1-one with 1-(6-bromo-3-chloro-2-fluorophenyl)prop-2-en-1-one, Intermediate 12. ¹H NMR (400 MHz, CD₃OD) d 8.72 (d, J=5.1 Hz, 1H), 7.59 (s, 1H), 7.52-7.37 (m, 4H), 5.93 (s, 1H), 5.65 (dd, J=12.7, 3.9 Hz, 1H), 4.04 (s, 3H), 3.91-3.69 (m, 2H), 2.65-2.53 (m, 3H), 2.27-2.13 (m, 1H), 2.04-1.80 (m, 2H), 1.66-1.51 (m, 1H), 1.37-1.17 (m, 1H), 1.05 (d, J=6.8 Hz, 3H), 1.02-0.93 (m, 1H). MS(ESI) m/z: 586.0 (M+H). Analytical HPLC (Method A): RT=7.46 min, purity=>95%; Factor XIa Ki=1.7 nM, Plasma Kallikrein Ki=5 nM.

Example 37

Preparation of (9R,13S)-13-[4-(2-bromo-5-chlorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one

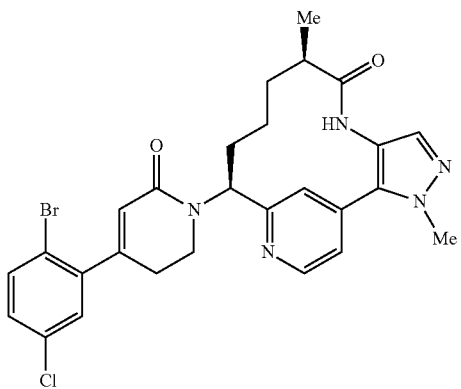 [SMILES: C[C@@H]1CCC[C@H](N2CCC(c3cc(Cl)ccc3Br)=CC2=O)c2cc(ccn2)-c2c(cnn2C)NC1=O]

(9R,13S)-13-[4-(2-Bromo-5-chlorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one trifluoroacetate (0.085 g, 20% yield) was prepared according to the procedures described in Example 1M by replacing 1-(5-chloro-2-(1H-1,2,3-triazol-1-yl)phenyl)prop-2-en-1-one with 1-(2-bromo-5-chlorophenyl)prop-2-en-1-one (0.15 g, 0.611 mmol), Intermediate 13. MS(ESI) m/z: 570.4 (M+2+H)⁺. ¹H NMR (400 MHz, CD₃OD) δ 8.79 (d, J=5.5 Hz, 1H), 7.80 (s, 1H), 7.75 (dd, J=5.5, 1.5 Hz, 1H), 7.63 (d, J=8.6 Hz, 1H), 7.54 (s, 1H), 7.34 (d, J=2.6 Hz, 1H), 7.30 (dd, J=8.5, 2.5 Hz, 1H), 5.91 (t, J=1.2 Hz, 1H), 5.56 (dd, J=12.7, 3.9 Hz, 1H), 4.08 (s, 3H), 3.72 (t, J=6.9 Hz, 2H), 2.73 (t, J=6.8 Hz, 2H), 2.62-2.53 (m, 1H), 2.31-2.20 (m, 1H), 2.04-1.91 (m, 2H), 1.67-1.56 (m, 1H), 1.27-1.16 (m, 2H), 1.10 (d, J=6.8 Hz, 3H). Analytical HPLC (Method A): RT=7.44 min, 96.5% purity; Factor XIa Ki=4.7 nM, Plasma Kallikrein Ki=16 nM.

Example 38

Preparation of (9R,13S)-13-(4-{5-chloro-2-[1-(difluoromethyl)-1H-pyrazol-4-yl]phenyl}-6-oxo-1,2,3,6-tetrahydropyridin-1-yl)-3,9-dimethyl-3,4,7,15-tetraazatricyclo[12.3.1.0²,⁶]octadeca-1(18),2(6),4,14,16-pentaen-8-one

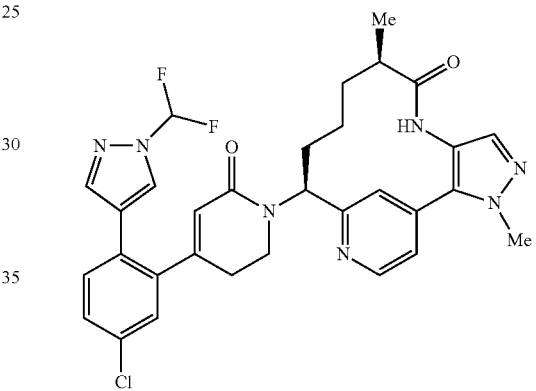

To a sealable tube was added (9R,13S)-13-[4-(2-bromo-5-chlorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one trifluoroacetate (0.02 g, 0.029 mmol), prepared as described in Example 37, 1-(difluoromethyl)-4-(4,4,5,5-tetramethyl-1,3,2-dioxaborolan-2-yl)-1H-pyrazole (7.86 mg, 0.032 mmol), 3 M aq K₃PO₄ (0.039 ml, 0.117 mmol) and THF (1 ml). Ar was bubbled through the reaction mixture for several min and (DtBPF)PdCl₂ (0.95 mg, 1.464 µmol) was added. The reaction was sealed and heated at 90° C. After 18 h, the reaction was cooled to rt and concentrated. Purification by reverse phase chromatography afforded (9R,13S)-13-(4-{5-chloro-2-[1-(difluoromethyl)-1H-pyrazol-4-yl]phenyl}-6-oxo-1,2,3,6-tetrahydropyridin-1-yl)-3,9-dimethyl-3,4,7,15-tetraazatricyclo[12.3.1.0²,⁶]octadeca-1(18),2(6),4,14,16-pentaen-8-one trifluoroacetate (6.5 mg, 30% yield) as a white solid. MS(ESI) m/z: 606.5 (M+H)⁺. ¹H NMR (500 MHz, CD₃OD) δ 8.77 (br. s., 1H), 8.22 (s, 1H), 7.83 (s, 1H), 7.78-7.66 (m, 2H), 7.52 (s, 1H), 7.50 (t, J=59.6 Hz, 1H), 7.45-7.43 (m, 2H), 7.35 (t, J=1.2 Hz, 1H), 5.99 (s, 1H), 5.54 (d, J=9.4 Hz, 1H), 4.07 (s, 3H), 3.49 (t, J=6.3 Hz, 2H), 2.60-2.52 (m, 1H), 2.37 (t, J=6.9 Hz, 2H), 2.22-2.13 (m, 1H), 1.99-1.88 (m, 2H), 1.63-1.54 (m, 1H), 1.23-1.14 (m, 2H), 1.09 (d, J=6.9 Hz, 3H). ¹⁹F NMR (376 MHz, CD₃OD) δ −77.60 (s), −96.03 (s). Analytical HPLC (Method A): RT=7.39 min, 98.5% purity; Factor XIa Ki=1.8 nM, Plasma Kallikrein Ki=120 nM.

Example 39

Preparation of 4-chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,2,3,6-tetrahydropyridin-4-yl}-3-fluorobenzonitrile

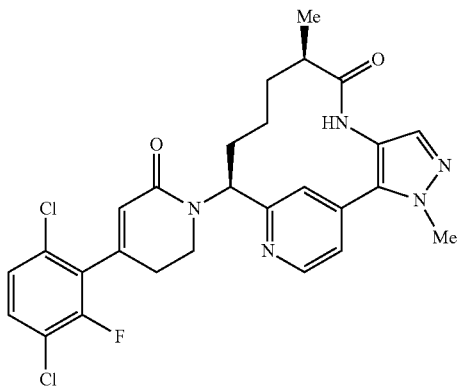 [SMILES: C[C@@H]1CCC[C@H](N2CCC(c3c(Cl)ccc(Cl)c3F)=CC2=O)c2cc(ccn2)-c2c(cnn2C)NC1=O]

4-Chloro-2-{1-[(9R,13S)-3,9-dimethyl-8-oxo-3,4,7,15-tetraazatricyclo[12.3.1.0²,⁶]octadeca-1(18),2(6),4,14,16-pentaen-13-yl]-6-oxo-1,2,3,6-tetrahydropyridin-4-yl}-3-fluorobenzonitrile was prepared according to the procedures described in Example 19 by substituting, (9R,13S)-13-[4-(2-bromo-5-chlorophenyl)-6-oxo-1,2,3,6-tetrahydropyridin-1-yl]-3-(difluoromethyl)-9-methyl-3,4,7,15-tetraazatricyclo[12.3.1.0²,⁶]octadeca-1(18),2(6),4,14,16-pentaen-8-one with (9R,13S)-13-[4-(6-bromo-3-chloro-2-fluorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one, Example 36. ¹H NMR (400 MHz, CD₃OD) δ 8.80 (d, J=5.5 Hz, 1H), 7.79 (s, 1H), 7.75-7.63 (m, 3H), 7.54 (s, 1H), 6.19 (t, J=1.2 Hz, 1H), 5.59 (dd, J=12.5, 4.0 Hz, 1H), 4.09 (s, 3H), 3.81-3.71 (m, 2H), 2.84-2.69 (m, 2H), 2.63-2.52 (m, 1H), 2.31-2.18 (m, 1H), 2.05-1.91 (m, 2H), 1.70-1.55 (m, 1H), 1.21 (d, J=4.2 Hz, 2H), 1.09 (d, J=6.8 Hz, 3H). MS(ESI) m/z: 533.1 (M+H). Analytical HPLC (Method A): RT=6.62 min, purity=>95%; Factor XIa Ki=1.1 nM, Plasma Kallikrein Ki=120 nM.

Example 40

Preparation of (9R,13S)-13-(4-{5-chloro-2-[4-(trifluoromethyl)-1H-1,2,3-triazol-1-yl]phenyl}-6-oxo-1,2,3,6-tetrahydropyridin-1-yl)-3,9-dimethyl-3,4,7,15-tetraazatricyclo[12.3.1.0²,⁶]octadeca-1(18),2(6),4,14,16-pentaen-8-one

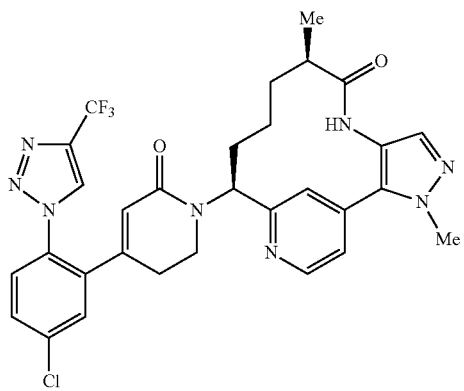 [SMILES: C[C@@H]1CCC[C@H](N2CCC(c3cc(Cl)ccc3-n3cc(C(F)(F)F)nn3)=CC2=O)c2cc(ccn2)-c2c(cnn2C)NC1=O]

40A. Preparation of 5-chloro-2-(4-(trifluoromethyl)-1H-1,2,3-triazol-1-yl)benzaldehyde 3,3,3-Trifluoroprop-1-yne gas was bubbled gently for 3 min into a suspension of 2-azido-5-chlorobenzaldehyde (160 mg, 0.881 mmol) and Cu₂O (14 mg, 0.098 mmol) in CH₃CN (6 ml). The reaction vessel was capped and the reaction was stirred at rt overnight. The reaction was diluted with EtOAc and washed with sat NH₄Cl and brine. The organic layer was dried over MgSO₄, filtered and concentrated to give 5-chloro-2-(4-(trifluoromethyl)-1H-1,2,3-triazol-1-yl)benzaldehyde (241 mg, 99% yield) as a beige solid. MS(ESI) m/z: 276.3 (M+H)⁺. ¹H NMR (400 MHz, CDCl₃) δ 9.88 (s, 1H), 8.26 (d, J=0.9 Hz, 1H), 8.10 (d, J=2.4 Hz, 1H), 7.78 (dd, J=8.4, 2.4 Hz, 1H), 7.52 (d, J=8.4 Hz, 1H).

40B. Preparation of 1-(5-chloro-2-(4-(trifluoromethyl)-1H-1,2,3-triazol-1-yl)phenyl)prop-2-en-1-ol To a solution of 5-chloro-2-(4-(trifluoromethyl)-1H-1,2,3-triazol-1-yl)benzaldehyde (241 mg, 0.874 mmol) and THF (10 mL) at 0° C. was added dropwise 1.6 M vinylmagnesium chloride in THF (1.137 mL, 1.137 mmol). The reaction was stirred at 0° C. for 30 min and then at rt for 1 h. The reaction was then quenched with 1 N HCl. The reaction was partitioned between EtOAc and water and the layers were separated. The organic layer was washed with brine, concentrated and purified on normal phase chromatography to give 1-(5-chloro-2-(4-(trifluoromethyl)-1H-1,2,3-triazol-1-yl)phenyl)prop-2-en-1-ol (224 mg, 84% yield) as a yellow oil. MS(ESI) m/z: 304.4 (M+H)⁺. ¹H NMR (400 MHz, CDCl₃) δ 8.18 (d, J=0.7 Hz, 1H), 7.72 (d, J=2.2 Hz, 1H), 7.47 (dd, J=8.4, 2.4 Hz, 1H), 7.32 (d, J=8.4 Hz, 1H), 5.87 (ddd, J=17.3, 10.3, 5.4 Hz, 1H), 5.20 (dt, J=6.0, 1.2 Hz, 1H), 5.18-5.14 (m, 1H), 5.11 (d, J=4.0 Hz, 1H), 2.82 (br. s., 1H).

40C. Preparation of 1-(5-chloro-2-(4-(trifluoromethyl)-1H-1,2,3-triazol-1-yl)phenyl)prop-2-en-1-one To a solution of 1-(5-chloro-2-(4-(trifluoromethyl)-1H-1,2,3-triazol-1-yl)phenyl)prop-2-en-1-ol (124 mg, 0.408 mmol) in acetone (5 mL) at 0° C. was added dropwise Jones reagent (0.16 mL, 0.408 mmol) until a brown color persisted. The reaction mixture was quenched with IPA, diluted with EtOAc and basified with sat NaHCO₃ to pH 8. The organic layer was separated and the aqueous layer was extracted with EtOAc (2×). The combined organic layers were washed with brine, concentrated, and then purified on normal phase chromatography to give 1-(5-chloro-2-(4-(trifluoromethyl)-1H-1,2,3-triazol-1-yl)phenyl)prop-2-en-1-one (112 mg, 91% yield) as a yellow oil. ¹H NMR (400 MHz, CDCl₃) δ 8.11 (s, 1H), 7.71-7.66 (m, 1H), 7.65 (d, J=2.2 Hz, 1H), 7.54 (d, J=8.4 Hz, 1H), 6.41 (dd, J=17.5, 10.7 Hz, 1H), 6.10-5.91 (m, 2H). MS(ESI) m/z: 302.3 (M+H)⁺.

40D. Preparation of (9R,13S)-13-(4-{5-chloro-2-[4-(trifluoromethyl)-1H-1,2,3-triazol-1-yl]phenyl}-6-oxo-1,2,3,6-tetrahydropyridin-1-yl)-3,9-dimethyl-3,4,7,15-tetraazatricyclo[12.3.1.0²,⁶]octadeca-1(18),2(6),4,14,16-pentaen-8-one trifluoroacetate (9R,13S)-13-(4-{5-Chloro-2-[4-(trifluoromethyl)-1H-1,2,3-triazol-1-yl]phenyl}-6-oxo-1,2,3,6-tetrahydropyridin-1- yl)-3,9-dimethyl-3,4,7,15-tetraazatricyclo[12.3.1.0²,⁶]octadeca-1(18),2(6),4,14,16-pentaen-8-one trifluoroacetate (14 mg, 36% yield) was prepared according to the procedures described in Example 1 by replacing 1-(5-chloro-2-(1H-1, 2,3-triazol-1-yl)phenyl)prop-2-en-1-one with 1-(5-chloro-2-(4-(trifluoromethyl)-1H-1,2,3-triazol-1-yl)phenyl)prop-2-en-1-one. ¹H NMR (400 MHz, CD₃OD) δ 8.93 (d, J=0.7 Hz, 1H), 8.72 (br. s., 1H), 7.69-7.55 (m, 5H), 7.50 (s, 1H), 5.80 (s, 1H), 5.52 (d, J=11.9 Hz, 1H), 4.05 (s, 3H), 3.56-3.42 (m, 2H), 2.60-2.48 (m, 1H), 2.24 (t, J=6.6 Hz, 2H), 2.13 (m, 1H), 2.03-1.78 (m, 2H), 1.62-1.51 (m, 1H), 1.18 (m., 1H), 1.07 (d, J=6.8 Hz, 3H). MS(ESI) m/z: 625.1 (M+H). Analytical HPLC (Method A): RT=7.44 min, purity=97%; Factor XIa Ki=0.1 nM, Plasma Kallikrein Ki=6 nM.

Example 41

Preparation of (9R,13S)-13-(4-{3-chloro-6-[1-(difluoromethyl)-1H-pyrazol-4-yl]-2-fluorophenyl}-6-oxo-1,2,3,6-tetrahydropyridin-1-yl)-3,9-dimethyl-3,4,7,15-tetraazatricyclo[12.3.1.0²,⁶]octadeca-1(18),2(6),4,14,16-pentaen-8-one

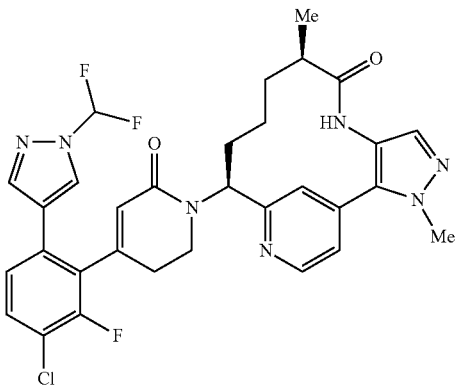 [SMILES: C[C@@H]1CCC[C@H](N2CCC(c3c(-c4cnn(C(F)F)c4)ccc(Cl)c3F)=CC2=O)c2cc(ccn2)-c2c(cnn2C)NC1=O]

(9R,13S)-13-(4-{3-Chloro-6-[1-(difluoromethyl)-1H-pyrazol-4-yl]-2-fluorophenyl}-6-oxo-1,2,3,6-tetrahydropyridin-1-yl)-3,9-dimethyl-3,4,7,15-tetraazatricyclo[12.3.1.0²,⁶]octadeca-1(18),2(6),4,14,16-pentaen-8-one trifluoroacetate (9.5 mg, 38% yield) was prepared according to the procedure described in Example 38 by replacing (9R,13S)-13-[4-(2-bromo-5-chlorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one trifluoroacetate with (9R,13S)-13-[4-(6-bromo-3-chloro-2-fluorophenyl)-6-oxo-1,2,3,6-tetrahydropyridin-1-yl]-3,9-dimethyl-3,4,7,15-tetraazatricyclo[12.3.1.0²,⁶]octadeca-1(18),2(6),4,14,16-pentaen-8-one (0.02 g, 0.034 mmol), prepared as described in Example 36. MS(ESI) m/z: 624.5 (M+H)⁺. ¹H NMR (400 MHz, CD₃OD) δ 8.73 (d, J=5.1 Hz, 1H), 8.24 (s, 1H), 7.83 (s, 1H), 7.60 (s, 1H), 7.56-7.52 (m, 2H), 7.50 (s, 1H), 7.49 (t, J=59.0 Hz, 1H), 7.30 (dd, J=8.4, 1.3 Hz, 1H), 5.96 (s, 1H), 5.59 (dd, J=12.8, 3.7 Hz, 1H), 4.05 (s, 3H), 3.64-3.49 (m, 2H), 2.62-2.51 (m, 1H), 2.42 (t, J=6.7 Hz, 2H), 2.22-2.11 (m, 1H), 2.01-1.83 (m, 2H), 1.64-1.53 (m, 1H), 1.27-1.03 (m, 5H). ¹⁹F NMR (376 MHz, CD₃OD) δ -77.45 (s), -96.21 (s), -117.57 (s). Analytical HPLC (Method A): RT=7.47 min, 100% purity. Factor XIa Ki=1 nM, Plasma Kallikrein Ki=34 nM.

Example 42

Preparation of (9R,13S)-13-(4-{5-chloro-2-[4-(trifluoromethyl)-1H-1,2,3-triazol-1-yl]phenyl}-6-oxo-1,2,3,6-tetrahydropyridin-1-yl)-3-(²H₃)methyl-9-methyl-3,4,7,15-tetraazatricyclo[12.3.1.0²,⁶]octadeca-1(18),2(6),4,14,16-pentaen-8-one

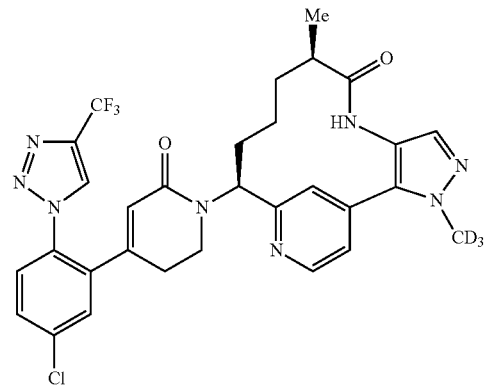 [SMILES: [2H]C([2H])([2H])n1ncc2c1-c1ccnc(c1)[C@@H](N1CCC(c3cc(Cl)ccc3-n3cc(C(F)(F)F)nn3)=CC1=O)CCC[C@@H](C)C(=O)N2]

(9R,13S)-13-(4-{5-Chloro-2-[4-(trifluoromethyl)-1H-1,2,3-triazol-1-yl]phenyl}-6-oxo-1,2,3,6-tetrahydropyridin-1-yl)-3-(²H₃)methyl-9-methyl-3,4,7,15-tetraazatricyclo[12.3.1.0²,⁶]octadeca-1(18),2(6),4,14,16-pentaen-8-one trifluoroacetate (21 mg, 41% yield) was prepared according to the procedures described in Example 1 by using 1-(5-chloro-2-(4-(trifluoromethyl)-1H-1,2,3-triazol-1-yl)phenyl)prop-2-en-1-one, prepared as described in Example 40C, and (9R, 13S)-13-amino-3-(²H₃)methyl-9-methyl-3,4,7,18-tetraazatricyclo[12.3.1.0²,⁶]octadeca-1(18),2(6),4,14,16-pentaen-8-one, prepared as described in Example 18. ¹H NMR (400 MHz, CD₃OD-d₄) δ 8.94 (d, J=0.7 Hz, 1H), 8.77 (br. s., 1H), 7.75 (br. s., 2H), 7.69-7.59 (m, 4H), 7.52 (s, 1H), 5.79 (s, 1H), 5.47 (d, J=10.3 Hz, 1H), 3.50 (t, J=6.6 Hz, 2H), 2.55 (ddd, J=9.3, 6.5, 3.3 Hz, 1H), 2.27 (t, J=6.7 Hz, 2H), 2.22-2.11 (m, 1H), 1.99-1.83 (m, 2H), 1.64-1.52 (m, 1H), 1.17 (br. s., 2H), 1.08 (d, J=6.8 Hz, 3H) MS(ESI) m/z: 628.2 (M+H). Analytical HPLC (Method A): RT=7.43 min, purity=99%; Factor XIa Ki=0.1 nM, Plasma Kallikrein Ki=7 nM.

Example 43

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7,18-tetraazatricyclo[12.3.1.0²,⁶]octadeca-1(18),2(6),4,14,16-pentaen-8-one

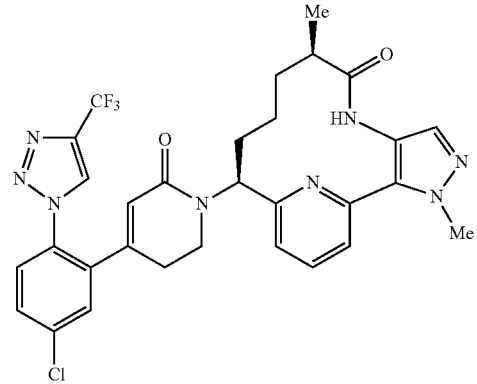 [SMILES: C[C@@H]1CCC[C@H](N2CCC(c3cc(Cl)ccc3-n3cc(C(F)(F)F)nn3)=CC2=O)c2cccc(n2)-c2c(cnn2C)NC1=O]

43A. Preparation of (S)—N-[(1E)-(6-chloropyridin-2-yl)methylidene]-2-methylpropane-2-sulfinamide To a solution of (S)-2-methylpropane-2-sulfinamide (1.712 g, 14.13 mmol) in DCM (61.4 mL) was added sequentially $Cs_2CO_3$ (6.91 g, 21.19 mmol) and 6-chloropicolinaldehyde (2.0 g, 14.13 mmol). The resulting white suspension was stirred at rt. After 17 h, the reaction was stopped and filtered. The filtrate was diluted with EtOAc (100 ml) and washed with brine (50 mL×3). The organic layer was dried over $MgSO_4$, filtered and concentrated to give (S)—N-[(1E)-(6-chloropyridin-2-yl)methylidene]-2-methylpropane-2-sulfinamide (3.58 g, 104%) as a yellow oil. $^1$H NMR (400 MHz, $CDCl_3$) δ 8.65 (s, 1H), 7.99-7.94 (m, 1H), 7.79 (t, J=7.7 Hz, 1H), 7.45 (dd, J=7.9, 0.7 Hz, 1H), 1.28 (s, 10H).

43B. Preparation of(S)—N-[(1S)-1-(6-chloropyridin-2-yl)but-3-en-1-yl]-2-methylpropane-2-sulfinamide, and

43C. Preparation of (S)—N-[(1R)-1-(6-chloropyridin-2-yl)but-3-en-1-yl]-2-methylpropane-2-sulfinamide To a mixture of (S)—N-[(1E)-(6-chloropyridin-2-yl)methylidene]-2-methylpropane-2-sulfinamide (1.73 g, 7.07 mmol) and In (0.92 g, 10.60 mmol) in THF (17.7 ml) was slowly added 3-bromoprop-1-ene (0.92 g, 10.60 mmol). The reaction was heated at 60° C. overnight. The reaction mixture was cooled to rt, filtered through CELITE® and the filtrate was concentrated. The resulting residue was purified by normal phase chromatography, using hexanes and EtOAc, which gave a 5.6:1 of (S)—N-[(1S)-1-(6-chloropyridin-2-yl)but-3-en-1-yl]-2-methylpropane-2-sulfinamide:(S)—N-[(1R)-1-(6-chloropyridin-2-yl)but-3-en-1-yl]-2-methylpropane-2-sulfinamide (2.42 g, 58%) as the major product and as a brown semi-solid. MS(ESI) m/z: 287.4 (M+H)$^+$.

43D. Preparation of (S)-2-methyl-N-[(1R)-1-[6-(1-methyl-4-nitro-1H-pyrazol-5-yl)pyridin-2-yl]but-3-en-1-yl]propane-2-sulfinamide (Diastereomer A), and

43E. Preparation of (S)-2-methyl-N-[(1S)-1-[6-(1-methyl-4-nitro-1H-pyrazol-5-yl)pyridin-2-yl]but-3-en-1-yl]propane-2-sulfinamide (Diastereomer B)

To a $N_2$ flushed pressure vial was added 5.6:1 of (S)—N-[(1S)-1-(6-chloropyridin-2-yl)but-3-en-1-yl]-2-methylpropane-2-sulfinamide: (S)—N-[(1R)-1-(6-chloropyridin-2-yl)but-3-en-1-yl]-2-methylpropane-2-sulfinamide (2.18 g, 7.60 mmol), 1-methyl-4-nitro-1H-pyrazole (0.966 g, 7.60 mmol), prepared as described in Example 1D, di(adamant-1-yl)(butyl)phosphine (0.954 g, 2.66 mmol), PvOH (0.300 ml, 2.58 mmol), $K_2CO_3$ (3.62 g, 26.2 mmol), Pd(OAc)$_2$ (0.341 g, 1.52 mmol) and DMF (15.2 mL). The vial was purged with Ar. The vial was sealed and heated in oil bath at 120° C. overnight. The reaction mixture was cooled to rt, partitioned between water and EtOAc, and the layers were separated. The aqueous layer was extracted with EtOAc (3×) and the organic layers were combined and concentrated. The crude product was purified using normal phase chromatography followed a second purification by reverse phase chromatography to give (S)-2-methyl-N-[(1R)-1-[6-(1-methyl-4-nitro-1H-pyrazol-5-yl)pyridin-2-yl]but-3-en-1-yl] propane-2-sulfinamide (Diastereomer A) (0.275 g, 13%) MS(ESI) m/z: 274.4 (M+H)$^+$. And (S)-2-methyl-N-[(1S)-1-[6-(1-methyl-4-nitro-1H-pyrazol-5-yl)pyridin-2-yl]but-3-en-1-yl]propane-2-sulfinamide (Diastereomer B) (1.2 g, 57%) MS(ESI) m/z: 274.4 (M+H)$^+$.

43F. Preparation of tert-butyl N-[(1S)-1-[6-(1-methyl-4-nitro-1H-pyrazol-5-yl)pyridin-2-yl]but-3-en-1-yl]carbamate (1S)-1-(6-(1-Methyl-4-nitro-1H-pyrazol-5-yl)pyridin-2-yl)but-3-en-1-amine (Diastereomer B) (1.2 g, 3.18 mmol) was dissolved in MeOH (5 mL) and dioxane (25 ml). 4 N HCl in dioxane (4.8 ml, 19.1 mmol) was added. The reaction was stirred at rt for 3 h and then the reaction was concentrated. The residue was coevaporated with toluene, dissolved in DCM (40 mL), and cooled to 0° C. TEA (4.43 mL, 31.8 mmol) was added followed by $BOC_2O$ (0.738 mL, 3.18 mmol). The reaction was stirred at 0° C. for 15 min and then the reaction was allowed to warm to rt. After 2 h, the reaction was diluted with DCM, washed with sat $NaHCO_3$, brine, and concentrated. Purification by normal phase chromatography gave tert-butyl N-[(1S)-1-[6-(1-methyl-4-nitro-1H-pyrazol-5-yl)pyridin-2-yl]but-3-en-1-yl]carbamate (393 mg, 33% yield) as an orange oil. MS(ESI) m/z: 374.5 (M+H)$^+$. $^1$H NMR (400 MHz, $CDCl_3$) δ 8.19 (s, 1H), 7.84 (t, J=7.8 Hz, 1H), 7.55 (d, J=7.7 Hz, 1H), 7.38 (d, J=7.7 Hz, 1H), 5.77-5.58 (m, 1H), 5.40 (br. s., 1H), 5.13-5.01 (m, 2H), 4.92 (d, J=6.8 Hz, 1H), 3.86 (s, 3H), 2.71-2.51 (m, 2H), 1.43 (s, 9H).

43G. Preparation of tert-butyl N-[(1S)-1-[6-(4-amino-1-methyl-1H-pyrazol-5-yl)pyridin-2-yl]but-3-en-1-yl]carbamate To a solution of tert-butyl N-[(1S)-1-[6-(1-methyl-4-nitro-1H-pyrazol-5-yl) pyridin-2-yl]but-3-en-1-yl]carbamate (393 mg, 1.05 mmol) in MeOH (6.4 mL) was added AcOH (0.64 mL). The reaction flask was put in a preheated bath at 45° C. then Zn powder (206 mg, 3.16 mmol) was added portionwise. After 1 h, additional Zn (198 mg) was added. Upon completion of the reaction, the mixture was cooled to rt, partitioned between DCM and sat $NaHCO_3$, and the layers were separated. The aqueous layer was extracted with DCM (2×). The organic layers were combined and washed with brine, dried over $MgSO_4$, filtered and concentrated to give tert-butyl N-[(1S)-1-[6-(4-amino-1-methyl-1H-pyrazol-5-yl) pyridin-2-yl]but-3-en-1-yl]carbamate (343 mg, 95% yield) as a yellow foam. MS(ESI) m/z: 344.5 (M+H)$^+$. $^1$H NMR (400 MHz, $CDCl_3$) δ 7.74 (t, J=7.8 Hz, 1H), 7.39 (dd, J=7.8, 0.8 Hz, 1H), 7.25-7.18 (m, 1H), 7.14 (d, J=7.7 Hz, 1H), 5.70 (ddt, J=17.1, 10.2, 7.0 Hz, 1H), 5.46 (d, J=6.8 Hz, 1H), 5.13-4.99 (m, 2H), 4.89 (d, J=6.8 Hz, 1H), 4.01 (s, 3H), 2.71-2.53 (m, 2H), 1.49-1.30 (m, 9H).

43H. Preparation of tert-butyl N-[(1S)-1-(6-{1-methyl-4-[(2R)-2-methylbut-3-enamido]-1H-pyrazol-5-yl)}pyridin-2-yl)but-3-en-1-yl]carbamate To tert-butyl N-[(1S)-1-[6-(4-amino-1-methyl-1H-pyrazol-5-yl)pyridin-2-yl]but-3-en-1-yl]carbamate (343 mg, 0.999 mmol) in EtOAc (3.33 ml) was added a solution of (R)-2-methylbut-3-enoic acid (0.150 g, 1.498 mmol), Intermediate 6, in EtOAc (1 ml). The mixture was cooled to 0° C. and pyridine (0.24 ml, 3.0 mmol) was added, followed by the addition of a solution of 50% T3P® in EtOAc (1.19 ml, 1.50 mmol). After 2 h, the reaction was partitioned between sat NaHCO$_3$ and EtOAc, and the layers were separated. The aqueous layer was extracted with EtOAc (2×). The organic layers were combined and washed with brine and then concentrated. Purification by normal phase chromatography gave tert-butyl N-[(1S)-1-(6-{1-methyl-4-[(2R)-2-methylbut-3-enamido]-1H-pyrazol-5-yl}pyridin-2-yl)but-3-en-1-yl]carbamate (360 mg, 85%) as a yellow solid. MS(ESI) m/z: 426.5 (M+H)$^+$. $^1$H NMR (400 MHz, CDCl$_3$) δ 9.35 (br. s., 1H), 8.30 (s, 1H), 7.82 (t, J=7.8 Hz, 1H), 7.40 (d, J=7.9 Hz, 1H), 7.32-7.19 (m, 1H), 6.01 (ddd, J=17.4, 10.0, 7.6 Hz, 1H), 5.78-5.57 (m, 1H), 5.35-5.04 (m, 5H), 4.91 (br. s., 1H), 4.06 (s, 3H), 3.26-3.06 (m, 1H), 2.81-2.54 (m, 2H), 1.54-1.30 (m, 12H).

43I. Preparation of tert-butyl N-[(9R,10E,13S)-3,9-dimethyl-8-oxo-3,4,7,18-tetraazatricyclo[12.3.1.0$^{2,6}$]octadeca-1(18),2(6),4,10,14,16-hexaen-13-yl]carbamate A solution of tert-butyl N-[(1S)-1-(6-{1-methyl-4-[(2R)-2-methylbut-3-enamido]-1H-pyrazol-5-yl}pyridin-2-yl)but-3-en-1-yl]carbamate (140 mg, 0.329 mmol) in EtOAc (25 ml) was purged with Ar for 20 min. Second Generation Grubbs Catalyst (0.112 g, 0.132 mmol) was added and the reaction mixture heated at 80° C. overnight. The reaction mixture was cooled to rt and concentrated. Purification by normal phase chromatography and then by reverse phase chromatography was done. The fractions containing the desired product were made basic (pH ~8) with sat NaHCO$_3$ and then concentrated. The residue was partitioned between water and EtOAc and the layers were separated. The aqueous layer was extracted with DCM (3×) and EtOAc (3×). The organic layers were combined and washed with brine, dried MgSO$_4$, filtered and concentrated to give tert-butyl N-[(9R,10E,13S)-3,9-dimethyl-8-oxo-3,4,7,18-tetraazatricyclo[12.3.1.0$^{2,6}$]octadeca-1(18),2(6),4,10,14,16-hexaen-13-yl]carbamate (96 mg, 66% yield). MS(ESI) m/z: 398.2 (M+H)$^+$. $^1$H NMR (400 MHz, CDCl$_3$) δ 11.12 (br. s., 1H), 8.08 (s, 1H), 7.84 (t, J=7.9 Hz, 1H), 7.39 (dd, J=7.9, 0.7 Hz, 1H), 7.32-7.24 (m, 1H), 5.98-5.83 (m, 1H), 5.55 (dd, J=15.7, 7.4 Hz, 1H), 5.41 (d, J=6.6 Hz, 1H), 5.04 (m, 1H), 4.10-4.03 (m, 3H), 3.15 (quin, J=7.3 Hz, 1H), 2.84-2.56 (m, 2H), 1.51-1.32 (m, 12H).

43J. Preparation of tert-butyl N-[(9R,13S)-3,9-dimethyl-8-oxo-3,4,7,18-tetraazatricyclo[12.3.1.0$^{2,6}$]octadeca-1(18),2(6),4,14,16-pentaen-13-yl]carbamate, and 43K. Preparation of tert-Butyl N-[(9R,13S)-3,9-dimethyl-8-oxo-3,4,7,18-tetraazatricyclo[12.3.1.0$^{2,6}$]octadeca-2(6),4-dien-13-yl]carbamate A solution of tert-butyl N-[(9R,10E,13S)-3,9-dimethyl-8-oxo-3,4,7,18-tetraazatricyclo[12.3.1.0$^{2,6}$]octadeca-1(18),2(6),4,10,14,16-hexaen-13-yl]carbamate (0.096 g, 0.024 mmol) in EtOH (4 ml) was hydrogenated at 20 psi H$_2$ in the presence of PtO$_2$ (20 mg) for 20 h. The mixture was filtered, washing with MeOH and EtOAc. The filtrate was concentrated and then purified by reverse phase chromatography to give, following neutralization of the fractions and extraction, tert-butyl-N-[(9R,13S)-3,9-dimethyl-8-oxo-3,4,7,18-tetraazatricyclo[12.3.1.0$^{2,6}$]octadeca-2(6),4-dien-13-yl]carbamate (20 mg, 20.4% yield), MS(ESI) m/z: 406.2 (M+H)$^+$; and tert-butyl N-[(9R,13S)-3,9-dimethyl-8-oxo-3,4,7,18-tetraazatricyclo[12.3.1.0$^{2,6}$]octadeca-1(18),2(6),4,14,16-pentaen-13-yl]carbamate (68 mg, 70.5% yield), MS(ESI) m/z: 400.2 (M+H)$^+$.

43L. Preparation of (9R,13S)-13-amino-3,9-dimethyl-3,4,7,18-tetraazatricyclo[12.3.1.0$^{2,6}$]octadeca-1(18),2(6),4,14,16-pentaen-8-one To a solution of tert-butyl N-[(9R,13S)-3,9-dimethyl-8-oxo-3,4,7,18-tetraazatricyclo[12.3.1.0$^{2,6}$]octadeca-1(18),2(6),4,14,16-pentaen-13-yl]carbamate (0.035 g, 0.088 mmol) in DCM (0.5 ml) was added TFA (0.2 mL, 2.60 mmol). After stirring for 1 h, the reaction mixture was concentrated to dryness, and coevaporated with CH$_3$CN. The residue was neutralized by dissolving in MeOH, passing through NaHCO$_3$ cartridge (StratoSpheres SPE; 500 mg, 0.90 mmol loading), and concentrating the filtrate to give (9R,13S)-13-amino-3,9-dimethyl-3,4,7,18-tetraazatricyclo[12.3.1.0$^{2,6}$]octadeca-1(18),2(6),4,14,16-pentaen-8-one (15 mg, 57% yield) as clear glass which was used without further purification. MS(ESI) m/z: 300.5 (M+H)$^+$.

43M. Preparation of (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7,18-tetraazatricyclo[12.3.1.0$^{2,6}$]octadeca-1(18),2(6),4,14,16-pentaen-8-one (9R,13S)-13-{4-[5-Chloro-2-(4-chloro-1H-1,2,3-triazol-1-yl)phenyl]-6-oxo-1,2,3,6-tetrahydropyridin-1-yl}-3,9-dimethyl-3,4,7,18-tetraazatricyclo[12.3.1.0$^{2,6}$]octadeca-1(18),2(6),4,14,16-pentaen-8-one (7 mg, 32% yield) was prepared according to the procedures described in Example 1 by using 1-(5-chloro-2-(4-chloro-1H-1,2,3-triazol-1-yl)phenyl)prop-2-en-1-one, prepared as described in Intermediate 4, and (9R,13S)-13-amino-3,9-dimethyl-3,4,7,18-tetraazatricyclo[12.3.1.0$^{2,6}$]octadeca-1(18),2(6),4,14,16-pentaen-8-one. MS(ESI) m/z: 591.2 (M+H)$^+$. $^1$H NMR (400 MHz, CD$_3$OD) δ 8.43 (s, 1H), 7.95 (t, J=7.8 Hz, 1H), 7.66-7.60 (m, 3H), 7.58-7.53 (m, 2H), 7.34 (d, J=7.7 Hz, 1H), 5.83 (s, 1H), 5.68 (dd, J=11.1, 1.9 Hz, 1H), 4.05 (s, 3H), 2.93 (ddd, J=13.1, 7.8, 5.5 Hz, 1H), 2.65-2.52 (m, 1H), 2.51-2.39 (m, 1H), 2.19-2.09 (m, 1H), 2.02-1.91 (m, 1H), 1.83-1.64 (m, 3H), 1.60-1.49 (m, 1H), 1.32-1.19 (m, 1H), 1.16 (d, J=6.8 Hz, 3H). Analytical HPLC (Method A): RT=8.46 min, purity=99.6%; Factor XIa Ki=4.1 nM, Plasma Kallikrein Ki=110 nM.

Example 44

Preparation of (9R,13S)-13-[4-(3,6-dichloro-2-fluorophenyl)-2-oxo-1,2-dihydropyridin-1-yl]-3,9-dimethyl-3,4,7,15-tetraazatricyclo[12.3.1.0$^{2,6}$]octadeca-1(18),2(6),4,14,16-pentaen-8-one

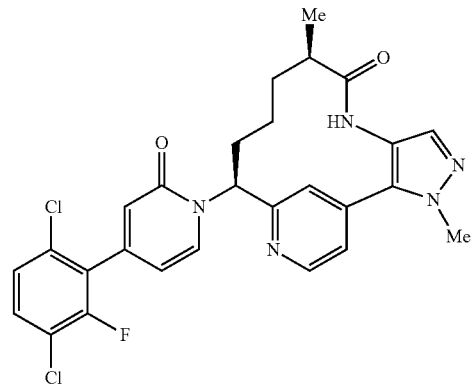 [SMILES: C[C@@H]1CCC[C@H](n2ccc(-c3c(Cl)ccc(Cl)c3F)cc2=O)c2cc(ccn2)-c2c(cnn2C)NC1=O]

To a sealable tube containing (9R,13S)-13-[4-(3,6-dichloro-2-fluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one), prepared as described in Example 24, CuI (0.368 mg, 1.935 μmol) in DMSO (1 ml) was added 3-iodopyridine (7.93 mg, 0.039 mmol) and Cs$_2$CO$_3$ (0.025 g, 0.077 mmol). The reaction mixture was purged with Ar (3×), then warmed to 80° C. After 44 h, the reaction was cooled to rt. Purification by reverse phase chromatography afforded (9R,13S)-13-[4-(3,6-dichloro-2-fluorophenyl)-2-oxo-1,2-dihydropyridin-1-yl]-3,9-dimethyl-3,4,7,15-tetraazatricyclo[12.3.1.0$^{2,6}$]octadeca-1(18),2(6),4,14,16-pentaen-8-one trifluoroacetate (1.91 mg, 15% yield) as a white solid. MS(ESI) m/z: 540.1 (M+H)$^+$. $^1$H NMR (400 MHz, CD$_3$OD) δ 8.74 (d, J=5.1 Hz, 1H), 8.23 (d, J=7.0 Hz, 1H), 7.75 (s, 1H), 7.59-7.50 (m, 3H), 7.39 (dd, J=8.8, 1.5 Hz, 1H), 6.55 (d, J=2.0 Hz, 1H), 6.42 (dd, J=7.0, 1.5 Hz, 1H), 6.17 (dd, J=12.8, 4.2 Hz, 1H), 4.06 (s, 3H), 2.74-2.64 (m, 1H), 2.38-2.26 (m, 1H), 2.15-1.99 (m, 2H), 1.70-1.58 (m, 1H), 1.52-1.39 (m, 1H), 1.03 (d, J=7.0 Hz, 3H), 0.89-0.72 (m, 1H). Analytical HPLC (Method A): RT=7.43 min, 97.9% purity; Factor XIa Ki=2.2 nM, Plasma Kallikrein Ki=5.7 nM.

Example 45

Preparation of (9R,13S)-13-[4-(3-chloro-2,6-difluorophenyl)-6-oxo-1,2,3,6-tetrahydropyridin-1-yl]-3-ethyl-9-methyl-3,4,7,15-tetraazatricyclo[12.3.1.0$^{2,6}$]octadeca-1(18),2(6),4,14,16-pentaen-8-one

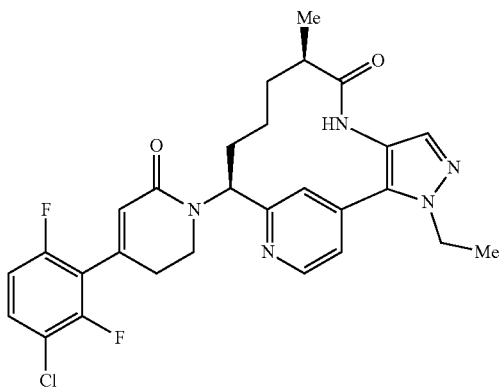 [SMILES: CCn1ncc2c1-c1ccnc(c1)[C@@H](N1CCC(c3c(F)ccc(Cl)c3F)=CC1=O)CCC[C@@H](C)C(=O)N2]

(9R,13S)-13-[4-(3-Chloro-2,6-difluorophenyl)-6-oxo-1,2,3,6-tetrahydropyridin-1-yl]-3-ethyl-9-methyl-3,4,7,15-tetraazatricyclo[12.3.1.0$^{2,6}$]octadeca-1(18),2(6),4,14,16-pentaen-8-one was prepared according to the procedures described in Example 1 by using 1-(3-chloro-2,6-difluorophenyl)prop-2-en-1-one, Intermediate 1, and 1-ethyl-4-nitro-1H-pyrazole, Intermediate 8. $^1$H NMR (400 MHz, CD$_3$OD) δ 8.84 (d, J=5.5 Hz, 1H), 7.86 (s, 1H), 7.76 (dd, J=5.7, 1.5 Hz, 1H), 7.61 (s, 1H), 7.56 (td, J=8.7, 5.5 Hz, 1H), 7.12 (td, J=9.2, 1.8 Hz, 1H), 6.13 (s, 1H), 5.56 (dd, J=12.5, 4.0 Hz, 1H), 4.43 (q, J=7.1 Hz, 2H), 3.74 (t, J=6.8 Hz, 2H), 2.85-2.69 (m, 2H), 2.65-2.54 (m, 1H), 2.38-2.20 (m, 1H), 2.10-1.88 (m, 2H), 1.71-1.58 (m, 1H), 1.53 (t, J=7.3 Hz, 3H), 1.22 (br. s., 2H), 1.12 (d, J=6.8 Hz, 3H). MS(ESI) m/z: 540.2 (M+H)$^+$. Analytical HPLC (Method A): RT=11.04 min, purity=97%; Factor XIa Ki=13 nM, Plasma Kallikrein Ki=54 nM.

Example 46

Preparation of (9R,13S)-13-[4-(6-acetyl-3-chloro-2-fluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one

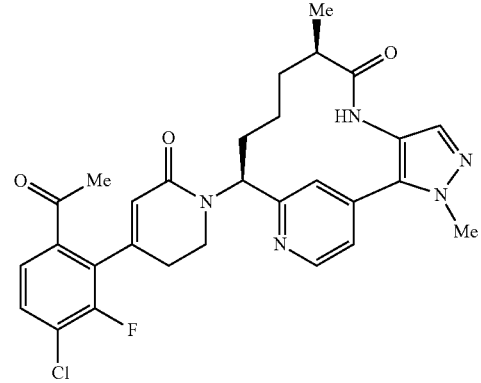 [SMILES: CC(=O)c1ccc(Cl)c(F)c1C1=CC(=O)N([C@H]2CCC[C@@H](C)C(=O)Nc3cnn(C)c3-c3ccnc2c3)CC1]

A mixture of (9R,13S)-13-[4-(6-bromo-3-chloro-2-fluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one (18 mg, 0.031 mmol), tributyl(1-ethoxyvinyl)stannane (20.72 μl, 0.061 mmol) and Pd(PPh$_3$)$_2$Cl$_2$ (2.153 mg, 3.07 μmol) in toluene (767 μl) was degassed and heated at 110° C. overnight. The solvent was removed and 2 ml of a 1:1 mixture of 1 N HCl and THF was added. The mixture was stirred at rt for 0.5 h and was concentrated. The crude product was then purified using reverse phase HPLC to afford (9R,13S)-13-[4-(6-acetyl-3-chloro-2-fluorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one trifluoroacetate (9.6 mg, 46%). $^1$H NMR (500 MHz, DMSO-d$_6$) δ 9.24 (s, 1H), 8.74 (d, J=5.2 Hz, 1H), 7.85-7.73 (m, 2H), 7.59-7.44 (m, 3H), 7.27-7.00 (m, 1H), 5.71 (s, 1H), 5.60 (d, J=8.9 Hz, 1H), 4.02 (s, 3H), 3.88 (br. s., 1H), 3.70 (d, J=5.5 Hz, 1H), 3.51-3.38 (m, 5H), 2.17-1.93 (m, 2H), 1.69 (br. s., 1H), 1.48 (br. s., 1H), 1.28-1.10 (m, 1H), 0.93 (d, J=6.7 Hz, 3H), 0.66 (br. s., 1H). MS(ESI) m/z: 550.4 (M+H). Analytical HPLC (Method C): RT=1.40 min, purity=>95%; Factor XIa Ki=3.5 nM, Plasma Kallikrein Ki=46 nM.

Example 47

Preparation of (9R,13S)-13-{4-[3-chloro-2-fluoro-6-(trifluoromethyl)phenyl]-6-oxo-1,2,3,6-tetrahydropyridin-1-yl}-9-methyl-4-(pyrimidin-5-yl)-3,4,7,15-tetraazatricyclo[12.3.1.0$^{2,6}$]octadeca-1(18),2,5,14,16-pentaen-8-one

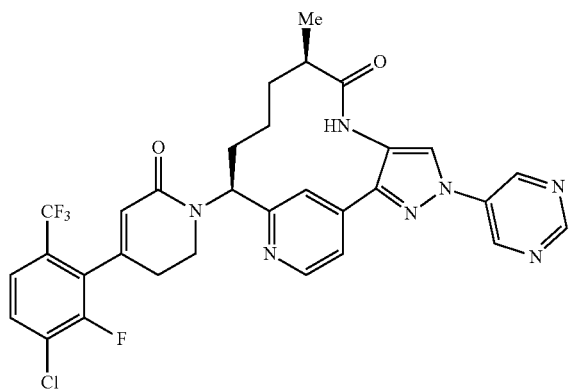 [SMILES: C[C@@H]1CCC[C@H](N2CCC(c3c(C(F)(F)F)ccc(Cl)c3F)=CC2=O)c2cc(ccn2)-c2nn(-c3cncnc3)cc2NC1=O]

47A. Preparation of (9R,13S)-13-{4-[3-chloro-2-fluoro-6-(trifluoromethyl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one trifluoroacetate (9R,13S)-13-{4-[3-Chloro-2-fluoro-6-(trifluoromethyl)phenyl]-6-oxo-1,2,3,6-tetrahydropyridin-1-yl}-9-methyl-3,4,7,15-tetraazatricyclo[12.3.1.0²,⁶]octadeca-1(18),2(6),4,14,16-pentaen-8-one trifluoroacetate (262 mg, 0.387 mmol, 65% yield) was prepared according to the procedures described in Example 1 by substituting, 1-(5-chloro-2-(1H-1,2,3-triazol-1-yl)phenyl)prop-2-en-1-one with 1-(3-chloro-2-fluoro-6-(trifluoromethyl)phenyl)prop-2-en-1-one, Intermediate 2. $^1$H NMR (500 MHz, DMSO-d$_6$) δ 9.25 (s, 1H), 8.59 (d, J=4.3 Hz, 1H), 7.91-7.79 (m, 2H), 7.74-7.65 (m, 2H), 7.44 (d, J=4.9 Hz, 1H), 7.26-6.96 (m, 1H), 5.91 (s, 1H), 5.65 (d, J=8.9 Hz, 1H), 3.91-3.81 (m, 1H), 3.60 (br. s., 1H), 2.65 (br. s., 2H), 2.20-1.97 (m, 2H), 1.76 (br. s., 1H), 1.51 (br. s., 1H), 1.31 (br. s., 1H), 0.95 (d, J=7.0 Hz, 3H), 0.81 (br. s., 1H). MS(ESI) m/z: 562.3 [M+H]$^+$. Analytical HPLC (Method B): RT=1.72 min, purity=100.0%.

47B. Preparation of (9R,13S)-13-{4-[3-chloro-2-fluoro-6-(trifluoromethyl)phenyl]-6-oxo-1,2,3,6-tetrahydropyridin-1-yl}-9-methyl-4-(pyrimidin-5-yl)-3,4,7,15-tetraazatricyclo[12.3.1.0²,⁶]octadeca-1(18),2,5,14,16-pentaen-8-one trifluoroacetate (9R,13S)-13-{4-[3-Chloro-2-fluoro-6-(trifluoromethyl)phenyl]-6-oxo-1,2,3,6-tetrahydropyridin-1-yl}-9-methyl-4-(pyrimidin-5-yl)-3,4,7,15-tetraazatricyclo[12.3.1.0²,⁶]octadeca-1(18),2,5,14,16-pentaen-8-one trifluoroacetate (7.5 mg, 9.85 μmol, 18% yield) was prepared according to the procedures described in Example 11 by substituting (2-bromoethoxy)(tert-butyl)dimethylsilane with 5-iodopyrimidine. $^1$H NMR (500 MHz, DMSO-d$_6$) δ 9.58 (s, 1H), 9.39 (s, 2H), 9.19 (s, 1H), 8.80 (s, 1H), 8.68 (d, J=4.9 Hz, 1H), 7.85 (t, J=7.8 Hz, 1H), 7.76 (s, 1H), 7.70 (d, J=8.5 Hz, 1H), 7.60 (d, J=4.3 Hz, 1H), 7.26-6.97 (m, 1H), 5.92 (s, 1H), 5.71 (d, J=8.8 Hz, 1H), 3.97 (br. s., 1H), 3.67 (br. s., 1H), 3.44-3.36 (m, 1H), 2.73 (br. s., 1H), 2.19 (br. s., 1H), 2.06 (br. s., 1H), 1.76 (br. s., 1H), 1.56 (br. s., 1H), 1.34 (br. s., 1H), 0.97 (d, J=6.7 Hz, 3H), 0.69 (br. s., 1H). MS(ESI) m/z: 640.1 [M+H]$^+$. Analytical HPLC (Method B): RT=1.84 min, purity=99.0%; Factor XIa Ki=5.4 nM, Plasma Kallikrein Ki=13 nM.

Example 48

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7-triazatricyclo[12.3.1.0²,⁶]octadeca-1(18),2(6),4,14,16-pentaen-8-one

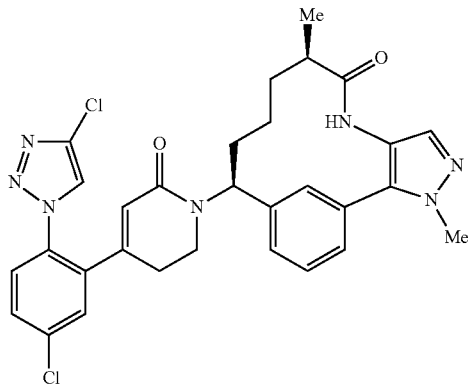 [SMILES: C[C@@H]1CCC[C@H](N2CCC(c3cc(Cl)ccc3-n3cc(Cl)nn3)=CC2=O)c2cccc(c2)-c2c(cnn2C)NC1=O]

48A. Preparation of tert-butyl N-[(1S)-1-[3-(1-methyl-4-nitro-1H-pyrazol-5-yl)phenyl]but-3-en-1-yl]carbamate To tert-butyl N-[(1S)-1-(3-bromophenyl)but-3-en-1-yl]carbamate (2 g, 6.13 mmol), 1-methyl-4-nitro-1H-pyrazole (0.779 g, 6.13 mmol), di(adamantan-1-yl)(butyl) phosphine (0.659 g, 1.839 mmol), pivalic acid (0.213 ml, 1.839 mmol), K$_2$CO$_3$ (2.54 g, 18.39 mmol) was added DMF (9 ml). The mixture was degassed with Ar for 10 min. Pd(OAc)$_2$ (0.275 g, 1.226 mmol) was added and the reaction was heated in oil bath at 120° C. for 15 h. The reaction was partitioned between water (50 ml) and EtOAc (50 ml) and solution was filtered through paper and the layers were separated. The aqueous layer was extracted with EtOAc (2×50 ml). The combined organic layers were washed with brine (50 ml), dried over MgSO$_4$, filtered and concentrated. The residue was purified by normal phase chromatography using hexanes and EtOAc as eluents to afford (S)-tert-butyl (1-(3-(1-methyl-4-nitro-1H-pyrazol-5-yl)phenyl)but-3-en-1-yl)carbamate (1.186 g, 3.18 mmol, 51.9% yield) as a yellow oil. MS(ESI) m/z: 371.1 (M–H)$^+$.

48B. Preparation of tert-butyl N-[(1S)-1-[3-(4-amino-1-methyl-1H-pyrazol-5-yl)phenyl]but-3-en-1-yl]carbamate To tert-butyl N-[(1S)-1-[3-(1-methyl-4-nitro-1H-pyrazol-5-yl)phenyl]but-3-en-1-yl]carbamate (0.097 g, 0.260 mmol) in acetone (5 ml)/water (1 ml), cooled to 0° C., was added NH$_4$Cl (0.070 g, 1.302 mmol) and Zn (0.170 g, 2.60 mmol). The ice bath was removed. After 3 h, the reaction was filtered and the filtrate was partitioned between water (10 ml) and EtOAc (30 ml). The aqueous layer was extracted with EtOAc (2×20 ml). The combined organic layers were washed with brine (10 ml), dried over MgSO$_4$, filtered and concentrated. The residue was purified by normal phase chromatography using DCM and 0-10% MeOH as eluents to afford tert-butyl N-[(1S)-1-[3-(4-amino-1-methyl-1H-pyrazol-5-yl)phenyl]but-3-en-1-yl]carbamate (76.6 mg, 86%). MS(ESI) m/z: 343.2 (M+H)$^+$.

48C. Preparation of tert-butyl N-[(1S)-1-(3-{1-methyl-4-[(2R)-2-methylbut-3-enamido]-1H-pyrazol-5-yl}phenyl)but-3-en-1-yl]carbamate To tert-butyl N-[(1S)-1-[3-(4-amino-1-methyl-1H-pyrazol-5-yl)phenyl]but-3-en-1-yl]carbamate (0.076 g, 0.222 mmol) in EtOAc (0.58 ml) was added (R)-2-methylbut-3-enoic acid (0.027 g, 0.266 mmol), Intermediate 6, in 0.3 ml EtOAc. The mixture was cooled to 0° C. and Hunig's Base (0.116 ml, 0.666 mmol) followed by a solution of 50% T3P® in EtOAc (0.264 ml, 0.444 mmol) were added. After 3 h, the reaction was partitioned with sat NaHCO$_3$ (5 ml) and EtOAc (5 ml). The aqueous layer was extracted with EtOAc (2×10 ml). The combined organic layers were washed with brine (5 ml), dried over MgSO$_4$, filtered and concentrated. The residue was purified by normal phase chromatography using hexanes and EtOAc as eluents to afford (69 mg, 73%) of tert-butyl N-[(1S)-1-(3-{1-methyl-4-[(2R)-2-methylbut-3-enamido]-1H-pyrazol-5-yl}phenyl)but-3-en-1-yl]carbamate as a yellow oil. MS(ESI) m/z: 425.2 (M+H)$^+$. $^1$H NMR (400 MHz, CDCl$_3$) δ 8.04 (s, 1H), 7.52-7.45 (m, 1H), 7.37 (d, J=7.9 Hz, 1H), 7.26-7.18 (m, 2H), 7.05 (br. s., 1H), 5.96-5.85 (m, 1H), 5.69 (ddt, J=17.0, 10.1, 7.0 Hz, 1H), 5.21-5.09 (m, 4H), 4.95 (br. s., 1H), 4.77 (br. s., 1H), 3.76

(s, 3H), 3.07 (quin, J=7.2 Hz, 1H), 2.61-2.48 (m, 2H), 1.45-1.38 (m, 9H), 1.30 (d, J=7.0 Hz, 3H).

48D. Preparation of tert-butyl N-[(9R,10E,13S)-3,9-dimethyl-8-oxo-3,4,7-triazatricyclo[12.3.1.0²,⁶]octadeca-1(18),2(6),4,10,14,16-hexaen- 13-yl]carbamate A solution of tert-butyl N-[(1S)-1-(3-{1-methyl-4-[(2R)-2-methylbut-3-enamido]-1H-pyrazol-5-yl}phenyl)but-3-en-1-yl]carbamate (0.069 g, 0.163 mmol) in degassed DCE (10 ml) was heated to 120° C. for 30 min in a microwave in the presence of Second Generation Grubbs Catalyst (0.055 g, 0.065 mmol). The reaction mixture was directly purified by normal phase chromatography twice using hexanes and EtOAc as eluents to afford desired tert-butyl N-[(9R,10E, 13S)-3,9-dimethyl-8-oxo-3,4,7-triazatricyclo [12.3.1.0²,⁶] octadeca-1(18),2(6),4,10,14,16-hexaen-13-yl]carbamate (33 mg, 51.2%) as a dark solid. MS(ESI) m/z: 397.1 (M+H)⁺. ¹H NMR (400 MHz, CDCl₃) δ 7.61-7.52 (m, 1H), 7.46-7.40 (m, 1H), 7.33-7.25 (m, 1H), 7.20 (d, J=7.5 Hz, 1H), 6.93 (br. s., 1H), 6.83 (s, 1H), 5.63 (ddd, J=15.1, 9.4, 5.6 Hz, 1H), 5.18 (br. s., 1H), 4.89 (dd, J=15.2, 8.8 Hz, 1H), 4.69 (br. s., 1H), 3.93-3.86 (m, 3H), 3.09-2.99 (m, 1H), 2.69-2.58 (m, 1H), 2.17-2.08 (m, 1H), 1.53-1.32 (m, 9H), 1.18 (d, J=6.8 Hz, 3H).

48E. Preparation of tert-butyl N-[(9R,13S)-3,9-dimethyl-8-oxo-3,4,7-triazatricyclo[12.3.1.0²,⁶]octadeca-1(18),2(6),4,14,16-pentaen-13- yl]carbamate A solution of tert-butyl N-[(9R,10E,13S)-3,9-dimethyl-8-oxo-3,4,7-triazatricyclo[12.3.1.0²,⁶]octadeca-1(18),2(6),4,10,14,16-hexaen-13-yl]carbamate (0.089 g, 0.224 mmol) in EtOH (5 ml) was hydrogenated under a H₂ atmosphere at 55 psi for 3 h. The reaction mixture was filtered through small plug of CELITE® and rinsed with EtOH/MeOH/DCM to give tert-butyl N-[(9R,13S)-3,9-dimethyl-8-oxo-3,4,7-triazatricyclo[12.3.1.0²,⁶]octadeca-1(18),2(6),4,14,16-pentaen-13-yl]carbamate (89 mg, 99%) as a white solid. MS(ESI) m/z: 399.4 (M+H)⁺. ¹H NMR (400 MHz CDCl₃) δ 7.53-7.43 (m, 2H), 7.43-7.36 (m, 1H), 7.29 (s, 1H), 6.44 (s, 1H), 4.90 (br. s., 1H), 4.68 (br. s., 1H), 3.98 (s, 3H), 2.44 (br. s., 1H), 1.93 (d, J=7.7 Hz, 1H), 1.85-1.63 (m, 2H), 1.42 (br. s., 9H), 1.28-1.19 (m, 2H), 1.07 (d, J=6.8 Hz, 3H), 0.96 (br. s., 1H).

48F. Preparation of (9R,13S)-13-amino-3,9-dimethyl-3,4,7-triazatricyclo[12.3.1.0²,⁶]octadeca-1(18),2(6),4,14,16-pentaen-8-one, hydrochloride

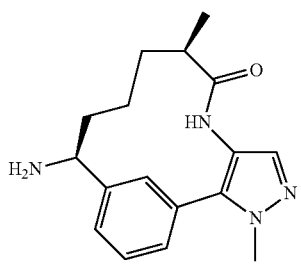 [SMILES: C[C@@H]1CCC[C@H](N)c2cccc(c2)-c2c(cnn2C)NC1=O]

tert-Butyl N-[(9R,13S)-3,9-dimethyl-8-oxo-3,4,7-triazatricyclo[12.3.1.0²,⁶]octadeca-1(18),2(6),4,14,16-pentaen-13-yl]carbamate (88 mg, 0.221 mmol) was deprotected with 4 N HCl in dioxane (3 ml) for 5 h. The reaction was concentrated to afford (70 mg, 95%) of (9R,13S)-13-amino-3,9-dimethyl-3,4,7-triazatricyclo[12.3.1.0²,⁶]octadeca-1(18),2(6),4,14,16-pentaen-8-one, hydrochloride as a dark solid. MS(ESI) m/z: 299.08 (M+H)⁺. ¹H NMR (500 MHz, CD₃OD) δ 7.81 (s, 1H), 7.77-7.70 (m, 1H), 7.70-7.58 (m, 3H), 4.46 (dd, J=12.0, 4.5 Hz, 1H), 4.19-4.07 (m, 3H), 3.45-3.26 (m, 1H), 2.75-2.59 (m, 1H), 2.21-2.09 (m, 1H), 1.99-1.86 (m, 2H), 1.58 (td, J=14.3, 8.3 Hz, 1H), 1.29-1.17 (m, 1H), 1.03 (d, J=6.9 Hz, 3H), 0.94-0.82 (m, 1H).

48G. Preparation of (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7-triazatricyclo[12.3.1.0²,⁶]octadeca-1(18),2(6),4,14,16-pentaen-8-one (9R,13S)-13-{4-[5-Chloro-2-(4-chloro-1H-1,2,3-triazol-1-yl)phenyl]-6-oxo-1,2,3,6-tetrahydropyridin-1-yl}-3,9-dimethyl-3,4,7-triazatricyclo[12.3.1.0²,⁶]octadeca-1(18),2(6),4,14,16-pentaen-8-one (23 mg, 86%), a white solid, was prepared in a similar manner as Example 1 by using 1-[5-chloro-2-(1H-1,2,3-triazol-1-yl)phenyl]prop-2-en-1-one and 13-amino-3,9-dimethyl-3,4,7,15-tetraazatricyclo[12.3.1.0²,⁶]octadeca-1(18),2(6),4,14,16-pentaen-8-one. MS(ESI) m/z: 590.3 (M+H)⁺. ¹H NMR (400 MHz, CD₃OD) δ 8.33 (s, 1H), 7.58-7.51 (m, 2H), 7.51-7.35 (m, 6H), 7.25 (d, J=7.7 Hz, 1H), 5.72 (s, 1H), 5.46 (dd, J=12.8, 3.1 Hz, 1H), 3.97-3.85 (m, 3H), 2.94-2.81 (m, 1H), 2.36-2.25 (m, 1H), 2.13-1.98 (m, 2H), 1.98-1.86 (m, 1H), 1.79-1.63 (m, 2H), 1.57-1.40 (m, 2H), 1.05 (d, J=6.8 Hz, 3H), 0.93 (t, J=12.7 Hz, 1H). Analytical HPLC (Method A) RT=8.52 min, purity=97%; Factor XIa Ki=0.13 nM, Plasma Kallikrein Ki=5.5 nM.

Example 49

Preparation of (9R,13S)-13-{4-[3-chloro-2-fluoro-6-(trifluoromethyl)phenyl]-6-oxo-1,2,3,6-tetrahydropyridin-1-yl}-3,9-dimethyl-3,4,7-triazatricyclo[12.3.1.0²,⁶]octadeca-1(18),2(6),4,14,16-pentaen-8-one

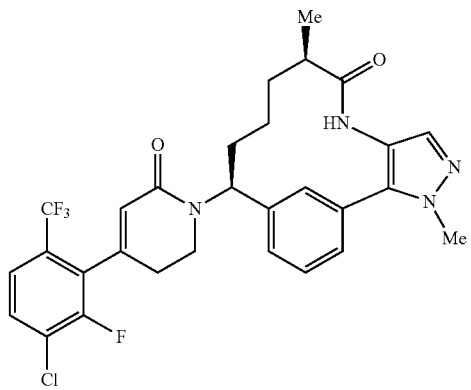 [SMILES: C[C@@H]1CCC[C@H](N2CCC(c3c(C(F)(F)F)ccc(Cl)c3F)=CC2=O)c2cccc(c2)-c2c(cnn2C)NC1=O]

(9R,13S)-13-{4-[3-Chloro-2-fluoro-6-(trifluoromethyl)phenyl]-6-oxo-1,2,3,6-tetrahydropyridin-1-yl}-3,9-dimethyl-3,4,7-triazatricyclo[12.3.1.0²,⁶]octadeca-1(18),2(6),4,14,16-pentaen-8-one (10.3 mg, 59.1%), a white solid, was prepared in a similar manner as Example 48, using 1-[5-chloro-2-(4-chloro-1H-1,2,3-triazol-1-yl)phenyl]prop-2-en-1-one and 13-amino-3,9-dimethyl-3,4,7,15-tetraazatricyclo

[12.3.1.0$^{2,6}$]octadeca-1(18),2(6),4,14,16-pentaen-8-one. MS(ESI) m/z: 575.3 (M+H)$^+$. $^1$H NMR (400 MHz, CD$_3$OD) δ 7.78-7.69 (m, 1H), 7.65-7.58 (m, 3H), 7.56-7.51 (m, 2H), 7.46 (d, J=7.7 Hz, 1H), 5.99 (s, 1H), 5.68 (dd, J=13.0, 3.1 Hz, 1H), 4.04 (s, 3H), 3.60-3.47 (m, 1H), 3.23-3.14 (m, 1H), 2.66-2.39 (m, 3H), 2.33-2.20 (m, 1H), 1.98-1.89 (m, 1H), 1.89-1.81 (m, 1H), 1.73-1.66 (m, 1H), 1.66-1.56 (m, 1H), 1.19 (d, J=6.8 Hz, 3H), 1.09 (t, J=12.8 Hz, 1H). Analytical HPLC (Method A) RT=9.56 min, purity=95%; Factor XIa Ki=3.2 nM, Plasma Kallikrein Ki=69 nM.

Example 50

Preparation of (9S,13S)-13-{4-[5-chloro-2-(4-chloro-1H-1,2,3-triazol-1-yl)phenyl]-6-oxo-1,2,3,6-tetrahydropyridin-1-yl}-10,16-difluoro-3,9-dimethyl-3,4,7-triazatricyclo[12.3.1.0$^{2,6}$]octadeca-1(18),2(6),4,14,16-pentaen-8-one

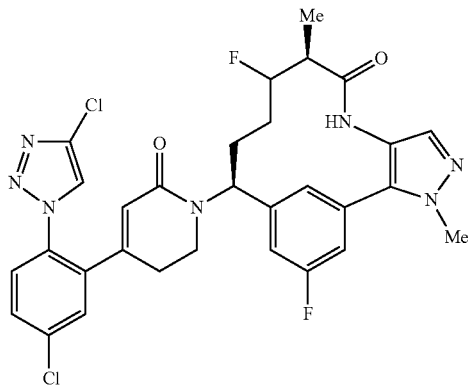 [SMILES: C[C@H]1C(=O)Nc2cnn(C)c2-c2cc(F)cc(c2)[C@@H](N2CCC(c3cc(Cl)ccc3-n3cc(Cl)nn3)=CC2=O)CCC1F]

50A. Preparation of N-[(9S,13S)-10,16-difluoro-3,9-dimethyl-8-oxo-3,4,7-triazatricyclo[12.3.1.0$^{2,6}$]octadeca-1(18),2(6),4,14,16-pentaen-13-yl]carbamate Fe$_2$(C$_2$O$_4$)$_3$·6H$_2$O (2.16 g, 4.46 mmol) was added to a RBF containing H$_2$O (30 ml). The suspension was warmed by a water bath (50° C.) to aid dissolution. After 3 h, the clear yellow solution was cooled to 0° C. and purged with Ar. After 20 min, SELECTFLUOR® (1.58 g, 4.46 mmol) in ACN (5 ml) was added followed by dropwise addition of tert-butyl N-[(9R,10E,13S)-16-fluoro-3,9-dimethyl-8-oxo-3,4,7-triazatricyclo[12.3.1.0$^{2,6}$]octadeca-1(18),2(6),4,10,14,16-hexaen-13-yl]carbamate (0.370 g, 0.893 mmol) in ACN (10 ml). After 5 min, NaBH$_4$ (0.270 g, 7.14 mmol) was added in two separate portions over a 5 min period. After 15 min, the reaction mixture was allowed to come to rt. After 1 h, the reaction mixture was quenched with aq 28-30% NH$_4$OH (15 mL). After 30 min, the reaction mixture was filtered, solids washed with EtOAc, organics washed with brine, dried over Na$_2$SO$_4$, filtered, and concentrated to give a crude mixture of isomers. The material was subjected chiral purification using CHIRALPAK® IC, 21×250 mm, 5μ, using 10% EtOH/90% CO$_2$ at 45 ml/min, 150 Bar, 40° C. The early eluting isomer was assigned tert-butyl N-[(9S,13S)-10,16-difluoro-3,9-dimethyl-8-oxo-3,4,7triazatricyclo[12.3.1.0$^{2,6}$]octadeca-1(18),2(6),4,14,16-pentaen-13-yl]carbamate (99.5% ee; 68 mg, 17.50%) and the second eluting isomer, tert-butyl N-[(9R,13S)-11,16-difluoro-3,9-dimethyl-8-oxo-3,4,7-triazatricyclo[12.3.1.0$^{2,6}$]octadeca-1(18),2(6),4,14,16-pentaen-13-yl]carbamate (99.5% ee; 32 mg, 8.3%). 435 (M+H)$^+$.

50B. Preparation of (9S,13S)-13-{4-[5-chloro-2-(4-chloro-1H-1,2,3-triazol-1-yl)phenyl]-6-oxo-1,2,3,6-tetrahydropyridin-1-yl}-10,16-difluoro-3,9-dimethyl-3,4,7-triazatricyclo[12.3.1.0$^{2,6}$]octadeca-1(18),2(6),4,14,16-pentaen-8-one trifluoroacetate (9S,13S)-13-{4-[5-Chloro-2-(4-chloro-1H-1,2,3-triazol-1-yl)phenyl]-6-oxo-1,2,3,6-tetrahydropyridin-1-yl}-10,16-difluoro-3,9-dimethyl-3,4,7-triazatricyclo[12.3.1.0$^{2,6}$]octadeca-1(18),2(6),4,14,16-pentaen-8-one trifluoroacetate (10 mg, 6%) was prepared by similar methods described in Example 1 by using Boc-deprotected tert-butyl N-[(9R,13S)-11,16-difluoro-3,9-dimethyl-8-oxo-3,4,7-triazatricyclo[12.3.1.0$^{2,6}$]octadeca-1(18),2(6),4,14,16-pentaen-13-yl]carbamate (early eluting isomer) and 1-(5-chloro-2-(4-chloro-1H-1,2,3-triazol-1-yl)phenyl)prop-2-en-1-one, prepared as described for Intermediate 4. The major diastereomer was isolated by chiral purification using CHIRALPAK® IC, 21×250 mm, 5μ, using 15% MeOH/85% CO$_2$ at 45 ml/min, 150 Bar, 40° C. and subsequent reverse phase chromatography (PHENOMENEX® Luna Axia C18 5μ 30×100 mm column, 10-minute gradient; Solvent A: 20% MeOH—80% H$_2$O—0.1% TFA; Solvent B: 90% MeOH—10% H$_2$O—0.1% TFA). MS(ESI) m/z: 626 (M+H)$^+$. $^1$H NMR: (400 MHz, DMSO-d$_6$) δ 9.40 (s, 1H), 8.62-8.56 (m, 1H), 8.12 (d, J=7.5 Hz, 1H), 7.75-7.67 (m, 3H), 7.41-7.32 (m, 2H), 7.26 (s, 1H), 6.88 (d, J=9.9 Hz, 1H), 6.30-6.23 (m, 1H), 5.97-5.82 (m, 2H), 5.43-5.24 (m, 1H), 3.93-3.88 (m, 3H), 3.00 (ddd, J=10.8, 6.9, 4.1 Hz, 1H), 2.34-2.23 (m, 1H), 1.89-1.78 (m, 1H), 1.65-1.49 (m, 1H), 1.25-1.10 (m, 1H), 0.81 (d, J=7.0 Hz, 3H), 0.66-0.44 (m, 1H). Analytical HPLC (method X): RT=6.25 min, purity=100%; Factor XIa Ki=0.1 nM, Plasma Kallikrein Ki=8 nM.

Example 51

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-($^2$H$_3$)methyl-9-methyl-3,4,7-triazatricyclo[12.3.1.0$^{2,6}$]octadeca-1(18),2(6),4,14,16-pentaen-8-one

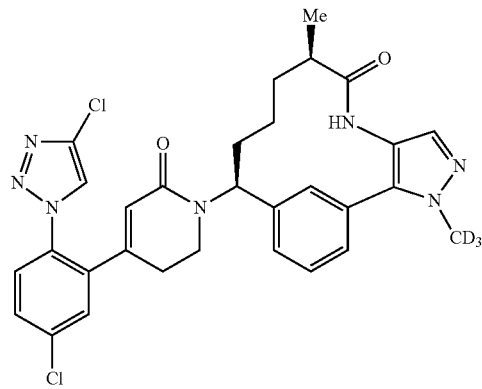 [SMILES: [2H]C([2H])([2H])n1ncc2c1-c1cccc(c1)[C@@H](N1CCC(c3cc(Cl)ccc3-n3cc(Cl)nn3)=CC1=O)CCC[C@@H](C)C(=O)N2]

51A. Preparation of (9R,13S)-13-amino-3-($^2H_3$)methyl-9-methyl-3,4,7-triazatricyclo[12.3.1.0$^{2,6}$]octadeca-1(18),2(6),4,14,16-pentaen-8-one

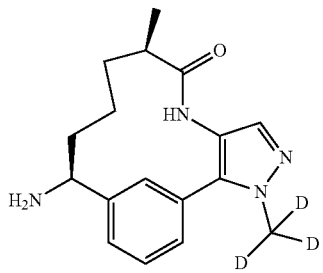 [SMILES: [2H]C([2H])([2H])n1ncc2c1-c1cccc(c1)[C@@H](N)CCC[C@@H](C)C(=O)N2]

(9R,13S)-13-Amino-3-($^2H_3$)methyl-9-methyl-3,4,7-triazatricyclo[12.3.1.0$^{2,6}$]octadeca-1(18),2(6),4,14,16-pentaen-8-one (0.28 g, 98%), a gray solid, was prepared in the same manner as (9R,13S)-13-amino-3,9-dimethyl-3,4,7-triazatricyclo[12.3.1.0$^{2,6}$]octadeca-1(18),2(6),4,14,16-pentaen-8-one, described in Example 48F, by substituting 1-($^2H_3$)methyl-4-nitro-1H-pyrazole for 1-methyl-4-nitro-1H-pyrazole. MS (ESI) m/z: 302.5 (M+H)$^+$.

51B. Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-($^2H_3$)methyl-9-methyl-3,4,7-triazatricyclo[12.3.1.0$^{2,6}$]octadeca-1(18),2(6),4,14,16-pentaen-8-one (9R,13S)-13-{4-[5-Chloro-2-(4-chloro-1H-1,2,3-triazol-1-yl)phenyl]-6-oxo-1,2,3,6-tetrahydropyridin-1-yl}-3-($^2H_3$)methyl-9-methyl-3,4,7-triazatricyclo[12.3.1.0$^{2,6}$]octadeca-1(18),2(6),4,14,16-pentaen-8-one (3 mg, 56.7%) was made in a similar manner as (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7-triazatricyclo[12.3.1.0$^{2,6}$]octadeca-1(18),2(6),4,14,16-pentaen-8-one, described in Example 48, by substituting (9R,13S)-13-amino-3-($^2H_3$)methyl-9-methyl-3,4,7-triazatricyclo[12.3.1.0$^{2,6}$]octadeca-1(18),2(6),4,14,16-pentaen-8-one for (9R,13S)-13-amino-3,9-dimethyl-3,4,7-triazatricyclo[12.3.1.0$^{2,6}$]octadeca-1(18),2(6),4,14,16-pentaen-8-one. MS(ESI) m/z: 593.5 (M+H)$^+$. $^1$H NMR (400 MHz, CD$_3$OD) δ 8.49-8.44 (m, 1H), 8.14 (s, 1H), 7.69-7.64 (m, 2H), 7.60-7.56 (m, 2H), 7.56-7.49 (m, 3H), 7.38 (d, J=7.7 Hz, 1H), 5.92-5.82 (m, 1H), 5.59 (dd, J=12.7, 3.0 Hz, 1H), 3.07-2.94 (m, 1H), 2.51-2.38 (m, 1H), 2.25-2.11 (m, 2H), 2.12-2.00 (m, 1H), 1.91-1.78 (m, 2H), 1.72-1.53 (m, 2H), 1.41-1.32 (m, 1H), 1.18 (d, J=6.8 Hz, 3H), 1.10-1.00 (m, 1H). Analytical HPLC (Method A) RT=8.17 min, purity=90%; Factor XIa Ki=0.18 nM, Plasma Kallikrein Ki=5 nM.

Example 52

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-(2,2-difluoroethyl)-9-methyl-3,4,7,15-tetraazatricyclo[12.3.1.0$^{2,6}$]octadeca-1(18),2(6),4,14,16-pentaen-8-one

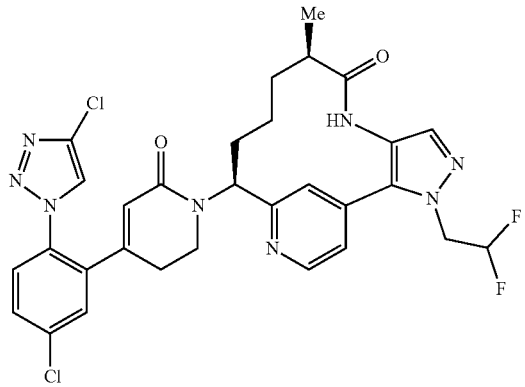 [SMILES: C[C@@H]1CCC[C@H](N2CCC(c3cc(Cl)ccc3-n3cc(Cl)nn3)=CC2=O)c2cc(ccn2)-c2c(cnn2CC(F)F)NC1=O]

(9R,13S)-13-{4-[5-Chloro-2-(4-chloro-1H-1,2,3-triazol-1-yl)phenyl]-6-oxo-1,2,3,6-tetrahydropyridin-1-yl}-3-(2,2-difluoroethyl)-9-methyl-3,4,7,15-tetraazatricyclo[12.3.1.0$^{2,6}$]octadeca-1(18),2(6),4,14,16-pentaen-8-one was prepared according to the procedures described in Example 1 by using 1-(5-chloro-2-(4-chloro-1H-1,2,3-triazol-1-yl)phenyl)prop-2-en-1-one, Intermediate 4, and 1-(2,2-difluoroethyl)-4-nitro-1H-pyrazole, Intermediate 9. $^1$H NMR (400 MHz, CD$_3$CN) δ 8.81 (d, J=5.3 Hz, 1H), 8.47 (s, 1H), 7.74 (s, 1H), 7.71-7.63 (m, 4H), 7.62-7.55 (m, 1H), 6.50-6.15 (m, 1H), 5.84 (s, 1H), 5.52 (dd, J=12.7, 4.1 Hz, 1H), 4.83-4.71 (m, 2H), 3.63-3.49 (m, 2H), 2.64-2.53 (m, 1H), 2.32-2.13 (m, 3H), 1.99-1.84 (m, 2H), 1.66-1.52 (m, 1H), 1.41-1.29 (m, 1H), 1.24-1.14 (m, 1H), 1.09 (d, J=6.8 Hz, 3H). MS(ESI) m/z: 641.1 (M+H)$^+$. Analytical HPLC (Method A): RT=11.43 min, purity=95%; Factor XIa Ki=0.76 nM, Plasma Kallikrein Ki=22 nM.

Example 53

Preparation of (9R)-13-{4-[5-chloro-2-(1H-1,2,3-triazol-1-yl)phenyl]-6-oxo-1,2,3,6-tetrahydropyridin-1-yl}-3-(difluoromethyl)-9-methyl-3,4,7,15-tetraazatricyclo[12.3.1.0$^{2,6}$]octadeca-1(18),2(6),4,14,16-pentaen-8-one

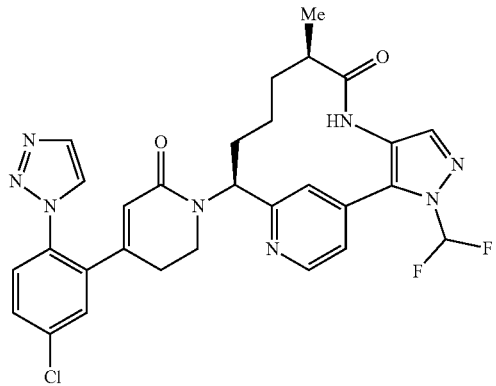 [SMILES: C[C@@H]1CCC[C@H](N2CCC(c3cc(Cl)ccc3-n3ccnn3)=CC2=O)c2cc(ccn2)-c2c(cnn2C(F)F)NC1=O]

(9R,13S)-13-{4-[5-Chloro-2-(1H-1,2,3-triazol-1-yl)phenyl]-6-oxo-1,2,3,6-tetrahydropyridin-1-yl}-3-(difluoromethyl)-9-methyl-3,4,7,15-tetraazatricyclo[12.3.1.0$^{2,6}$]octadeca-1(18),2(6),4,14,16-pentaen-8-one (6 mg, 9%), as a white solid, was prepared in a manner similar to Example 1 by substituting 1-methyl-4-nitro-1H-pyrazole with 1-(difluoromethyl)-4-nitro-1H-pyrazole MS(ESI) m/z: 593.2 (M+H)$^+$. $^1$H NMR (400 MHz, CD$_3$OD) δ 8.93-8.64 (m, 1H), 8.32 (s, 1H), 7.92 (s, 1H), 7.77 (s, 2H), 7.72-7.50 (m, 6H), 5.83 (s, 1H), 5.67-5.49 (m, 1H), 4.34-4.08 (m, 1H), 3.75-3.62 (m, 1H), 3.60-3.48 (m, 1H), 2.67-2.54 (m, 1H), 2.27-2.09 (m, 3H), 1.96 (s, 2H), 1.90-1.76 (m, 1H), 1.67-1.52 (m, 1H), 1.50-1.29 (m, 1H), 1.28-1.15 (m, 1H), 1.06 (d, J=7.0 Hz, 3H), 1.01-0.86 (m, 1H). Analytical HPLC (Method A): RT=7.19 min, purity=100%; Factor XIa Ki=0.87 nM, Plasma Kallikrein Ki=37 nM.

Example 54

Preparation of (9R,13S)-13-{4-[5-chloro-2-(1H-1,2,3-triazol-1-yl)phenyl]-6-oxo-1,2,3,6-tetrahydropyridin-1-yl}-3-cyclobutyl-9-methyl-3,4,7,15-tetraazatricyclo[12.3.1.0$^{2,6}$]octadeca-1(18),2(6),4,14,16-pentaen-8-one

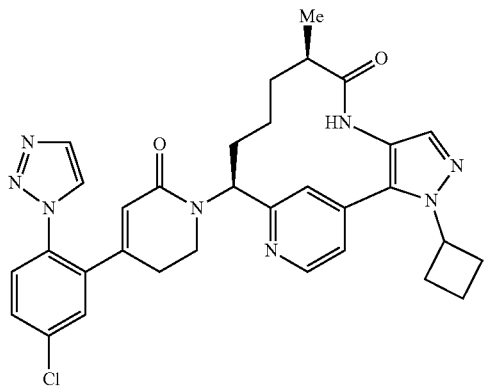 [SMILES: C[C@@H]1CCC[C@H](N2CCC(c3cc(Cl)ccc3-n3ccnn3)=CC2=O)c2cc(ccn2)-c2c(cnn2C2CCC2)NC1=O]

85A. Preparation of 1-cyclobutyl-4-nitro-1H-pyrazole

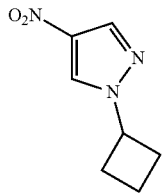 [SMILES: O=[N+]([O-])c1cnn(C2CCC2)c1]

To a dry RBF was added 4-nitro-1H-pyrazole (2 g, 17.69 mmol) and DMF (40 mL). The reaction was cooled to 0° C. and NaH (1.415 g, 35.4 mmol) was added to the reaction followed by bromocyclobutane (3.58 g, 26.5 mmol). The reaction was slowly warmed to rt and stirred at rt overnight. HPLC showed the majority still starting material. Then one more eq. of NaH and bromocyclobutane were added and the reaction was stirred at 65° C. for additional 4 h. The reaction was carefully quenched with water (5 ml) and the reaction was then partitioned between water (50 ml) and EtOAc (50 ml). The aqueous layer was extracted with EtOAc (2×20 ml). The combined EtOAc layer was washed with water (2×40 ml) and brine (40 ml), dried over MgSO$_4$, filtered and concentrated. The residue was purified using ISCO system (0-50% EtOAc/Hex gradient) to give 1-cyclobutyl-4-nitro-1H-pyrazole (640 mg, 3.83 mmol, 21.65% yield) as a clear oil. $^1$H NMR (400 MHz, CDCl$_3$) δ 88.16 (s, 1H), 8.09 (s, 1H), 4.78 (quin, J=8.3 Hz, 1H), 2.65-2.39 (m, 4H), 2.04-1.79 (m, 2H). MS(ESI) m/z: 167.1 (M+H)$^+$.

54B. Preparation of (9R,13S)-13-{4-[5-chloro-2-(1H-1,2,3-triazol-1-yl)phenyl]-6-oxo-1,2,3,6-tetrahydropyridin-1-yl}-3-cyclobutyl-9-methyl-3,4,7,15-tetraazatricyclo[12.3.1.0$^{2,6}$]octadeca-1(18),2(6),4,14,16-pentaen-8-one (9R,13S)-13-{4-[5-Chloro-2-(1H-1,2,3-triazol-1-yl)phenyl]-6-oxo-1,2,3,6-tetrahydropyridin-1-yl}-3-cyclobutyl-9-methyl-3,4,7,15-tetraazatricyclo[12.3.1.0$^{2,6}$]octadeca-1(18),2(6),4,14,16-pentaen-8-one was prepared according to the procedures described in Example 1 by substituting 1-methyl-4-nitro-1H-pyrazole with 1-cyclobutyl-4-nitro-1H-pyrazole. $^1$H NMR (400 MHz, CD$_3$OD) δ 8.59 (d, J=5.1 Hz, 1H), 8.21 (s, 1H), 7.80 (s, 1H), 7.58-7.43 (m, 4H), 7.39 (s, 1H), 7.29-7.17 (m, 1H), 5.72 (s, 1H), 5.44 (dd, J=12.5, 3.7 Hz, 1H), 4.99 (t, J=8.3 Hz, 1H), 3.45 (br. s., 1H), 3.42-3.30 (m, 1H), 2.74-2.57 (m, 2H), 2.51-2.41 (m, 1H), 2.35 (dd, J=7.7, 5.7 Hz, 2H), 2.07-1.93 (m, 3H), 1.87-1.75 (m, 3H), 1.73-1.61 (m, 1H), 1.52-1.39 (m, 1H), 1.25-1.17 (m, 2H), 1.07 (d, J=5.3 Hz, 1H), 0.94 (d, J=6.8 Hz, 3H). MS(ESI) m/z: 597.1 (M+H)$^+$. Analytical HPLC (Method B): RT=1.87 min, purity=96%; Factor XIa Ki=7.1 nM, Plasma Kallikrein Ki=150 nM.

Example 55

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-(difluoromethyl)-9-methyl-3,4,7,15-tetraazatricyclo[12.3.1.0$^{2,6}$]octadeca-1(18),2(6),4,14,16-pentaen-8-one

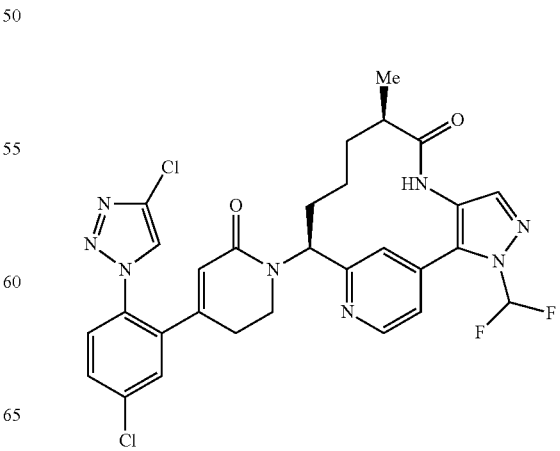

(9R,13S)-13-{4-[5-Chloro-2-(4-chloro-1H-1,2,3-triazol-1-yl)phenyl]-6-oxo-1,2,3,6-tetrahydropyridin-1-yl}-3-(difluoromethyl)-9-methyl-3,4,7,15-tetraazatricyclo[12.3.1.0$^{2,6}$]octadeca-1(18),2(6),4,14,16-pentaen-8-one (45 mg, 66%). was prepared in a similar manner to Example 1 by substituting 1-methyl-4-nitro-1H-pyrazole with 1-(difluoromethyl)-4-nitro-1H-pyrazole and substituting 1-(5-chloro-2-(1H-1,2,3-triazol-1-yl)phenyl)prop-2-en-1-one with 1-(5-chloro-2-(4-chloro-1H-1,2,3-triazol-1-yl)phenyl)prop-2-en-1-one. MS(ESI) m/z: 627.3 (M+H). $^1$H NMR (500 MHz, CD$_3$OD) δ 8.77 (d, J=5.2 Hz, 1H), 8.47 (s, 1H), 7.78 (s, 1H), 7.73-7.62 (m, 4H), 7.62-7.55 (m, 2H), 5.88-5.78 (m, 1H), 5.63-5.50 (m, 1H), 3.76-3.64 (m, 1H), 3.63-3.51 (m, 1H), 2.67-2.53 (m, 1H), 2.27 (d, J=6.1 Hz, 2H), 2.24-2.11 (m, 1H), 2.02-1.91 (m, 1H), 1.91-1.80 (m, 1H), 1.65-1.53 (m, 1H), 1.40-1.29 (m, 1H), 1.28-1.18 (m, 1H), 1.07 (d, J=6.9 Hz, 3H), 1.03-0.86 (m, 1H). Analytical HPLC (Method A): RT=8.36 min, purity=98.8%; Factor XIa Ki=0.1 nM, Plasma Kallikrein Ki=6 nM.

Example 56

Preparation of (9R,13S)-13-{4-[5-chloro-2-(4-chloro-1H-1,2,3-triazol-1-yl)phenyl]-6-oxo-1,2,3,6-tetrahydropyridin-1-yl}-3-(2,2-difluorocyclopropyl)-9-methyl-3,4,7,15-tetraazatricyclo[12.3.1.0$^{2,6}$]octadeca-1(18),2(6),4,14,16-pentaen-8-one

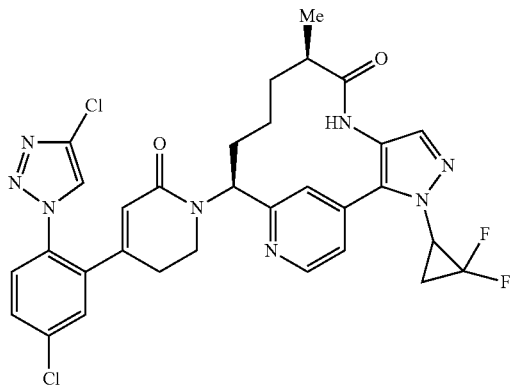 [SMILES: C[C@@H]1CCC[C@H](N2CCC(c3cc(Cl)ccc3-n3cc(Cl)nn3)=CC2=O)c2cc(ccn2)-c2c(cnn2C2CC2(F)F)NC1=O]

(9R,13S)-13-{4-[5-Chloro-2-(4-chloro-1H-1,2,3-triazol-1-yl)phenyl]-6-oxo-1,2,3,6-tetrahydropyridin-1-yl}-3-(2,2-difluorocyclopropyl)-9-methyl-3,4,7,15-tetraazatricyclo[12.3.1.0$^{2,6}$]octadeca-1(18),2(6),4,14,16-pentaen-8-one (26 mg, 49%) was prepared in a similar manner to Example 1 by using 1-(2,2-difluorocyclopropyl)-4-nitro-1H-pyrazole, Intermediate 15, and 1-(5-chloro-2-(4-chloro-1H-1,2,3-triazol-1-yl)phenyl)prop-2-en-1-one. MS(ESI) m/z: 653.3 (M+H). $^1$H NMR (400 MHz, CD$_3$CN) δ 8.79 (d, J=5.5 Hz, 1H), 8.16 (s, 1H), 7.80 (d, J=8.1 Hz, 2H), 7.77-7.68 (m, 1H), 7.67-7.60 (m, 2H), 7.58-7.52 (m, 2H), 5.87 (d, J=9.7 Hz, 1H), 5.40-5.24 (m, 1H), 4.63-4.43 (m, 1H), 3.72-3.42 (m, 2H), 2.64-2.50 (m, 1H), 2.44-2.07 (m, 5H), 1.31 (br. s., 3H), 1.01 (d, J=6.8 Hz, 3H). Analytical HPLC (Method A): RT=8.10 min, purity=99%; Factor XIa Ki=0.36 nM, Plasma Kallikrein Ki=30 nM.

Example 57

Preparation of 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,2,3,6-tetrahydropyridin-4-yl}benzonitrile

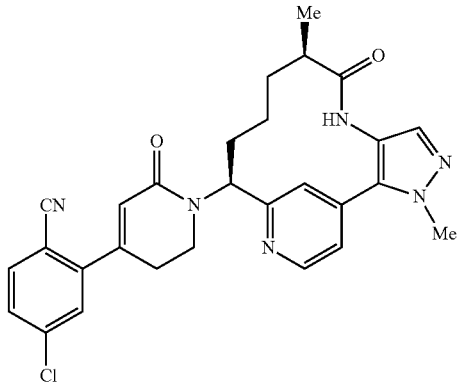 [SMILES: C[C@@H]1CCC[C@H](N2CCC(c3cc(Cl)ccc3C#N)=CC2=O)c2cc(ccn2)-c2c(cnn2C)NC1=O]

(9R,13S)-13-[4-(2-Bromo-5-chlorophenyl)-6-oxo-1,2,3,6-tetrahydropyridin-1-yl]-3,9-dimethyl-3,4,7,15-tetraazatricyclo[12.3.1.0$^{2,6}$]octadeca-1(18),2(6),4,14,16-pentaen-8-one trifluoroacetate, prepared as Example 37, (0.0094 g, 0.012 mmol), Zn(CN)$_2$ (0.0007 g, 5.90 µmol), Pd(P(t-Bu)$_3$)$_2$ (0.0012 g, 2.36 µmol) in DMF (0.5 mL) was flushed with Ar, sealed and heated at 80° C. for 3 days. The reaction mixture was cooled down to rt, filtered and concentrated. Purification by reverse phase chromatography afforded 4-chloro-2-{1-[(9R,13S)-3,9-dimethyl-8-oxo-3,4,7,15-tetraazatricyclo[12.3.1.0$^{2,6}$]octadeca-1(18),2(6),4,14,16-pentaen-13-yl]-6-oxo-1,2,3,6-tetrahydropyridin-4-yl}benzonitrile trifluoroacetate (0.0015 g, 17%) as a white solid product. MS(ESI) m/z: 515.3 (M+H). $^1$H NMR (400 MHz, CD$_3$OD) δ 8.79 (d, J=5.1 Hz, 1H), 7.88-7.81 (m, 1H), 7.75-7.59 (m, 4H), 7.55 (s, 1H), 6.26 (s, 1H), 5.65 (dd, J=12.4, 3.4 Hz, 1H), 4.12-4.08 (m, 3H), 3.88-3.70 (m, 2H), 2.85 (t, J=6.6 Hz, 2H), 2.67-2.56 (m, 1H), 2.32-2.17 (m, 1H), 2.09-1.90 (m, 2H), 1.71-1.58 (m, 1H), 1.40-1.21 (m, 2H), 1.12 (d, J=6.8 Hz, 3H) Analytical HPLC (Method A): RT=6.41 min, purity=>95%; Factor XIa Ki=4.0 nM, Plasma Kallikrein Ki=14 nM.

Example 58

Preparation of (9R,13S)-13-{4-[5-chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one

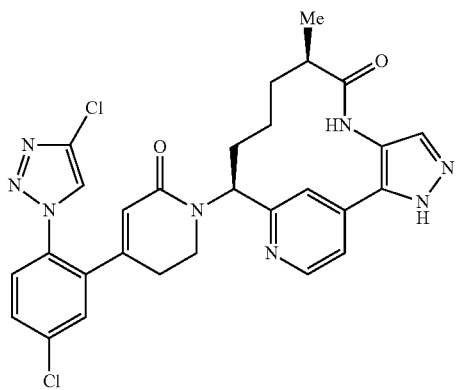 [SMILES: C[C@@H]1CCC[C@H](N2CCC(c3cc(Cl)ccc3-n3cc(Cl)nn3)=CC2=O)c2cc(ccn2)-c2[nH]ncc2NC1=O]

(9R,13S)-13-{4-[5-Chloro-2-(4-chloro-1H-1,2,3-triazol-1-yl)phenyl]-6-oxo-1,2,3,6-tetrahydropyridin-1-yl}-9-methyl-3,4,7,15-tetraazatricyclo[12.3.1.0$^{2,6}$]octadeca-1(18),2(6),4,14,16-pentaen-8-one trifluoroacetate (140 mg, 0.174 mmol, 73% yield) was prepared in a similar way as described in Example 10 by replacing 1-[5-chloro-2-(1H-1,2,3-triazol-1-yl)phenyl]prop-2-en-1-one with 1-[5-chloro-2-(4-chloro-1H-1,2,3-triazol-1-yl)phenyl]prop-2-en-1-one, Intermediate 4. $^1$H NMR (500 MHz, DMSO-d$_6$) δ 9.31 (s, 1H), 8.82 (s, 1H), 8.60 (d, J=5.2 Hz, 1H), 7.94 (s, 1H), 7.81 (s, 1H), 7.78-7.63 (m, 5H), 7.56 (d, J=4.6 Hz, 1H), 7.27-6.99 (m, 1H), 5.71 (s, 1H), 5.48 (d, J=11.3 Hz, 1H), 3.54 (br. s., 1H), 3.38 (br. s., 1H), 2.61 (br. s., 1H), 1.72 (br. s., 1H), 1.51 (d, J=6.4 Hz, 1H), 1.24 (br. s., 1H), 0.96 (d, J=6.7 Hz, 3H), 0.88 (br. s., 1H). MS(ESI) m/z: 577.1 [M+H]$^+$. Analytical HPLC (Method B): RT=1.431 min, purity=96.0%; Factor XIa Ki=2.4 nM, Plasma Kallikrein Ki=46 nM.

Example 59

Preparation of (9R,13S)-13-{4-[5-chloro-2-(4-chloro-1H-1,2,3-triazol-1-yl)phenyl]-6-oxo-1,2,3,6-tetrahydropyridin-1-yl}-16-fluoro-3,9-dimethyl-3,4,7-triazatricyclo[12.3.1.0$^{2,6}$]octadeca-1(18),2(6),4,14,16-pentaen-8-one

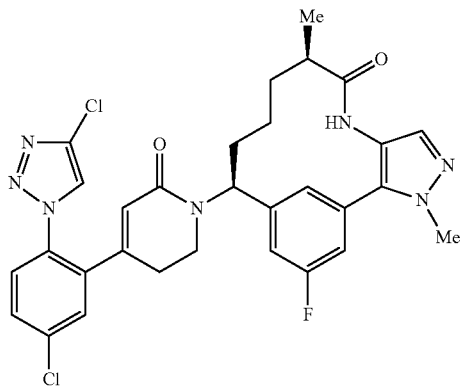 [SMILES: C[C@@H]1CCC[C@H](N2CCC(c3cc(Cl)ccc3-n3cc(Cl)nn3)=CC2=O)c2cc(F)cc(c2)-c2c(cnn2C)NC1=O]

59A. Preparation of (R)—N-[(1E)-(3-bromo-5-fluorophenyl)methylidene]-2-methylpropane-2-sulfinamide To 3-bromo-5-fluorobenzaldehyde (25 g, 123 mol) dissolved in DCM (200 mL) was added (R)-2-methylpropane-2-sulfinamide (14.96 g, 123 mol) and Cs$_2$CO$_3$ (40.2 g, 123 mol). The reaction mixture was stirred at rt overnight. After this time, the reaction mixture was filtered and concentrated to give a yellow oil. The yellow oil was purified using a 120 g silica gel ISCO column eluted with hexanes and EtOAc to give (R)—N-[(1E)-(3-bromo-5-fluorophenyl)methylidene]-2-methylpropane-2-sulfinamide (35 g, 93%) as a yellow oil. $^1$H NMR (500 MHz, DMSO-d$_6$) δ 8.58-8.55 (m, 1H), 8.05-7.98 (m, 1H), 7.84-7.76 (m, 2H), 1.20 (s, 9H). LCMS m/z 306.1 (M+H).

59B. Preparation of (R)—N-[(1S)-1-(3-bromo-5-fluorophenyl)but-3-en-1-yl]-2-methylpropane-2-sulfinamide N-[(1E)-(3-Bromo-5-fluorophenyl)methylidene]-2,2-dimethylpropanamide (35 g, 114 mol) was dissolved in THF (500 mL) in a large 3 neck RB flask and flushed with Ar. The solution was cooled to 0° C. and In (18.4 g, 160 mol) was added followed by the dropwise addition of allylbromide (15.2 g, 126 mol). The reaction was stirred at 0° C. for 2 h, then the ice bath was removed and the reaction mixture was stirred at rt overnight. The reaction was quenched with water (2 L) and the gelatinous material was filtered through CELITE®. The filtrate was concentrated in vacuo to an oily mass. The crude material was dissolved in water (2 L) and the organics were extracted with EtOAc (4×200 mL), dried over MgSO$_4$, filtered and concentrated to give an oil. The oily liquid was purified via a silica gel ISCO column and eluted with DCM/MeOH to afford (R)—N-[(1S)-1-(3-bromo-5-fluorophenyl)but-3-en-1-yl]-2-methylpropane-2-sulfinamide (34.9 g, 88% yield) as a semi solid mass. LCMS m/z 348.2 (M+H). $^1$H NMR (500 MHz, DMSO-d$_6$) δ 7.44-7.38 (m, 2H), 7.26-7.20 (m, 1H), 5.79-5.65 (m, 1H), 5.46-5.42 (m, 1H), 5.04-4.98 (m, 2H), 4.41-4.34 (m, 1H), 2.69-2.59 (m, 1H), 2.49-2.43 (m, 1H), 1.09 (s, 9H).

59C. Preparation of tert-butyl N-[(1S)-1-(3-bromo-5-fluorophenyl)but-3-en-1-yl]carbamate

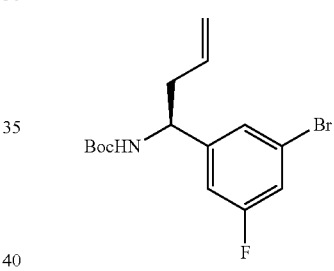

To a cooled 0° C. solution of (R)—N-[(1S)-1-(3-bromo-5-fluorophenyl)but-3-en-1-yl]-2-methylpropane-2-sulfinamide (21.9 g, 100 mol) dissolved in MeOH (100 mL) was added conc. HCl (50 mL) dropwise and then stirred at 0° C. for 48 h. After this time, the reaction mixture was concentrated to give a white solid mass. The residue was dissolved in water (1000 mL) and the organics were extracted with EtOAc (2×200 mL), dried over MgSO$_4$, filtered and concentrated to a brown oil (11.5 g). The aqueous layer was basified with 1 N NaOH and the organics were extracted with EtOAc (2×300 mL), dried over MgSO$_4$, filtered and concentrated to a brown oil (18 g). The combined oils were dissolved in DCM (500 mL) and to this was added Boc$_2$O (22 g) followed by TEA (15 mL) and the reaction mixture was stirred at rt overnight. The reaction mixture was concentrated in vacuo and purified via a 330 g silica gel Isco column eluting with hexanes and EtOAc to give a white solid. The white solid was triturated with hexanes and the precipitate was collected by filtration to give tert-butyl-N-[(1S)-1-(3-bromo-5-fluorophenyl)but-3-en-1-yl]carbamate (29.5 g, 87% yield).

153

59D. Preparation of (9R,13S)-13-amino-16-fluoro-3,9-dimethyl-3,4,7-triazatricyclo[12.3.1.0²,⁶]octadeca-1 (18),2(6),4,14,16-pentaen-8- one

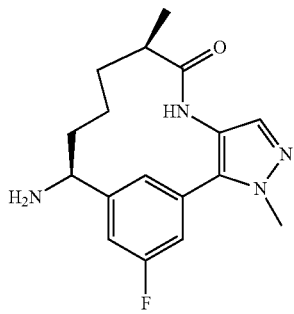 [SMILES: C[C@@H]1CCC[C@H](N)c2cc(F)cc(c2)-c2c(cnn2C)NC1=O]

(9R,13S)-13-Amino-16-fluoro-3,9-dimethyl-3,4,7-triazatricyclo[12.3.1.0²,⁶]octadeca-1(18),2(6),4,14,16-pentaen-8-one (19 mg, 92%), a dark solid, was prepared in the same manner as (9R,13S)-13-amino-3,9-dimethyl-3,4,7-triazatricyclo[12.3.1.0²,⁶]octadeca-1(18),2(6),4,14,16-pentaen-8-one, described in Example 48, substituting tert-butyl-N-[(1S)-1-(3-bromo-5-fluorophenyl)but-3-en-1-yl]carbamate, for tert-butyl-N-[(1S)-1-(3-bromophenyl)but-3-en-1-yl]carbamate. MS(ESI) m/z: 317.4 (M+H)⁺.

59E. Preparation of (9R,13S)-13-{4-[5-chloro-2-(4-chloro-1H-1,2,3-triazol-1-yl)phenyl]-6-oxo-1,2,3,6-tetrahydropyridin-1-yl}-16-fluoro-3,9-dimethyl-3,4, 7-triazatricyclo[12.3.1.0²,⁶]octadeca-1(18),2(6),4,14, 16-pentaen-8-one (9R,13S)-13-{4-[5-Chloro-2-(4-chloro-1H-1,2,3-triazol-1-yl)phenyl]-6-oxo-1,2,3,6-tetrahydropyridin-1-yl}-16-fluoro-3,9-dimethyl-3,4,7-triazatricyclo[12.3.1.0²,⁶]octadeca-1(18),2(6),4,14,16-pentaen-8-one (32 mg, 63.5%), a white solid, was made in a similar manner as (9R,13S)-13-{4-[5-chloro-2-(4-chloro-1H-1,2,3-triazol-1-yl)phenyl]-6-oxo-1,2,3,6-tetrahydropyridin-1-yl}-3,9-dimethyl-3,4,7-triazatricyclo[12.3.1.0²,⁶]octadeca-1(18),2(6),4,14,16-pentaen-8-one, described in Example 48, substituting (9R,13S)-13-amino-16-fluoro-3,9-dimethyl-3,4,7-triazatricyclo[12.3.1.0²,⁶]octadeca-1(18),2(6),4,14,16-pentaen-8-one for (9R,13S)-13-amino-3,9-dimethyl-3,4,7-triazatricyclo[12.3.1.0²,⁶]octadeca-1(18),2(6),4,14,16-pentaen-8-one. MS(ESI) m/z: 608.3 (M+H)⁺. ¹H NMR (400 MHz, CD₃OD) δ 8.46 (s, 1H), 7.69-7.63 (m, 2H), 7.62-7.57 (m, 1H), 7.53-7.48 (m, 1H), 7.37 (s, 1H), 7.32 (d, J=8.6 Hz, 1H), 7.13 (d, J=9.5 Hz, 1H), 5.87-5.84 (m, 1H), 5.55 (dd, J=12.5, 3.1 Hz, 1H), 4.03 (s, 3H), 3.07-3.00 (m, 1H), 2.47-2.40 (m, 1H), 2.26-2.06 (m, 3H), 1.88-1.79 (m, 2H), 1.68-1.55 (m, 2H), 1.17 (d, J=6.8 Hz, 3H), 1.09-1.00 (m, 1H). Analytical HPLC (Method A) RT=8.82 min, purity=95%; Factor XIa Ki=0.1 nM, Plasma Kallikrein Ki=4 nM.

154

Example 60

Preparation of (9R,13S)-13-{4-[3-chloro-2-fluoro-6-(trifluoromethyl)phenyl]-6-oxo-1,2,3,6-tetrahydropyridin-1-yl}-3-cyclopropyl-9-methyl-3,4,7,15-tetraazatricyclo[12.3.1.0²,⁶]octadeca-1(18),2(6),4,14, 16-pentaen-8-one

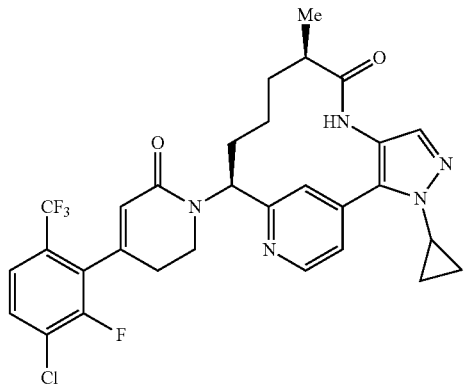 [SMILES: C[C@@H]1CCC[C@H](N2CCC(c3c(C(F)(F)F)ccc(Cl)c3F)=CC2=O)c2cc(ccn2)-c2c(cnn2C2CC2)NC1=O]

(9R,13S)-13-{4-[3-Chloro-2-fluoro-6-(trifluoromethyl)phenyl]-6-oxo-1,2,3,6-tetrahydropyridin-1-yl}-3-cyclopropyl-9-methyl-3,4,7,15-tetraazatricyclo[12.3.1.0²,⁶]octadeca-1(18),2(6),4,14,16-pentaen-8-one (30 mg, 39%). was prepared in a similar manner to Example 1 by substituting 1-methyl-4-nitro-1H-pyrazole with 1-cyclopropyl-4-nitro-1H-pyrazole and substituting 1-(5-chloro-2-(1H-1,2,3-triazol-1-yl)phenyl)prop-2-en-1-one with 1-(3-chloro-2-fluoro-6-(trifluoromethyl)phenyl)prop-2-en-1-one. MS(ESI) m/z: 602.4 (M+H). ¹H NMR (400 MHz, CD₃CN) δ 8.79 (d, J=5.7 Hz, 1H), 7.91 (br. s., 1H), 7.81 (s, 1H), 7.76 (s, 1H), 7.69 (d, J=7.3 Hz, 1H), 7.64-7.58 (m, 1H), 7.43 (s, 1H), 5.95 (s, 1H), 5.54-5.41 (m, 1H), 3.90-3.68 (m, 5H), 2.79-2.48 (m, 3H), 2.38-2.21 (m, 1H), 1.66-1.50 (m, 1H), 1.30 (br. s., 2H), 1.22-1.08 (m, 4H), 1.04 (d, J=6.8 Hz, 3H). Analytical HPLC (Method A): RT=8.19 min, purity=92%; Factor XIa Ki=7.2 nM, Plasma Kallikrein Ki=22 nM.

Example 61

Preparation of (9R,13S)-13-(4-{5-chloro-2-[4-(trifluoromethyl)-1H-1,2,3-triazol-1-yl]phenyl}-6-oxo-1, 6-dihydropyridazin-1-yl)-3,9-dimethyl-3,4,7,15-tetraazatricyclo[12.3.1.02,6]octadeca-1(18),2(6),4, 14,16-pentaen-8-one trifluoroacetate

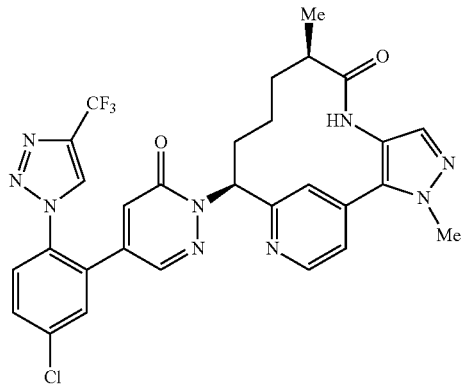 [SMILES: C[C@@H]1CCC[C@H](n2ncc(-c3cc(Cl)ccc3-n3cc(C(F)(F)F)nn3)cc2=O)c2cc(ccn2)-c2c(cnn2C)NC1=O]

61A. Preparation of 1-(4-chloro-2-ethenylphenyl)-4-(trifluoromethyl)-1H-1,2,3-triazole To a cooled (−20° C.) suspension of methyltriphenylphosphonium bromide (1.540 g, 4.31 mmol) in Et$_2$O (12 mL) was added dropwise a solution of 2.5 M nBuLi in hexane (1.58 mL, 3.95 mmol). The resulting yellow suspension was allowed to warm to 0° C. and stir for 2 h. Then a solution of 5-chloro-2-[4-(trifluoromethyl)-1H-1,2,3-triazol-1-yl]benzaldehyde (0.99 g, 3.59 mmol), prepared as described in Example 40A, in Et$_2$O (5 mL) was added dropwise to give a brown suspension. The suspension was stirred at 0° C. for 30 min and then the reaction was allowed to warm to rt. After 17 h, the reaction was cooled to 0° C. and then sat NH$_4$Cl was added. The reaction was warmed to rt and the layers were separated. The aqueous layer was extracted with Et$_2$O. The organic layers were combined and washed with brine, dried over Na$_2$SO$_4$, filtered and concentrated to give a black foam. Purification by normal phase chromatography provided 1-(4-chloro-2-ethenylphenyl)-4-(trifluoromethyl)-1H-1,2,3-triazole (0.357 g, 36% yield) as a white solid. MS(ESI) m/z: 274.0 (M+H)$^+$ and 276.0 (M+2+H)$^+$.

61B. Preparation of 4-{5-chloro-2-[4-(trifluoromethyl)-1H-1,2,3-triazol-1-yl]phenyl}-5-hydroxy-2,5-dihydrofuran-2-one To a cooled (−5° C.) clear, colorless solution of Pb(OAc)$_4$ (0.567 g, 1.28 mmol) in TFA (1.3 ml) was added dropwise a clear, colorless solution of 1-(4-chloro-2-ethenylphenyl)-4-(trifluoromethyl)-1H-1,2,3-triazole (0.350 g, 1.28 mmol) in DCM (1.3 mL). During the addition, the reaction temperature did not go above 2° C. Following the addition, the resulting clear, pale yellow solution was allowed to warm to rt. After 2 h the reaction was cooled to −5° C. and additional Pb(OAc)$_4$ (0.283 g) in TFA (0.65 mL) was added dropwise. The reaction was allowed to warm to rt. After 2 h, water (10 mL) was added dropwise to give a red-brown suspension. The suspension was filtered through CELITE®, eluting with DCM. The biphasic filtrate was separated and the aqueous layer was extracted with DCM. The organic layers were combined and concentrated to give a yellow oil. The oil was dissolved in DCM and washed with water, brine, dried over Na$_2$SO$_4$, filtered and concentrated to give 2-{5-chloro-2-[4-(trifluoromethyl)-1H-1,2,3-triazol-1-yl]phenyl}acetaldehyde (0.370 g) as a pale, yellow foam. This material was used in the next step without further purification. MS(ESI) m/z: 290.3 (M+H)$^+$ and 292.3 (M+2+H)$^+$. To a solution of morpholine (0.12 mL, 1.34 mmol) in dioxane (1.7 mL) was added 6 M HCl (0.22 ml, 1.30 mmol) followed by glyoxylic acid monohydrate (0.112 g, 1.21 mmol). Next, a solution of 2-{5-chloro-2-[4-(trifluoromethyl)-1H-1,2,3-triazol-1-yl]phenyl}acetaldehyde (0.370 g, 1.28 mmol) in dioxane (1.7 mL) was added. The reaction mixture was warmed to reflux. After 5 h, the reaction was stopped and cooled to rt. Water and EtOAc were added and the layers were separated. The aqueous layer was extracted with EtOAc (1×). The organic layers were combined and washed with brine, dried over Na$_2$SO$_4$, filtered and concentrated to give a golden brown foam. Purification by normal phase chromatography gave 4-(3-chloro-2,6-difluorophenyl)-5-hydroxy-2,5-dihydrofuran-2-one (0.112 g, 28% yield) as a pale, yellow foam. MS(ESI) m/z: 346.2 (M+H)$^+$ and 348.3 (M+2+H)$^+$.

61C. Preparation of N'-[(9R,13S)-3,9-dimethyl-8-oxo-3,4,7,15-tetraazatricyclo[12.3.1.0$^{2,6}$]octadeca-1(18),2(6),4,14,16-pentaen-13-yl](tert-butoxy)carbohydrazide To a cooled (0° C.), purple suspension of (9R,13S)-13-amino-3,9-dimethyl-3,4,7,15-tetraazatricyclo[12.3.1.0$^{2,6}$]octadeca-1(18),2(6),4,14,16-pentaen-8-one (0.083 g, 0.277 mmol), prepared as described in Example 1, in DCM (1.848 ml) was added dropwise a clear, colorless solution of tert-butyl 3-(4-cyanophenyl)-1,2-oxaziridine-2-carboxylate (0.068 g, 0.277 mmol) in DCM (1 mL). Following the addition, the reaction was allowed to warm to rt. After 5.5 h, the reaction was stopped and it was concentrated. Purification by normal phase chromatography gave N'-[(9R,13S)-3,9-dimethyl-8-oxo-3,4,7,15-tetraazatricyclo[12.3.1.0$^{2,6}$]octadeca-1(18),2(6),4,14,16-pentaen-13-yl](tert-butoxy)carbohydrazide (0.0310 g, 27% yield) as a white solid. MS(ESI) m/z: 415.5 (M+H)$^+$.

61D. Preparation of (9R,13S)-13-hydrazinyl-3,9-dimethyl-3,4,7,15-tetraazatricyclo[12.3.1.0$^{2,6}$]octadeca-1(18),2(6),4,14,16-pentaen-8-one, bis-hydrochloride A suspension of N'-[(9R,13S)-3,9-dimethyl-8-oxo-3,4,7,15-tetraazatricyclo[12.3.1.0$^{2,6}$]octadeca-1(18),2(6),4,14,16-pentaen-13-yl](tert-butoxy)carbohydrazide (0.0310 g, 0.075 mmol) in 4 M HCl in dioxane (0.94 ml, 3.74 mmol) was stirred at rt. MeOH (0.2 mL) was added to give a clear, bright yellow solution. After 1 h the reaction was concentrated to give a yellow residue. The residue was dissolved in MeOH and concentrated. This was repeated two more times to give (9R,13S)-13-hydrazinyl-3,9-dimethyl-3,4,7,15-tetraazatricyclo[12.3.1.0$^{2,6}$]octadeca-1(18),2(6),4,14,16-pentaen-8-one, bis-hydrochloride (0.029 g, 100% yield) as a yellow solid. This material was used without further purification. MS(ESI) m/z: 315.5 (M+H)$^+$.

61E. Preparation of (9R,13S)-13-(4-{5-chloro-2-[4-(trifluoromethyl)-1H-1,2,3-triazol-1-yl]phenyl}-6-oxo-1,6-dihydropyridazin-1-yl)-3,9-dimethyl-3,4,7,15-tetraazatricyclo[12.3.1.0$^{2,6}$]octadeca-1(18),2(6),4,14,16-pentaen-8-one trifluoroacetate A slightly cloudy yellow solution of (9R,13S)-13-hydrazinyl-3,9-dimethyl-3,4,7,15-tetraazatricyclo[12.3.1.0$^{2,6}$]octadeca-1(18),2(6),4,14,16-pentaen-8-one bis-hydrochloride (0.029 g, 0.075 mm) and 4-{5-chloro-2-[4-(trifluoromethyl)-1H-1,2,3-triazol-1-yl]phenyl}-5-hydroxy-2,5-dihydrofuran-2-one (0.026 g, 0.075 mmol) in MeOH (0.75 ml) was heated at 150° C. in a microwave for 30 min. Upon cooling to rt, DMF (0.75 mL) was added to the reaction mixture. Purification by reverse phase chromatography gave (9R,13S)-13-(4-{5-chloro-2-[4-(trifluoromethyl)-1H-1,2,3-triazol-1-yl]phenyl}-6-oxo-1,6-dihydropyridazin-1-yl)-3,9-dimethyl-3,4,7,15-tetraazatricyclo[12.3.1.0$^{2,6}$]octadeca-1(18),2(6),4,14,16-pentaen-8-one trifluoroacetate (0.0021 g, 3.7% yield), as a white solid. MS(ESI) m/z: 624.4 (M+H)$^+$ and 626.4 (M+2+H)$^+$. $^1$H NMR (500 MHz, CD$_3$OD) δ 8.85 (d, J=0.6 Hz, 1H), 8.62 (d, J=5.2 Hz, 1H), 7.81 (d, J=2.2 Hz, 1H), 7.79-7.76 (m, 2H), 7.74-7.70 (m, 1H), 7.58-7.54 (m, 2H), 7.51 (s, 1H), 6.82 (d, J=2.5 Hz, 1H), 6.00 (dd, J=12.1, 4.1 Hz, 1H), 4.05 (s, 3H), 2.63-2.55 (m, 1H), 2.48-2.39 (m, 1H), 2.10-2.00 (m, 1H), 2.00-1.91 (m, 1H), 1.63-1.55 (m, 1H), 1.36-1.26 (m, 1H), 1.11-1.03 (m, 4H). $^{19}$F NMR (471 MHz, CD$_3$OD) δ −62.65 (s), −77.57 (s). Analytical HPLC (Method A): RT=7.42 min, purity=99.5%. Factor XIa Ki=0.51 nM, Plasma Kallikrein Ki=66 nM.

Example 62

(9R,13S)-13-(4-{5-Chloro-2-[4-(trifluoromethyl)-1H-1,2,3-triazol-1-yl]phenyl}-2-oxo-1,2-dihydro-pyridin-1-yl)-3-($^2$H$_3$)methyl-9-methyl-3,4,7,15-tetraazatricyclo[12.3.1.0$^{2,6}$]octadeca-1(18),2(6),4,14,16-pentaen-8-one, trifluoroacetate

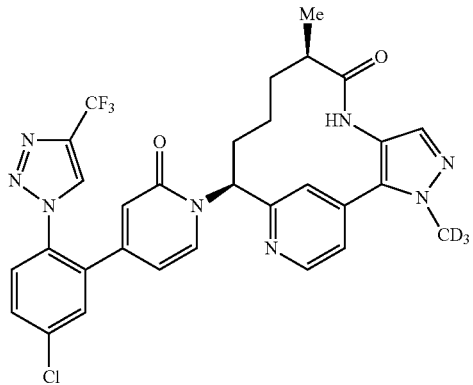 [SMILES: [2H]C([2H])([2H])n1ncc2c1-c1ccnc(c1)[C@@H](n1ccc(-c3cc(Cl)ccc3-n3cc(C(F)(F)F)nn3)cc1=O)CCC[C@@H](C)C(=O)N2]

A suspension of (9R,13S)-13-(4-{5-chloro-2-[4-(trifluoromethyl)-1H-1,2,3-triazol-1-yl]phenyl}-6-oxo-1,2,3,6-tetrahydropyridin-1-yl)-3-($^2$H$_3$)methyl-9-methyl-3,4,7,15-tetraazatricyclo[12.3.1.0$^{2,6}$]octadeca-1(18),2(6),4,14,16-pentaen-8-one (30 mg, 0.048 mmol), prepared as described in Example 42, in DMF (0.5 mL) was added K$_2$CO$_3$ (66.0 mg, 0.478 mmol), Pearlman's catalyst (6.71 mg, 0.048 mmol) and tert-butyl hydroperoxide (70% in water, 0.066 mL, 0.478 mmol). After 67 h, the reaction was stopped with the addition of 3 drops of 10% Na$_2$S$_2$O$_3$. The reaction was purified by reverse phase chromatography which gave (9R,13S)-13-(4-{5-chloro-2-[4-(trifluoromethyl)-1H-1,2,3-triazol-1-yl]phenyl}-2-oxo-1,2-dihydropyridin-1-yl)-3-($^2$H$_3$)methyl-9-methyl-3,4,7,15-tetraazatricyclo[12.3.1.0$^{2,6}$]octadeca-1(18),2(6),4,14,16-pentaen-8-one, trifluoroacetate (0.0030 g, 8.4% yield) as a white solid. MS(ESI) m/z: 626.4 (M+H)$^+$. $^1$H NMR (400 MHz, CD$_3$OD) δ 8.72 (d, J=0.9 Hz, 1H), 8.67 (d, J=5.1 Hz, 1H), 8.01 (d, J=7.0 Hz, 1H), 7.75-7.66 (m, 4H), 7.52-7.48 (m, 2H), 6.38 (d, J=2.0 Hz, 1H), 6.10-6.01 (m, 2H), 2.67 (td, J=7.0, 3.2 Hz, 1H), 2.27-2.15 (m, 1H), 2.11-2.00 (m, 1H), 1.93 (tt, J=11.6, 5.9 Hz, 1H), 1.66-1.53 (m, 1H), 1.47-1.34 (m, 1H), 1.02 (d, J=7.0 Hz, 3H), 0.77 (m, 1H). Analytical HPLC (Method A): RT=8.28 min, purity=99.7%. Factor XIa Ki=0.10 nM, Plasma Kallikrein Ki=6 nM.

Example 63

(9R,13S)-13-(4-{5-Chloro-2-[4-(trifluoromethyl)-1H-1,2,3-triazol-1-yl]phenyl}-6-oxo-1,6-dihydro-pyridazin-1-yl)-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate

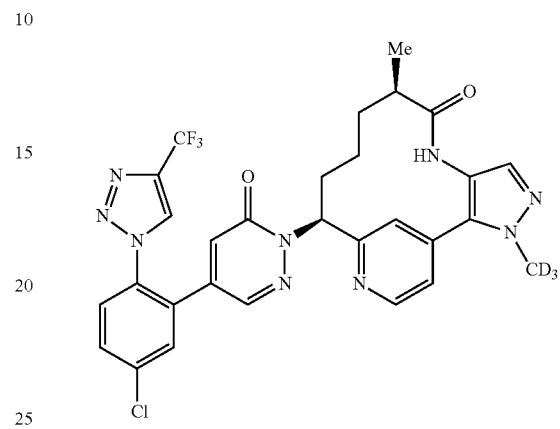

63A. Preparation of (9R,13S)-13-hydrazinyl-3-($^2$H$_3$)methyl-9-methyl-3,4,7,15-tetraazatricyclo[12.3.1.0$^{2,6}$]octadeca-1(18),2(6),4,14,16-pentaen-8-one, bis-hydrochloride (9R,13S)-13-Hydrazinyl-3-($^2$H$_3$)methyl-9-methyl-3,4,7,15-tetraazatricyclo[12.3.1.0$^{2,6}$]octadeca-1(18),2(6),4,14,16-pentaen-8-one bis-hydrochloride (0.088 g, 43% over two steps, yellow solid) was prepared according to the procedures described in Examples 61C and 61D, by replacing (9R,13S)-13-amino-3,9-dimethyl-3,4,7,15-tetraazatricyclo[12.3.1.0$^{2,6}$]octadeca-1(18),2(6),4,14,16-pentaen-8-one with (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one. MS(ESI) m/z: 318.5 (M+H)$^+$.

63B. Preparation of (9R,13S)-13-(4-{5-chloro-2-[4-(trifluoromethyl)-1H-1,2,3-triazol-1-yl]phenyl}-6-oxo-1,6-dihydropyridazin-1-yl)-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate (9R,13S)-13-(4-{5-Chloro-2-[4-(trifluoromethyl)-1H-1,2,3-triazol-1-yl]phenyl}-6-oxo-1,6-dihydropyridazin-1-yl)-3-($^2$H$_3$)methyl-9-methyl-3,4,7,15-tetraazatricyclo[12.3.1.0$^{2,6}$]octadeca-1(18),2(6),4,14,16-pentaen-8-one trifluoroacetate (0.0034 g, 4.4% yield) was prepared as described in Example 61E by replacing (9R,13S)-13-hydrazinyl-3,9-dimethyl-3,4,7,15-tetraazatricyclo[12.3.1.0$^{2,6}$]octadeca-1(18),2(6),4,14,16-pentaen-8-one bis-hydrochloride with (9R,13S)-13-hydrazinyl-3-($^2$H$_3$)methyl-9-methyl-3,4,7,15-tetraazatricyclo[12.3.1.0$^{2,6}$]octadeca-1(18),2(6),4,14,16-pentaen-8-one, bis-hydrochloride. MS(ESI) m/z: 627.4 (M+H)$^+$. $^1$H NMR (500 MHz, CD$_3$OD) δ 8.86 (d, J=0.8 Hz, 1H), 8.64 (d, J=5.2 Hz, 1H), 7.82-7.80 (m, 2H), 7.77 (dd, J=8.5, 2.5 Hz, 1H), 7.72 (d, J=8.5 Hz, 1H), 7.60-7.58 (m, 1H), 7.57 (d, J=2.2 Hz, 1H), 7.51 (s, 1H), 6.83 (d, J=2.2 Hz, 1H), 6.01 (dd, J=12.4, 4.1 Hz, 1H), 2.63-2.55 (m, 1H), 2.48-2.38 (m, 1H), 2.11-2.01 (m, 1H), 2.00-1.91

(m, 1H), 1.64-1.55 (m, 1H), 1.36-1.26 (m, 1H), 1.13-1.02 (m, 4H). $^{19}$F NMR (471 MHz, CD$_3$OD) δ -62.46, -77.66. Analytical HPLC (Method A): RT=7.39 min, purity=99.7%. Factor XIa Ki=0.52 nM, Plasma Kallikrein Ki=77 nM.

Example 64

(9R,13S)-13-(4-{5-Chloro-2-[4-(trifluoromethyl)-1H-1,2,3-triazol-1-yl]phenyl}-6-oxo-1,6-dihydropyridazin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one

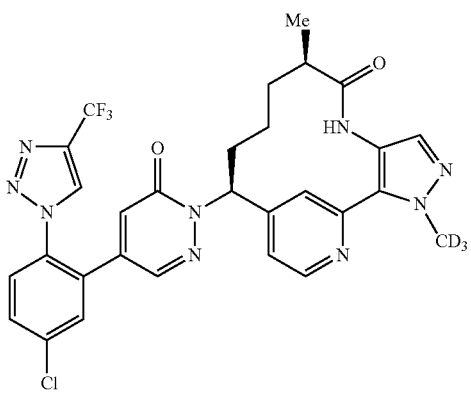 [SMILES: [2H]C([2H])([2H])n1ncc2c1-c1cc(ccn1)[C@@H](n1ncc(-c3cc(Cl)ccc3-n3cc(C(F)(F)F)nn3)cc1=O)CCC[C@@H](C)C(=O)N2]

64A. Preparation of (R)—N-[(1E)-(2-bromopyridin-4-yl)methylidene]-2-methylpropane-2-sulfinamide To a stirred suspension of (R)-2-methylpropane-2-sulfinamide (13.03 g, 108 mmol) and Cs$_2$CO$_3$ (52.5 g, 161 mmol) in DCM (400 ml) was added 2-bromopyridine-4-carbaldehyde (20 g, 108 mmol) over 10 min. The reaction mixture was then stirred for 18.5 h at rt. The reaction mixture was concentrated and the residue was diluted with EtOAc (50 ml) and washed with brine (3×20 ml). The organic layer was dried over MgSO$_4$ and filtered and then the filtrate was concentrated. The residue was purified by normal phase chromatography using hexanes and EtOAc as eluents to afford (27.2 g, 87%) of (R)—N-[(1E)-(2-bromopyridin-4-yl)methylidene]-2-methylpropane-2-sulfinamide as a white solid. MS(ESI) m/z: 289-291.0 (M+H)$^+$.

64B. Preparation of (R)—N-[(1S)-1-(2-bromopyridin-4-yl)but-3-en-1-yl]-2-methylpropane-2-sulfonamide To a solution of (R)—N-[(1E)-(2-bromopyridin-4-yl)methylidene]-2-methylpropane-2-sulfinamide (0.73 g, 2.52 mmol) and indium (0.435 g, 3.79 mmol) in THF (6 ml) was slowly added 3-bromoprop-1-ene (0.458 g, 3.79 mmol) and resulting solution was heated at 60° C. for 18 h. The reaction mixture was cooled, filtered through CELITE® and the filtrate was concentrated. To the residue was added EtOAc (100 ml) and 5% NaHCO$_3$ (aq) (1000 ml) and an emulsion formed immediately. The suspension was filtered through paper. The organic layer was washed with brine, dried over Na$_2$SO$_4$ filtered, and concentrated. The resulting residue was purified by normal phase chromatography using hexanes and EtOAc as eluents to afford (0.62 g, 74%) of (R)—N-[(1S)-1-(2-bromopyridin-4-yl)but-3-en-1-yl]-2-methylpropane-2-sulfonamide as a yellow liquid. MS(ESI) m/z: 331-333.0 (M+H)$^+$.

64C. Preparation of tert-butyl N-[(1S)-1-(2-bromopyridin-4-yl)but-3-en-1-yl]carbamate To a solution of (R)—N-[(1S)-1-(2-bromopyridin-4-yl)but-3-en-1-yl]-2-methylpropane-2-sulfinamide (1.38 g, 4.17 mmol) in MeOH (10 ml) was added 4N HCl in dioxane (5.21 mL, 20.83 mmol). The reaction mixture was stirred for 1.5 h at rt, then was concentrated. To the resulting residue was added ACN (10 ml), TEA (5.81 ml, 41.7 mmol) and Boc$_2$O (1.818 g, 8.33 mmol). After 18 h, the reaction mixture was concentrated and the residue was taken up in EtOAc, washed with water, brine, dried over MgSO$_4$, filtered and concentrated. The resulting residue was purified by normal phase chromatography using hexanes and EtOAc as eluents to afford (0.80 g, 58.7%) of tert-butyl N-[(1S)-1-(2-bromopyridin-4-yl)but-3-en-1-yl]carbamate as a pale yellow oil. MS(ESI) m/z: 324-326.1 (M+H)$^+$.

64D. Preparation of (9R,13S)-13-amino-3-($^2$H$_3$)methyl-9-methyl-3,4,7,17-tetraazatricyclo[12.3.1.0$^{2,6}$]octadeca-1(18),2(6),4,14,16-pentaen-8-one (9R,13S)-13-Amino-3-($^2$H$_3$)methyl-9-methyl-3,4,7,17-tetraazatricyclo[12.3.1.0$^{2,6}$]octadeca-1(18),2(6),4,14,16-pentaen-8-one was prepared in a similar manner as (9R,13S)-13-amino-3-($^2$H$_3$)methyl-9-methyl-3,4,7,15-tetraazatricyclo[12.3.1.0$^{2,6}$]octadeca-1(18),2(6),4,14,16-pentaen-8-one, as described in Example 17B through 17G, replacing (S)-tert-butyl(1-(4-chloropyridin-2-yl)but-3-en-1-yl)carbamate, with (S)-tert-butyl(1-(2-bromopyridin-4-yl)but-3-en-1-yl)carbamate. MS(ESI) m/z: 303.3 (M+H)$^+$. $^1$H NMR (400 MHz, CD$_3$OD) δ 8.70 (d, J=5.3 Hz, 1H), 7.58 (s, 1H), 7.50-7.42 (m, 2H), 4.14-4.05 (m, 1H), 2.72 (td, J=6.7, 3.5 Hz, 1H), 2.06-1.94 (m, 2H), 1.65-1.50 (m, 2H), 1.41-1.26 (m, 1H), 1.02 (d, J=6.8 Hz, 3H), 0.70-0.53 (m, 1H).

64E. Preparation of (9R,13S)-13-hydrazinyl-3-($^2$H$_3$)methyl-9-methyl-3,4,7,17-tetraazatricyclo[12.3.1.0$^{2,6}$]octadeca-1(18),2(6),4,14,16-pentaen-8-one, bis-hydrochloride (9R,13S)-13-Hydrazinyl-3-($^2$H$_3$)methyl-9-methyl-3,4,7,17-tetraazatricyclo[12.3.1.0$^{2,6}$]octadeca-1(18),2(6),4,14,16-pentaen-8-one, bis-hydrochloride (0.067 g, 35% over two steps, yellow solid) was prepared according to the procedures described in Examples 61C and 61D, by replacing (9R,13S)-13-amino-3,9-dimethyl-3,4,7,15-tetraazatricyclo[12.3.1.0$^{2,6}$]octadeca-1(18),2(6),4,14,16-pentaen-8-one with (9R,13S)-13-amino-3-($^2$H$_3$)methyl-9-methyl-3,4,7,17 tetraazatricyclo[12.3.1.0$^{2,6}$]octadeca-1(18),2(6),4,14,16-pentaen-8-one. MS(ESI) m/z: 318.5 (M+H)$^+$.

64F. Preparation of (9R,13S)-13-(4-{5-chloro-2-[4-(trifluoromethyl)-1H-1,2,3-triazol-1-yl]phenyl}-6-oxo-1,6-dihydropyridazin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one (9R,13S)-13-(4-{5-Chloro-2-[4-(trifluoromethyl)-1H-1,2,3-triazol-1-yl]pheny}-6-oxo-1,6-dihydropyridazin-1-yl)-3-($^2$H$_3$)methyl-9-methyl-3,4,7,17-tetraazatricyclo[12.3.1.0$^{2,6}$]octadeca-1(18),2(6),4,14,16-pentaen-8-one (2.7 mg, 2.7%) was prepared in a similar manner as Example 61E, by replacing (9R,13S)-13-hydrazinyl-3-($^2$H$_3$) methyl-9-methyl-3,4,7,15-tetraazatricyclo[12.3.1.0$^{2,6}$]octadeca-1(18),2(6),4,14,16-pentaen-8-one, bis-hydrochloride as described in Example 61D with (9R,13S)-13-hydrazinyl-3-($^2$H$_3$)methyl-9-methyl-3,4,7,17-tetraazatricyclo[12.3.1.0$^{2,6}$] octadeca-1(18),2(6),4,14,16-pentaen-8-one, bis-hydrochloride. MS(ESI) m/z: 627.4 (M+H)$^+$. $^1$H NMR (400 MHz, CD$_3$OD) δ 8.90 (d, J=0.7 Hz, 1H), 8.70-8.64 (m, 1H), 7.91-7.75 (m, 4H), 7.64-7.58 (m, 1H), 7.53-7.48 (m, 1H), 7.21 (dd, J=5.3, 1.5 Hz, 1H), 6.90 (d, J=2.4 Hz, 1H), 6.10 (dd, J=12.1, 4.2 Hz, 1H), 2.67 (dt, J=6.9, 3.6 Hz, 1H), 2.57-2.45 (m, 1H), 2.09-1.97 (m, 2H), 1.64 (dd, J=14.1, 5.7 Hz, 1H), 1.42-1.32 (m, 1H), 1.25-1.19 (m, 1H), 1.10 (d, J=7.0 Hz, 3H), contains minor diastereomer. Analytical HPLC (Method A): RT=8.32 min, purity=95%. Factor XIa Ki=0.71 nM, Plasma Kallikrein Ki=52.6 nM.

What is claimed is:
1. A compound of Formula (Ia):

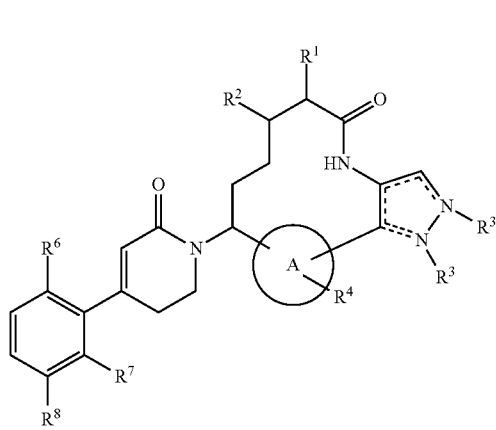

(Ia)

or a stereoisomer, a tautomer, a pharmaceutically acceptable salt thereof, wherein:
--- is an optional bond;
ring A is independently selected from

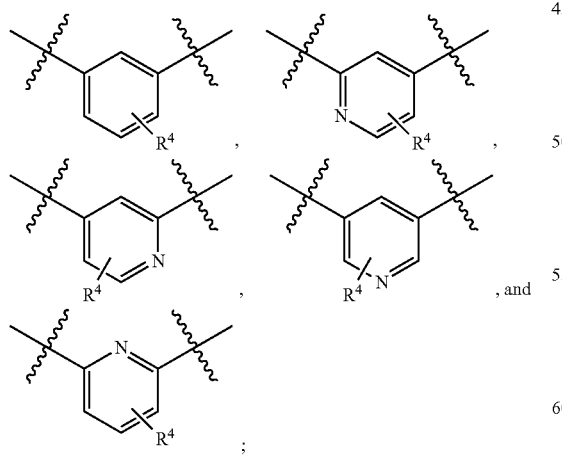

R$^1$ is independently selected from H, F, OH, and C$_{1-4}$ alkyl;
R$^2$ is independently selected from H, F, and OH;
R$^3$ is absent or independently selected from H, C$_{1-4}$alkyl, C$_{1-4}$haloalkyl, —(CH$_2$)$_n$—OR$^5$, —(CH$_2$)$_n$—C(O)OR$^5$, C$_{3-6}$ cycloalkyl optionally substituted with halogen, and 5- to 6-membered heteroaryl comprising carbon atoms and 1-2 nitrogen atoms and optionally substituted with R$^1$; provided only one R$^3$ group is present on the ring;
R$^4$ is independently selected from H, OH, F, OC$_{1-4}$ alkyl, C$_{1-4}$ alkyl, and CN;
R$^5$ is independently selected from H and C$_{1-4}$ alkyl;
R$^6$ is independently selected from H, F, Cl, Br, CN, OCH$_3$, CH$_3$, C(O)CH$_3$, CHF$_2$, CCH$_3$F$_2$, CF$_3$, OCHF$_2$, NHC(O)C$_{1-4}$ alkyl, C$_{3-6}$ cycloalkyl, and 5-membered heterocycle substituted with R$^9$;
R$^7$ is independently selected from H and F;
R$^8$ is independently selected from H, F, Cl, and OCH$_3$;
R$^9$ is independently selected from H, cyano, C$_{1-4}$ alkyl, haloalkyl, and halogen; and
n, at each occurrence, is an integer selected from 1 and 2.

2. The compound of claim 1 having Formula (IIa):

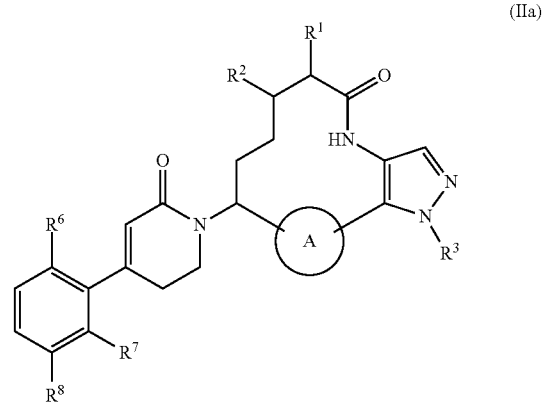

(IIa)

or a stereoisomer, a tautomer, a pharmaceutically acceptable salt thereof, wherein:
ring A is independently selected from

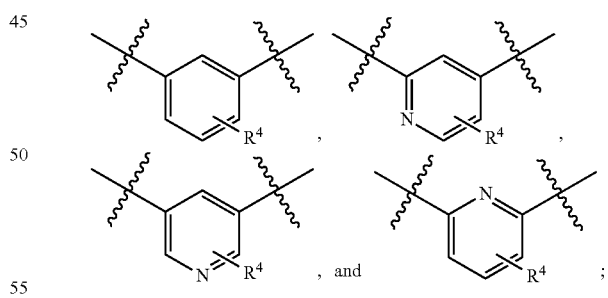

R$^1$ is independently selected from H and C$_{1-3}$alkyl;
R$^2$ is independently selected from H and F;
R$^3$ is independently selected from H, C$_{1-3}$alkyl, C$_{1-3}$haloalkyl, —(CH$_2$)$_n$—OR$^5$, —(CH$_2$)$_n$—C(O)OR$^5$, and C$_{3-4}$ cycloalkyl optionally substituted with halogen;
R$^4$ is independently selected from H and F;
R$^5$ is independently selected from H and C$_{1-4}$ alkyl;
R$^6$ is independently selected from H, F, Cl, Br, CN, CF$_3$, C(O)CH$_3$, CHF$_2$, CCH$_3$F$_2$, CF$_3$, OCHF$_2$,

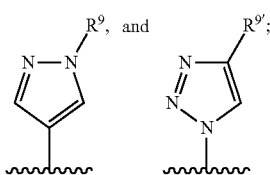

R[7] is independently selected from H and F;
R[8] is independently selected from H, F, Cl, and OCH$_3$;
R[9] is independently selected from H, CHF$_2$, and CF$_3$;
R[9'] is independently selected from H, F, Cl, CN, CHF$_2$, and CF$_3$; and
n, at each occurrence, is an integer selected from 1 and 2.

3. The compound of claim 2, or a stereoisomer, a tautomer, a pharmaceutically acceptable salt thereof, wherein:
R[1] is independently selected from H, CH$_3$, and CH(CH$_3$)$_2$;
R[2] is independently selected from H and F;
R[3] is independently selected from H, CH$_3$, CD$_3$, CH$_2$CH$_3$, —CHF$_2$, —CH$_2$CHF$_2$, —CH$_2$CF$_3$, —CH$_2$CH$_2$OH, CH$_2$CH$_2$OC(CH$_3$)$_3$, —CH$_2$C(O)OH, cyclopropyl optionally substituted with F, and cyclobutyl;
R[6] is independently selected from H, F, Cl, Br, CN, CF$_3$, C(O)CH$_3$, CHF$_2$, CCH$_3$F$_2$, CF$_3$, OCHF$_2$,

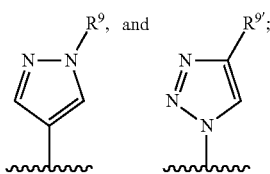

R[7] is independently selected from H and F;
R[8] is independently selected from H, F, Cl, and OCH$_3$;
R[9] is independently selected from H, CHF$_2$, and CF$_3$; and
R[9'] is independently selected from H, F, Cl, CN, CHF$_2$, and CF$_3$.

4. The compound of claim 1 having Formula (IIIa):

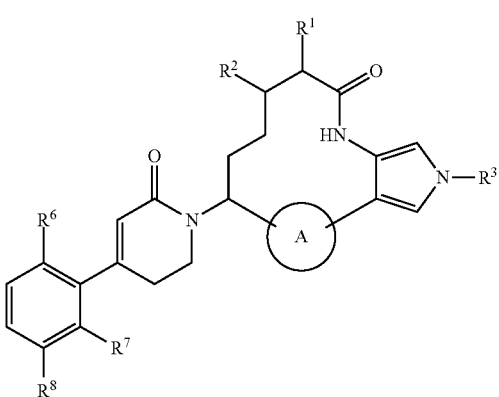

(IIIa)

or a stereoisomer, a tautomer, a pharmaceutically acceptable salt thereof, wherein:
ring A is independently selected from

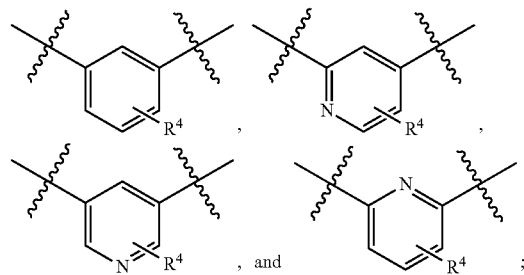

R[1] is independently selected from H, CH$_3$, and CH(CH$_3$)$_2$;
R[2] is independently selected from H and F;
R[3] is independently selected from H, CH$_2$C(=O)OH, CH$_2$C(=O)OCH$_2$CH$_3$,

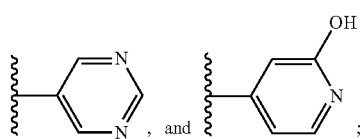

R[4] is independently selected from H and F;
R[6] is independently selected from H, F, Cl, Br, CN, CF$_3$, C(O)CH$_3$, CHF$_2$, CCH$_3$F$_2$, CF$_3$, OCHF$_2$,

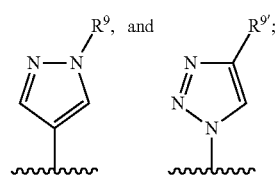

R[7] is independently selected from H and F;
R[8] is independently selected from H, F, Cl, and OCH$_3$;
R[9] is independently selected from H, CHF$_2$, and CF$_3$; and
R[9'] is independently selected from H, F, Cl, CN, CHF$_2$, and CF$_3$.

5. The compound of claim 1, or a stereoisomer, a tautomer, a pharmaceutically acceptable salt thereof, wherein:
R[3] is independently selected from H, CH$_3$, CD$_3$, CH$_2$CH$_3$, —CHF$_2$, —CH$_2$CHF$_2$, —CH$_2$CF$_3$, —CH$_2$CH$_2$OH, CH$_2$CH$_2$OC(CH$_3$)$_3$, —CH$_2$C(O)OH, CH$_2$C(=O)OH, CH$_2$C(=O)OCH$_2$CH$_3$, cyclopropyl optionally substituted with F, and cyclobutyl,

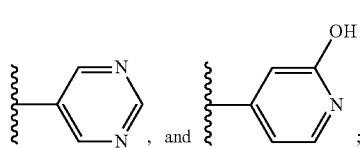

R[6] is independently selected from H, F, Cl, Br, CN, CF$_3$, C(O)CH$_3$, CHF$_2$, CCH$_3$F$_2$, CF$_3$, OCHF$_2$,

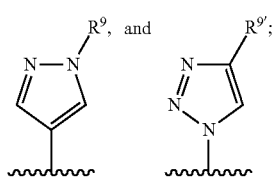

$R^7$ is independently selected from H and F;
$R^8$ is Cl;
$R^9$ is independently selected from H, $CHF_2$, and $CF_3$; and
$R^{9'}$ is independently selected from H, F, Cl, CN, $CHF_2$, and $CF_3$.

6. A compound having Formula (IV):

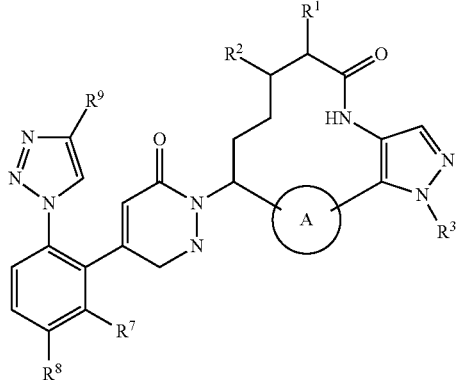

or a stereoisomer, a tautomer, a pharmaceutically acceptable salt thereof, wherein:
ring A is independently selected from

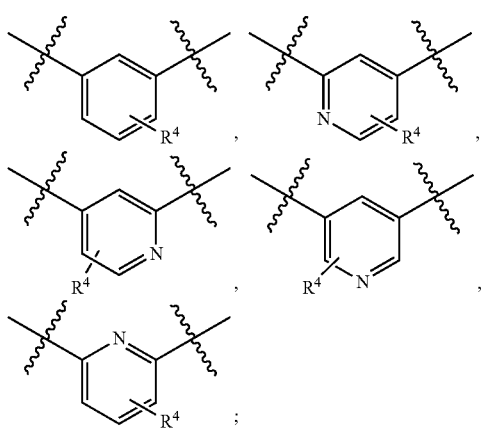

$R^1$ is independently selected from H and $C_{1-3}$alkyl;
$R^2$ is independently selected from H and F;
$R^3$ is independently selected from H, $CD_3$, $CHF_2$, and $CH_3$;
$R^4$ is independently selected from H and halogen;
$R^7$ is independently selected from H and F;
$R^8$ is independently selected from H, F, Cl, and $OCH_3$; and
$R^9$ is independently selected from H, F, Cl, CN, and $CF_3$.

7. A compound having Formula (V):

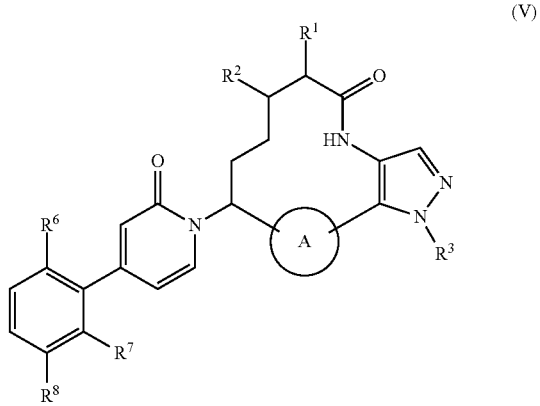

or a stereoisomer, a tautomer, a pharmaceutically acceptable salt thereof, wherein:
ring A is independently selected from

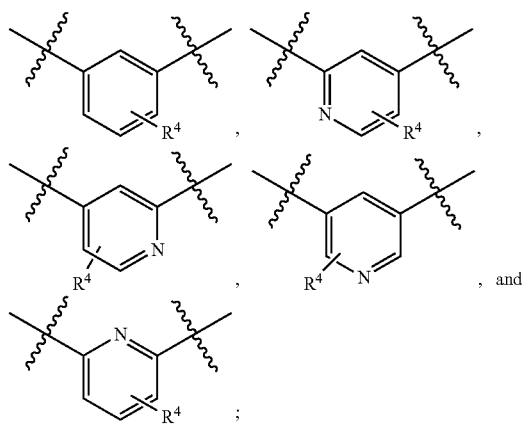

$R^1$ is independently selected from H and $C_{1-3}$alkyl;
$R^2$ is independently selected from H and F;
$R^3$ is independently selected from H, $CD_3$, $CHF_2$, and $CH_3$;
$R^4$ is independently selected from H and halogen;
$R^6$ is independently selected from H, F, Cl, Br, CN, $CF_3$, $C(O)CH_3$, $CHF_2$, $CCH_3F_2$, $CF_3$, $OCHF_2$,

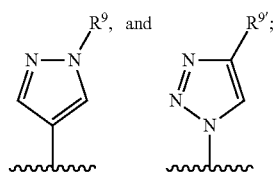

$R^7$ is independently selected from H and F;
$R^8$ is independently selected from H, F, Cl, and $OCH_3$;
$R^9$ is independently selected from H, $CHF_2$, and $CF_3$; and
$R^{9'}$ is independently selected from H, F, Cl, CN, $CHF_2$, and $CF_3$.

8. A compound of claim 1 selected from
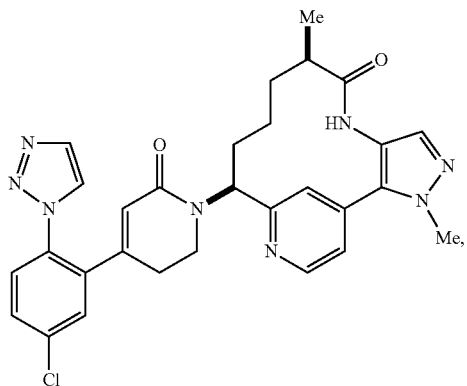
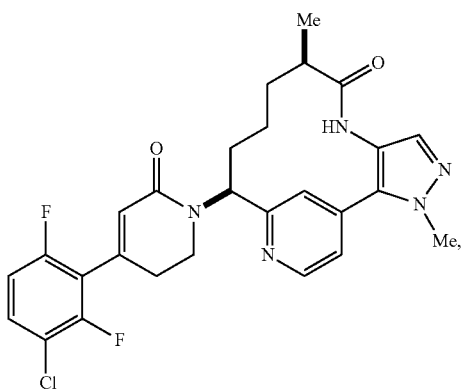
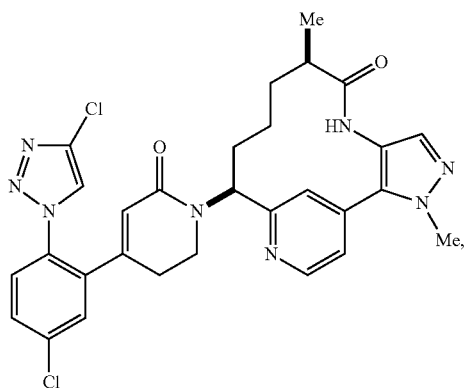
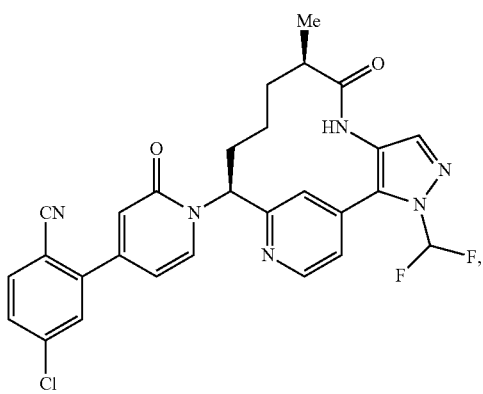
-continued
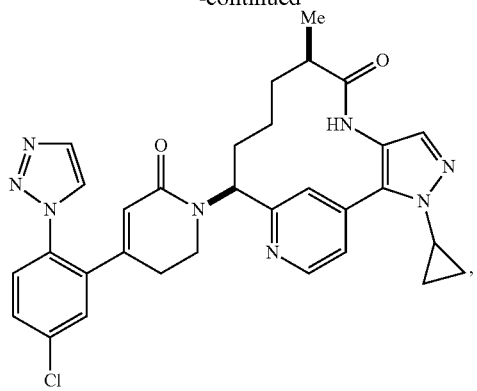
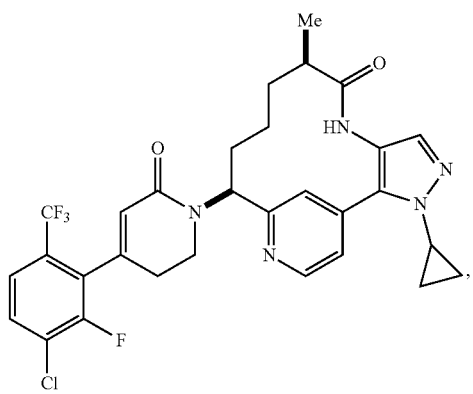
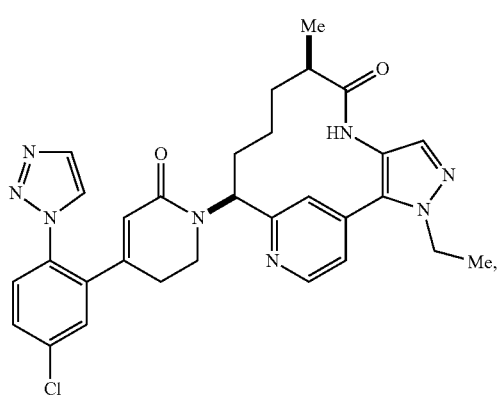
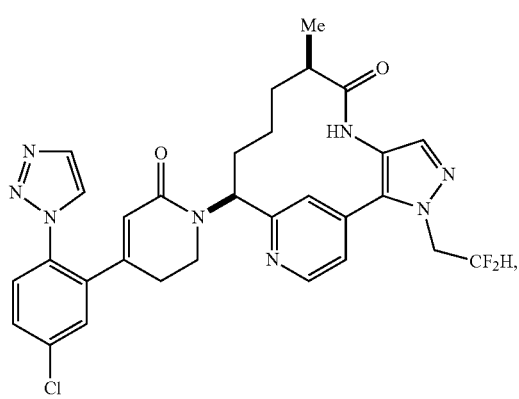

169
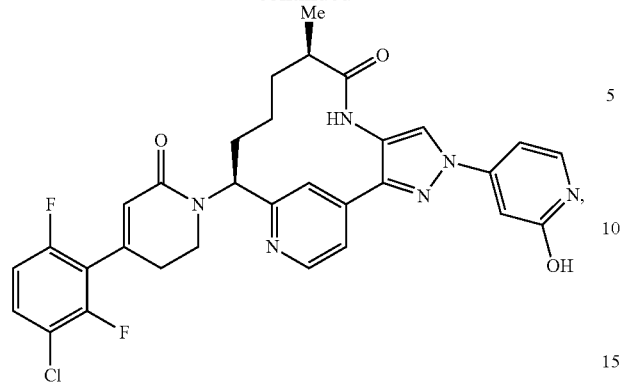
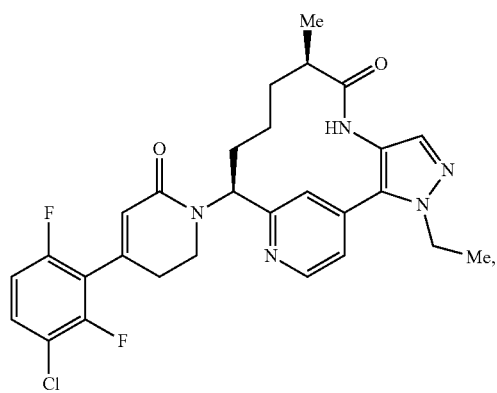
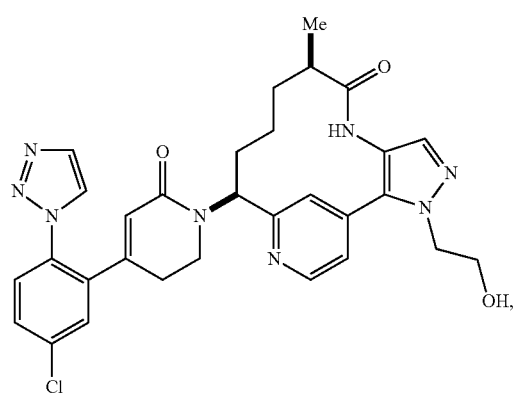
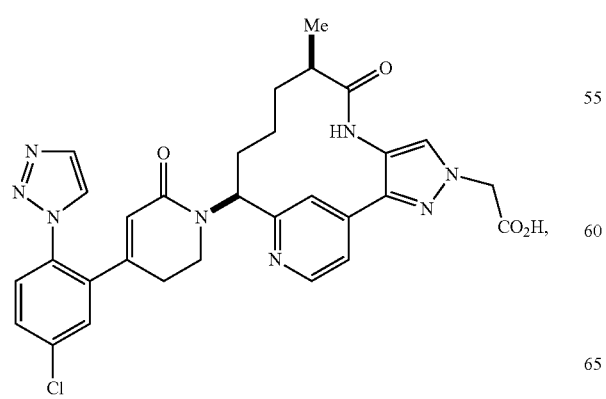
170
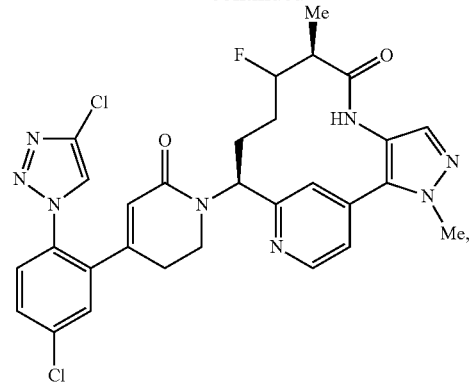
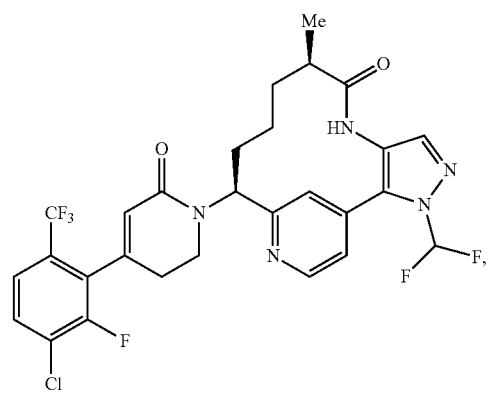
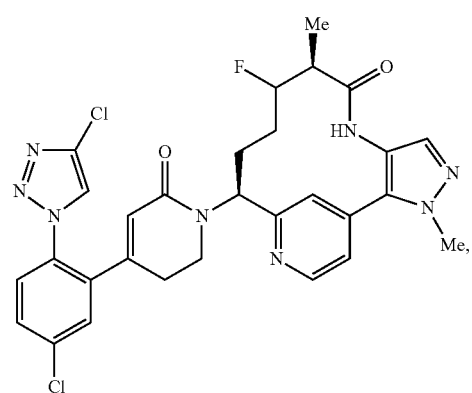
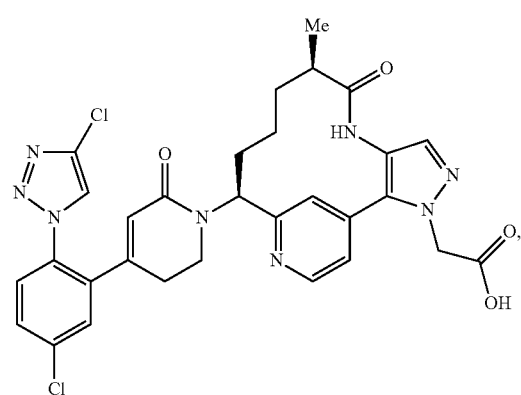

171
-continued
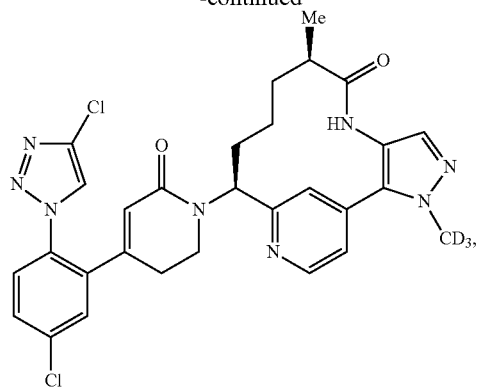
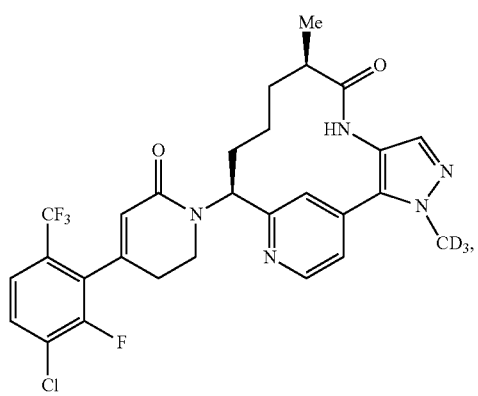
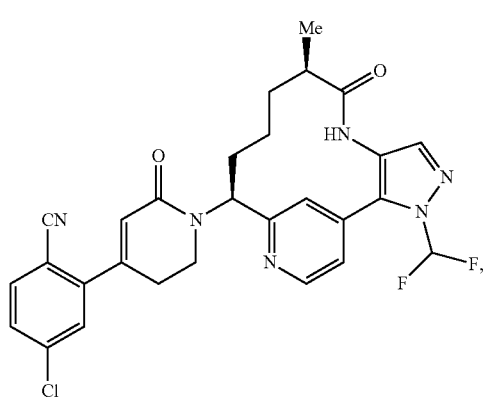
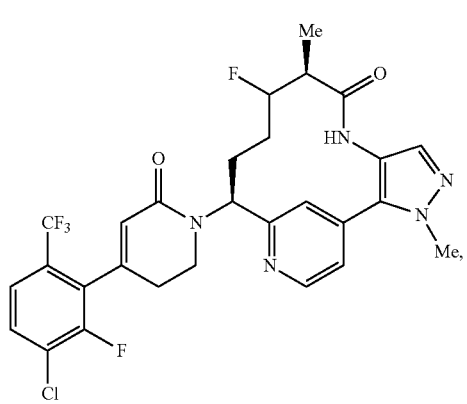
172
-continued
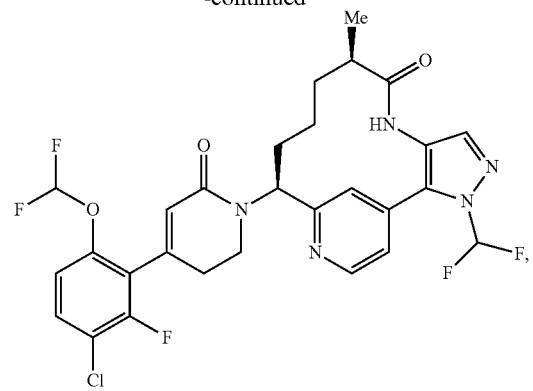
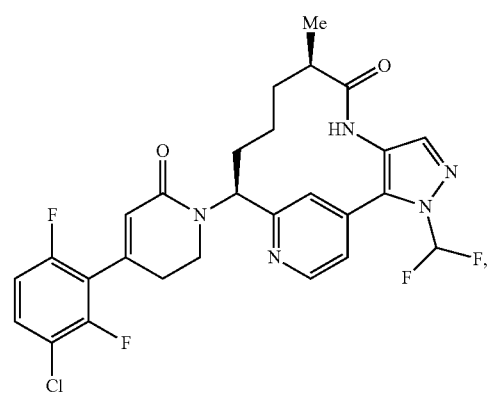
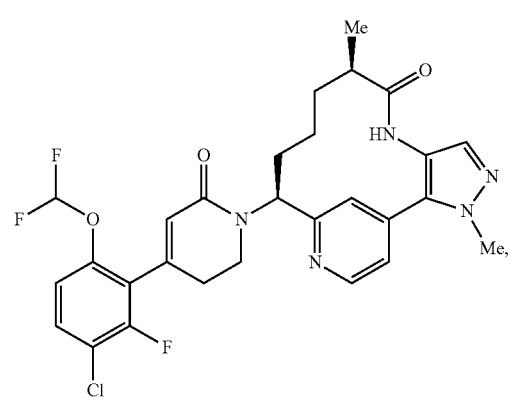
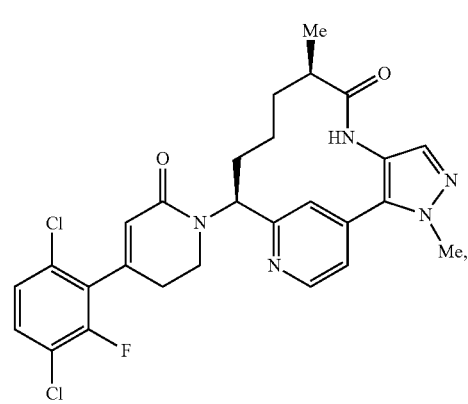

173
-continued
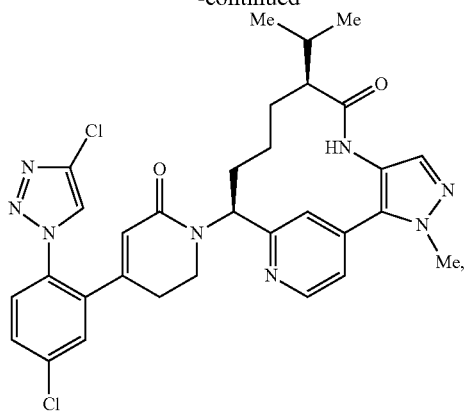
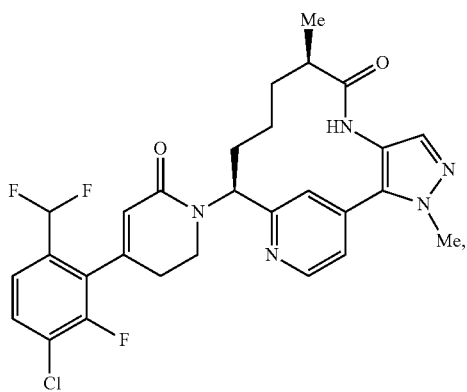
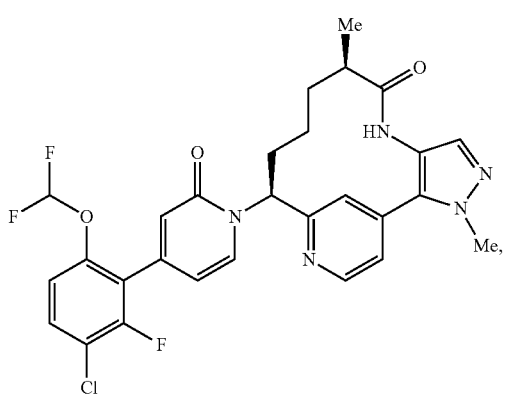
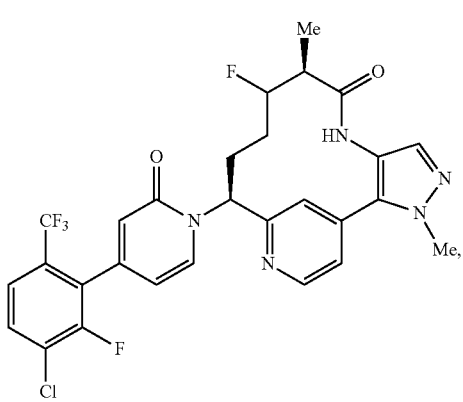
174
-continued
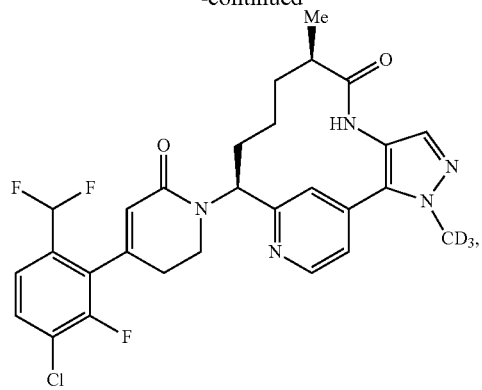
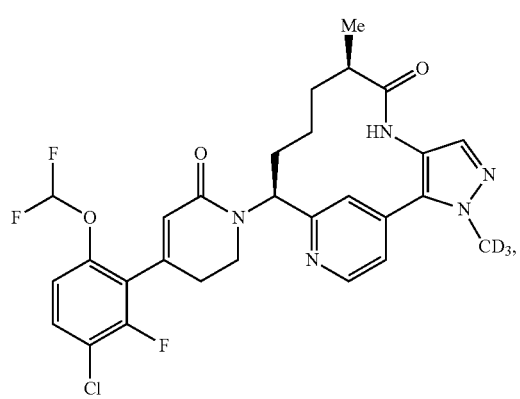
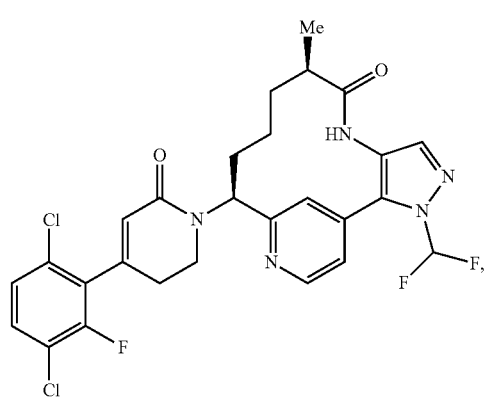
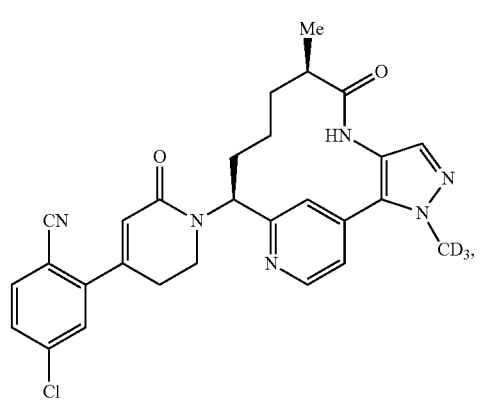

175
-continued
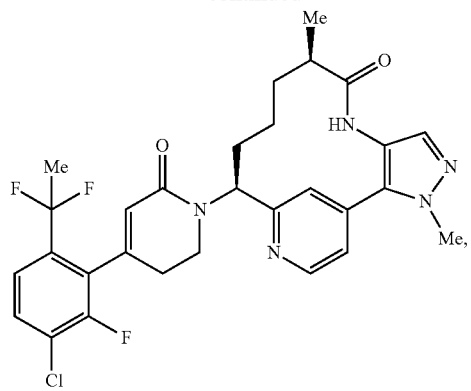
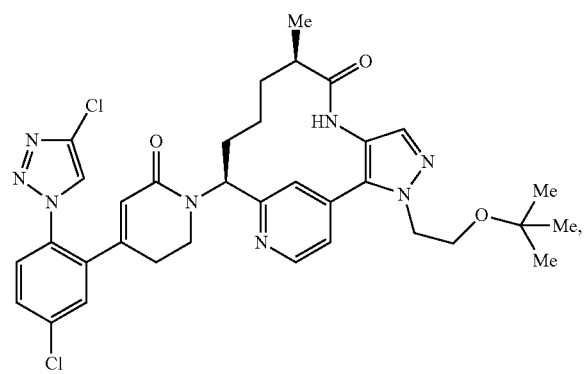
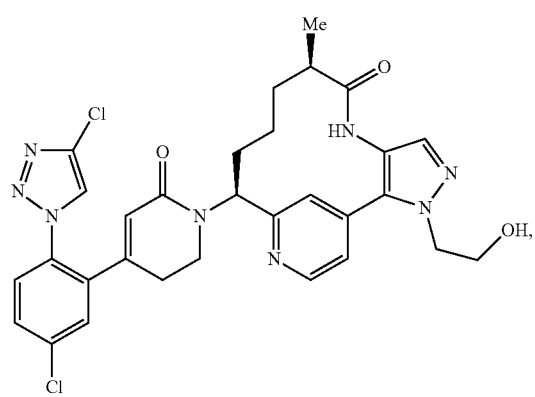
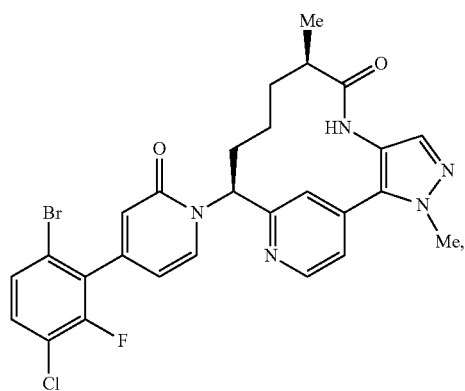
176
-continued
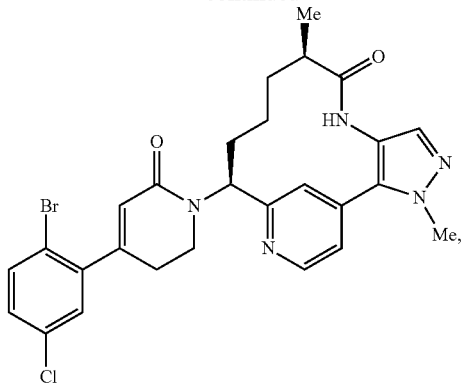
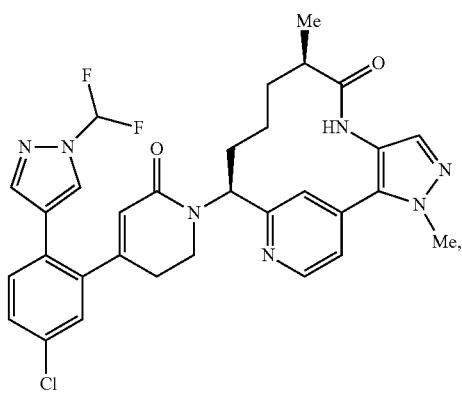
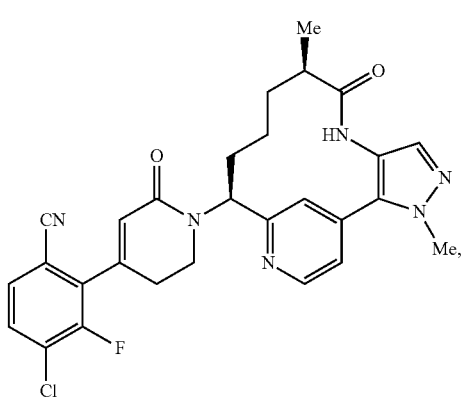
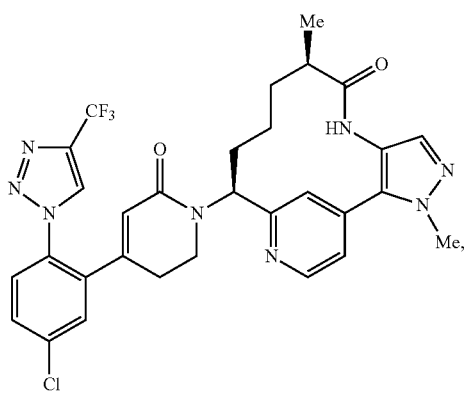

177
-continued
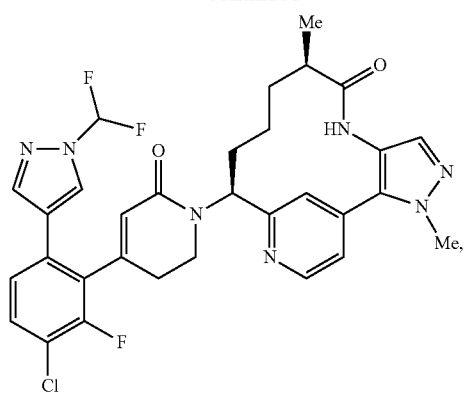
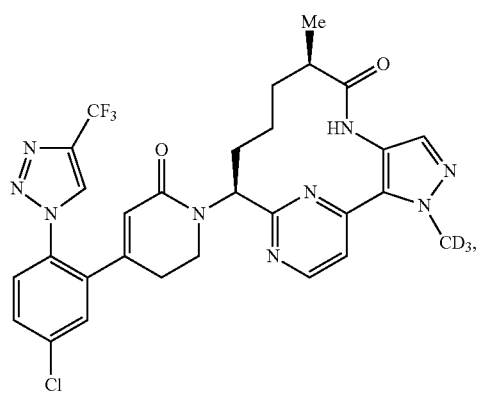
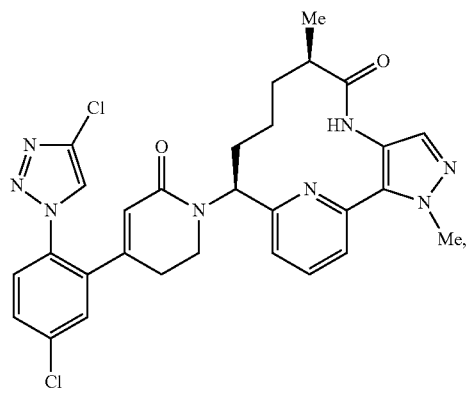
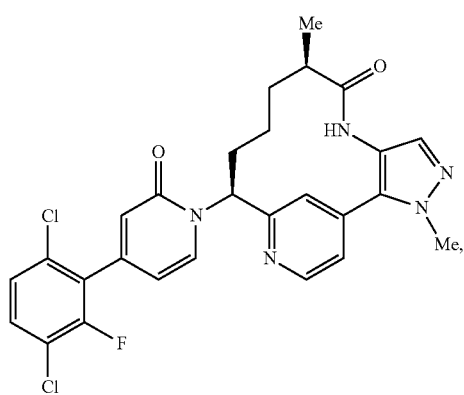
178
-continued
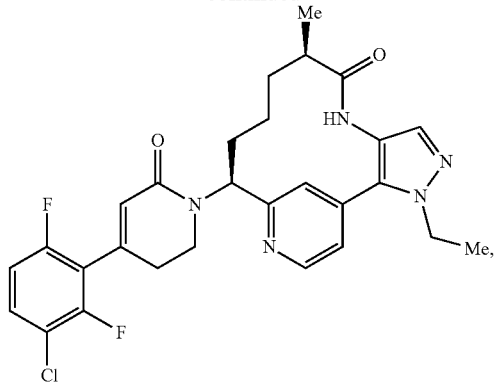
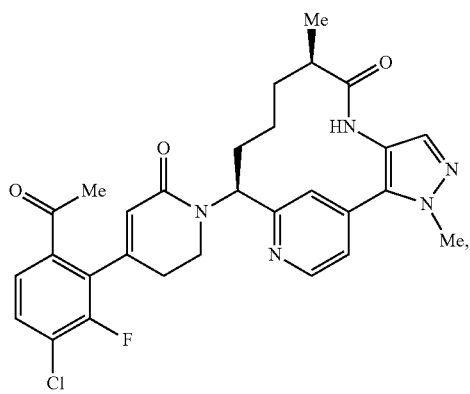
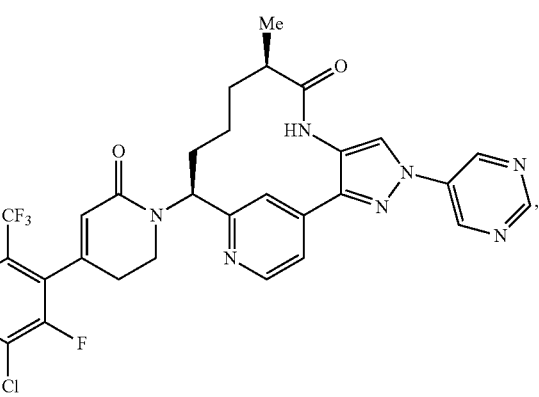
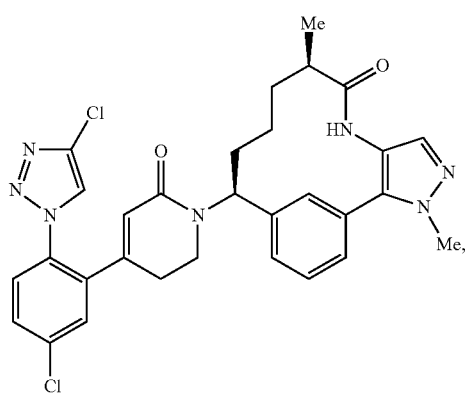

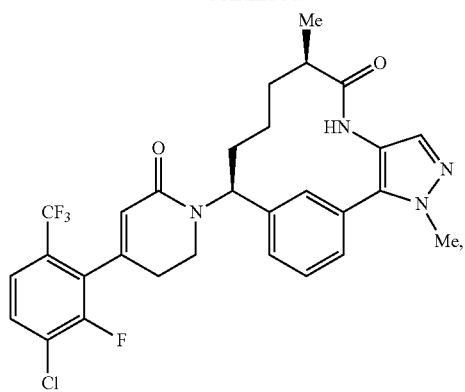
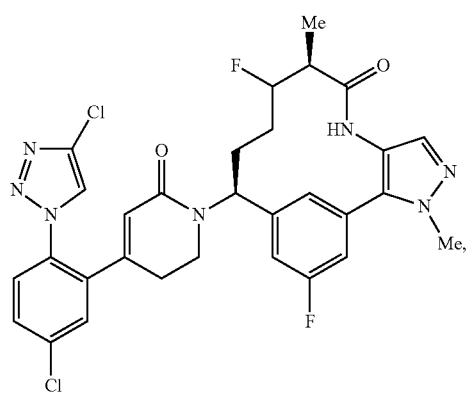
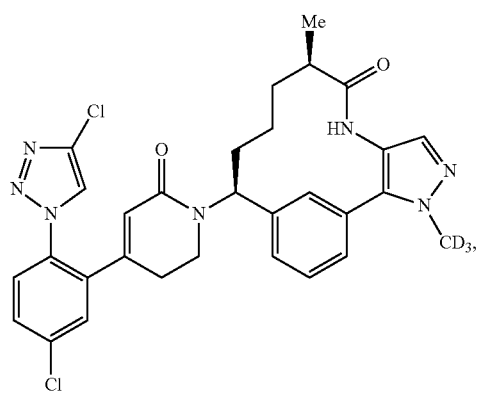
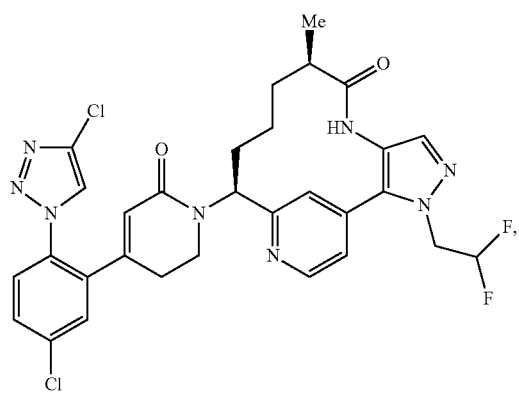
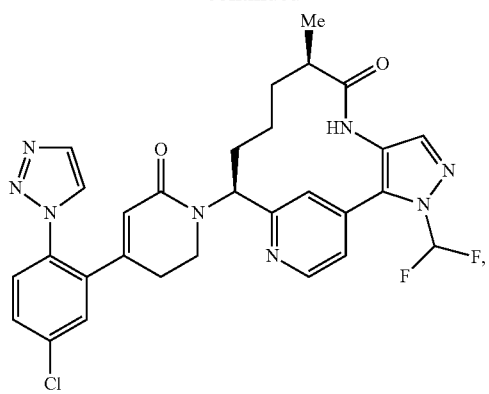
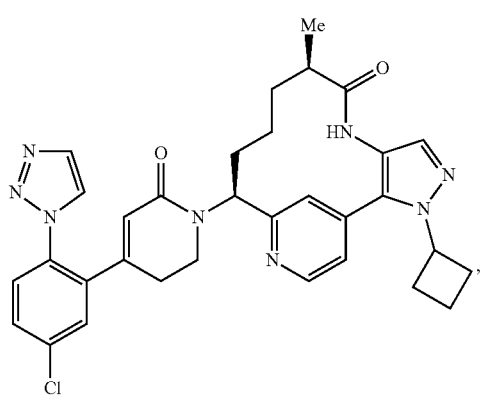
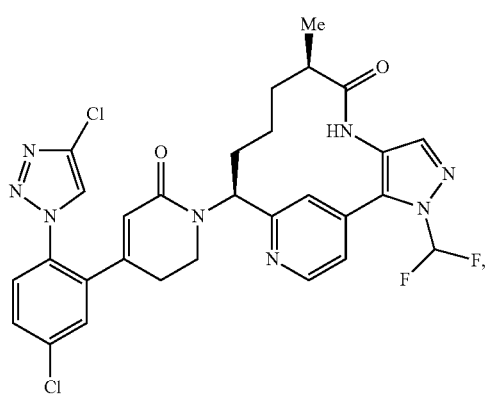
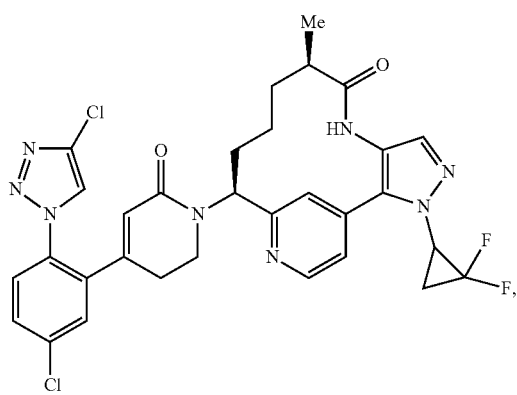

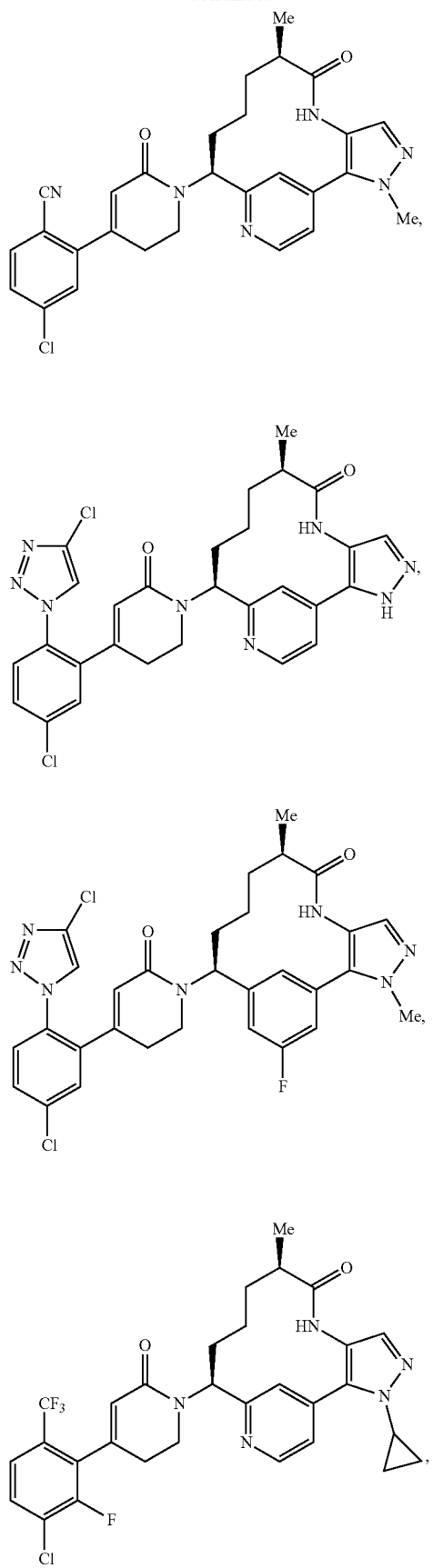
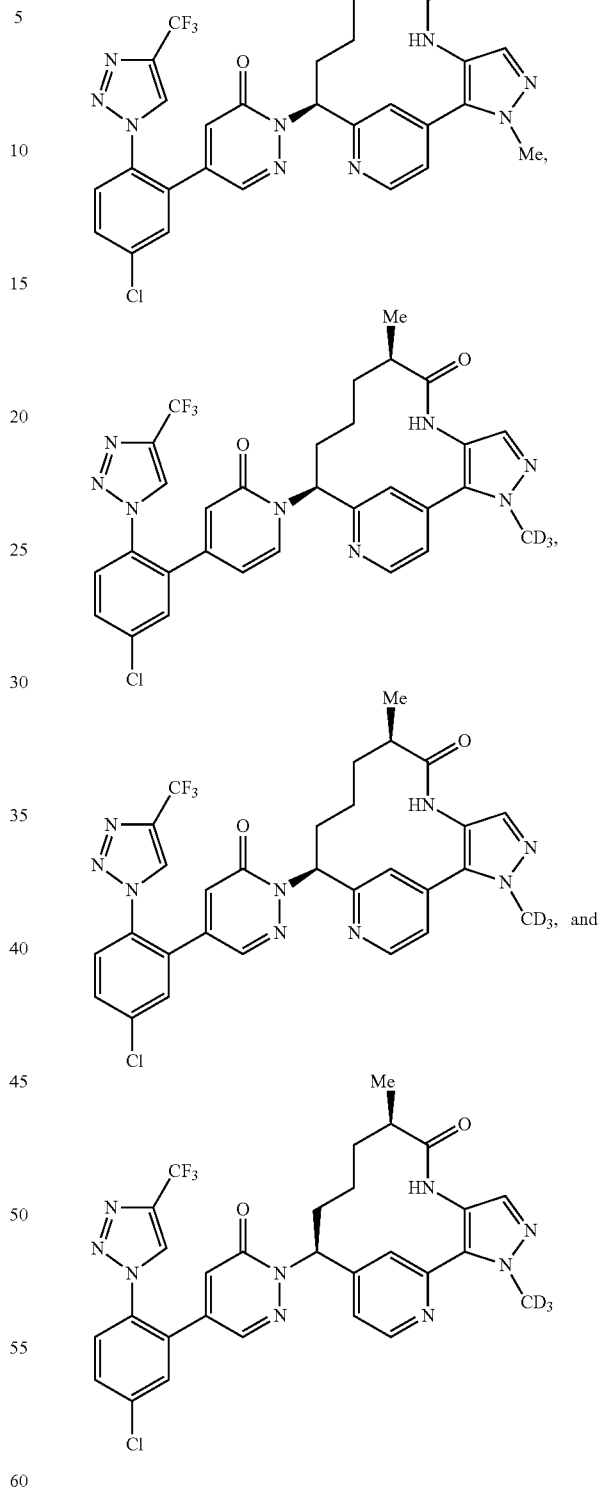
or a stereoisomer, a tautomer, a pharmaceutically acceptable salt thereof.
9. A pharmaceutical composition comprising one or more compounds according to claim 1 and a pharmaceutically acceptable carrier or diluent.
10. A method for the treatment and/or prophylaxis of a thromboembolic disorder, comprising: administering to a patient in need thereof a therapeutically effective amount of a compound of claim 1, or a stereoisomer, a tautomer, or a pharmaceutically acceptable salt thereof, wherein the thromboembolic disorder is selected from arterial cardiovascular thromboembolic disorders, venous cardiovascular thromboembolic disorders, and thromboembolic disorders in the chambers of the heart or in the peripheral circulation.

11. A method according to claim 10, wherein the thromboembolic disorder is selected from unstable angina, an acute coronary syndrome, atrial fibrillation, myocardial infarction, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from medical implants, devices, or procedures in which blood is exposed to an artificial surface that promotes thrombosis.

\* \* \* \* \*